US007115611B2

(12) United States Patent
Ackermann et al.

(10) Patent No.: US 7,115,611 B2
(45) Date of Patent: Oct. 3, 2006

(54) PHENYL DERIVATIVES, THEIR MANUFACTURE AND USE AS PHARMACEUTICAL AGENTS

(75) Inventors: Jean Ackermann, Riehen (CH); Johannes Aebi, Basel (CH); Alfred Binggeli, Binningen (CH); Uwe Grether, Loerrach (DE); Georges Hirth, Colmar (FR); Bernd Kuhn, Liestal (CH); Hans-Peter Maerki, Basel (CH); Markus Meyer, Neuenburg (DE); Peter Mohr, Basel (CH); Matthew Blake Wright, Basel (CH)

(73) Assignee: Hoffmann-la Roche Inc., Nutley, NJ (US)

( * ) Notice: Subject to any disclaimer, the term of this patent is extended or adjusted under 35 U.S.C. 154(b) by 0 days.

(21) Appl. No.: 10/978,155

(22) Filed: Oct. 29, 2004

(65) Prior Publication Data
US 2005/0096337 A1    May 5, 2005

(30) Foreign Application Priority Data
Nov. 5, 2003    (EP)    ................... 03104081
Feb. 26, 2004    (EP)    ................... 04100759

(51) Int. Cl.
A61K 31/4965    (2006.01)
A61K 31/44    (2006.01)
A61N 43/54    (2006.01)
C07D 239/00    (2006.01)
C07D 241/04    (2006.01)

(52) U.S. Cl. ................. 514/255.02; 514/256; 514/334; 544/242; 544/224; 544/384; 544/402; 546/334

(58) Field of Classification Search ................. 544/384, 544/402, 242, 224; 514/255.02, 277, 256; 546/334
See application file for complete search history.

(56) References Cited
FOREIGN PATENT DOCUMENTS

| EP | 1 266 888 A1 | 12/2002 |
|---|---|---|
| WO | WO 97/27857 A1 | 8/1997 |
| WO | WO 02/08188 A1 | 1/2002 |
| WO | WO 02/092084 A1 | 11/2002 |
| WO | WO 03/072100 A1 | 9/2003 |
| WO | WO 03/074495 A1 | 9/2003 |
| WO | WO 03/084916 | 10/2003 |
| WO | WO 03084916 | * 10/2003 |
| WO | WO 2004/000315 | 12/2003 |
| WO | WO 2004/007439 | 1/2004 |

OTHER PUBLICATIONS

Anal. Biochem. 257: 112-119.
Belostotskii, Anatoly M., et. al., Tetrahedron Lett (1994), 35(28), 5075-6.
E.J. Corey, et. al., Am. Chem. Soc (1987) 109, 5551-5553.
Guerre-Millo, et. al., J. Biol Chem (2000) 275: 16638-16642.
Lobiner, et. al., Tetrahedron Lett. (1984), 25, 2535-3536.
S.W. Mccombie, et. al., Bioorganic & Medicinal Chemistry Ltrs 13 (2003) 567-571.
Oliver, et. al., Proc Nat Acad Sci USA (2001) 98: 5306-11.
P.V. Ramachandran, e.t al., Tetrahedron: Asymmetry (1994) 5, 1061-1074.
Tetrahedron Letters 43 (42), 7617-7619 (2002).
J. Labelled Compounds & Radiopharmaceutical 43 (7), 683-691 (2000).
P. Keller, Bull. Soc. Fr. (1994) 131, 27-29.
W. Zhi-Liang, et. al., J. Org. Chem. (2003)web publication release October 10, 2003.
Al-Saleh, B., et. al., Journal of Heterocyclic Chemistry (2002), 39 (5), 1035-1038.
Katsuyama, I, et. al., Synthesis (1997), (11), 1321-1324.
Netherton, M.R., et. al., Organic Letters 2001, 3(26), 4295-4298.
Patent Abstracts of Japan, vol. 2003, No. 10, (2003) & JP 2003 171275 A (Sumitomo Pharmaceut Co Ltd), (2003) Abstract.
Patent Abstracts of Japan, vol. 2003, No. 12, (2003) & JP 2003 292439 A (Sumitomo Pharmaceut Co Ltd), (2003) Abstract.

* cited by examiner

*Primary Examiner*—Cecilia J. Tsang
*Assistant Examiner*—Binta Robinson
(74) *Attorney, Agent, or Firm*—George W. Johnston; Patricia S. Rocha-Tramaloni

(57) ABSTRACT

This invention relates to compounds of the formula

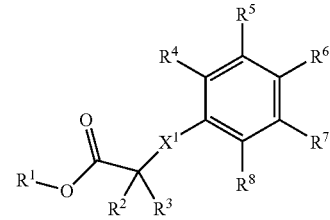

wherein one of $R^5$, $R^6$ and $R^7$ is

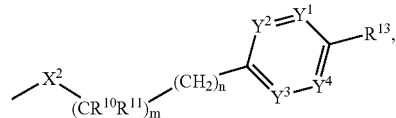

and $X^1$, $X^2$, $Y^1$ to $Y^4$, $R^1$ to $R^{13}$ and m and n are defined in the description, and to all enantiomers and pharmaceutically acceptable salts and/or esters thereof. The invention further relates to pharmaceutical compositions containing such compounds, to a process for their preparation and to their use for the treatment and/or prevention of diseases which are modulated by PPARδ and/or PPARα agonists.

28 Claims, No Drawings

PHENYL DERIVATIVES, THEIR MANUFACTURE AND USE AS PHARMACEUTICAL AGENTS

SUMMARY OF THE INVENTION

The present invention is concerned with novel phenyl derivatives of the formula

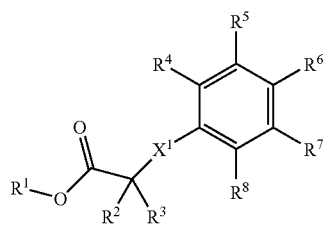

and enantiomers and pharmaceutically acceptable salts and esters thereof, wherein $R^{1-8}$ and $X^1$ are as described herein.

Compounds such as {5-methoxy-2-methyl-4-[6-(4-trifluoromethyl-phenyl)-pyridin-3-ylmethyl-sulfanyl]-phenoxy}-acetic acid have been described in PCT patent application WO 03/084916.

Compounds of formula I are useful as lipid modulators and insulin sensitizers. In particular, compounds of formula I are PPAR activators.

BACKGROUND OF THE INVENTION

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described which are PPARα, PPARδ (also known as PPARβ), and PPARγ. PPARδ is ubiquitously expressed. PPARα is predominantly expressed in the liver, kidney and heart. There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose- and lipid-homeostasis and metabolism, energy balance, cell differentiation, inflammation and cardiovascular events.

Approximately half of all patients with coronary artery disease have low concentrations of plasma HDL cholesterol. The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels. The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol>240 mg/dl is 37% in diabetic men and 44% in women. The respective rates for LDL-C>160 mg/dl are 31% and 44%, respectively, and for HDL-C<35 mg/dl 28% and 11%, respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and afflicts 80–90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2D is a cardiovascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance. A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (Actos™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients. Therefore, new, more efficacious drugs with greater safety and lower side effects are urgently needed. Recent studies provide evidence that agonism of PPARδ would result in compounds with enhanced therapeutic potential, i. e. such compounds should improve the lipid profile, with a superior effect on HDL-C raising compared to current treatments and with additional positive effects on normalization of insulin-levels (Oliver et al; Proc Nat Acad Sci USA 2001; 98: 5306–11). Recent observations also suggest that there is a independent PPARα mediated effect on insulin-sensitzation in addition to its well known role in reducing triglycerides (Guerre-Millo et al; J Biol Chem 2000; 275: 16638–16642). Thus selective PPARδ agonists or PPARδ agonists with additional PPARα activity may show superior therapeutic efficacy without the side-effects such as the weight gain seen with PPARγ agonists.

The novel compounds of the present invention exceed the compounds known in the art, inasmuch as they bind to and selectively activate PPARδ or coactivate PPARδ and PPARα simultaneously and very efficiently, and with much improved pharmacokinetic properties. Therefore, these compounds combine the anti-dyslipidemic and anti-glycemic effects of PPARδ and PPARα activation with no effect on PPARγ. Consequently, HDL cholesterol is increased, triglycerides lowered (=improved lipid profile) and plasma glucose and insulin are reduced (=insulin sensitization). In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2D disease syndrome are addressed by PPARδ-selective agonists and PPARδ and α coagonists, they are expected to have an enhanced therapeutic potential compared to the compounds already known in the art.

Object of the present invention therefore is to provide compounds which must have the criteria mentioned above. Furthermore, the compounds of the present invention exhibit improved pharmacological properties compared to known compounds.

DETAILED DESCRIPTION OF THE INVENTION

In detail, the present invention relates to compounds of formula I

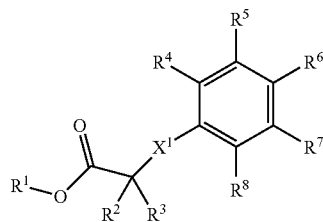

I and enantiomers and pharmaceutically acceptable salts and esters thereof, wherein $X^1$ is O, S, $CH_2$ $R^1$ is hydrogen or $C_{1-7}$-alkyl;

$R^2$ is hydrogen or $C_{1-7}$-alkyl, or, if $X^1$ is $CH_2$, then $R^2$ is hydrogen, $C_{1-7}$-alkyl or $C_{1-7}$-alkoxy;

$R^3$ is hydrogen or $C_{1-7}$-alkyl;

$R^4$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

$R^5$, $R^6$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^5$, $R^6$ and $R^7$ is

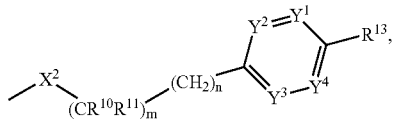

wherein $X^2$ is selected from the group consisting of S, O, $NR^9$, $(CH_2)_p NR^9 CO$, or $(CH_2)_p CONR^9$;

$R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl, or$C_{1-7}$-alkoxy-$C_{2-7}$-alkyl;

$Y^1$, $Y^2$, $Y^3$ and $Y^4$ are N or C—$R^{12}$ and 1 or 2 of $Y^1$, $Y^2$, $Y^3$ and $Y^4$ are N and the other ones are C—$R^{12}$;

$R^{10}$ is $C_{1-7}$-alkyl, $C_{3-7}$-cycloalkyl, fluoro-$C_{1-7}$-alkyl, or $C_{1-7}$-alkoxy-$C_{1-7}$-alkyl;

$R^{11}$ is hydrogen, $C_{1-7}$-alkyl or $C_{1-7}$-alkoxy-$C_{1-7}$-alkyl;

$R^{12}$ independently from each other in each occurrence is selected from the group consisting of hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;

$R^{13}$ is aryl or heteroaryl;

m is 0 or 1, n is 0, 1, 2 or 3, and p is 0, 1 or 2, and the sum of m, n and p is 1, 2, 3 or 4; provided that compounds of formula I are excluded, wherein $X^1$ is O, $R^2$ and $R^3$ are hydrogen, $R^6$ is equal to

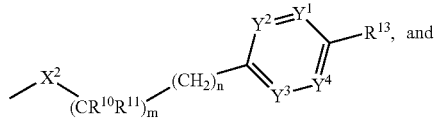

$X^2$ is O or S, and m is 0.

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono- or multiply substituted with fluorine. Examples of fluoro-lower alkyl groups are e.g. —$CF_3$, —$CH_2CF_3$, —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Preferred are the lower-alkoxy groups specifically exemplified herein.

The term "alkylthio" refers to the group R'—S—, wherein R' is alkyl. The term "lower-alkylthio" or "$C_{1-7}$-alkylthio" refers to the group R'—S—, wherein R' is lower-alkyl. Examples of $C_{1-7}$-alkylthio groups are e.g. methylthio or ethylthio. Preferred are the lower-alkylthio groups specifically exemplified herein.

The term "mono- or di-$C_{1-7}$-alkyl-amino" refers to an amino group, which is mono- or disubstituted with $C_{1-7}$-alkyl. A mono-$C_{1-7}$-alkyl-amino group includes for example methylamino or ethylamino. The term "di-$C_{1-7}$-alkyl-amino" includes for example dimethylamino, diethylamino or ethylmethylamino. Preferred are the mono- or di-$C_{1-7}$-alkylamino groups specifically exemplified herein.

The term "carboxy-lower alkyl" or "carboxy-$C_{1-7}$-alkyl" refers to lower alkyl groups which are mono- or multiply substituted with a carboxy group (—COOH). Examples of carboxy-lower alkyl groups are e.g. —$CH_2$—COOH (carboxymethyl), —$(CH_2)_2$—COOH (carboxyethyl) and the groups specifically exemplified herein.

The term "alkanoyl" refers to the group R'—CO—, wherein R' is alkyl. The term "lower-alkanoyl" or "$C_{1-7}$-alkanoyl" refers to the group R'—O—, wherein R' is lower-alkyl. Examples of lower-alkanoyl groups are e.g. ethanoyl (acetyl) or propionyl. Preferred are the lower-alkoxy groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower fluoroalkyl, lower-alkoxy, lower fluoroalkoxy, aryl and/or aryloxy. Preferred substituents are halogen, $CF_3$, lower-alkyl, and/or lower-alkoxy. Preferred are the specifically exemplified aryl groups.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

The term "protecting group" refers to groups such as e.g. acyl, alkoxycarbonyl, aryloxycarbonyl, benzyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups. Protecting groups which can be used for the protection of hydroxy groups are e.g. benzyl, trimethylsilyl or tert-butyldimethylsilyl.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Preferred compounds of formula I of the present invention are compounds, wherein $X^2$ is $NR^9$, $(CH_2)_p NR^9 CO$ or $(CH_2)_p CONR^9$, $R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl; and p is 0, 1 or 2.

Especially preferred are those compounds of formula I in accordance with the present invention, wherein $X^2$ is $NR^9$, and $R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl.

Also preferred are compounds of formula I, wherein $X^2$ is $(CH_2)_p NR^9 CO$, or $(CH_2)_p CONR^9$, $R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl, and p is 0, 1 or 2.

Preferred examples of such compounds include the following:

2-methyl-2-(3-{methyl-[2-methyl-6-(4-trifluoromethyl-phenyl)-pyridin-3-ylmethyl]-carbamoyl}-phenoxy)-propionic acid, 2-[3-({2-[4-cyclopropyl-2-(4-trifluoromethyl-phenyl)-pyrimidin-5-yl]-acetyl}-methyl-amino)-phenoxy]-2-methyl-propionic acid, 2-methyl-2-[3-(methyl-{2-[2-methyl-6-(4-trifluoromethyl-phenyl)-pyridin-3-yl]-acetyl}-amino)-5-trifluoromethyl-phenoxy]-propionic acid, 2-[4-({[4-cyclopropyl-2-(4-trifluoromethyl-phenyl)-pyrimidine-5-carbonyl]-amino}-methyl)-phenoxy]-2-methyl-propionic acid, and 2-methyl-2-(4-{[2-methyl-6-(4-trifluoromethyl-phenyl)-pyridin-3-ylcarbamoyl]-methyl}-phenoxy)-propionic acid.

Further preferred examples of such compounds are the following:

2-[3-chloro-4-({[4-trifluoromethyl-2-(4-trifluoromethyl-phenyl)-pyrimidine-5-carbonyl]-amino}-methyl)-phenoxy]-2-methyl-propionic acid, 2-methyl-2-[4-({[4-trifluoromethyl-2-(4-trifluoromethyl-phenyl)-pyrimidine-5-carbonyl]-amino}-methyl)-phenoxy]-propionic acid; and 2-(4-{[4-cyclopropyl-2-(4-trifluoromethyl-phenyl)-pyrimidin-5-ylcarbamoyl]-methyl}-phenoxy)-2-methyl-propionic acid.

Compounds of formula I, wherein $X^2$ is $NR^9$, $(CH_2)_p NR^9CO$ or $(CH_2)_p CONR^9$ and $R^9$ is $C_{1-7}$-alkyl, are more preferred.

Examples of especially preferred compounds, wherein $X^2$ is $NR^9$, $(CH_2)_p NR^9CO$ or $(CH_2)_p CONR^9$, are the following:

(2-(3-methoxy-propyl)-4-{methyl-[2-methyl-6-(4-trifluoromethyl-phenyl)-pyridin-3-ylmethyl]-amino}-phenoxy)-acetic acid,

[rac]-[2-methyl-4-(methyl-{1-[2-methyl-6-(3-trifluoromethyl-phenyl)-pyridin-3-yl]-butyl}-amino)-phenoxy]-acetic acid, (4-{[6-(4-chloro-phenyl)-pyridin-3-ylmethyl]-methyl-amino}-2-methyl-phenoxy)-acetic acid, 2-methyl-2-[3-(methyl-{2-[2-methyl-6-(4-trifluoromethyl-phenyl)-pyridin-3-yl]-acetyl}-amino)-phenoxy]-propionic acid, and (4-{[4-cyclopropyl-2-(4-trifluoromethyl-phenyl)-pyrimidin-5-ylmethyl]-methyl-amino}-2-methyl-phenoxy)-acetic acid.

Furthermore, compounds of formula I in accordance with the present invention are preferred, wherein $X^1$ and $X^2$ are O and $R^2$ is $C_{1-7}$-alkyl, with those compounds of formula I, wherein $R^2$ and $R^3$ are $C_{1-7}$-alkyl, being especially preferred.

Examples of such compounds are the following:

2-methyl-2-{2-methyl-4-[2-methyl-6-(3-trifluoromethyl-phenyl)-pyridin-3-ylmethoxy]-phenoxy}-propionic acid, 2-methyl-2-{2-methyl-4-[6-(4-trifluoromethoxy-phenyl)-pyridin-3-ylmethoxy]-phenoxy}-propionic acid, and 2-{4-[4-cyclopropyl-2-(4-trifluoromethyl-phenyl)-pyrimidin-5-ylmethoxy]-2-methyl-phenoxy}-2-methyl-propionic acid.

Further preferred examples of such kind of compounds include 2-methyl-2-{2-methyl-4-[2-methyl-6-(4-trifluoromethoxy-phenyl)-pyridin-3-ylmethoxy]-phenoxy}-propionic acid, 2-{4-[4-cyclopropyl-2-(3-trifluoromethyl-phenyl)-pyrimidin-5-ylmethoxy]-2-methyl-phenoxy}-2-methyl-propionic acid, and 2-{4-[4-(2-methoxy-ethyl)-6-methyl-2-(4-trifluoromethyl-phenyl)-pyrimidin-3-ylmethoxy]-2-methyl-phenoxy}-2-methyl-propionic acid.

Furthermore, the following compounds are examples thereof:

2-{4-[2-cyclopropyl-6-(4-trifluoromethoxy-phenyl)-pyridin-3-ylmethoxy-2-methyl-phenoxy}-2-methyl-propionic acid, 2-{4-[4-methoxymethyl-6-methyl-2-(3-trifluoromethyl-phenyl)-pyrimidin-5-ylmethoxy]-2-methyl-phenoxy}-2-methyl-propionic acid, 2-{4-[2-cyclopropyl-6-(4-trifluoromethoxy-phenyl)-4-trifluoromethyl-pyridin-3-ylmethoxy]-2-methyl-phenoxy}-2-methyl-propionic acid, 2-{4-[4-methoxymethyl-2-(4-trifluoromethoxy-phenyl)-pyrimidin-5-ylmethoxy]-2-methyl-phenoxy}-2-methyl-propionic acid, 2-{4-[2-cyclopropyl-6-(4-trifluoromethoxy-phenyl)-4-trifluoromethyl-pyridin-3-ylmethoxy]-2-methyl-phenoxy}-2-methyl-propionic acid, and 2-{4-[4-methoxymethyl-2-(4-trifluoromethoxy-phenyl)-pyrimidin-5-ylmethoxy]-2-methyl-phenoxy}-2-methyl-propionic acid.

Further preferred compounds of formula I of the present invention are those, wherein $X^1$ and $X^2$ are O and m is 1.

The following compounds, wherein $X^1$ and $X^2$ are O and m is 1, are especially preferred:

[rac]-(4-{1-[4-Cyclopropyl-2-(4-trifluoromethyl-phenyl)-pyrimidin-5-yl]-ethoxy}-2-methyl-phenoxy)-acetic acid, and

[rac]-(4-{1-[4-Cyclopropyl-2-(4-trifluoromethyl-phenyl)-pyrimidin-5-yl]-butoxy}-2-methyl-phenoxy)-acetic acid.

Also preferred are compounds of formula I according the present invention, wherein $X^1$ is S.

Examples of such compounds are the following:

[rac]-(2-methyl-4-{1-[2-methyl-6-(4-trifluoromethyl-phenyl)-pyridin-3-yl]-ethoxy}-phenylsulfanyl)-acetic acid, and

[rac]-(2-methyl-4-{1-[2-methyl-6-(4-trifluoromethyl-phenyl)-pyridin-3-yl]-butoxy}-phenylsulfanyl)-acetic acid.

Further preferred compounds of formula I according to the present invention are those, wherein $X^1$ is O, $X^2$ is S and m is 1.

The following compounds, wherein $X^1$ is O, $X^2$ is S and m is 1, are especially preferred:

[rac]-(2-methyl-4-{1-[2-methyl-6-(4-trifluoromethyl-phenyl)-pyridin-3-yl]-ethylsulfanyl}-phenoxy)-acetic acid, and

[rac]-(4-{1-[4-Cyclopropyl-2-(4-trifluoromethyl-phenyl)-pyrimidin-5-yl]-ethylsulfanyl}-2-methyl-phenoxy)-acetic acid.

Compounds of formula I, wherein $R^{13}$ is aryl, are preferred. More preferred are those compounds of formula I, wherein $R^{13}$ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano, with those compounds, wherein $R^{13}$ is $C_{1-7}$-alkyl, $C_{1-7}$-alkoxy, halogen, fluoro-$C_{1-7}$-alkyl or cyano, being more preferred, and with those compounds, wherein $R^{13}$ is phenyl substituted with halogen or fluoro-$C_{1-7}$-alkyl, being particularly preferred. Especially preferred are those compounds, wherein $R^{13}$ is 4-trifluoromethylphenyl. Also preferred are those compounds, wherein $R^{13}$ is 4-trifluoromethoxyphenyl.

Especially preferred are furthermore compounds of formula I, wherein $R^1$ is hydrogen.

Preferred compounds of formula I of the present invention are those, wherein $R^6$ is

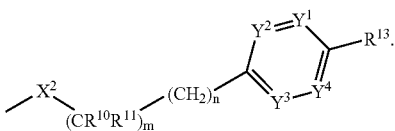

These compounds have the formula I-A:

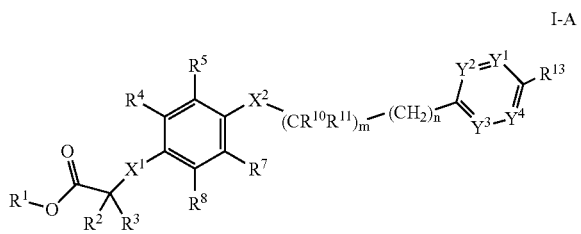

I-A

However, compounds of formula I-A, wherein $X^1$ is O, $R^2$ and $R^3$ are hydrogen, $X^2$ is O or S and m is 0, are excluded.

Furthermore, compounds of formula I are preferred, wherein $R^5$ or $R^7$ is

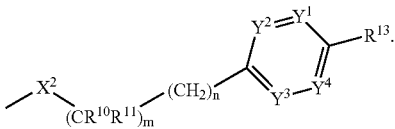

These compounds have the formula I-B or I-C:

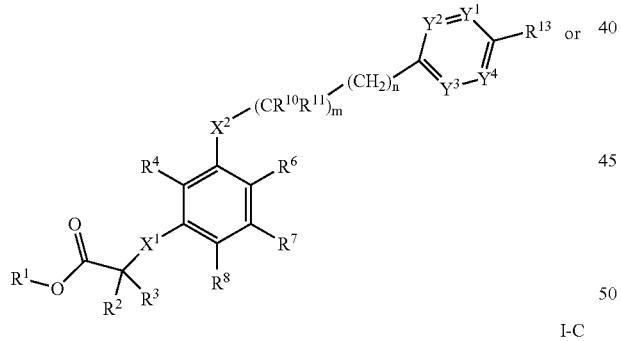

I-B

I-C

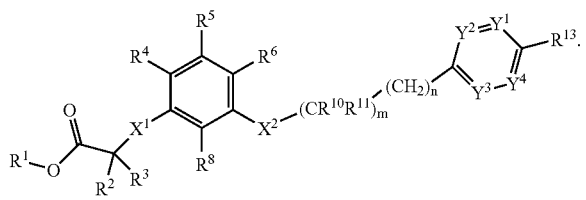

The integer m is 0 or 1, the integer n is 0, 1, 2 or 3 and the integer p is 0, 1 or 2, provided that the sum of m, n and p is 1, 2, 3 or 4. Especially preferred are compounds of formula I, wherein the sum of m, n and p is 1.

$Y^1$, $Y^2$, $Y^3$ and $Y^4$ signify N or C—$R^{12}$, provided that 1 or 2 of $Y^1$, $Y^2$, $Y^3$ and $Y^4$ are N and the other ones are C—$R^{12}$. $R^{12}$ independently from each other in each occurrence is selected from hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl. Preferably, $R^{12}$ independently from each other in each occurrence is selected from hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, and $C_{1-7}$-alkylthio-$C_{1-7}$-alkyl. More preferably, $R^{12}$ is selected from hydrogen, $C_{1-7}$-alkyl, and $C_{3-7}$-cycloalkyl.

Preferred compounds of the present invention are for example those, wherein 1 of $Y^1$, $Y^2$, $Y^3$ and $Y^4$ is N and the other ones are C—$R^{12}$, thus meaning compounds containing a pyridyl group.

Especially preferred are those compounds of formula I, wherein $Y^1$ is N and $Y^2$, $Y^3$ and $Y^4$ are C—$R^{12}$, e. g. compounds of formula I containing the group

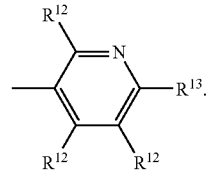

Further preferred compounds of the present invention are those, wherein 2 of $Y^1$, $Y^2$, $Y^3$ and $Y^4$ are N and the other ones are C—$R^{12}$, thus meaning compounds containing a pyrazinyl group or a pyrimidinyl group or a pyridazinyl group.

Especially preferred are compounds of formula I, wherein $Y^1$ and $Y^4$ are N and $Y^2$ and $Y^3$ are C—$R^{12}$, e. g. compounds of formula I containing the pyrimidinyl group

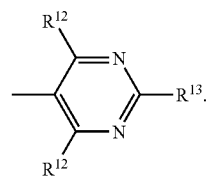

Also preferred are compounds of formula I, wherein $Y^1$ and $Y^3$ are N and $Y^2$ and $Y^4$ are C—$R^{12}$, e. g. compounds of formula I containing the pyrazinyl group

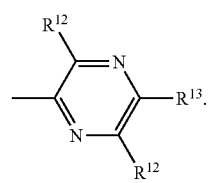

$R^{12}$ is preferably hydrogen, $C_{1-7}$-alkyl, or $C_{3-7}$-cycloalkyl.

Examples of preferred compounds of formula I are the following:

(2-(3-methoxy-propyl)-4-{methyl-[2-methyl-6-(4-trifluoromethyl-phenyl)-pyridin-3-ylmethyl]-amino}-phenoxy)-acetic acid, (2-(3-methoxy-propyl)-4-{methyl-[2-methyl-6-(3-trifluoromethyl-phenyl)-pyridin-3-ylmethyl]-amino}-phenoxy)-acetic acid,

[rac]-[2-(3-methoxy-propyl)-4-(methyl-{1-[2-methyl-6-(3-trifluoromethyl-phenyl)-pyridin-3-yl]-ethyl}-amino)-phenoxy]-acetic acid,

[rac]-[2-(3-methoxy-propyl)-4-(methyl-{1-[2-methyl-6-(3-trifluoromethyl-phenyl)-pyridin-3-yl]-butyl}-amino)-phenoxy]-acetic acid,

[rac]-[2-methyl-4-(methyl-{1-[2-methyl-6-(3-trifluoromethyl-phenyl)-pyridin-3yl]-butyl}-amino)-phenoxy]-acetic acid,

[rac]-(4-{methyl-[2-methyl-6-(4-trifluoromethyl-phenyl)-pyridin-3-ylmethyl]-amino}-2-trifluoromethyl-phenoxy)-acetic acid, (2,6-dimethyl-4-{methyl-[2-methyl-6-(4-trifluoromethyl-phenyl)-pyridin-3-ylmethyl]-amino}-phenoxy)-acetic acid, 2-methyl-2-{2-methyl-4-[2-methyl-6-(3-trifluoromethyl-phenyl)-pyridin-3-ylmethoxy]-phenoxy}-propionic acid, 2-methyl-2-{2-methyl-4-[6-(4-trifluoromethyl-phenyl)-pyridin-3-ylmethoxy]-phenoxy}-propionic acid, 2-methyl-2-{2-methyl-4-[6-(4-trifluoromethoxy-phenyl)-pyridin-3-ylmethoxy]-phenoxy}-propionic acid,

[rac]-[2-methyl-4-(methyl-{1-[2-methyl-6-(3-trifluoromethyl-phenyl)-pyridin-3-yl]-propyl}-amino)-phenoxy]-acetic acid, (4-{[6-(4-chloro-phenyl)-pyridin-3-ylmethyl]-methyl-amino}-2-methyl-phenoxy)-acetic acid, (2-methyl-4-{methyl-[6-(4-trifluoromethoxy-phenyl)-pyridin-3-ylmethyl]-amino}-phenoxy)-acetic acid, (2-(3-methoxy-propyl)-4-{methyl-[6-(4-trifluoromethoxy-phenyl)-pyridin-3-ylmethyl]-amino}-phenoxy)-acetic acid, (2-methyl-4-{methyl-[6-(4-trifluoromethyl-phenyl)-pyridin-3-ylmethyl]-amino}-phenoxy)-acetic acid, (2-(3-methoxy-propyl)-4-{methyl-[6-(4-trifluoromethyl-phenyl)-pyridin-3-ylmethyl]-amino}-phenoxy)-acetic acid,

[rac]-(2-methyl-4-{1-[2-methyl-6-(4-trifluoromethyl-phenyl)-pyridin-3-yl]-ethylsulfanyl]-phenoxy)-acetic acid,

[rac]-(2-methyl-4-{1-[2-methyl-6-(4-trifluoromethyl-phenyl)-pyridin-3-yl]-propylsulfanyl}-phenoxy)-acetic acid,

[rac]-(2-methyl-4-{1-[2-methyl-6-(3-trifluoromethyl-phenyl)-pyridin-3-yl]-ethylsulfanyl}-phenoxy)-acetic acid,

[rac]-(2-methyl-4-{1-[2-methyl-6-(4-trifluoromethyl-phenyl)-pyridin-3-yl]-ethoxy}-phenylsulfanyl)-acetic acid,

[rac]-(2-methyl-4-{1-[2-methyl-6-(4-trifluoromethyl-phenyl)-pyridin-3-yl]-butoxy}-phenylsulfanyl)-acetic acid,

[rac]-(2-methyl-4-{1-[2-methyl-6-(4-trifluoromethyl-phenyl)-pyridin-3-yl]-butylsulfanyl}-phenoxy)-acetic acid,

[rac]-(4-{cyclopentyl-[2-methyl-6-(4-trifluoromethyl-phenyl)-pyridin-3-yl]-methylsulfanyl}-2-methyl-phenoxy)-acetic acid, 2-{4-[6-(4-fluoro-3-trifluoromethyl-phenyl)-2-methyl-pyridin-3-ylmethoxy]-2-methyl-phenoxy}-2-methyl-propionic acid,

[rac]-2-methyl-2-(2-methyl-4-{1-[2-methyl-6-(3-trifluoromethyl-phenyl)-pyridin-3-yl]-ethoxy}-phenoxy)-propionic acid, 2-methyl-2-[3-(methyl-{2-[2-methyl-6-(4-trifluoromethyl-phenyl)-pyridin-3-yl]-acetyl}-amino)-phenoxy]-propionic acid, (4-{[4-cyclopropyl-2-(4-trifluoromethyl-phenyl)-pyrimidin-5-ylmethyl]-methyl-amino}-2-methyl-phenoxy)-acetic acid,

[rac]-(4-{1-[4-Cyclopropyl-2-(4-trifluoromethyl-phenyl)-pyrimidin-5-yl]-ethylsulfanyl}-2-methyl-phenoxy)-acetic acid,

[rac]-(4-{1-[4-Cyclopropyl-2-(4-trifluoromethyl-phenyl)-pyrimidin-5-yl]-ethoxy}-2-methyl-phenoxy)-acetic acid,

[rac]-(4-{1-[4-Cyclopropyl-2-(4-trifluoromethyl-phenyl)-pyrimidin-5-yl]-butylsulfanyl}-2-methyl-phenoxy)-acetic acid,

[rac]-(4-{1-[4-Cyclopropyl-2-(4-trifluoromethyl-phenyl)-pyrimidin-5-yl]-butoxy}-2-methyl-phenoxy)-acetic acid, 2-{4-[4-cyclopropyl-2-(4-trifluoromethyl-phenyl)-pyrimidin-5-ylmethoxy]-2-methyl-phenoxy}-2-methyl-propionic acid, and (2-methyl-4-{methyl-[5-(4-trifluoromethyl-phenyl)-pyrazin-2-ylmethyl-amino}-phenoxy)-acetic acid.

Further examples of preferred compounds include the following:

2-methyl-2-{2-methyl-4-[2-methyl-6-(4-trifluoromethyl-phenyl)-pyridin-3-ylmethoxy]-phenoxy}-propionic acid, phenoxy-propionic acid,

[rac]-2-methyl-2-(2-methyl-4-{1-[2-methyl-6-(4-trifluoromethyl-phenyl)-pyridin-3-yl]-butoxyl}-phenoxy)-propionic acid,

[rac]-2-methyl-2-(2-methyl-4-{1-[2-methyl-6-(4-trifluoromethyl-phenyl)-pyridin-3-yl]-propoxyl-phenoxy)-propionic acid,

[rac]-2-methyl-2-(2-methyl-4-{1-[2-methyl-6-(4-trifluoromethyl-phenyl)-pyridin-3-yl]-ethoxy}-phenoxy)-propionic acid, 2-{4-[6-(3-fluoro-4-trifluoromethyl-phenyl)-2-methyl-pyridin-3-ylmethoxy]-2-methyl-phenoxy-2-methyl-propionic acid, 2-methyl-2-{2-methyl-4-[2-methyl-6-(4-trifluoromethoxy-phenyl)-pyridin-3-ylmethoxy]-phenoxy}-propionic acid, 2-{4-[2-cyclopropyl-6-(4-trifluoromethyl-phenyl)-pyridin-3-ylmethoxy]-2-methyl-phenoxy}-2-methyl-propionic acid,

[rac]-2-methyl-2-(2-methyl-4-{1-[2-methyl-6-(3-trifluoromethyl-phenyl)-pyridin-3-yl]-butoxy}-phenoxy)-propionic acid, 2-{4-[4-cyclopropyl-2-(3-trifluoromethyl-phenyl)-pyrimidin-5-ylmethoxy]-2-methyl-phenoxy}-2-methyl-propionic acid, 2-methyl-2-(2-methyl-4-{2-[2-methyl-6-(4-trifluoromethyl-phenyl)-pyridin-3-yl]-ethoxy}-phenoxy)-propionic acid, 2-methyl-2-{2-methyl-4-[6-(4-trifluoromethyl-phenyl)-pyridazin-3-ylmethoxy]-phenoxy}-propionic acid, 2-{4-[2-methoxymethyl-6-(4-trifluoromethyl-phenyl)-pyridin-3-ylmethoxy]-2-methyl-phenoxy}-2-methyl-propionic acid,

[rac]-(2-methyl-4-{1-[2-methyl-6-(4-trifluoromethyl-phenyl)-pyridin-3-yl]-butoxy}-phenoxy)-acetic acid,

[rac]-(2-methyl-4-{1-[2-methyl-6-(3-trifluoromethyl-phenyl)-pyridin-3-yl]-ethoxy}-phenoxy)-acetic acid,

[rac]-(2-methyl-4-{1-[2-methyl-6-(3-trifluoromethyl-phenyl)-pyridin-3-yl]-butoxy}-phenoxy)-acetic acid,

[rac]-(2-methyl-4-{1-[2-methyl-6-(4-trifluoromethyl-phenyl)-pyridin-3-yl]-propoxy}-phenoxy)-acetic acid,

[rac]-(2-methyl-4-{1-[2-methyl-6-(4-trifluoromethyl-phenyl)-pyridin-3-yl]-ethoxy}-phenoxy)-acetic acid, 2-{4-[2-dimethylaminomethyl-6-(4-trifluoromethyl-phenyl)-pyridin-3-ylmethoxy]-2-methyl-phenoxy}-2-methyl-propionic acid, 2-methyl-2-{3-[(methyl-{2-[2-methyl-6-(4-trifluoromethyl-phenyl)-pyridin-3-yl]-acetyl}-amino)-methyl]-phenoxy}-propionic acid, 2-[3-({[4-cyclopropyl-2-(4-trifluoromethyl-phenyl)-pyrimidine-5-carbonyl]-methyl-amino}-methyl)-phenoxy]-2-methyl-propionic acid,
2-methyl-2-[3-({methyl-[2-methyl-6-(4-trifluoromethyl-phenyl)-pyridine-3-carbonyl]-amino}-methyl)-phenoxy]-propionic acid,
2-methyl-2-[3-(2-{2-[2-methyl-6-(4-trifluoromethyl-phenyl)-pyridin-3-yl]-acetylamino}-ethyl)-phenoxy]-propionic acid,
2-methyl-2-[3-(2-{[2-methyl-6-(4-trifluoromethyl-phenyl)-pyridine-3-carbonyl]-amino}-ethyl)-phenoxy]-propionic acid,
2-[3-(2-{[4-cyclopropyl-2-(4-trifluoromethyl-phenyl)-pyrimidine-5-carbonyl]-amino}-ethyl)-phenoxy]-2-methyl-propionic acid,
2-[3-({2-[4-butyl-2-(4-trifluoromethyl-phenyl)-pyrimidin-5-yl]-acetyl}-methyl-amino)-phenoxy]-2-methyl-propionic acid,
2-methyl-2-(3-{methyl-[2-methyl-6-(4-trifluoromethyl-phenyl)-pyridin-3-ylmethyl]-carbamoyl}-phenoxy)-propionic acid,
3-{4-[4-cyclopropyl-2-(4-trifluoromethyl-phenyl)-pyrimidin-5-ylmethoxy]-2-methyl-phenyl}-propionic acid,
3-{4-[4-cyclopropyl-2-(4-trifluoromethyl-phenyl)-pyrimidin-5-ylmethoxy]-3-ethoxy-phenyl}-propionic acid,
3-{3-ethoxy-4-[2-methyl-6-(4-trifluoromethyl-phenyl)-pyridin-3-ylmethoxy]-phenyl}-propionic acid,
3-{2-methyl-4-[5-(4-trifluoromethyl-phenyl)-pyrimidin-2-ylmethoxy]-phenyl}-propionic acid,
2-[3-({2-[4-cyclopropyl-2-(4-trifluoromethyl-phenyl)-pyrimidin-5-yl]-acetyl}-methyl-amino)-phenoxy]-2-methyl-propionic acid,
2-[3-(2-{2-[4-cyclopropyl-2-(4-trifluoromethyl-phenyl)-pyrimidin-5-yl]-acetylamimo}-ethyl)-phenoxy]-2-methyl-propionic acid,
2-[3-({[4-cyclopropyl-2-(4-trifluoromethyl-phenyl)-pyrimidine-5-carbonyl]-amino}-methyl)-phenoxy]-2-methyl-propionic acid,
2-methyl-2-[3-({2-[2-methyl-6-(4-trifluoromethyl-phenyl)-pyridin-3-yl]-acetylamino}-methyl)-phenoxy]-propionic acid,
2-[3-({2-[4-cyclopropyl-2-(4-trifluoromethyl-phenyl)-pyrimidin-5-yl]-acetylamino}-methyl)-phenoxy]-2-methyl-propionic acid,
2-methyl-2-[3-({[2-methyl-6-(4-trifluoromethyl-phenyl)-pyridine-3-carbonyl]-amino}-methyl)-phenoxy]-propionic acid,
2-methyl-2-(2-methyl-5-{2-[2-methyl-6-(4-trifluoromethyl-phenyl)-pyridin-3-yl]-ethoxy}-phenoxy)-propionic acid,
2-methyl-2-{2-methyl-5-[2-methyl-6-(4-trifluoromethyl-phenyl)-pyridin-3-ylmethoxy]-phenoxy}-propionic acid,
[rac]-3-(2-methyl-4-{1-[2-methyl-6-(4-trifluoromethyl-phenyl)-pyridin-3-yl]-ethoxy}-phenyl)-propionic acid,
3-{3-methyl-4-[2-methyl-6-(4-trifluoromethyl-phenyl)-pyridin-3-ylmethoxy]-phenyl}-propionic acid,
[rac]-3-(3-methyl-4-{1-[2-methyl-6-(4-trifluoromethyl-phenyl)-pyridin-3-yl]-ethoxy}-phenyl)-propionic acid,
2-[3-({2-[4-cyclopropyl-2-(4-trifluoromethyl-phenyl)-pyrimidin-5-yl]-acetyl}-methyl-amino)-5-trifluoromethyl-phenoxy]-2-methyl-propionic acid,
2-methyl-2-[3-(methyl-{2-[2-methyl-6-(4-trifluoromethyl-phenyl)-pyridin-3-yl]-acetyl}-amino)-5-trifluoromethyl-phenoxy]-propionic acid,
2-[4-({2-[4-cyclopropyl-2-(4-trifluoromethyl-phenyl)-pyrimidin-5-yl]-acetylamino}-methyl)-phenoxy]-2-methyl-propionic acid,
2-methyl-2-[4-({2-[2-methyl-6-(4-trifluoromethyl-phenyl)-pyridin-3-yl]-acetylamino}-methyl)-phenoxy]-propionic acid,
2-[4-({[4-cyclopropyl-2-(4-trifluoromethyl-phenyl)-pyrimidine-5-carbonyl]-amino}-methyl)-phenoxy]-2-methyl-propionic acid,
2-methyl-2-[4-({[2-methyl-6-(4-trifluoromethyl-phenyl)-pyridine-3-carbonyl]-amino}-methyl)-phenoxy]-propionic acid,
2-methyl-2-(3-{methyl-[4-methyl-2-(4-trifluoromethyl-phenyl)-pyrimidin-5-ylmethyl]-carbamoyl}-phenoxy)-propionic acid,
2-(3-{[4-(2-methoxy-ethyl)-6-methyl-2-(4-trifluoromethyl-phenyl)-pyrimidin-5-ylmethyl]-methyl-carbamoyl}-phenoxy)-2-methyl-propionic acid,
2-methyl-2-{4-[(methyl-{2-[2-methyl-6-(4-trifluoromethyl-phenyl)-pyridin-3-yl]-acetyl}-amino)-methyl]-phenoxy}-propionic acid,
2-methyl-2-[4-(2-{[2-methyl-6-(4-trifluoromethyl-phenyl)-pyridine-3-carbonyl]-amino}-ethyl)-phenoxy]-propionic acid,
2-[4-(2-{[4-cyclopropyl-2-(4-trifluoromethyl-phenyl)-pyrimidine-5-carbonyl]-amino}-ethyl)-phenoxy]-2-methyl-propionic acid,
2-methyl-2-[4-(2-{2-[2-methyl-6-(4-trifluoromethyl-phenyl)-pyridin-3-yl]-acetylamino}-ethyl)-phenoxy]-propionic acid,
2-[4-(2-{2-[4-cyclopropyl-2-(4-trifluoromethyl-phenyl)-pyrimidin-5-yl]-acetylamino}-ethyl)-phenoxy]-2-methyl-propionic acid,
2-methyl-2-{4-[2-(methyl-{2-[2-methyl-6-(4-trifluoromethyl-phenyl)-pyridin-3-yl]-acetyl}-amino) -ethyl]-phenoxy}-propionic acid,
2-methyl-2-[4-(2-{methyl-[2-methyl-6-(4-trifluoromethyl-phenyl)-pyridine-3-carbonyl]-amino}-ethyl)-phenoxy]-propionic acid,
2-{2-methoxy-4-[2-methyl-6-(4-trifluoromethyl-phenyl)-pyridin-3-ylmethoxy]-phenoxy}-2-methyl-propionic acid,
[rac]-2-(2-methoxy-4-{1-[2-methyl-6-(4-trifluoromethyl-phenyl)-pyridin-3-yl]-ethoxy}-phenoxy)-2-methyl-propionic acid,
3-{2-methoxy-4-[2-methyl-6-(4-trifluoromethyl-phenyl)-pyridin-3-ylmethoxy]-phenyl}-propionic acid,
2-[3-methoxy-5-(2-{[2-methyl-6-(4-trifluoromethyl-phenyl)-pyridine-3-carbonyl]-amino}-ethyl)-phenoxy]-2-methyl-propionic acid,
2-[3-(2-{[4-cyclopropyl-2-(4-trifluoromethyl-phenyl)-pyrimidine-5-carbonyl]-amino}-ethyl)-5-methoxy-phenoxy]-2-methyl-propionic acid,
2-[3-(2-{[4-cyclopropyl-2- (4-trifluoromethyl-phenyl)-pyrimidin-5-yl]-acetylamino}-ethyl)-5-methoxy-phenoxy]-2-methyl-propionic acid,
2-[3-methoxy-5-(2-{2-[2-methyl-6-(4-trifluoromethyl-phenyl)-pyridin-3-yl]-acetylamino}-ethyl)-phenoxy]-2-methyl-propionic acid,
2-methyl-2-[2-methyl-4-({[2-methyl-6-(4-trifluoromethyl-phenyl)-pyridine-3-carbonyl]-amino}-methyl)-phenoxy]-propionic acid,
2-[4-({[4-cyclopropyl-2-(4-trifluoromethyl-phenyl)-pyrimidine-5-carbonyl]-amino}-methyl)-2-methyl-phenoxy]-2-methyl-propionic acid,
2-[4-({[4-methoxymethyl-2-(4-trifluoromethyl-phenyl)-pyrimidine-5-carbonyl]-amino}-methyl)-2-methyl-phenoxy]-2-methyl-propionic acid, 2-[4-({[4-(2-methoxy-ethyl)-2-(4-trifluoromethyl-phenyl)-pyrimidine-5-carbonyl]-amino}-methyl)-2-methyl-phenoxy]-2-methyl-propionic acid, 2-{4-[4-(2-ethoxy-ethyl)-2-(6-trifluoromethyl-pyridin-3-yl)-pyrimidin-5-ylmethoxy]-2-methyl-phenoxy}-2-methyl-propionic acid, 2-{4-[4-(2-methoxy-ethyl)-2-(6-trifluoromethyl-pyridin-3-yl)-pyrimidin-5-ylmethoxy]-2-methyl-phenoxy}-2-methyl-propionic acid, 2-{4-[4-(2-hydroxy-ethyl)-2-(6-trifluoromethyl-pyridin-3-yl)-pyrimidin-5-ylmethoxy]-2-methyl-phenoxy}-2-methyl-propionic acid, 2-{4-[4-methoxymethyl-2-(4-trifluoromethyl-phenyl)-pyrimidin-5-ylmethoxy]-2-methyl-phenoxy}-2-methyl-propionic acid, 2-{4-[4-cyclopropyl-2-(6-trifluoromethyl-pyridin-3-yl)-pyrimidin-5-ylmethoxy]-2-methyl-phenoxy}-2-methyl-propionic acid, 2-{4-[4-cyclopropyl-2-(4-trifluoromethyl-phenyl)-pyrimidin-5-ylmethoxy]-2,3-dimethyl-phenoxy}-2-methyl-propionic acid, 2-methyl-2-{2-methyl-4-[4-trifluoromethyl-2-(4-trifluoromethyl-phenyl)-pyrimidin-5-ylmethoxy]-phenoxy}-propionic acid, 2-methyl-2-{2-methyl-4-[4-trifluoromethyl-6-(4-trifluoromethyl-phenyl)-pyridin-3-ylmethoxy]-phenoxy}-propionic acid, 2-{4-[4-chloro-6-(4-trifluoromethoxy-phenyl)-pyridin-3-ylmethoxy]-2-methyl-phenoxy}-2-methyl-propionic acid, 2-{4-[4-(2-hydroxy-ethyl)-2-(4-trifluoromethyl-phenyl)-pyrimidin-5-ylmethoxy]-2-methyl-phenoxy}-2-methyl-propionic acid, 2-methyl-2-{2-methyl-4-[2-(4-trifluoromethoxy-phenyl)-4-trifluoromethyl-pyrimidin-5-ylmethoxy]-phenoxy}-propionic acid, 2-methyl-2-{2-methyl-4-[2-methyl-6-(4-trifluoromethoxy-phenyl)-4-trifluoromethyl-pyridin-3-ylmethoxy]-phenoxy}-propionic acid, 2-{4-[4-cyclopropyl-6-methoxymethyl-2-(4-trifluoromethyl-phenyl)-pyrimidin-5-ylmethoxy]-2-methyl-phenoxy}-2-methyl-propionic acid, 2-{4-[4-cyclopropyl-6-methoxymethyl-2-(4-trifluoromethyl-phenyl)-pyrimidin-5-ylmethoxy]-phenoxy}-2-methyl-propionic acid, 2-{4-[4-butyl-2-(4-trifluoromethyl-phenyl)-pyrimidin-5-ylmethoxy]-2-methyl-phenoxy}-2-methyl-propionic acid, 2-{4-[4-butyl-2-(4-trifluoromethyl-phenyl)-pyrimidin-5-ylmethoxy]-phenoxy}-2-methyl-propionic acid, 2-{4-[4-cyclopropyl-2-(4-trifluoromethyl-phenyl)-pyrimidin-5-ylmethoxy]-phenoxy}-2-methyl-propionic acid, 2-{4-[4-(2-methoxy-ethyl)-6-methyl-2-(4-trifluoromethyl-phenyl)-pyrimidin-5-ylmethoxy]-2-methyl-phenoxy}-2-methyl-propionic acid, 2-{4-[4-(2-ethoxy-ethyl)-2-(4-trifluoromethyl-phenyl)-pyrimidin-5-ylmethoxy]-2-methyl-phenoxy}-2-methyl-propionic acid and 2-{4-[4-(2-methoxy-ethyl)-2-(4-trifluoromethyl-phenyl)-pyrimidin-5-ylmethoxy]-2-methyl-phenoxy}-2-methyl-propionic acid (3:2),

[rac]-3-(2-methyl-4-{3-methyl-1-[2-methyl-6-(4-trifluoromethyl-phenyl)-pyridin-3-yl]-butoxy}-phenyl)-propionic acid, 2-[4-({[4-methoxymethyl-2-(4-trifluoromethyl-phenyl)-pyrimidine-5-carbonyl]-amino}-methyl)-phenoxy]-2-methyl-propionic acid, 2-[4-({[4-(2-methoxy-ethyl)-2-(4-trifluoromethyl-phenyl)-pyrimidine-5-carbonyl]-amino}-methyl)-phenoxy]-2-methyl-propionic acid, 2-(3-methoxy-5-{methyl-[2-methyl-6-(4-trifluoromethyl-phenyl)-pyridin-3-ylmethyl]-carbamoyl}-phenoxy)-2-methyl-propionic acid, 2-methyl-2-[4-({[2-methyl-6-(4-trifluoromethyl-phenyl)-pyridin-3-ylmethyl]-carbamoyl}-methyl)-phenoxy]-propionic acid, 2-methyl-2-(4-{[2-methyl-6-(4-trifluoromethyl-phenyl)-pyridin-3-ylcarbamoyl]-methyl}-phenoxy)-propionic acid, 2-[3-chloro-4-({[2-methyl-6-(4-trifluoromethyl-phenyl)-pyridine-3-carbonyl]-amino}-methyl)-phenoxy]-2-methyl-propionic acid, 2-[3-chloro-4-({[4-cyclopropyl-2-(4-trifluoromethyl-phenyl)-pyrimidine-5-carbonyl]-amino}-methyl)-phenoxy]-2-methyl-propionic acid, 2-[3-chloro-4-({[4-methoxymethyl-2-(4-trifluoromethyl-phenyl)-pyrimidine-5-carbonyl]-amino}-methyl)-phenoxy]-2-methyl-propionic acid, and 2-[3-chloro-4-({[4-(2-methoxy-ethyl)-2-(4-trifluoromethyl-phenyl)-pyrimidine-5-carbonyl]-amino}-methyl)-phenoxy]-2-methyl-propionic acid.

Further examples of preferred compounds are the following:

2-(3-{[4-cyclopropyl-2-(4-trifluoromethyl-phenyl)-pyrimidin-5-ylmethyl]-methyl-carbamoyl}-5-methoxy-phenoxy)-2-methyl-propionic acid, 2-methyl-2-[4-({methyl-[2-methyl-6-(4-trifluoromethyl-phenyl)-pyridin-3-yl]-carbamoyl}-methyl)-phenoxy]-propionic acid, 2-[3-chloro-4-({[4-trifluoromethyl-6-(4-trifluoromethyl-phenyl)-pyridine-3-carbonyl]-amino}-methyl)-phenoxy]-2-methyl-propionic acid, 2-[3-chloro-4-({[4-trifluoromethyl-2-(4-trifluoromethyl-phenyl)-pyrimidine-5-carbonyl]-amino}-methyl)-phenoxy]-2-methyl-propionic acid, 2-methyl-2-[4-({[4-trifluoromethyl-6-(4-trifluoromethyl-phenyl)-pyridine-3-carbonyl]-amino}-methyl)-phenoxy]-propionic acid, 2-methyl-2-[4-({[4-trifluoromethyl-2-(4-trifluoromethyl-phenyl)-pyrimidine-5-carbonyl]-amino}-methyl)-phenoxy]-propionic acid, 2-(4-{[4-cyclopropyl-2-(4-trifluoromethyl-phenyl)-pyrimidin-5-ylcarbamoyl]-methyl}-phenoxy)-2-methyl-propionic acid, 2-(3-{[4-cyclopropyl-2-(4-trifluoromethyl-phenyl)-pyrimidin-5-ylcarbamoyl]-methyl}-phenoxy)-2-methyl-propionic acid, 2-methyl-2-(3-{[2-methyl-6-(4-trifluoromethyl-phenyl)-pyridin-3-ylcarbamoyl]-methyl}-phenoxy)-propionic acid, 2-methyl-2-(4-{[4-trifluoromethyl-6-(4-trifluoromethyl-phenyl)-pyridin-3-ylcarbamoyl]-methyl}-phenoxy)-propionic acid, 2-{4-[4-(2-methoxy-ethyl)-2-(4-trifluoromethyl-phenyl)-pyrimidin-5-ylmethoxy]-2-methyl-phenoxy}-2-methyl-propionic acid, 2-{4-[4-cyclopropyl-2-(4-trifluoromethyl-phenyl)-pyrimidin-5-ylmethoxy]-3-fluoro-phenoxy}-2-methyl-propionic acid, 2-{4-[4-cyclopropyl-2-(4-trifluoromethoxy-phenyl)-pyrimidin-5-ylmethylsulfanyl]-2-methyl-phenoxy}-2-methyl-propionic acid, 2-{4-[2-cyclopropyl-6-(4-trifluoromethoxy-phenyl)-pyridin-3-ylmethylsulfanyl]-2-methyl-phenoxy}-2-methyl-propionic acid, 2-{4-[4-cyclopropyl-2-(4-trifluoromethyl-phenyl)-pyrimidin-5-ylmethylsulfanyl]-2-methyl-phenoxy}-2-methyl-propionic acid, 2-{4-[2-cyclopropyl-6-(4-trifluoromethoxy-phenyl)-pyridin-3-ylmethoxy]-2-methyl-phenoxy}-2-methyl-propionic acid,
{2-methyl-4-[2-methyl-6-(4-trifluoromethyl-phenyl)-pyridin-3-ylmethoxy]-phenylsulfanyl}-acetic acid,
2-{4-[4-methoxymethyl-6-methyl-2-(4-trifluoromethyl-phenyl)-pyrimidin-5-ylmethoxy]-2-methyl-phenoxy}-2-methyl-propionic acid,
2-{4-[4-methoxymethyl-6-methyl-2-(3-trifluoromethyl-phenyl)-pyrimidin-5-ylmethoxy]-2-methyl-phenoxy}-2-methyl-propionic acid,
2-{4-[4-methoxymethyl-6-methyl-2-(4-trifluoromethoxy-phenyl)-pyrimidin-5-ylmethoxy]-2-methyl-phenoxy}-2-methyl-propionic acid,
2-{4-[4-cyclopropyl-2-(4-trifluoromethoxy-phenyl)-pyrimidin-5-ylmethoxy]-2-methyl-phenoxy}-2-methyl-propionic acid,
2-methyl-2-{2-methyl-4-[6-(4-trifluoromethoxy-phenyl)-4-trifluoromethyl-pyridin-3-ylmethoxy]-phenoxy}-propionic acid,
2-{4-[2-cyclopropylmethyl-6-(4-trifluoromethoxy-phenyl)-4-trifluoromethyl-pyridin-3-ylmethoxy]-2-methyl-phenoxy}-2-methyl-propionic acid,
2-{4-[2-cyclopropyl-6-(4-trifluoromethoxy-phenyl)-4-trifluoromethyl-pyridin-3-ylmethoxy]-2-methyl-phenoxy}-2-methyl-propionic acid,
2-methyl-2-{2-methyl-4-[6-(4-trifluoromethoxy-phenyl)-2-trifluoromethyl-pyridin-3-ylmethoxy]-phenoxy}-propionic acid, and
2-{4-[4-methoxymethyl-2-(4-trifluoromethoxy-phenyl)-pyrimidin-5-ylmethoxy]-2-methyl-phenoxy}-2-methyl-propionic acid.

Particularly preferred compounds of formula I of the present invention are the following:
2-methyl-2-{2-methyl-4-[2-methyl-6-(3-trifluoromethyl-phenyl)-pyridin-3-ylmethoxy]phenoxy}-propionic acid,
2-methyl-2-{2-methyl-4-[6-(4-trifluoromethoxy-phenyl)-pyridin-3-ylmethoxy]-phenoxy}-propionic acid,
[rac]-(2-methyl-4-{1-[2-methyl-6-(4-trifluoromethyl-phenyl)-pyridin-3-yl]-ethoxy}-phenylsulfanyl)-acetic acid,
2-methyl-2-[3-(methyl-{2-[2-methyl-6-(4-trifluoromethyl-phenyl)-pyridin-3-yl]-acetyl}-amino)-phenoxy]-propionic acid,
(4-{[4-cyclopropyl-2-(4-trifluoromethyl-phenyl)-pyrimidin-5-ylmethyl]-methyl-amino}-2-methyl-phenoxy)-acetic acid,
[rac]-(4-{1-[4-Cyclopropyl-2-(4-trifluoromethyl-phenyl)-pyrimidin-5-yl]-ethylsulfanyl}-2-methyl-phenoxy)-acetic acid,
[rac]-(4-{1-[4-Cyclopropyl-2-(4-trifluoromethyl-phenyl)-pyrimidin-5-yl]-ethoxy}-2-methyl-phenoxy)-acetic acid,
2-{4-[4-cyclopropyl-2-(4-trifluoromethyl-phenyl)-pyrimidin-5-ylmethoxy]-2-methyl-phenoxy}-2-methyl-propionic acid,
2-methyl-2-{2-methyl-4-[2-methyl-6-(4-trifluoromethoxy-phenyl)-pyridin-3-ylmethoxy]-phenoxy}-propionic acid,
2-{4-[4-cyclopropyl-2-(3-trifluoromethyl-phenyl)-pyrimidin-5-ylmethoxy]-2-methyl-phenoxy}-2-methyl-propionic acid,
2-{4-[4-(2-methoxy-ethyl)-6-methyl-2-(4-trifluoromethyl-phenyl)-pyrimidin-5-ylmethoxy]-2-methyl-phenoxy}-2-methyl-propionic acid,
2-methyl-2-(3-{methyl-[2-methyl-6-(4-trifluoromethyl-phenyl)-pyridin-3-ylmethyl]-carbamoyl}-phenoxy)-propionic acid,
2-[3-({2-[4-cyclopropyl-2-(4-trifluoromethyl-phenyl)-pyrimidin-5-yl]-acetyl}-methyl-amino)-phenoxy]-2-methyl-propionic acid,
2-methyl-2-[3-(methyl-{2-[2-methyl-6-(4-trifluoromethyl-phenyl)-pyridin-3-yl]-acetyl}-amino)-5-trifluoromethyl-phenoxy]-propionic acid,
2-[4-({[4-cyclopropyl-2-(4-trifluoromethyl-phenyl)-pyrimidine-5-carbonyl]-amino}-methyl)-phenoxy]-2-methyl-propionic acid,
2-methyl-2-(4-{[2-methyl-6-(4-trifluoromethyl-phenyl)-pyridin-3-ylcarbamoyl]-methyl}-phenoxy)-propionic acid,
2-[3-chloro-4-({[4-trifluoromethyl-2-(4-trifluoromethyl-phenyl)-pyrimidine-5-carbonyl]-amino}-methyl)-phenoxy]-2-methyl-propionic acid,
2-methyl-2-[4-({[4-trifluoromethyl-2-(4-trifluoromethyl-phenyl)-pyrimidine-5-carbonyl]-amino}-methyl)-phenoxy]-propionic acid,
2-(4-{[4-cyclopropyl-2-(4-trifluoromethyl-phenyl)-pyrimidin-5-ylcarbamoyl]-methyl}-phenoxy)-2-methyl-propionic acid,
-{4-[2-cyclopropyl-6-(4-trifluoromethoxy-phenyl)-pyridin-3-ylmethoxy]-2-methyl-phenoxy}-2-methyl-propionic acid,
2-{4-[4-methoxymethyl-6-methyl-2-(3-trifluoromethyl-phenyl)-pyrimidin-5-ylmethoxy]-2-methyl-phenoxy}-2-methyl-propionic acid,
2-{4-[2-cyclopropyl-6-(4-trifluoromethoxy-phenyl)-4-trifluoromethyl-pyridin-3-ylmethoxy]-2-methyl-phenoxy}-2-methyl-propionic acid,
2-{4-[4-methoxymethyl-2-(4-trifluoromethoxy-phenyl)-pyrimidin-5-ylmethoxy]-2-methyl-phenoxy}-2-methyl-propionic acid,
2-{4-[2-cyclopropyl-6-(4-trifluoromethoxy-phenyl)-4-trifluoromethyl-pyridin-3-ylmethoxy]-2-methyl-phenoxy}-2-methyl-propionic acid, and
2-{4-[4-methoxymethyl-2-(4-trifluoromethoxy-phenyl)-pyrimidin-5-ylmethoxy]-2-methyl-phenoxy}-2-methyl-propionic acid.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a compound of formula

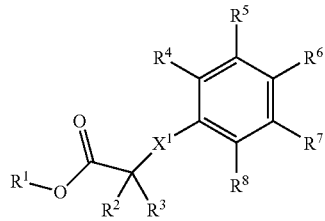

II wherein $R^1$ is $C_{1-7}$-alkyl, $R^2$ to $R^8$ are as defined above and one of $R^5$, $R^6$ or $R^7$ is selected from —OH, —SH or —NHR$^9$, wherein $R^9$ is as defined above, with a compound of formula

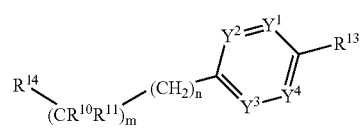

III wherein $Y^1$ to $Y^4$, $R^{10}$, $R^{11}$, $R^{13}$, m and n are as defined above and $R^{14}$ is —OH, —Cl, —Br, —I or another leaving group, to obtain a compound of formula

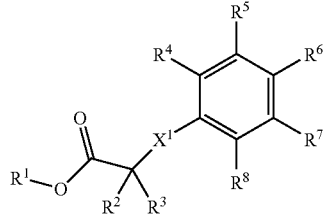

I-1 wherein one of $R^5$, $R^6$ and $R^7$ is

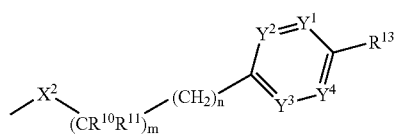

and wherein $X^2$ is O, S or —NR$^9$, $R^1$ is $C_{1-7}$-alkyl and $X^1$, $Y^1$ to $Y^4$, $R^2$ to $R^{13}$ and m and n are as defined above, and optionally hydrolysing the ester group to obtain a compound of formula I, wherein $R^1$ is hydrogen;

or, alternatively, b) reacting a compound of formula

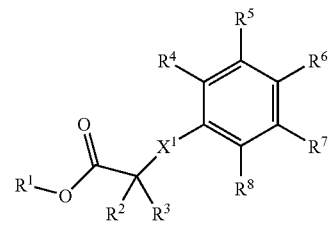

IV wherein $R^1$ is $C_{1-7}$-alkyl, $R^2$ to $R^8$ are as defined above and one of $R^5$, $R^6$ or $R^7$ is $(CH_2)_p$-NHR$^9$, wherein $R^9$ and p are as defined above, with a compound of formula

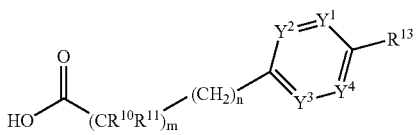

V wherein $Y^1$ to $Y^4$, $R^{10}$, $R^{11}$, $R^{13}$, m and n are as defined above, to obtain a compound of formula

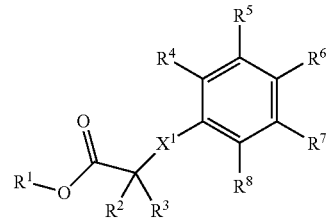

I-2 wherein one of $R^5$, $R^6$ and $R^7$ is

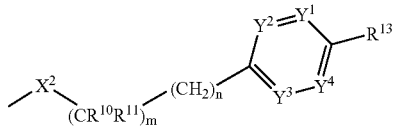

and wherein $X^2$ is $-(CH_2)_p$—NR$^9$CO—, $R^1$ is $C_{1-7}$-alkyl and $X^1$, $Y^1$ to $Y^4$, $R^2$ to $R^{13}$ and m, n and p are as defined above, and optionally hydrolysing the ester group to obtain a compound of formula I, wherein $R^1$ is hydrogen;

or, alternatively, c) reacting a compound of formula

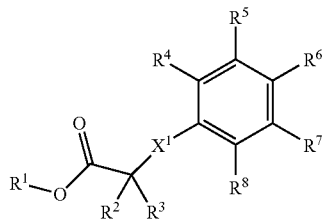
VI wherein $R^1$ is $C_{1-7}$-alkyl, $R^2$ to $R^8$ are as defined above and one of $R^5$, $R^6$ or $R^7$ is —$(CH_2)_p$—COOH, and p is defined above, with a compound of formula

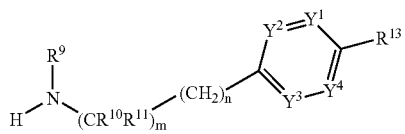
VII wherein $Y^1$ to $Y^4$, $R^9$, $R^{10}$, $R^{11}$, $R^{13}$, m and n are as defined above, to obtain a compound of formula

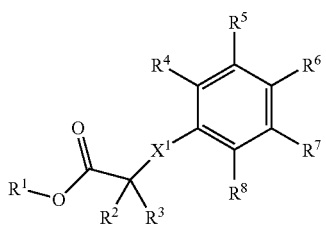
I-3 wherein one of $R^5$, $R^6$ and $R^7$ is

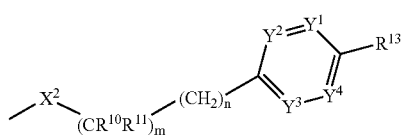

and wherein $X^2$ is —$(CH_2)_p$—$CONR^9$, $R^1$ is $C_{1-7}$-alkyl and $X^1$, $Y^1$ to $Y^4$, $R^2$ to $R^{13}$ and m, n and p are as defined above, and optionally hydrolysing the ester group to obtain a compound of formula I, wherein $R^1$ is hydrogen.

As described above, the compounds of formula (I) of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment of low HDL cholesterol levels, high LDL cholesterol levels, high triglyceride levels, and the metabolic syndrome (syndrome X) is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

The compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia to Iq, are described in scheme 1 to scheme 7. Scheme 8 to scheme 11 describe the synthesis of heterocycles 5 (scheme 1), identical to 11 (scheme 3), 8 (scheme 5) and 8 (scheme 6); 5 (scheme 4) identical to 8 (scheme 7) and 6 (scheme 4) identical to 9 (scheme 7 ).

The synthesis of compounds with the general structure I, particularly compounds according to formula Ia with $X^1$ and $X^2$ equal to oxygen can be accomplished according to scheme 1.

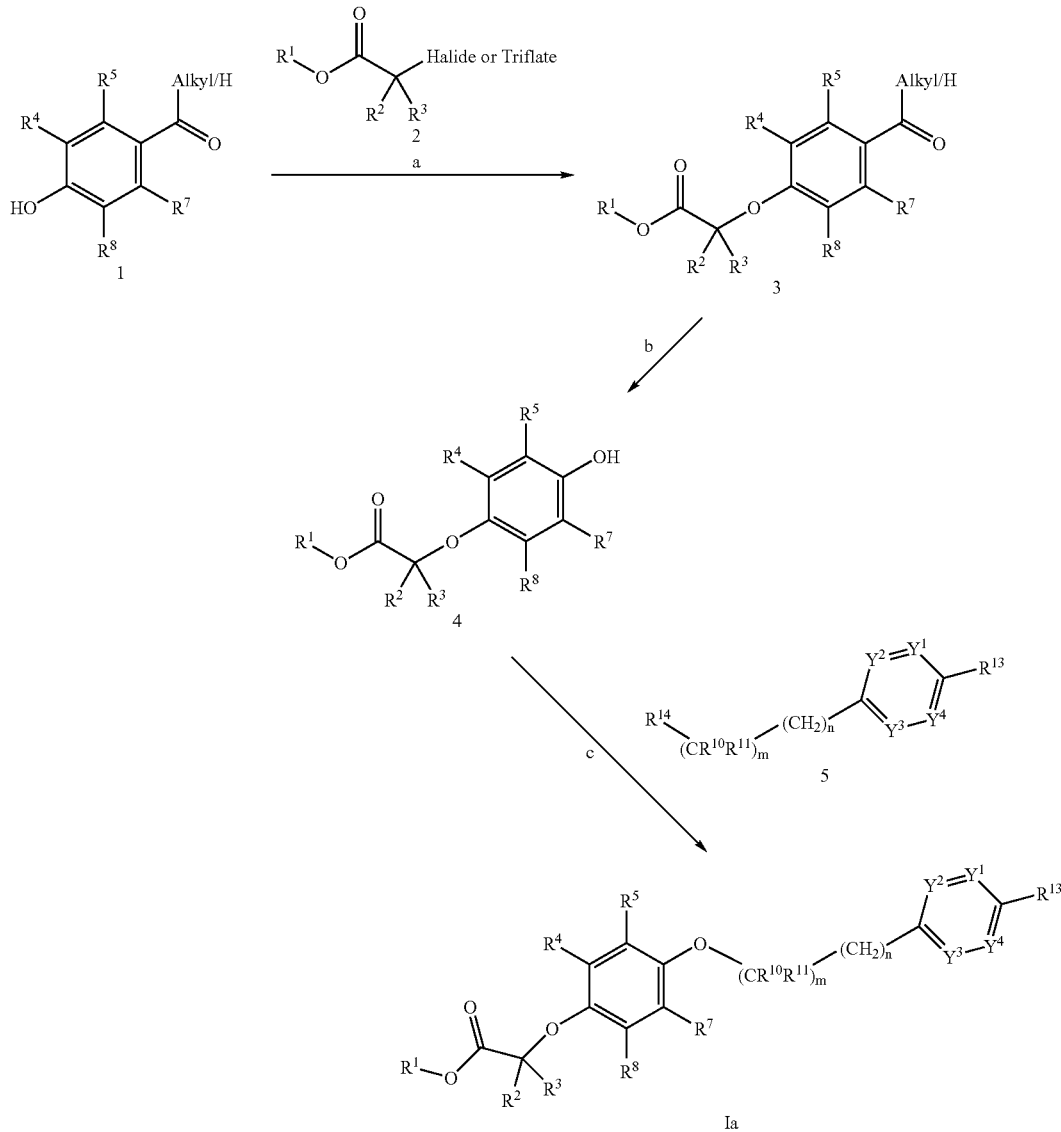

Scheme 1

Hydroxy aldehydes or hydroxy aryl alkyl ketones 1 are known or can be prepared by methods known in the art. Reaction of phenols 1 with alpha halo esters of formula 2 in the presence of a base like potassium or cesium carbonate in solvents like acetone, methyl-ethyl ketone, acetonitrile or N,N-dimethylformamide in a temperature range between room temperature and 140° C. leads to the corresponding ether compounds 3 (steps a). Baeyer Villiger oxidation e. g. with meta chloro perbenzoic acid in a solvent like dichloromethane, leads to compounds 4 (step. b). Heterocycles 5 (prepared as outlined in schemes 8 to 11) are condensed with phenols 4 according to well known procedures (step c): if $R^{14}$ represents a hydroxy group e. g. via Mitsunobu-reaction, with triphenylphosphine and di-tert-butyl-, diisopropyl- or diethyl-azodicarboxylate as reagents; this transformation is preferably carried out in a solvent like toluene, dichloromethane or tetrahydrofuran at ambient temperature. Alternatively, if $R^{14}$ represents a halide, mesylate, tosylate or triflate moiety, the heterocycles 5 can be reacted with phenols 4 in solvents like N,N-dimethylformamide, dimethylsulfoxide, acetonitrile, acetone or methyl-ethyl ketone in the presence of a weak base like cesium or potassium carbonate at a temperature ranging from room temperature to 140 °C., preferably around 50° C. to yield ether compounds Ia (step c). Those can optionally be hydrolyzed according to standard procedures, e. g. by treatment with an alkali hydroxide like LiOH or NaOH in a polar solvent mixture like tetrahydrofuran/ethanol/water leading to carboxylic acids Ia.

An analogous reaction scheme with the same reaction sequences applies for the isomeric compound series leading to compounds of general formula I, particularly compounds according to formula Ib:

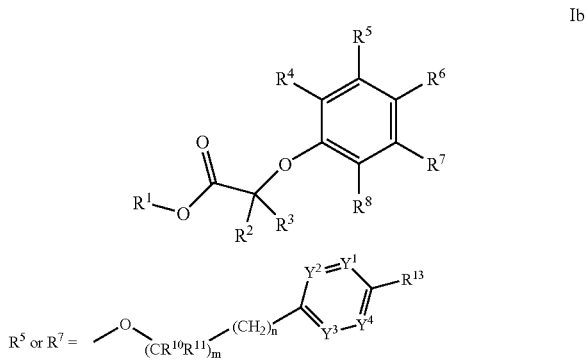

The synthesis of compounds with the general structure I, particularly compounds according to formula Ic, with $X^1$ equal to O and $X^2$ equal to nitrogen can be accomplished according to schemes 2 and 3.

Scheme 2

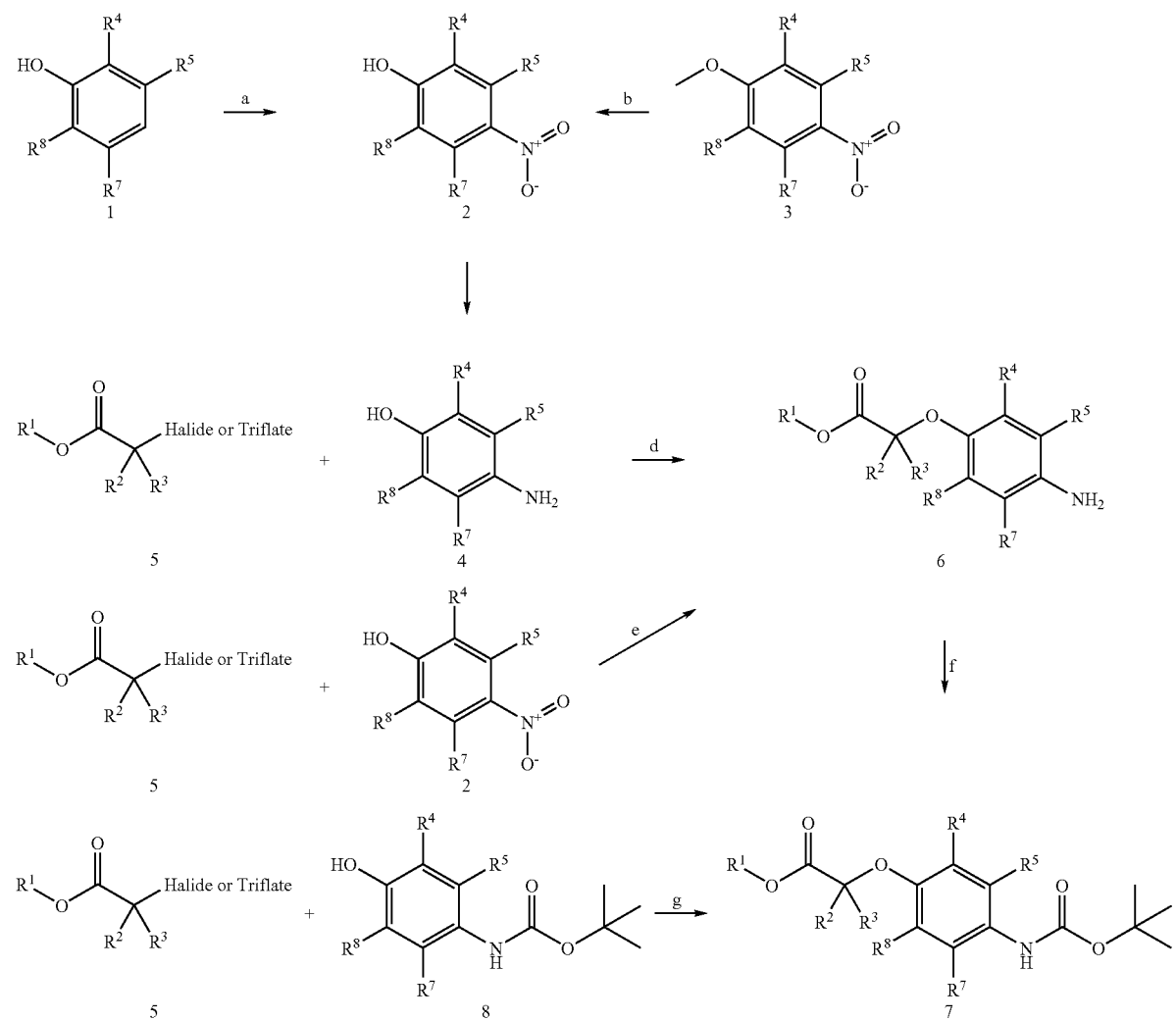

Nitro-phenols 2 of scheme 2 are commercial available, or known or can be synthesized from anisols 3 by demethylation with aqueous 62% HBr in acetic acid between RT and 120° C. (step b). Alternatively, phenols 1 can be nitrated in para-position according to well established methods, e. g. with a solution of $NaNO_3$ in water/concentrated hydrochloric acid in a solvent like $Et_2O$, followed by the addition of acetic acid anhydride at RT [following a procedure of P. Keller, *Bull. Soc. Fr.* 1994, 131, 27–29] leading to phenols 2 (step a). Nitro-phenols 2 are then hydrogenated in an alcohol like EtOH or MeOH with hydrogen in the presence of Pd/C and optionally an acid like HCl or AcOH at RT to give anilines 4 (step c). Intermediates 4 are then alkylated at oxygen with an activated ester compound 5, e.g. a bromoacetate 5, in the presence of $K_2CO_3$ or $Cs_2CO_3$ in a solvent like acetonitrile or acetone between 10° C. and RT to give intermediates 6 of scheme 2 (step d). Activated esters 5 are commercial available or can be synthesized by methods known in the art. Triflates 5 can be prepared from the corresponding alcohols. Anilines 6 can alternatively be synthesized from compounds 5 and nitrophenols 2 in a two step procedure: first by O-alkylation as described above, followed by hydrogenation with Pd/C in an alcohol like MeOH or EtOH optionally in the presence of AcOH or HCl (step e). BOC-protection with di-tert-butyl dicarbonate in tetrahydrofuran at RT to reflux yields compound 7 (step f). Compound 7 can also be synthesized directly from activated esters 5 and BOC-protected aniline 8 with $K_2CO_3$ or $Cs_2CO_3$ as described for the synthesis of compounds 6 (step g).

Intermediates 7 of scheme 3 can optionally be alkylated at nitrogen using sodium hydride and a reactive alkyl halogenide/mesylate or triflate to give compounds 9 (step h, scheme 3). Standard BOC-deprotection (TFA/$CH_2Cl_2$, or HCl in dioxane) at 0° C. to RT affords anilines 10 of (step i, scheme 3). Reaction with activated heterocycles 11 ($R^{14}$ being a halide or a methanesulfonate) using sodium hydride or sodium, potassium or cesium carbonate in N,N-dimethylformamide, dimethylsulfoxide, dimethylacetamide or tetrahydrofuran, at 0° C. to RT, leads to compounds Ic (step k). Alternatively, heterocycles 11 with $R^{14}$=OH can be transformed in situ to the coresponding triflate by treatment with trifluoromethanesulfonicr anhydride/2,6-di-tert-butylpyridine in $CH_2Cl_2$ at 0° C. This triflate is then reacted with anilines 10 in the presence of 2,6-di-tert-butylpyridine as base in nitromethane between RT and 60° C. to yield compounds Ic [following a procedure of Belostotskii, Anatoly M., Hassner, A., *Tetrahedron Lett.* 1994, 35(28), 5075–6] (step k). Secondary aniline compounds Ic ($R^9$=H) can be reductively methylated with an aqueous solution of $NaH_2PO_3$ and formaldehyde between RT and 65° C. [Loibner, H., Pruckner, A., Stuetz, A., *Tetrahedron Lett.* 1984, 25, 2535–2536] to give compounds Ic with $R^9$=Me. Ensuing hydrolysis with aqueous LiOH, NaOH or KOH in tetrahydrofuran/EtOH or another suitable solvent produces compounds Ic of scheme 3 in the form of the free acid.

Scheme 3

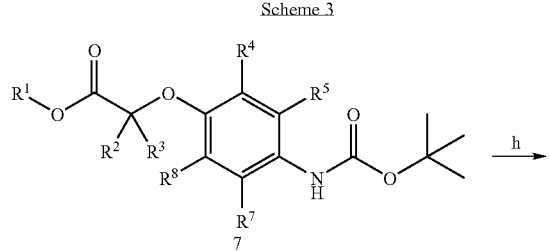

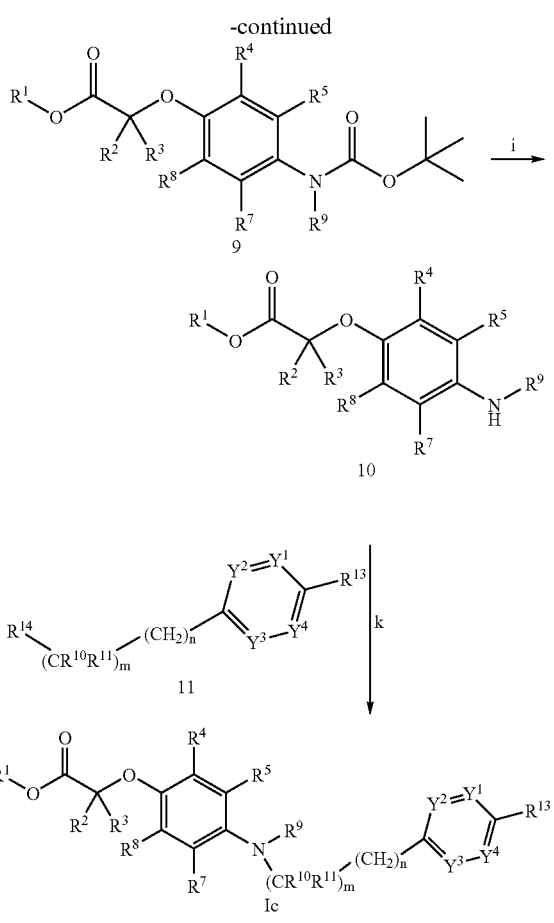

An analogous reaction scheme with the same reaction sequences applies for the isomeric compound series leading to compounds of general formula I, particularly compounds according to formula Id:

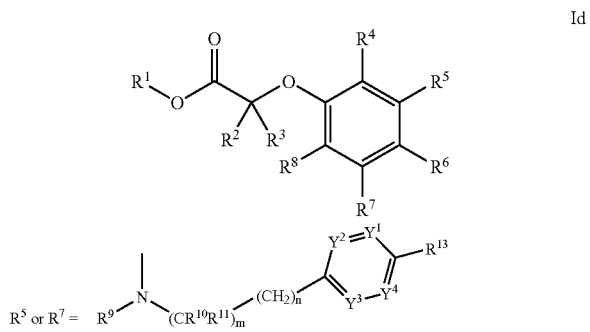

As alternative to the sequences described in scheme 2, the nitrogen containing intermediates can be prepared from suitable intermediates carrying a phenolic hydroxyl moiety. In such intermediates, optionally carrying one or more protective functions, the phenolic OH group can be replaced by the corresponding aromatic $NH_2$ function by methods known in the art. For example by a three step sequence as described in Tetrahedron Letters 43(42),7617–7619(2002): i) transformation of the phenol moiety into its trifluoromethanesulfonate (triflic anhydride, 2,6-lutidine, 4-dimethylamino-pyridine, dichloromethane, 0° C. to room temperature; ii) treatment of the triflate with benzophenone imine, di-palladium-tris(dibenzylideneacetone) complex, S-(–)-2,2'-bis(diphenylphosphino)-1,1'-binaphthyl, cesium carbonate, toluene, in a Schlenk tube at temperatures around 120° C.; iii) treatment with catalytic amounts of hydrochloric acid in wet tetrahydrofuran preferably at room temperature to liberate the aromatic $NH_2$ moiety.

The synthesis of compounds with the general structure I, particularly compounds according to formula Ie and If, with $X^1$ equal to O and $X^2$ equal to $(CH_2)_p NR^9 CO$, or $(CH_2)_p CONR^9$ can be accomplished according to schemes 4.

Nitriles 1 and aldehydes 2 can be prepared from the corresponding cyano- or formyl-phenols (which are known, commercially available or can be prepared by methods known in the art) by reaction with activated esters compounds (compounds 5 in scheme 2) in the presence of a base like potassium or cesium carbonate in solvents like acetone, methyl-ethyl ketone, acetonitrile or N,N-dimethylformamide in a temperature range between room temperature and 140° C. Hydrogenation of nitrile compounds 1, e. g. with palladium on charcoal in a mixture of acetic acid and ethanol, or, alternatively, transformation of aldehydes 2 into

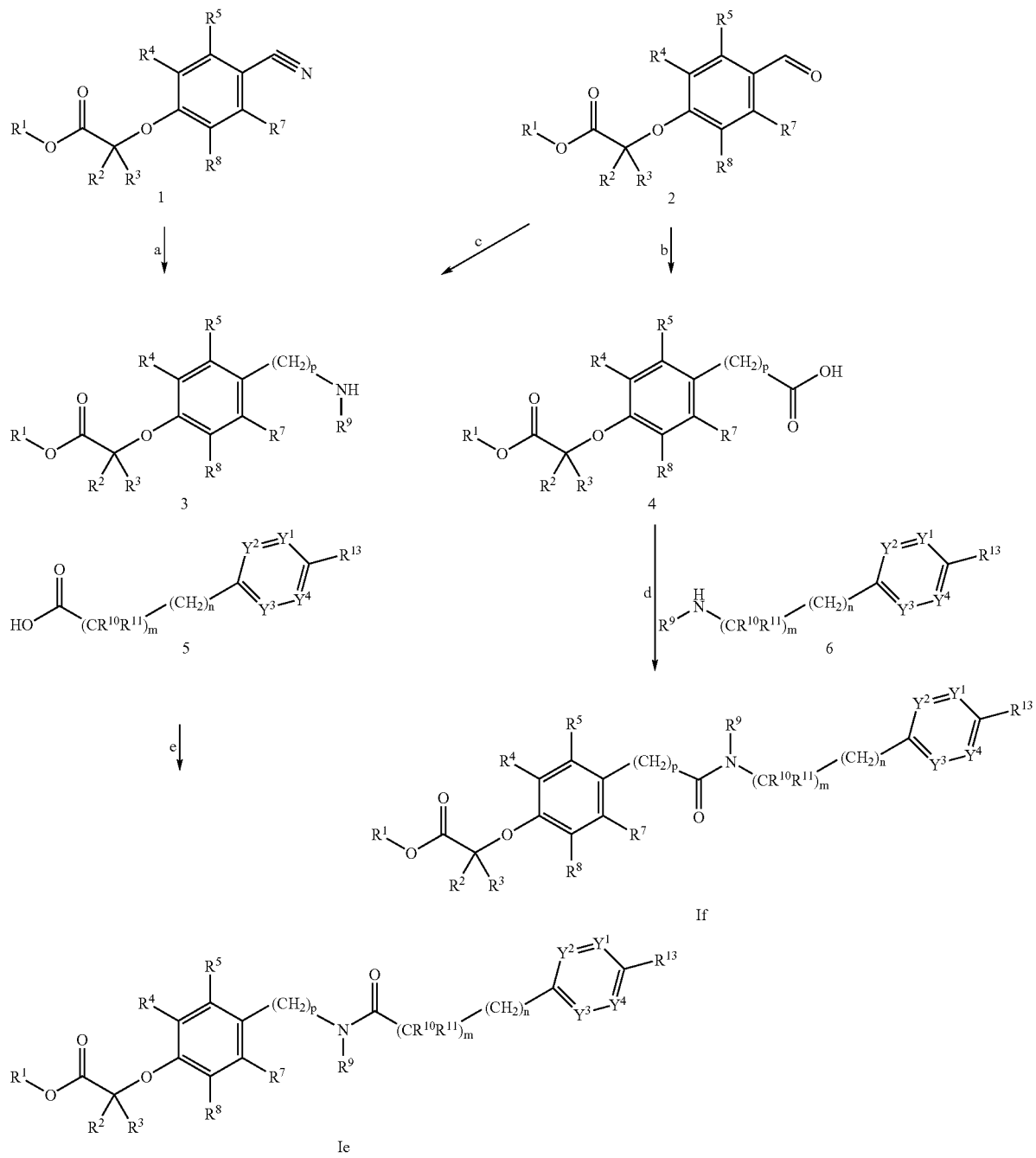

Scheme 4 the corresponding oximes followed by reduction with zinc in acetic acid preferably around 65° C. gives compounds 3 with p=1 (steps a, c). The preparation of compounds 3 with p=0 has been described in scheme 2 and 3 (compounds 6, scheme 2, and compounds 10, scheme 3). Compounds 3 with p=2 can be prepared from compounds 2 in a two step procedure: i) treatment with nitro-methane and ammonium acetate in acetic acid at a temperature around 110° C. to form the corresponding nitro styrene compounds; ii) hydrogenation with palladium on charcoal in the presence of a strong acid like sulfuric acid or hydrogen chloride in solvents like ethanol or acetic acid and in a temperature range between room temperature and 100° C. In order to introduce an $R^9$ substituent into compounds 3, BOC-protection followed by alkylation and subsequent removal of the BOC group can be performed similarly as described in schemes 2 and 3. Compounds 4 with p=0 can be prepared from compounds 2 by standard procedures of oxidation of an aromatic aldehyde to an aromatic acid (e. g. with sodium chlorite, sodium dihydrogen-phosphate in a mixture of tert butanol and water and in the presence of 3-methyl-2-butene at temperatures around room temperature). Compounds 4 with p=1 can be prepared from compounds 2 by a Wittig reaction using (methoxymethyl)-triphenylphosphonium chloride as reagent, treatment of the Wittig product with acid and oxidation of the aldehyde formed to the corresponding acid. Compounds 4 with p=2 can be prepared from compounds 2 by a Horner-Emmons reaction with e. g. dimethyl(benzyloxycarbonyl)methl phosphonate, followed by concomitant reduction of the double bond and liberation of the ester function by e. g. hydrogenation with palladium on charcoal. Condensation of amines 3 or acids 4 with acids 5 or amines 6 can be performed using well known procedures for amid formation, such as use of N-(3-dimethylaminopropyl)-N'-ethyl-carbodiimide-hydrochloride and 4-dimethylamino-pyridine in dichloromethane at temperatures between 0° C. and room temperature yielding compounds Ie (step e) or If (step d). Those can optionally be hydrolyzed according to standard procedures, e. g. by treatment with an alkali hydroxide like LiOH or NaOH in a polar solvent mixture like tetrahydrofuran/ethanol/water, giving carboxylic acids Ie or If.

An analogous reaction scheme with the same reaction sequences applies for the isomeric compound series leading to compounds of general formula I, particularly compounds according to formula Ig and Ih:

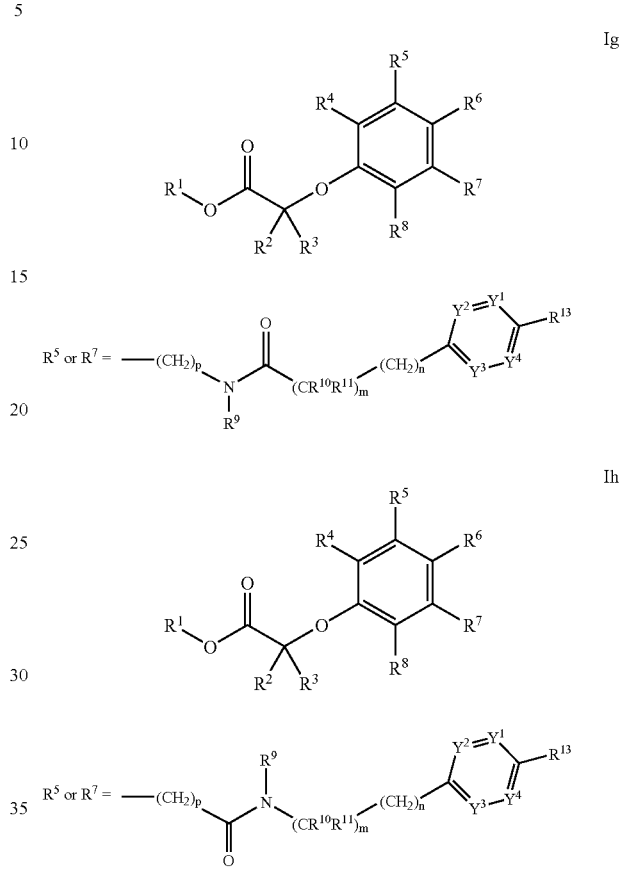

The synthesis of compounds with the general structure I, particularly compounds according to formula Ii, with $X^1$ equal to $CH_2$ and $X^2$ equal to oxygen can be accomplished according to schemes 5.

Scheme 5

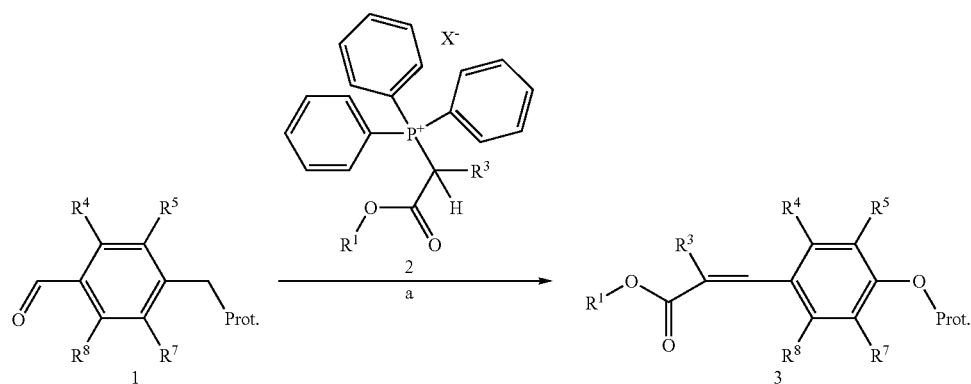

-continued

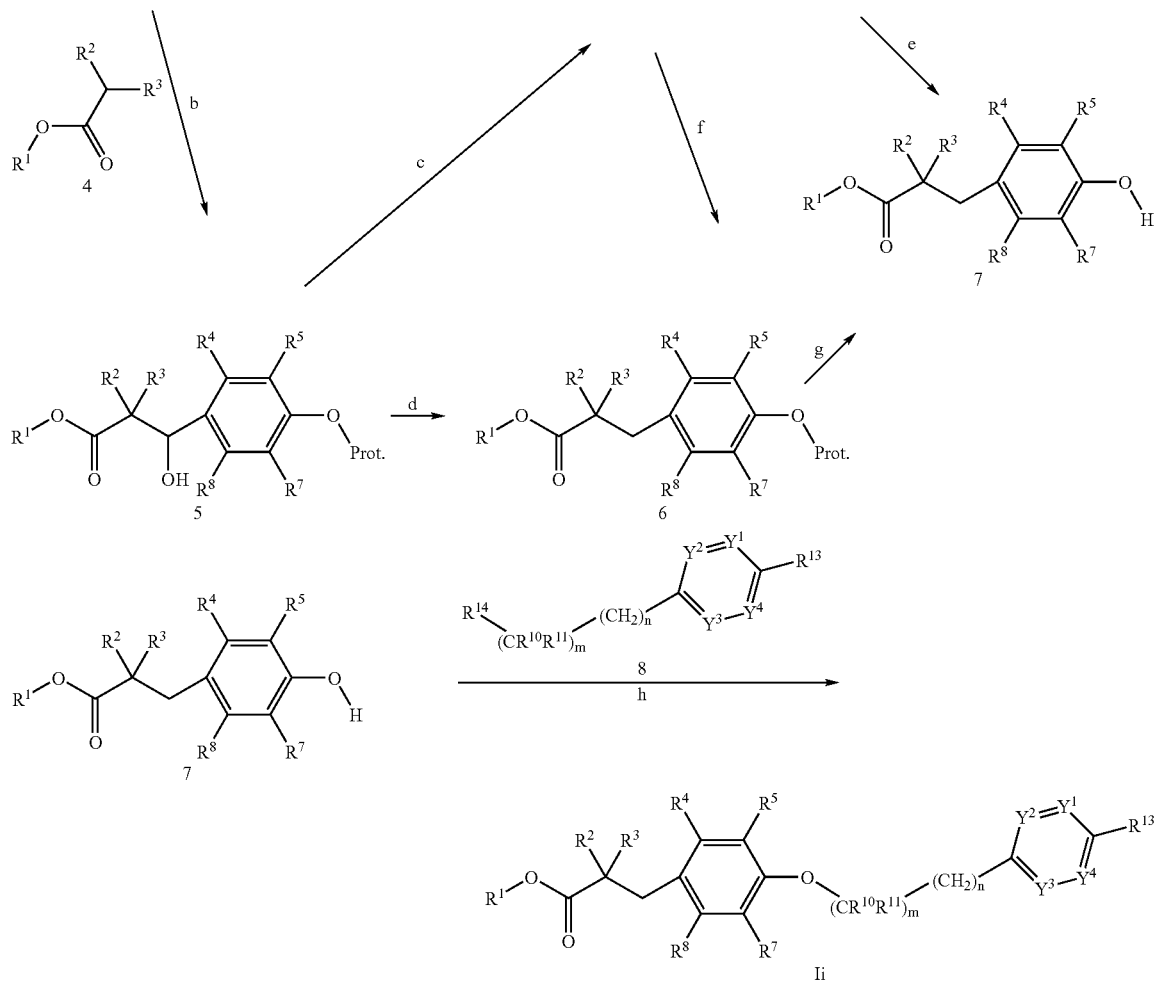

Aldehydes 1 are known, commercially available or can be prepared by methods known in the art. Aldehydes 1 can be reacted with a Wittig salt 2 such as (1,2-diethoxy-2-oxoethyl)triphenyl phosphonium chloride or (1,2-dimethoxy-2-oxoethyl)triphenyl phosphonium bromide in solvents like isopropanol, dichloromethane or tetrahydrofuran or mixtures thereof in the presence of a base like potassium carbonate, 1,8-diazabicyclo[5.4.0]undec-7-ene (DBU), 1,1,3,3-tetramethyl-guanidine or sodium tert butylate, preferably between 0° C. and the reflux temperature of the solvents, giving acrylic esters 3 as E and/or Z isomers (step a). Alternatively, a Horner-Emmons reaction can be used for the transformation of compounds 1 into unsaturated esters 3, e. g. using dimethyl(methoxycarbonyl)methl phosphonate, optionally substituted at the methylene group, a base like sodium hydride in a solvent like tetrahydrofuran. Hydrogenation of acrylic esters 3 using palladium on charcoal as catalyst, preferably at room temperature and 1 atm. pressure of hydrogen, in solvents like methanol, ethanol, tetrahydrofuran, acetic acid, dichloromethane and mixtures thereof, affords esters 7, provided that the protecting group can be cleaved reductively (step e).

Alternatively, aldehydes 1 are reacted with the enolate of an acetic acid esters 4 (preferably the lithium-enolate, prepared at −78° C. by treatment of 4 with a strong, non-nucleophilic base like lithium diisopropylamide in an inert solvent like tetrahydrofuran), preferably at temperatures around −78° C., in solvents like tetrahydrofuran giving the aldol product 5 as a mixture of diasteromers (step b). Removal of the benzylic hydroxy group in compounds 5 can be performed with a reducing agent like e. g. triethylsilane in the presence of a Lewis acid, like boron-trifluoride, or a protic acid, like trifluoroacetic acid, in a suitable solvent like trifluoroacetic acid itself or dichloromethane between 0° C. and 60° C. to yield protected phenol compounds 6 (step d). Subsequent removal of the protecting group, e. g. a benzyl group, by standard technology, e. g. catalytic hydrogenation using hydrogen and a catalyst like palladium or by using dimethyl sulfide and boron trifluoride diethyl etherate in a solvent like dichloromethane between room temperature and the reflux temperature of the solvent gives phenolic compounds 7 (step g). Catalytic hydrogenation can be used to transform unsaturated esters 3 into compounds 6 (step f). In case the protective group in compounds 3 is a benzyl group, then a one step hydrogenation procedure directly gives phenolic compounds 7. Catalytic hydrogenation can also be used for the simultaneous removal of the benzylic hydroxy function and a benzyl protecting group, preferably using palladium on charcoal as catalyst in the presence of an acid like oxalic acid in solvents like alcohols at temperatures around room temperature and a hydrogen pressure up to 100 bar, thus giving the transformation of compounds 5 into compounds 7 in one step (step d and g). As an alternative method, compounds 5 can be treated with catalytic amounts of an acid like para toluene sulfonic acid in a solvent like benzene or toluene, preferably under conditions allowing the removal of the water formed (e. g. with a Dean Stark trap or in the presence of molecular sieves) at temperatures between room temperature and the reflux temperature of the solvents to yield acrylic esters 3 (step c). The condensation of phenols 7 with heterocycles 8 to form compounds Ii can be performed as outlined in scheme 1.

An analogous reaction scheme with the same reaction sequences applies for the isomeric compound series leading to compounds of general formula I, particularly compounds according to formula Ik:

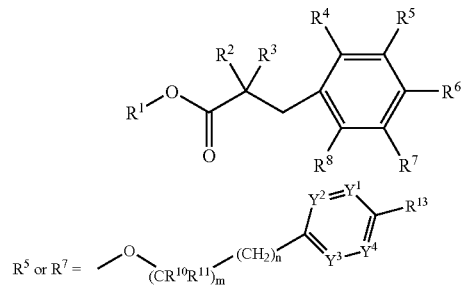

The synthesis of compounds with the general structure I, particularly compounds according to formula II, with $X^1$ equal to $CH_2$ and $X^2$ equal to nitrogen can be accomplished according to schemes 6.

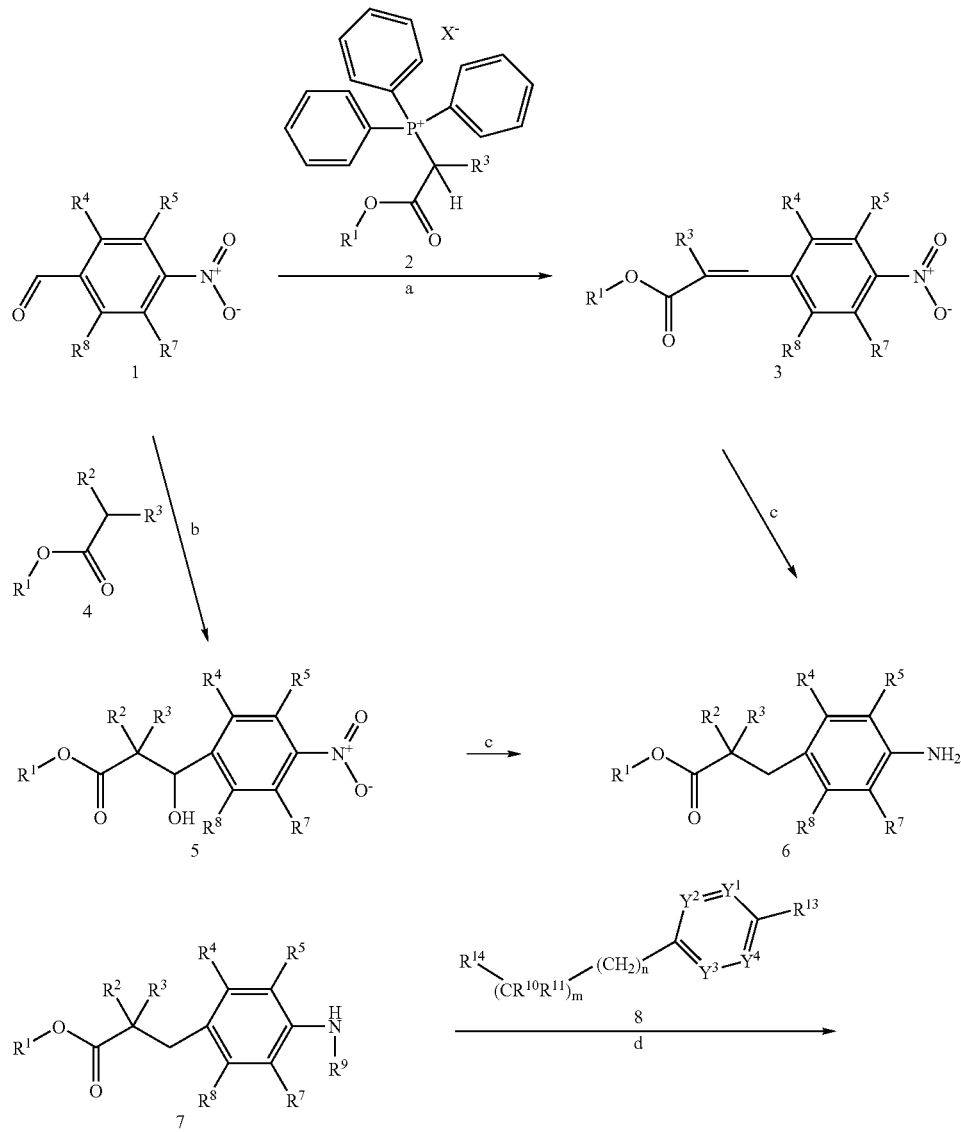

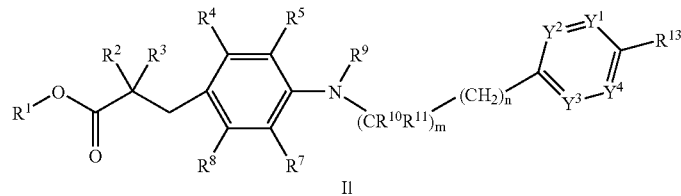

II

Nitro-phenyl compounds 3 and 5 are prepared from nitro aldehydes 1, which are known, commercially available or can be prepared by methods known in the art, by Wittig/Horner-Emmons or aldol reactions analogous to the reactions described for the synthesis of compounds 3 and 5 in scheme 5 (steps a and b). Catalytic hydrogenation can be used for the simultaneous removal of the benzylic hydroxy function (compounds 5) or the reduction of the double bond (compounds 3) and the reduction of the nitro group, preferably using palladium on charcoal as catalyst optionally in the presence of an acid like oxalic acid in solvents like alcohols at temperatures around room temperature and a hydrogen pressure up to 100 bar (step c). Compounds 7 with $R^9$ substituents different from hydrogen are obtained by first introduction of a BOC group, alkylation and removal of the BOC protective function as described in schemes 2 and 3. The condensation of anilines 7 with heterocycles 8 to form compounds II can be performed as outlined in scheme 3.

An analogous reaction scheme with the same reaction sequences applies for the isomeric compound series leading to compounds of general formula I, particularly compounds according to formula Im:

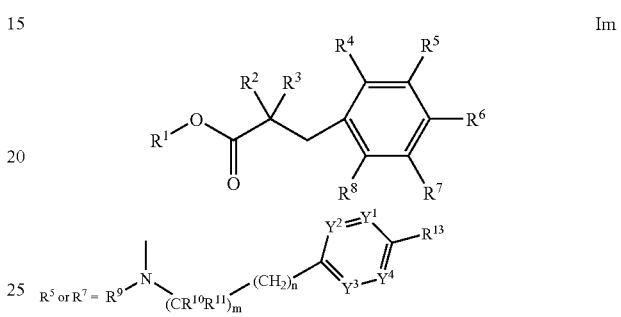

Im

As alternative to the sequences described in scheme 6, the nitrogen containing intermediates can be prepared from suitable intermediates carrying a phenolic hydroxyl function. In such intermediates, optionally carrying one or more protective functions, the phenolic OH group can be replaced by the corresponding aromatic $NH_2$ function by methods known in the art. For example by a three step sequence as described in Tetrahedron Letters 43(42), 7617–7619 (2002) and discussed in the context of schemes 2 and 3.

The synthesis of compounds with the general structure I, particularly compounds according to formula In and Io, with $X^1$ equal to $CH_2$ and $X^2$ equal to $(CH_2)_p NR^9 CO$, or $(CH_2)_p CONR^9$ can be accomplished according to schemes 7.

Scheme 7

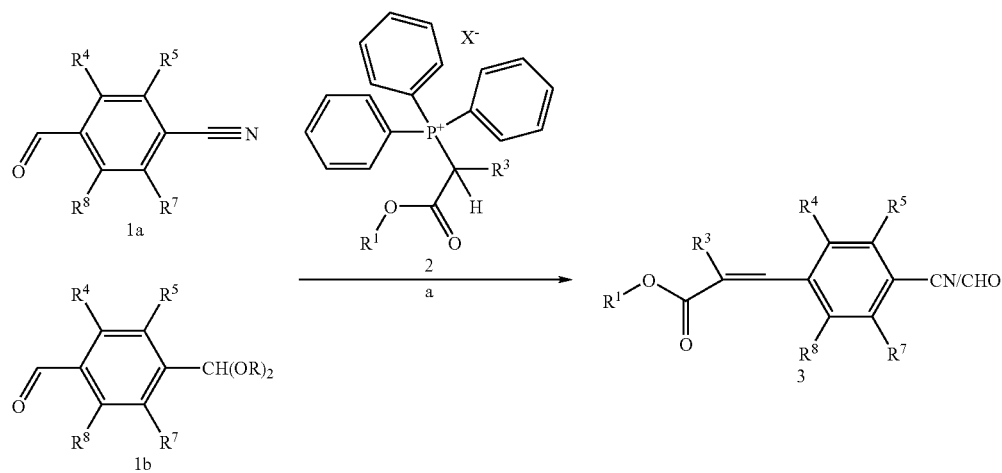

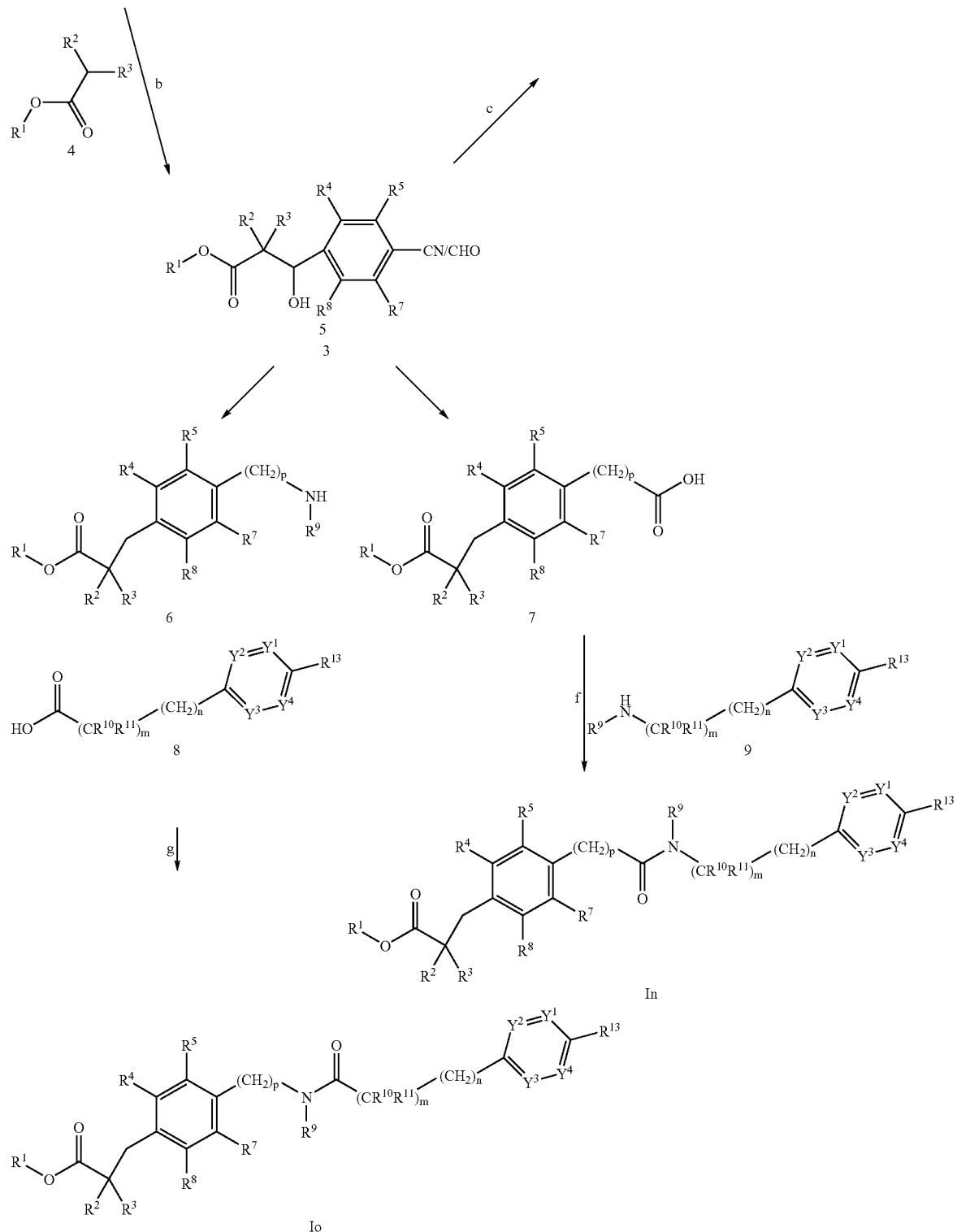

Formyl-nitriles 1a or aldehydes 1b, carrying a protected aldehyde function, are known, commercially available or can be prepared by methods known in the art. Compounds 3 and 5 are prepared from aldehydes 1 by Wittig/Horner-Emmons or aldol reactions analogous to the reactions described for the synthesis of compounds 3 and 5 in scheme 5 followed by removal of the aldehyde acetal protective function (if applicable) (steps a and b). Compounds 5 can be transformed into compounds 3 by treatment with catalytic amounts of an acid like para toluene sulfonic acid in a solvent like benzene or toluene, preferably under conditions allowing the removal of the water formed (e. g. with a Dean Stark trap or in the presence of molecular sieves) at temperatures between room temperature and the reflux temperature of the solvents to yield acrylic esters 3 (step c). Acrylic esters 3 carrying an aldehyde or a nitrile function can be further transformed into compounds of the general formula 6 or 7 using selective transformations as outlined for the transformation of nitrile 1 (scheme 4) and aldehyde 2 (scheme 4). Subsequent amide formation with heterocycles 5 and 6 can also be performed as outlined in scheme 4 thus yielding compound of the general formula In and Io as esters or acids.

An analogous reaction scheme with the same reaction sequences applies for the isomeric compound series leading to compounds of general formula I, particularly compounds according to formula Ip and Iq:

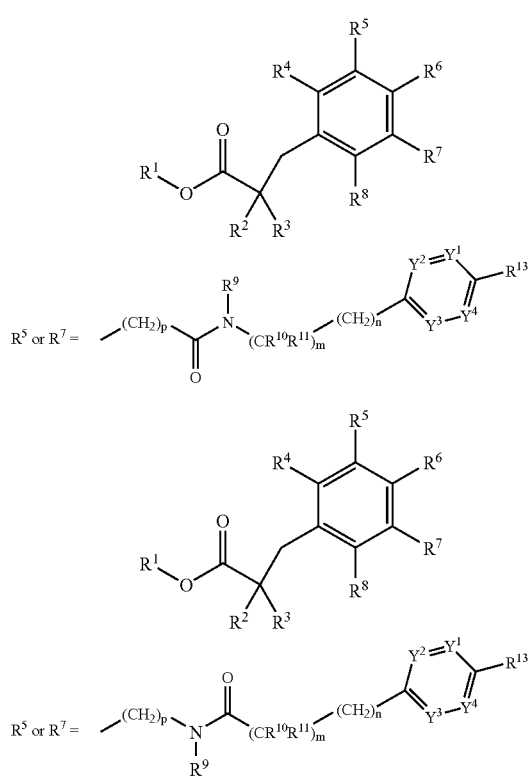

The synthesis of compounds with the general structure I, particularly compounds with $X^1$ and/or $X^2$ equal to S can be accomplished in close analogy to the synthesis of the corresponding analogues with $X^1$ and/or $X^2$ equal to oxygen. Suitable sulfur containing intermediates are known, can be prepared by methods known in the art or are prepared from phenolic intermediates as described by W Zhi-Liang and A P Kozikowski (J. Org. Chem. 2003, web publication release Oct. 10, 2003): treatment of a phenolic intermediate with sodium thiocyanate, sodium bromide and bromine in a solvent like methanol preferably between 0° C. and room temperature gives the corresponding 4-thiocyanato-phenols; subsequent reduction with lithiumaluminium hydride in a solvent like tetrahydrofuran at temperatures around 0° C. then liberates the corresponding 4-mercapto-phenol. Alternatively, intermediates carrying an aromatic SH moiety can be prepared from suitable intermediates carrying a phenolic hydroxyl function. In such intermediates, optionally carrying one or more protective functions, the phenolic OH group can be replaced by the corresponding aromatic SH function by methods known in the art. For example by a three step sequence as described in J. Labelled Compounds & Radiopharmaceuticals 43(7), 683–691, (2000): i) transformation of the phenol moiety into its trifluoromethanesulfonate (triflic anhydride, triethylamine, dichloromethane, at low temperature, preferably around −30° C.); ii) treatment of the triflate with triisopropylsilanethiolate, tetrakis(triphenylphosphine)-palladium(0) in solvent mixtures like toluene and tetrahydrofuran in a temperature range between 60° C. and 150° C.; iii) treatment of the silyl sulfide with hydrogen chloride in methanol preferably around 0° C. to liberate the phenolic SH moiety.

Compounds of the general formula I may be obtained in the form of racemates. Racemic compounds can be separated into their antipodes by methods known in the art, such as separation of the antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent.

Schemes 8 to 11 describe the synthesis of heterocycles 5 (scheme 1), identical to 11 (scheme 3), 8 (scheme 5) and 8 (scheme 6); 5 (scheme 4) identical to 8 (scheme 7) and 6 (scheme 4) identical to 9 (scheme 7).

Scheme 8

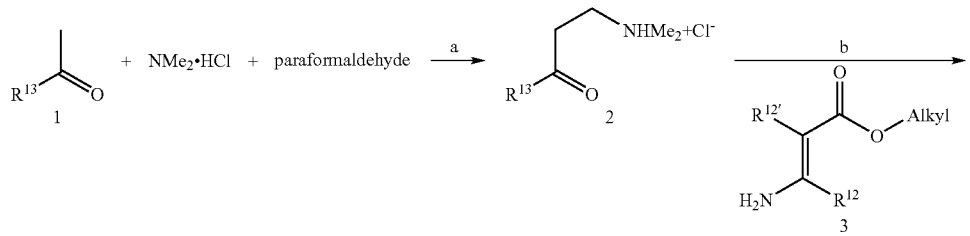

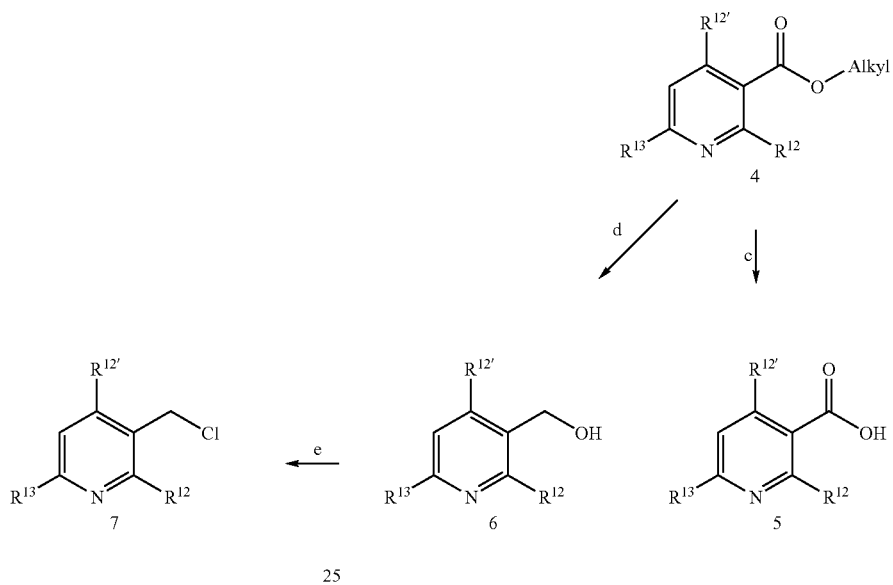

Pyridines 5 and 7 can be synthesized in a three step synthesis from ketones 1 (scheme 8). A mixture of ketones 1 with paraformaldehyde and dimethylamine hydrochloride in a solvent like ethanol in the presence of an acid like 37% HCl is heated to reflux for 2 to 10 hours to give aminoketones 2 (step a). Reaction of compounds 2 with 3-aminocrotonic acid esters 3 in acetic acid at reflux for 2 to 8 hours gives esters 4 (step b), which can be hydrolyzed (alkali hydroxide in solvents like THF, dioxane or DMSO) to give acids 5 (step c). Alternatively, esters 4 can be reduced with diisbutylaluminium hydride-solution (in toluene) at −30° C. to room temperature for 30 min to 3 h in solvents like THF to give alcohols 6. Reaction of alcohols 6 with thionyl chloride in dichloromethane at 0° C. to room temperature for 5 min to 1 h gives access to chlorides 7. Pyridines 4 can alternatively be synthesized following procedures described in Al-Saleh, Balkis; Abdelkhalik, Mervat Mohammed; Eltoukhy, Afaf Mohammed; Elnagdi, Mohammed Hilmy (Enaminones in heterocyclic synthesis: A new regioselective synthesis of 2,3,6-trisubstituted pyridines, 6-substituted-3-aroylpyridines and 1,3,5-triaroylbenzenes. Journal of Heterocyclic Chemistry (2002), 39(5), 1035–1038). Disubstituted pyridines 4 can be prepared according to procedures described in Katsuyama, Isamu; Ogawa, Seiya; Yamaguchi, Yoshihiro; Funabiki, Kazumasa; Matsui, Masaki; Muramatsu, Hiroshige; Shibata, Katsuyoshi (A convenient and regioselective synthesis of 4-(trifluoromethyl)pyridines. Synthesis (1997), (11), 1321–1324).

Scheme 9

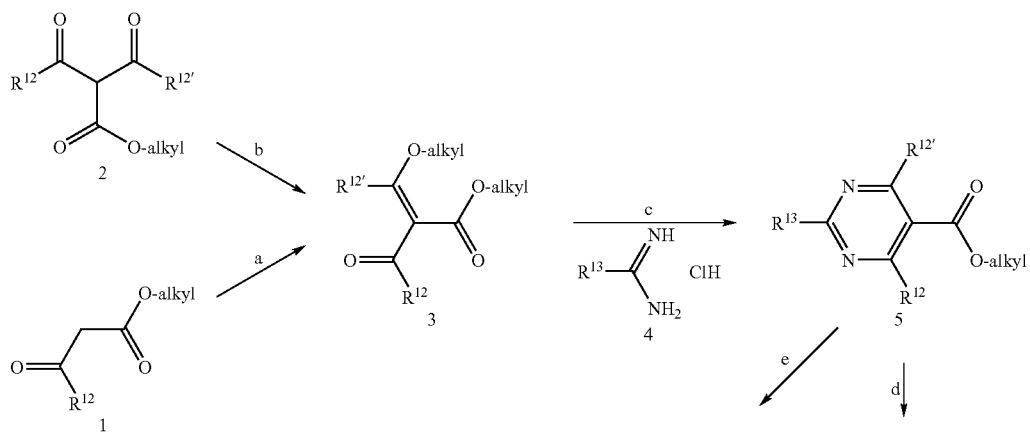

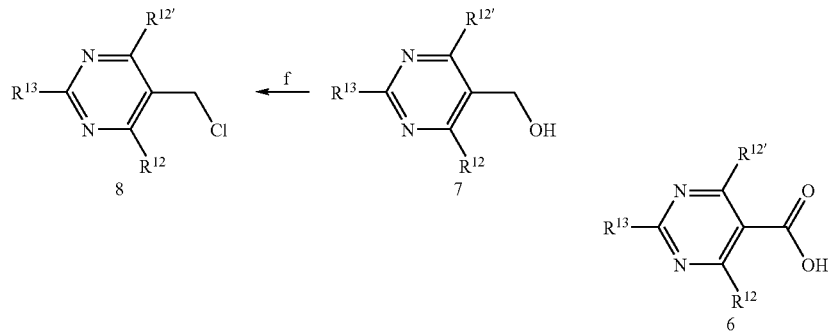

The synthesis of chlormethyl pyrimidines 8 and pyrimidine acids 6 is described in scheme 9. Reaction of 3-oxo-esters 1 with triethyl orthoformate in acetic anhydride at room temperature to reflux for 1 to 8 hours gives an E/Z mixture of the 3-ethoxy-acrylic acid esters 3 (step a). Diketo-esters 2 are reacted with methyl triflate in the presence of cesium carbonate in acetonitrile to give O-methylated products 3 (step b) [S. W. McCombie et al., Bioorganic & Medicinal Chemistry Letters 13 (2003), 567–571], thus yielding substituted enolethers 3 ($R^{12}$ not H). Reaction with amidine hydrochlorides 4 in ethanol in the presence of alkali tert-butoxide at room temperature gives access to esters 5 (step c). Esters 5 can be hydrolyzed (alkali hydroxide in solvents like THF, dioxane or DMSO) to give acids 6 (step d). Alternatively, esters 5 can be reduced with diisbutyl-aluminium hydride-solution (in toluene) at −30° C. to room temperature for 30 min to 3 h in solvents like THF to give alcohols 7 (step e). Reaction of alcohols 7 with thionyl chloride in dichloromethane at 0° C. to room temperature for 5 min to 1 h gives access to chlorides 8 (step f).

A general synthesis for acids 4 and chlorides 6 is depicted in scheme 10. Suzuki-coupling with boronic acides 1 and 6-halo-pyridazine-3-carboxylic acid esters 2,5-halo-pyrazine-2-carboxylic acid esters 2,6-halo-nicotinic acid esters 2,5-halo-pyridine-2-carboxylic acid esters 2,2-halo-pyrimidine-5-carboxylic acid esters 2 or 5-halo-pyrimidine-2-carboxylic acid esters 2 with $Pd(PhP)_4$ or $PdCl_2(dppf)$ [(1,1'-bis(diphenylphosphino)ferrocene)-dichloropalladium(II)× $CH_2Cl_2$ (1:1)] in toluene, dimethoxyethane, ethanol or DMF with cesium carbonate, potassium carbonate or cesium fluoride at room temperature to 90° C. for 2 to 8 h give esters 3 (step a). Esters 2 are either commercially available or can be prepared by methods known to a person skilled in the art. Esters 3 can be hydrolyzed (alkali hydroxide in solvents like THF, dioxane or DMSO) to give acids 4 (step b). A Curtius rearrangement can be used to transform acids 4 into the analogous BOC-protected anilines: first, the acid chlorides are synthesized with e.g. oxalyl chloride/DMF in dichloromethane. Then, reaction with sodium azide in DMF/dichloromethane followed by heating to reflux in the pres- Scheme 10

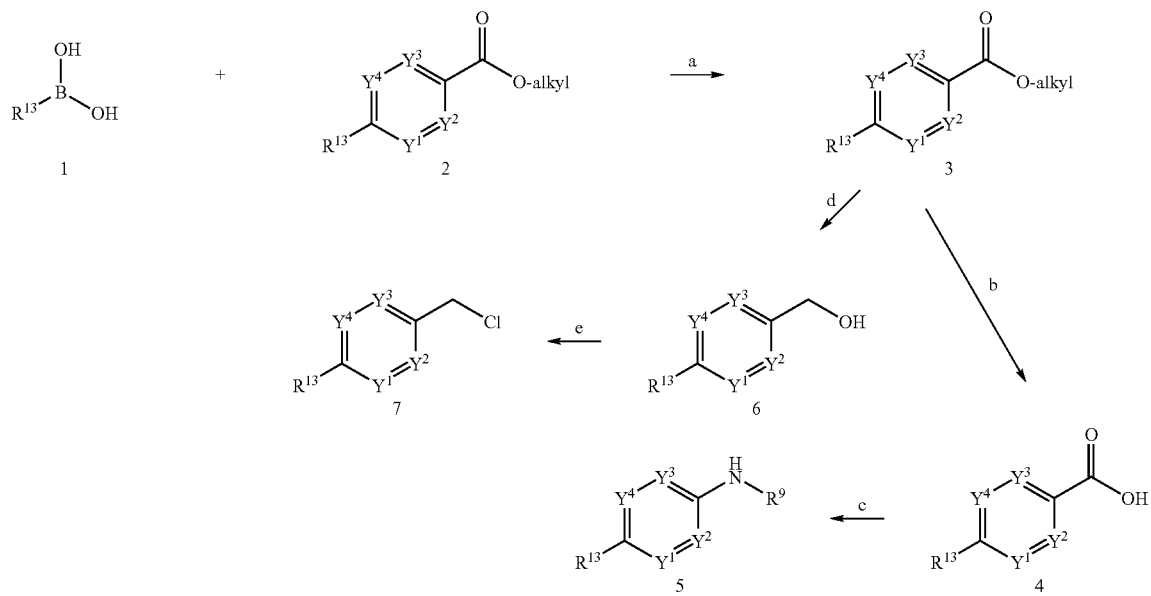

ence of 2-methyl-2-propanol gives the BOC protected anilines. Alternatively, such BOC protected anilines can be obtained from acids 4 in a one pot procedure by treatment with diphenylphosphoryl azide in 2-methyl-2-propanol in the presence of triethylamine and anhydrous 4-toluene sulfonic acid at temperatures around 100° C. Alkylation of these BOC protected anilines with $R^9$-halide in the presence of sodium hydride in solvents like DMF followed by BOC-deprotection with TFA or HCl in dioxane yields anilines 5 (step c). Alternatively, esters 3 can be reduced with diisbutylaluminium hydride-solution (in toluene) at −30° C. to room temperature for 30 min to 3 h in solvents like THF to give alcohols 6 (step d). Reaction of alcohols 6 with thionyl chloride in dichloromethane at 0° C. to room temperature for 5 min to 1 h gives access to chlorides 7 (step e).

solvents like ether or tetrahydrofuran gives alcohols 5 (step f); treatment of compounds 6 with lithium aluminium hydride in solvents like tetrahydrofuran or ether or with sodium borohydride in solvents like ethanol or methanol, preferably at temperatures between −15° C. and 40° C., gives alcohols 5 with $R^{11}$=H (step f). The alcohol compounds 5 which contain a chiral center can optionally be separated into optically pure antipodes by methods well known in the art, e. g. chromatography on a chiral HPLC column, or by derivatization with an optically pure acid to form esters, which can be separated by conventional HPLC chromatography and can then be converted back to the enantiomericaly pure alcohols 5. The reduction of ketones 6 to the corresponding secondary alcohols 5 of scheme 11 can also be carried out in an enantioselective fashion leading to

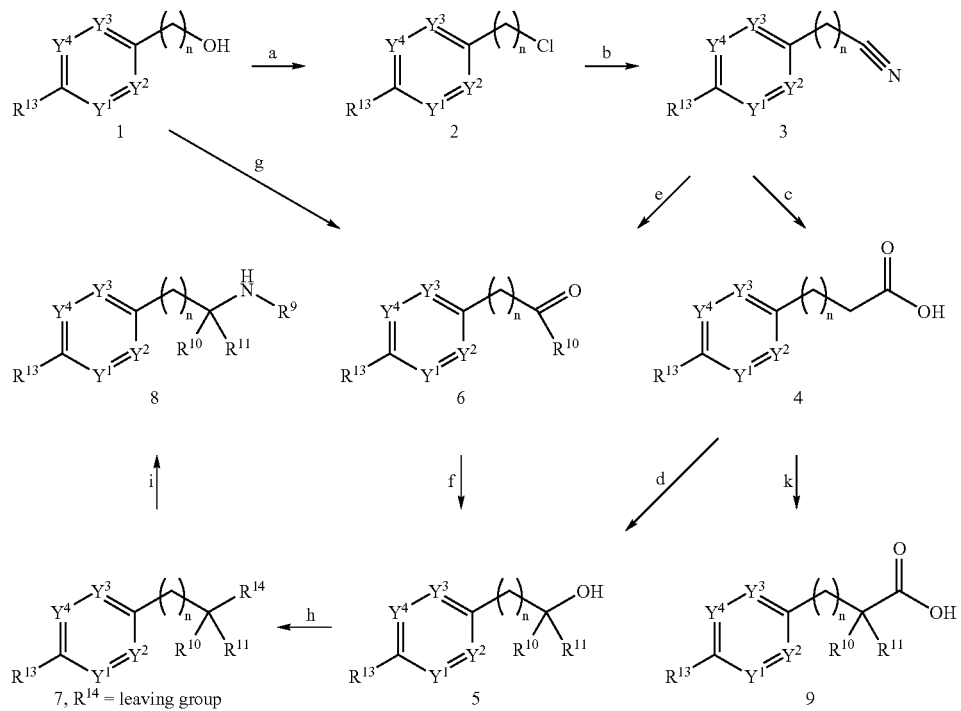

Scheme 11

Alcohols 1 in scheme 11 comprising a chain length n equal to one or two can be converted into analogues with a chain length of n+1 carbon atoms by methods well known in the art, e. g. by conversion of the primary alcohol into a suitable leaving group, e. g. a halide (2, step a), followed by reaction with cyanide to form nitriles 3 (step b) and saponification to acids 4 (step c). Acids 4 can be further transformed into the primary alcohols 5 ($R^{10}$=H, $R^{11}$=H), e. g. by using diborane in tetrahydrofuran (step d). Optionally, such alcohols 5 can be elongated to a chain length of n+1 carbon atoms by repeating the synthesis described for alcohols 1 to 5. In order to introduce substituents $R^{10}$ and/or $R^{11}$ different from hydrogen, cyano intermediates 3 can be reacted with alkyl Grignard reagents $R^{10}$MgX in solvents like ether or tetrahydrofuran between 0° C. and then reflux temperature of the solvent to form the corresponding $R^{10}$CO-alkyl ketones 6 (step e) or with diisbutylaluminium hydride the corresponding aldehydes 6 ($R^{10}$=H). Treatment of compounds 6 with an alkyllithium reagent $R^{11}$Li in the (R)— or (S)-alcohols 5, e. g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551–5553), or by treatment with (+)- or (−)-B-chlorodiisopinocampheyl-borane (DIP-Cl), according to Brown et al. (P. V. Ramachandran, B. Gong, A. V. Teodorovic, H. C. Brown, *Tetrahedron: Asymmetry* 1994, 5, 1061–1074). Aldehydes 6 ($R^{10}$=H, n=0) can also be synthesized from primary alcohols 1 by methods known in the art, e. g. by treatment with pyridinium chlorochromate in dichloromethane, preferably at temperatures between room temperature and the reflux temperature of dichloromethane, or by treatment with manganese dioxide in solvents like dichloromethane, preferably at room temperature (step g). These aldehydes 6 can be converted to the corresponding secondary alcohols 5 through reaction with alkyl organometallic compounds, preferably under the conditions discussed above. Finally, the alcohols 5 of scheme 11 can be converted into compounds of formula 7, e. g by treatment with methanesulfonyl chloride in dichloromethane in the presence of a base like triethylamine preferably in a temperature range between −20° C. and room temperature or thionyl chloride in dichloromethane at 0° C. to room temperature or by reaction with carbon tetrachloride or carbon tetrabromide and triphenylphosphine in solvents like tetrahydrofuran preferably in a temperature range between room temperature and the reflux temperature of the solvents or by treatment with triflic anhydride, 2,6-lutidine and 4-dimethylaminopyridine in dichloromethane between −30° C. and room temperature; thus yielding compounds of formula 7 as methanesulfonates, triflates, chlorides or bromides, respectively (step h). Compounds of formula 7 can further be converted (reaction step i) to the amines 8 in solvents like DMA, DMF or dichloromethane at room temperature with an excess of the corresponding amine.

Alpha mono- or di-substituted acids 9 ($R^{10}$ and/or $R^{11}$ not H) can be synthesized via esters of compounds 4, by treatment with a base like LDA or HMDS in solvents like tetrahydrofuran or 1,2-dimethoxyethane, followed by addition of one or sequentially two different alkyl halides, a reaction preferably performed between −78° C. and room temperature followed by hydrolysis to acid 9 (step k). Compounds 9 can be chiral and can optionally be separated into optically pure antipodes by methods well known in the art, e. g. chromatography on a chiral HPLC column, or by derivatization with an optically pure acid to form esters, which can be separated by conventional HPLC chromatography and then converted back to the enantiomerically pure alcohol. Additionally, the asymmetric alkylation can be done with chiral amides of 4 which are well known to a person skilled in the art.

The synthesis of compounds with the general structure I, particularly compounds according to formula Ir (scheme 12), with $X^1$ and/or $X^2$ equal to S can be accomplished in close analogy to the synthesis of the corresponding analogues with $X^1$ and/or $X^2$ equal to oxygen and is generally described on pages 41 to 42. In scheme 12, a general synthesis for $X^1$ equal to O and $X^2$ equal to S is shown.

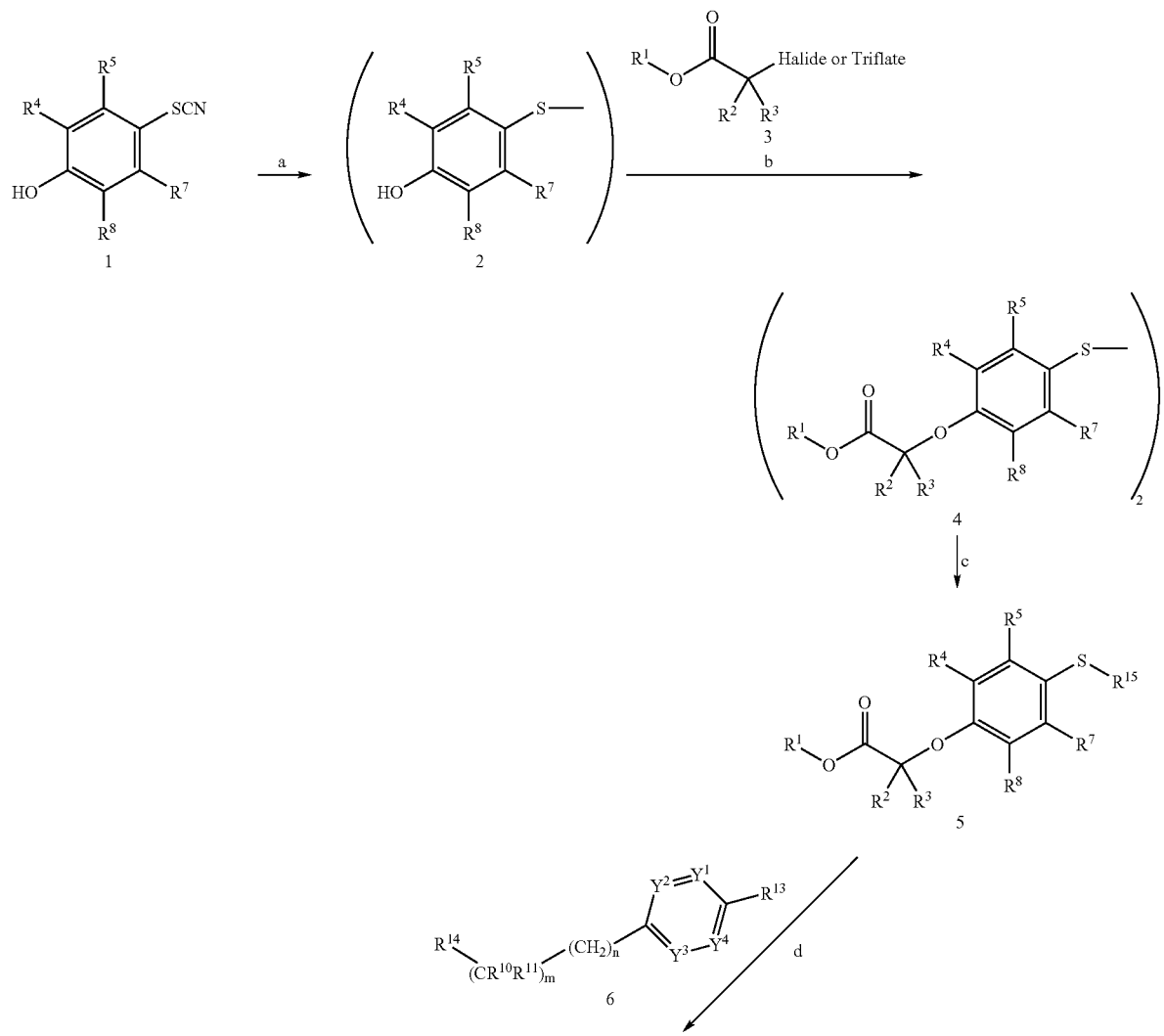

Scheme 12

-continued

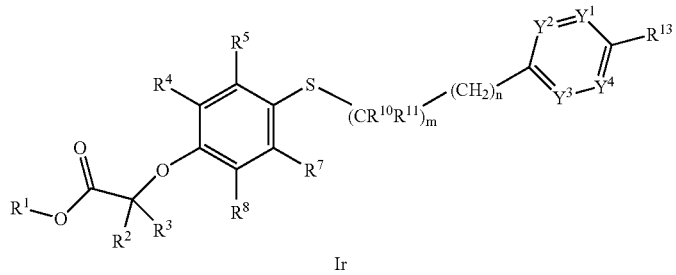

Ir

Thiocyanato phenols 1 which are known or can be prepared as discussed before (page 41–42) can be hydrolyzed with NaOH in water at room temperature to reflux temperature and oxidized in DMSO at higher temperature, preferably around 95° C. to the dithiols 2 (step a). Thiophenols 1 described before can be oxidized to the dithiols 2 as well (step a). Reaction of phenols 2 with alpha halo esters or triflates of formula 3 in the presence of a base like potassium or cesium carbonate in solvents like acetone, methyl-ethyl ketone, acetonitrile or N,N-dimethylformamide in a temperature range between room temperature and 100° C. leads to the corresponding ether compounds 4 (step b). Dithiol reduction with (n-Bu$_3$PH)BF$_4$ and Hünig's base in DMF at room temperature as described in the literature [Netherton, M. R.; Fu, G. C. Organic Letters 2001, 3(26), 4295–4298] yields thiophenols 5 (R$^{15}$=H) (step c). The reaction can also be carried out with acetic acid anhydride to give the stable compounds 5 (R$^{15}$=Ac) (step c).

Heterocycles 6 (prepared as outlined in schemes 8 to 11) are condensed with thiophenols 5 (R$^{15}$=H) according to well known procedures (step d): if R$^{13}$ represents a hydroxy group e. g. via Mitsunobu-reaction, with triphenylphosphine and di-tert-butyl-, diisopropyl- or diethyl-azodicarboxylate as reagents; this transformation is preferably carried out in a solvent like toluene, dichloromethane or tetrahydrofuran at ambient temperature. Alternatively, if R$^{13}$ represents a halide, mesylate or tosylate, heterocycles 6 can be reacted with S-acetyl protected 5 (R$^{15}$=Ac) in solvents like N,N-dimethylformamide, dimethylsulfoxide, acetonitrile, acetone or methyl-ethyl ketone in the presence of methanol and a weak base like cesium or potassium carbonate at a temperature ranging from 0° C. to 140° C., preferably around room temperature to yield ether compounds Ir (step d). Heterocycles 6 with R$^{13}$=OH can also be transformed in situ to the coresponding triflates by treatment with trifluoromethanesulfonic anhydride/2,6-di-tert-butylpyridine in CH$_2$Cl$_2$ at 0° C. to room temperature. The triflates are then reacted with thiophenols 5 (R$^{15}$=H) in solvents like N,N-dimethylformamide, dimethylsulfoxide, acetonitrile, acetone or methyl-ethyl ketone in the presence of a weak base like cesium or potassium carbonate at a temperature ranging from room temperature to 140° C., preferably around 50° C. to yield ether compounds Ir (step d). Esters of formula Ir can optionally be hydrolyzed according to standard procedures, e. g. by treatment with an alkali hydroxide like LiOH or NaOH in a polar solvent mixture like tetrahydrofuran/ethanol/water leading to carboxylic acids Ir.

An analogous reaction scheme with the same reaction sequence applies for the isomeric compound series leading to compounds of general formula I, particularly compounds according to formula Is:

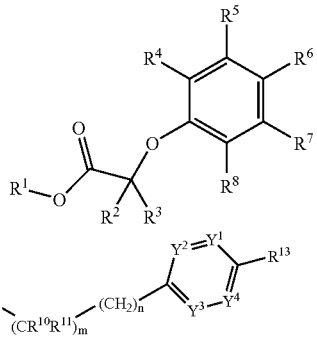

Is

Compounds of the general formula I with X$^1$=S can be prepared from the appropriate thiophenol precursors which themselves can be obtained by converting suitable phenol intermediates into the corresponding thiophenols applying methods described above.

Compounds of the general formula I can contain one or more stereocenters and can optionally be separated into optically pure enantiomers or diastereomers by methods well known in the art, e. g. by HPLC chromatography, chromatography on a chiral HPLC column, chromatography with a chiral eluant or by derivatization with an optically pure alcohol to form esters, which can be separated by conventional HPLC chromatography and then converted back to the enantiomerically pure acids I (R$^1$=H). In addition, racemic compounds can be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine.

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257:112–119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM $MgCl_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiomethylsulfanyl]-phenoxy}-acetic acid, was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resuspended in 50 ul of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using OptiPlates (Packard). Dose response curves were done in triplicates within a range of concentration from $10^{-10}$ M to $10^{-4}$ M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARα-LBD fusion protein was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resolved in 50 μl of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction a 140 ng equivalent of GST-PPARγ-LBD fusion protein was bound to 10 μg SPA beads (PharmaciaAmersham) in a final volume of 50 ul by shaking. The resulting slurry was incubated for 1 h at RT and centrifuged for 2 min at 1300g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 μl were added, the reaction incubated at RT for 1 h and scintillation proximity counting performed.

All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6 well plates at a density of $10^5$ Cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit $IC_{50}$ values of 0.5 nM to 10 μM, preferably 1 nM to 100 nM for PPARδ and $IC_{50}$ values of 1 nM to 10 μM, preferably 10 nM to 5 μM for PPARα. Compounds, in which $R^1$ is not hydrogen are converted in vivo to compounds in which $R^1$ is hydrogen. The following table shows measured values for some selected compounds of the present invention.

|  | PPARα $IC_{50}$ (μmol/l) | PPARγ $IC_{50}$ (μmol/l) | PPARδ $IC_{50}$ (μmol/l) |
| --- | --- | --- | --- |
| Example 8 | 0.013 | >10 | 0.026 |
| Example 20 | 0.454 | >10 | 0.002 |
| Example 27 | 0.289 | >10 | 0.031 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1–500 mg, preferably 0.5–100 mg, of a compound of formula (I).

The following examples serve to illustrate the present invention in more detail. They are, however, not intended to limit its scope in any manner.

EXAMPLES

Abbreviations:

AcOEt=ethyl acetate, n-BuLi=n-butyllithium, DBU=1,8-diazabicyclo[5.4.0]undec-7-ene, DEAD=diethyl azodicarboxylate, DIAD=diisopropyl azodicarboxylate, DIBAL-H solution=diisobutylaluminum hydride solution, DMF=N,N-dimethylformamide, DMPU=1,3-dimethyl-3,4,5,6-tetrahydro-2(1H)-pyrimidinone, eq.=equivalents, h=hour(s), DMSO=dimethyl sulfoxide, HPLC=high performance liquid chromatography, i. V.=in vacuo, LDA=lithium diisopropylamide, $PdCl_2(dppf)$=(1,1'-bis(diphenylphosphino)ferrocene)dichloro-palladium(II).$CH_2Cl_2$ (1:1), $Pd(Ph_3P)_4$=tetrakis(triphenylphosphine)palladium, $POCl_3$=phosphorous oxychloride, RT=room temperature, TFA=trifluoroacetic acid, TFAA=trifluoroacetic anhydride, THF=tetrahydrofuran.

Example 1

(2-(3-Methoxy-propyl)-4-{methyl-[2-methyl-6-(4-trifluoromethyl-phenyl)-pyridin-3-ylmethyl]-amino}-phenoxy)-acetic acid A] (2-Iodo-phenoxy)-acetic acid ethyl ester 9.10 g (41.4 mmol) of o-iodophenol was dissolved in 102 ml of acetone and treated subsequently at 0° C. with 14.8 g (1.1 eq.) of cesium carbonate and 4.57 ml (1.0 eq.) of ethyl bromoacetate. After vigorous stirring for 1 h at ambient temperature and filtration, the bulk of solvent was evaporated and the residue redissolved in AcOEt. Washing with water, drying over magnesium sulfate, and evaporation of the solvents finally produced 12.66 g of pure title compound as colorless oil.

MS: 306.0 $(M)^+$.

B] [2-(3-Methoxy-prop-1-ynyl)-phenoxy-acetic acid ethyl ester

A three neck reaction flask was successively charged with 12.65 g (41.3 mmol) of the above prepared (2-iodo-phenoxy)-acetic acid ethyl ester, 128 ml of acetonitrile, 5.793 g (2 eq.) of 3-methoxy-1-propyne, 17.28 ml (3 eq.) of $NEt_3$, 1.45 g (0.05 eq.) of $(PPh_3)_2PdCl_2$, and 0.394 g (0.05 eq.) of CuI. After stirring for 4 h the bulk of the solvent was removed i. V. and the residue distributed between HCl and AcOEt. Washing of the organic layer with cold water and brine, drying over magnesium sulfate, and evaporation of the solvents, followed by flash chromatography ($SiO_2$, hexane/AcOEt=8/2), yielded 9.54 g of the title compound as light brown oil.

MS: 248.2 $(M)^+$.

C] [2-(3-Methoxy-propyl)-phenoxy]acetic acid ethyl ester 9.54 g (38.4 mmol) of the above prepared [2-(3-methoxy-prop-1-ynyl)-phenoxy]-acetic acid ethyl ester was hydrogenated at RT in 130 ml of AcOEt over 2.39 g of Pd/C (10%) under 1 atm of $H_2$-pressure. After 2 h at ambient temperature, the reaction mixture was filtrated over Celite and carefully rinsed with AcOEt. Evaporation of the solvent left finally 9.39 g of the title compound as colorless oil.

MS: 252.2 $(M)^+$.

D] [2-(3-Methoxy-propyl)-4-nitro-phenoxy-acetic acid ethyl ester 4.00 g (15.9 mmol) of the above prepared [2-(3-methoxy-propyl)-phenoxy]-acetic acid ethyl ester was dissolved in 5.0 ml of TFAA and added slowly and carefully via dropping funnel to a mixture of 5 ml of TFAA and 4 ml of conc. $HNO_3$ (65%) kept at −10° C.; the reaction was then allowed to proceed for additional 30 Min. Careful quenching with ice, twofold extraction with AcOEt, washing with $NaHCO_3$ and brine, drying over magnesium sulfate, and evaporation of the solvents left a crude product which was purified by flash chromatography ($SiO_2$, hexane/AcOEt=75/25) to deliver finally 3.00 g of the title compound as light brown oil, contaminated according to NMR with roughly 35% of the ortho-isomer which was separated after the next step.

MS: 298.3 $(M+H)^+$.

E] [4-Amino-2-(3-methoxy-propyl)-phenoxy-acetic acid ethyl ester 3.00 g (roughly 65%, 6.56 mmol) of the above prepared [2-(3-methoxy-propyl)-4-nitro-phenoxy]-acetic acid ethyl ester was hydrogenated at RT in 50 ml of AcOEt over 0.60 g of Pd/C (10%) under 1 atm of $H_2$-pressure. After 3 h at ambient temperature, the reaction mixture was filtered over Celite and carefully rinsed with AcOEt. Evaporation of the solvent, followed by flash chromatography ($SiO_2$, hexane/AcOEt=1/1) produced 1.69 g of the title compound as light brown oil; from the more polar fractions, 0.784 g of 8-(3-methoxy-propyl)-4H-benzo[1,4]oxazin-3-one was isolated (cyclized reduced ortho-amino derivative).

MS: 268.3 $(M+H)^+$; side product: 221.1 $(M)^+$.

F] [4-tert-Butoxycarbonylamino-2-(3-methoxy-propyl)-phenoxy-acetic acid ethyl ester 1.68 g (6.28 mmol) of the above prepared [4-amino-2-(3-methoxy-propyl)-phenoxy]-acetic acid ethyl ester was dissolved in 7 ml of THF, treated with 1.646 g (1.2 eq.) of di-tert-butyl dicarbonate, and refluxed for 1 h. After cooling, the reaction mixture was poured onto crashed ice/AcOEt, the organic layer washed with water and brine, dried over magnesium sulfate, and evaporated to dryness. Flash chromatography ($SiO_2$, hexane/AcOEt=75/25) afforded 2.22 g of the title compound as light brown oil.

MS: 387.2 $(M)^+$.

G] [4-(tert-Butoxycarbonyl-methyl-amino)-2-(3-methoxy-propyl)-phenoxy-acetic acid ethyl ester To 2.21 g (6.01 mmol) of the above prepared [4-tert-butoxycarbonylamino-2-(3-methoxy-propyl)-phenoxy]-acetic acid ethyl ester, dissolved in 18 ml of abs. DMF, was added at 0° C. 0.313 g of NaH (60% in mineral oil, 1.3 eq.). 5 Min. later, 0.75 ml (2 eq.) of MeI was added and the reaction allowed to proceed for 10 Min. at 0° C. and for 1 h at ambient temperature. Pouring onto crashed ice/$KHSO_4$ solution, twofold extraction with AcOEt, washing with water and brine, drying over magnesium sulfate, and evaporation of the solvents, followed by flash chromatography ($SiO_2$, hexane/AcOEt=8/2), yielded 1.55 g of the title compound as light yellow oil.

H] [2-(3-Methoxy-propyl)-4-methylamino-phenoxy-acetic acid ethyl ester 1.55 g (4.06 mmol) of the above prepared [4-(tert-butoxycarbonyl-methyl-amino)-2-(3-methoxy-propyl)-phenoxy]-acetic acid ethyl ester was dissolved in 41 ml of $CH_2Cl_2$ and treated dropwise with 10 ml of TFA. After additional 30 Min. at RT, the bulk of the solvents was removed i. V. and the residue distributed between cold $NaHCO_3$-solution and AcOEt. Washing with cold water and brine, drying over magnesium sulfate, and evaporation of the solvents left 1.15 g of the title compound as brownish oil which was used as such for the next step.

I] (2-(3-Methoxy-propyl)-4-{methyl-[2-methyl-6-(4-trifluoromethyl-phenyl)-pyridin-3-ylmethyl]-amino}-phenoxy)-acetic acid ethyl ester To 0.102 g (0.36 mmol) of the above prepared [2-(3-methoxy-propyl)-4-methylamino-phenoxy]-acetic acid ethyl ester, dissolved in 1.4 ml of abs. DMF, were added successively at 0° C. 0.017 g of NaH (60% in mineral oil, 1.2 eq.), 0.054 g (1 eq.) of NaI and 0.100 g (1 eq.) of 3-chloromethyl-2-methyl-6-(4-trifluoromethyl-phenyl)-pyridine (see below 1K]). The reaction was allowed to proceed for 5 Min. at 0° C. and for 0.5 h at ambient temperature. Pouring onto crashed ice/$KHSO_4$, twofold extraction with AcOEt, washing with water and brine, drying over magnesium sulfate, and evaporation of the solvents, followed by flash chromatography ($SiO_2$, hexane/AcOEt=75/25), yielded 0.126 g of the title compound as light yellow oil.

MS: 531.5 $(M+H)^+$.

J] (2-(3-Methoxy-propyl)-4-{methyl-[2-methyl-6-(4-trifluoromethyl-phenyl)-pyridin-3-ylmethyl]-amino}-phenoxy)-acetic acid 0.125 g (0.24 mmol) of the above prepared (2-(3-methoxy-propyl)-4-{methyl-[2-methyl-6-(4-trifluoromethyl-phenyl)-pyridin-3-ylmethyl]-amino}-phenoxy)-acetic acid ethyl ester was dissolved in 1.44 ml of THF/EtOH=1/1, treated with 0.72 ml (3 eq.) of 1N NaOH, and kept at ambient temperature for 0.5 h. The reaction mixture was then poured onto crashed ice/AcOEt/HCl dil., the organic layer washed with water, dried over sodium sulfate, and evaporated to dryness. Crystallization from hexane/AcOEt produced finally 0.102 g of the title compound as off-white crystals of mp. 72–73° C.

MS: 501.1 $(M-H)^-$.

The reagent used in 1I] was prepared as follows:

K] 3-Dimethylamino-1-(4-trifluoromethyl-phenyl)-propan-1-one hydrochloride 4-(Trifluoromethyl) acetophenone (4.97 g, 26.4 mmol), paraformaldehyde (1.586 g, 2 eq.) and dimethylamine hydrochloride (3.231 g, 1.5 eq.) were mixed together in 7 ml of EtOH, treated with 0.08 ml of 37% HCl, and heated to reflux for 5 h. Cooling down to ambient temperature, filtration and washing with tiny amounts of cold EtOH delivered 4.59 g of the title compound as white crystals, mp. 128–42° C. (dec.).

MS: 246.3 $(M+H)^+$.

L] 2-Methyl-6-(4-trifluoromethyl-phenyl)-nicotinic acid methyl ester 4.59 g (16.3 mmol) of the above prepared 3-dimethylamino-1-(4-trifluoromethyl-phenyl)-propan-1-one hydrochloride and 1.86 g (1.0 eq.) of 3-aminocrotonic acid methyl ester was dissolved in 50 ml of AcOH and heated to reflux for 4 h. After cooling, the bulk of the solvent was evaporated i. V., the residue dissolved in AcOEt, and washed with water and brine. Drying over sodium sulfate, evaporation of the solvents and flash chromatography ($SiO_2$, hexane/AcOEt=8/2) delivered finally 2.40 g of the title compound as light yellow waxy solid.

MS: 296.1 $(M+H)^+$.

M] [2-Methyl-6-(4-trifluoromethyl-phenyl)-pyridin-3-yl]-methanol g (3.39 mmol) of the above synthesized 2-methyl-6-(4-trifluoromethyl-phenyl)-nicotinic acid methyl ester in 7 ml of abs. THF was cooled down to 0° C. and reacted with 7.06 ml of DIBAL-H-solution (1.2 M in toluene, 2.5 eq.) for 1 h. Careful quenching with ice/NH$_4$Cl, twofold extraction with AcOEt, washing with brine, drying over sodium sulfate, and evaporation of the solvents left a crude product which was purified by flash chromatography (SiO$_2$, hexane/AcOEt=7/3) to deliver finally 0.875 g of the title compound as off-white solid, mp. 76–78° C.

MS: 268.1 (M+H)$^+$.

N] 3-Chloromethyl-2-methyl-6-(4-trifluoromethyl-phenyl)-pyridine 0.875 g (3.27 mmol) of the above prepared [2-methyl-6-(4-trifluoromethyl-phenyl)-pyridin-3-yl]-methanol was dissolved in 16 ml of CH$_2$Cl$_2$ and treated dropwise at 0° C. with 0.48 ml (2 eq.) of SOCl$_2$. The reaction mixture was kept at 0° C. for 5 Min. and at RT for 30 Min. Pouring onto crashed ice/NaHCO$_3$, twofold extraction with AcOEt, washing with water, drying over sodium sulfate and evaporation of the solvents afforded 0.875 g of pure title compound as light yellow oil.

MS: 285.1, 287.1 (M)$^+$.

Example 2

(2-(3-Methoxy-propyl)-4-{methyl-[2-methyl-6-(3-trifluoromethyl-phenyl)-pyridin-3-ylmethyl]-amino}-phenoxy)-acetic acid

A] 3-Chloromethyl-2-methyl-6-(3-trifluoromethyl-phenyl)-pyridine was prepared in analogy to example 1N], but starting the whole reaction sequence with 3-(trifluoromethyl) acetophenone instead of 4-(trifluoromethyl) acetophenone, as white crystals of mp. 73–75° C.

MS: 285.1, 287.1 (M)$^+$.

B] (2-(3-Methoxy-propyl)-4-{methyl-[2-methyl-6-(3-trifluoromethyl-phenyl)-pyridin-3-ylmethyl]-amino}-phenoxy)-acetic acid The title compound was prepared in analogy to example 1, but using in step I] 3-chloromethyl-2-methyl-6-(3-trifluoromethyl-phenyl)-pyridine instead of 3-chloromethyl-2-methyl-6-(4-trifluoromethyl-phenyl)-pyridine, as light brown viscous oil.

MS: 501.1 (M–H)$^-$.

Example 3

[rac]-[2-(3-Methoxy-propyl)-4-(methyl-{1-[2-methyl-6-(3-trifluoromethyl-phenyl)-pyridin-3-yl]-ethyl}-amino}-phenoxy)-acetic acid

A] 2-Methyl-6-(3-trifluoromethyl-phenyl)-pyridine-3-carbaldehyde 3.00 g (11.2 mmol) of [2-methyl-6-(3-trifluoromethyl-phenyl)-pyridin-3-yl]-methanol (synthesized as described in example 1K]-M], but starting with 3-(trifluoromethyl) acetophenone instead of 4-(trifluoromethyl) acetophenone), was dissolved in 56 ml of CH$_2$Cl$_2$ and treated with 14.6 g (15 eq.) of MnO$_2$. After vigorous stirring for 2 h at ambient temperature, the reaction mixture was filtered over Celite and carefully rinsed with CH$_2$Cl$_2$. Evaporation of the solvent left 2.659 g of the title compound as white crystals of mp. 61–63° C.

MS: 266.2 (M+H)$^+$.

B] [rac]-1-[2-Methyl-6-(3-trifluoromethyl-phenyl)-pyridin-3-yl]-methanol 0.500 g (1.89 mmol) of the above prepared 2-methyl-6-(3-trifluoromethyl-phenyl)-pyridine-3-carbaldehyde was dissolved in 9.4 ml of abs. THF and treated at −10° C. with 0.94 ml of 3M methyl magnesium chloride solution (in THF). After 30 Min., the reaction mixture was carefully poured onto crashed ice/NH$_4$Cl, extracted twice with AcOEt, washed with water, dried over sodium sulfate, and evaporated to dryness to leave 0.532 g of the title product, pure according to NMR.

MS: 282.1 (M+H)$^+$.

C] [rac]-3-(1-Chloro-ethyl)-2-methyl-6-(3-trifluoromethyl-phenyl)-pyridine 0.530 g (1.89 mmol) of the above prepared [rac]-1-[2-methyl-6-(3-trifluoromethyl-phenyl)-pyridin-3-yl]-ethanol was dissolved in 9.5 ml of CH$_2$Cl$_2$ and treated dropwise at 0° C. with 0.275 ml (2 eq.) of SOCl$_2$. The reaction mixture was kept at 0° C. for 5 Min. and at RT for 30 Min. Pouring onto crashed ice/NaHCO$_3$, twofold extraction with EtOEt, washing with water, drying over sodium sulfate and evaporation of the solvents yielded 0.586 g of pure title compound as light yellow oil.

D] [rac]-[2-(3-Methoxy-propyl)-4-(methyl-}1-[2-methyl-6-(3-trifluoromethyl-phenyl)-pyridin-3-yl]-ethyl}-amino)-phenoxy-acetic acid ethyl ester To 0.082 g (0.29 mmol) of the above (example 1H]) prepared [2-(3-methoxy-propyl)-4-methylamino-phenoxy]-acetic acid ethyl ester, dissolved in 1.0 ml of abs. DMF, were added successively at 0° C. 0.014 g of NaH (60% in mineral oil, 1.2 eq.), 0.044 g (1 eq.) of NaI and 0.087 g (1 eq.) of the above prepared [rac]-3-(1-chloro-ethyl)-2-methyl-6-(3-trifluoromethyl-phenyl)-pyridine. The reaction was allowed to proceed for 5 Min. at 0° C. and for 0.5 h at ambient temperature. Pouring onto crashed ice/KHSO$_4$, twofold extraction with AcOEt, washing with water and brine, drying over magnesium sulfate, and evaporation of the solvents, followed by flash chromatography (SiO$_2$, hexane/AcOEt=8/2), yielded 0.015 g of the title compound as light yellow oil.

MS: 545.5 (M+H)$^+$.

E] [rac]-[2-(3-Methoxy-propyl)-4-(methyl-{1-[2-methyl-6-(3-trifluoromethyl-phenyl)-pyridin-3-yl]-ethyl}-amino)-phenoxy-acetic acid 0.015 g (0.03 mmol) of the above prepared [rac]-[2-(3-methoxy-propyl)-4-(methyl-{1-[2-methyl-6-(3-trifluoromethyl-phenyl)-pyridin-3-yl]-ethyl}-amino)-phenoxy]-acetic acid ethyl ester was dissolved in 0.2 ml of THF/EtOH=1/1, treated with 0.09 ml (3 eq.) of 1N NaOH, and kept at ambient temperature for 0.5 h. The reaction mixture was then poured onto crashed ice/AcOEt/HCl dil., the organic layer washed with water and brine, dried over sodium sulfate, and evaporated to dryness to leave 0.012 g of the title compound as light brown oil.

MS: 515.3 (M–H)$^-$.

Example 4

[rac]-[2-(3-Methoxy-propyl)-4-(methyl-{1-[2-methyl-6-(3-trifluoromethyl-phenyl)-pyridin-3-yl]-butyl}-amino)-phenoxy]-acetic acid

A] [rac]-1-[2-Methyl-6-(3-trifluoromethyl-phenyl)-pyridin-3-yl]-butan-1-ol 0.600 g (2.26 mmol) of the above prepared 2-methyl-6-(3-trifluoromethyl-phenyl)-pyridine-3-carbaldehyde (example 3A]) was dissolved in 11.3 ml of abs. THF and treated at −78° C. with 1.2 ml of 2M propyl magnesium chloride solution (in EtOEt, 1.06 eq.). After stirring for 15 Min. at 0° C., the reaction mixture was carefully poured onto crashed ice/$NH_4Cl$, extracted twice with AcOEt, washed with water, dried over sodium sulfate, and evaporated to dryness. Flash chromatography ($SiO_2$, hexane/AcOEt=8/2) yielded then 0.281 g of the title compound as white crystals of mp. 83–85° C.

MS: 309.2 $(M)^+$.

B] [rac]-3-(1-Chloro-butyl)-2-methyl-6-(3-trifluoromethyl-phenyl)-pyridine 0.276 g (0.892 mmol) of the above prepared [rac]-1-[2-methyl-6-(3-trifluoromethyl-phenyl)-pyridin-3-yl]-butan-1-ol was dissolved in 4.3 ml of $CH_2Cl_2$ and treated dropwise at 0° C. with 0.13 ml (2 eq.) of $SOCl_2$. The reaction mixture was kept at 0° C. for 5 Min. and at RT for 30 Min. Pouring onto crashed ice/$NaHCO_3$, twofold extraction with AcOEt, washing with water, drying over sodium sulfate, and evaporation of the solvents yielded 0.289 g of pure title compound as light yellow oil.

MS: 327.2, 329.1 $(M)^+$.

C] [rac]-[2-(3-Methoxy-propyl)-4-(methyl-{1-[2-methyl-6-(3-trifluoromethyl-phenyl)-pyridin-3-yl]-butyl}-amino)-phenoxy-acetic acid ethyl ester To 0.0944 g (0.336 mmol) of the above prepared (example 1H]) [2-(3-methoxy-propyl)-4-methylamino-phenoxy]-acetic acid ethyl ester and 0.100 g (0.305 mmol) of the above prepared [rac]-3-(1-chloro-butyl)-2-methyl-6-(3-trifluoromethyl-phenyl)-pyridine, dissolved in 1.9 ml of abs. DMSO, were added successively 0.0505 g of $K_2CO_3$ (0.366 mmol) and 0.0503 g (0.336 mmol) of NaI. The reaction was allowed to proceed for 5 h at 50° C. Pouring onto crashed ice/$NH_4Cl$, twofold extraction with AcOEt, washing with water, drying over sodium sulfate, and evaporation of the solvents, followed by flash chromatography ($SiO_2$, hexane/AcOEt=8/2), afforded 0.082 g of the title compound as light yellow oil.

MS: 573.5 $(M+H)^+$.

D] [rac]-[2-(3-Methoxy-propyl)-4-(methyl-{1-[2-methyl-6-(3-trifluoromethyl-phenyl)-pyridin-3-yl]-butyl}-amino)-phenoxy]-acetic acid 0.082 g (0.143 mmol) of the above prepared [rac]-[2-(3-methoxy-propyl)-4-(methyl-{1-[2-methyl-6-(3-trifluoromethyl-phenyl)-pyridin-3-yl]-butyl}-amino)-phenoxy]-acetic acid ethyl ester was dissolved in 1.64 ml of THF/EtOH=1/1, treated at 0° C. with 0.43 ml (3 eq.) of 1N NaOH, and kept at ambient temperature for 2 h. The reaction mixture was then neutralized with HCl dil. to pH 7, extracted with AcOEt, the organic layer was washed with water, dried over sodium sulfate, and evaporated to dryness to leave 0.070 g of the title compound as light brown oil.

MS: 543.3 $(M-H)^-$.

Example 5

[rac]-[2-Methyl-4-(methyl-{1-[2-methyl-6-(3-trifluoromethyl-phenyl)-pyridin-3-yl]-butyl}-amino)-phenoxy]-acetic acid

A] The title compound was prepared in analogy to example 4, but using in step C] (2-methyl-4-methylamino-phenoxy)-acetic acid methyl ester instead of [2-(3-methoxy-propyl)-4-methylamino-phenoxy]-acetic acid ethyl ester, as yellow foam

MS: 587.5 $(M+H)^+$.

The necessary building block was synthesized as follows:

B] (2-Methyl-4-nitro-phenoxy)-acetic acid methyl ester

A solution of 15.76 ml (171 mmol) of methyl bromoacetate and 25.0 g (163 mmol) of 2-methyl-4-nitrophenol in 300 ml dry acetonitrile was treated with 61.3 g (188 mmol) $Cs_2CO_3$ and stirred at RT for 4 h. The mixture was filtered, washed with acetonitrile and evaporated. The residue was suspended in 700 ml $CH_2Cl_2$, filtered and evaporated to give 36.4 g of (2-methyl-4-nitro-phenoxy)-acetic acid methyl ester as yellow crystals.

MS: 225 $(M^+)$.

C] (4-Amino-2-methyl-phenoxy)-acetic acid methyl ester

A solution of 36.3 g (161 mmol) of the above prepared (2-methyl-4-nitro-phenoxy)-acetic acid methyl ester in 400 ml MeOH and 11.2 ml (177 mmol) AcOH was hydrogenated in the presence of 3.63 g 10% Pd/C for 7 h at atmospheric pressure. After removal of the catalyst the reaction was evaporated, dissolved in toluene and evaporated (5×) to give 32.5g of (4-amino-2-methyl-phenoxy)-acetic acid methyl ester as a brown crystalline residue.

MS: 196 $(M+H^+)$.

D] (4-tert-Butoxycarbonylamino-2-methyl-phenoxy)-acetic acid methyl ester

A solution of 21.1 g (108 mmol) of (4-amino-2-methyl-phenoxy)-acetic acid methyl ester in 210 ml THF was treated with of 24.7 g (111 mmol) di-tert-butyl dicarbonate and heated for 3 h at 80° C. The solution was evaporated and purified by flash chromatography with a gradient of n-heptane: AcOEt (9:1 to 4:1) to yield 28.1 g of (4-tert-butoxycarbonylamino-2-methyl-phenoxy)-acetic acid methyl ester as a light pink crystalline residue.

MS: 295 $(M^+)$.

E] [4-(tert-Butoxycarbonyl-methyl-amino)-2-methyl-phenoxy-acetic acid methyl ester To an ice-cooled and stirred solution of 22.8 g (77 mmol) of the above prepared (4-tert-butoxycarbonylamino-2-methyl-phenoxy)-acetic acid methyl ester in 230 ml DMF was added within 10 min 3.7 g (55% in oil, 85 mmol) of NaH and, after 1 h, 14.5 ml (232 mmol) of CH$_3$I. The reaction was stirred at 0° C. for 2 h, neutralized with aqueous 10% KHSO$_4$, and extracted with aqueous 10% KHSO$_4$/Et$_2$O (3×). The organic phases were washed with aqueous 10% NaCl, dried over sodium sulfate, and evaporated to give 25.8 g of [4-(tert-butoxycarbonyl-methyl-amino)-2-methyl-phenoxy]-acetic acid methyl ester.

MS: 310 (M+H$^+$).

F] (2-Methyl-4-methylamino-phenoxy)-acetic acid methyl ester

A solution of crude 25.8 g (77 mmol) of the above prepared [4-(tert-butoxycarbonyl-methyl-amino)-2-methyl-phenoxy]-acetic acid methyl ester in 600 ml CH$_2$Cl$_2$ was treated at 0° C. with 198 ml TFA and stirred at RT for 30 min. The reaction was evaporated and treated with chilled aqueous saturated NaHCO$_3$ solution/Et$_2$O (3×). The organic phases were washed with aqueous 10% NaCl, dried over sodium sulfate, and evaporated to give 16.2 g of crude product. Purification by flash chromatography on SiO$_2$ with a gradient of n-heptane: AcOEt (9:1 to 4:1) yielded 12.7 g of (2-methyl-4-methylamino-phenoxy)-acetic acid methyl ester as an orange oil.

MS: 210 (M+H$^+$).

Example 6

[rac]-(4-{Methyl-[2-methyl-6-(4-trifluoromethyl-phenyl)-pyridin-3-ylmethyl]-amino}-2-trifluoromethyl-phenoxy)-acetic acid A] 4-Nitro-2-trifluoromethyl-phenol A solution of 24.73 g (110.7 mmol) 6-methoxy-5-nitrobenzotrifluoride in 260 ml acetic acid and 130 ml of aqueous HBr solution (62%) was heated to reflux for 96 h, cooled down, evaporated and taken up in aqueous saturated NaHCO$_3$ solution/Et$_2$O (3×). The organic phases were washed with aqueous 10% NaCl, dried over sodium sulfate, and evaporated to dryness to yield 19.27 g of the title compound as yellow solid of mp. 103–104° C.

MS: 207 (M$^+$).

B] (4-Methylamino-2-trifluoromethyl-phenoxy)-acetic acid ethyl ester

Analogously to example 5B] to 5F], 4-nitro-2-trifluoromethyl-phenol and ethyl bromoacetate were transformed to (4-methylamino-2-trifluoromethyl-phenoxy)-acetic acid ethyl ester containing some (4-methylamino-2-trifluoromethyl-phenoxy)-acetic acid methyl ester as light yellow waxy solid.

MS: 278 (M+H$^+$) and 264 (M+H$^+$).

C] [rac]-(4-{Methyl-[2-methyl-6-(4-trifluoromethyl-phenyl)-pyridin-3-ylmethyl]-amino}-2-trifluoromethyl-phenoxy)-acetic acid ethyl ester To 0.080 g (0.29 mmol) of the above prepared (4-methylamino-2-trifluoromethyl-phenoxy)-acetic acid ethyl ester and 0.124 g (0.43 mmol) of 3-chloromethyl-2-methyl-6-(4-trifluoromethyl-phenyl)-pyridine (see example 1N], dissolved in 1.0 ml of abs. DMSO, were added successively 0.048 g (0.32 mmol) of NaI and 0.066 g (0.43 mmol) of DBU. The reaction was allowed to proceed for 4 h at ambient temperature, when TLC still indicated some starting amine. Therefore, another 33 mg (0.4 eq.) of 3-chloromethyl-2-methyl-6-(4-trifluoromethyl-phenyl)-pyridine was added and stirring continued for 3 h. Pouring onto crashed ice, extraction with AcOEt, filtration over Celite, washing of the organic layer with water, drying over sodium sulfate, and evaporation of the solvents, followed by flash chromatography (SiO$_2$, hexane/AcOEt=8/2), afforded 0.046 g of the title compound as colorless oil.

MS: 527.5 (M+H)$^+$.

D] [rac]-(4-{Methyl-[2-methyl-6-(4-trifluoromethyl-phenyl)-pyridin-3-ylmethyl]-amino}-2-trifluoromethyl-phenoxy)-acetic acid 0.046 g (0.087 mmol) of the above prepared [rac]-(4-{methyl-[2-methyl-6-(4-trifluoromethyl-phenyl)-pyridin-3-ylmethyl]-amino}-2-trifluoromethyl-phenoxy)-acetic acid ethyl ester was dissolved in 0.52 ml of THF/EtOH=1/1, treated with 0.26 ml (3 eq.) of 1N NaOH and kept at ambient temperature for 3.5 h. The reaction mixture was then poured onto crashed ice/AcOEt/HCl dil., the organic layer was washed with water, dried over sodium sulfate, and evaporated to dryness to leave, after recrystallisation from AcOEt/hexane, 0.039 g of the title compound as off-white solid.

MS: 497.0 (M–H)$^-$.

Example 7

(2,6-Dimethyl-4-{methyl-[2-methyl-6-(4-trifluoromethyl-phenyl)-pyridin-3-ylmethyl]-amino}-phenoxy)-acetic acid A] The title compound was prepared in analogy to example 6, but using in step C](2,6-dimethyl-4-methylamino-phenoxy)-acetic acid ethyl ester (described in U.S. Pat. No. 5,905,068) instead of (4-methylamino-2-trifluoromethyl-phenoxy)-acetic acid ethyl ester, as brownish crystals of mp. 137–138° C.

MS: 459.6 (M+H)$^+$.

Example 8

2-Methyl-2-{2-methyl-4-[2-methyl-6-(3-trifluoromethyl-phenyl)-pyridin-3-ylmethoxy]-phenoxy}-propionic acid A] 2-Methyl-2-{2-methyl-4-[2-methyl-6-(3-trifluoromethyl-phenyl)-pyridin-3-ylmethoxy]-phenoxy}-propionic acid ethyl ester To 0.150 g (0.629 mmol) of 2-(4-hydroxy-2-methyl-phenoxy)-2-methyl-propionic acid ethyl ester (described in WO 02/092590) and 0.180 g (0.629 mmol) of the above prepared (example 2A]) 3-chloromethyl-2-methyl-6-(3-trifluoromethyl-phenyl)-pyridine, dissolved in 5.4 ml of abs. acetonitrile, was added 0.226 g of Cs$_2$CO$_3$ (0.692 mmol). The reaction was stirred for 3.5 h at ambient temperature. Pouring onto crashed ice, twofold extraction with AcOEt, washing with water, drying over sodium sulfate, and evaporation of the solvents, followed by flash chromatography (SiO$_2$, hexane/AcOEt=85/15) yielded 0.248 g of pure title compound as colorless oil.

MS: 488.4 (M+H)$^+$.

B] 2-Methyl-2-{2-methyl-4-[2-methyl-6-(3-trifluoromethyl-phenyl)-pyridin-3-ylmethoxy]-phenoxypropionic acid 0.248 g (0.509 mmol) of the above prepared 2-methyl-2-{2-methyl-4-[2-methyl-6-(3-trifluoromethyl-phenyl)-pyridin-3-ylmethoxy]-phenoxy}-propionic acid ethyl ester was dissolved in 5.0 ml of THF/EtOH=1/1, treated with 1.50 ml (3 eq.) of 1N NaOH and kept at ambient temperature for 20 h. The reaction mixture was then poured onto crashed ice/AcOEt/HCl dil. to bring the pH to 7, the organic layer was washed with water, dried over sodium sulfate, and evaporated to dryness to leave, after recrystallisation from AcOEt/hexane, 0.224 g of the title compound as white crystals of mp. 105–107° C.

MS: 458.2 (M−H)⁻.

Example 9

2-Methyl-2-{2-methyl-4-[6-(4-trifluoromethyl-phenyl)-pyridin-3-ylmethoxy]-phenoxy}-propionic acid A] The title compound was prepared in analogy to example 8, but using in step A] 5-chloromethyl-2-(4-trifluoromethyl-phenyl)-pyridine instead of 3-chloromethyl-2-methyl-6-(3-trifluoromethyl-phenyl)-pyridine, as white solid of mp. 149–151° C.

MS: 444.1 (M−H)⁻.

B] 5-Chloromethyl-2-(4-trifluoromethyl-phenyl)-pyridine

This reagent, necessary in step A], was prepared in analogy to example 1N] from [6-(4-trifluoromethyl-phenyl)-pyridin-3-yl]-methanol (described in WO 01/060805) as white solid of mp. 73° C.

MS: 272.1, 274.1 (M+H)⁺.

Example 10

2-Methyl-2-{2-methyl-4-[6-(4-trifluoromethoxy-phenyl)-pyridin-3-ylmethoxy]-phenoxy}-propionic acid A] The title compound was prepared in analogy to example 8, but using in step A] 5-chloromethyl-2-(4-trifluoromethoxy-phenyl)-pyridine instead of 3-chloromethyl-2-methyl-6-(3-trifluoromethyl-phenyl)-pyridine, as white solid of mp. 146–148° C.

MS: 460.2 (M−H)⁻.

The reagent, necessary in step A], was prepared as follows:

B] [6-(4-Trifluoromethoxy-phenyl)-pyridin-3-yl]-methanol 2.00 g (7.48 mmol) of commercially available 6-(4-trifluoromethoxy-phenyl)-pyridine-3-carbaldehyde was dissolved in 37 ml of EtOH and treated at 0° C. with 0.283 g (7.48 mmol) of NaBH$_4$. After 10 Min. the cooling bath was removed and stirring continued at ambient temperature. Pouring onto crashed ice, twofold extraction with AcOEt, washing with water, drying over sodium sulfate, and evaporation of the solvents afforded 2.08 g of pure title compound as off-white solid of mp. 57–58° C.

MS: 269.1 (M)⁺.

C] 5-Chloromethyl-2-(4-trifluoromethoxy-phenyl)-pyridine 0.400 g (1.49 mmol) of the above prepared [6-(4-trifluoromethoxy-phenyl)-pyridin-3-yl]-methanol was dissolved in 7.2 ml of CH$_2$Cl$_2$ and treated dropwise at 0° C. with 0.22 ml (2 eq.) of SOCl$_2$. The reaction mixture was kept at 0° C. for 5 Min. and at RT for 30 Min. Pouring onto crashed ice/NaHCO$_3$, twofold extraction with AcOEt, washing with water, drying over sodium sulfate, and evaporation of the solvents produced 0.419 g of pure title compound as off-white solid of mp. 34–36° C.

MS: 288.1, 290.1 (M+H)⁺.

Example 11

[rac]-[2-Methyl-4-(methyl-{1-[2-methyl-6-(3-trifluoromethyl-phenyl)-pyridin-3-yl]-propyl}-amino)-phenoxy]-acetic acid A] The title compound was prepared in analogy to example 5, but using in step C] [rac]-3-(1-chloro-propyl)-2-methyl-6-(3-trifluoromethyl-phenyl)-pyridine instead of [rac]-3-(1-chloro-butyl)-2-methyl-6-(3-trifluoromethyl-phenyl)-pyridine, as yellow solid.

MS: 471.1 (M−H)⁻.

The necessary intermediate

B] [rac -3-(1-Chloro-propyl)-2-methyl-6-(3-trifluoromethyl-phenyl)-pyridine

Was prepared as described in example 4A]-B], but using ethyl magnesium chloride instead of propyl magnesium chloride, as yellowish oil.

MS: 314.11, 316.2 (M+H)⁺.

Example 12

(4-{[6-(4-Chloro-phenyl)-pyridin-3-ylmethyl]-methyl-amino}-2-methyl-phenoxy)-acetic acid A] The title compound was prepared in analogy to example 4, but using in step C] (2-methyl-4-methylaminophenoxy)-acetic acid ethyl ester (prepared in analogy to example 5F])instead of [2-(3-methoxy-propyl)-phenoxy]-acetic acid ethyl ester and 5-chloromethyl-2-(4-chloro-phenyl)-pyridine instead of [rac]-3-(1-chloro-butyl)-2-methyl-6-(3-trifluoromethyl-phenyl)-pyridine, as off-white crystals of mp. 174–76° C.

MS: 397.2, 399.4 (M+H)⁺.

The necessary intermediate

B] 5-Chloromethyl-2-(4-chloro-phenyl)-pyridine

Was prepared in analogy to example 1N] from [6-(4-chloro-phenyl)-pyridin-3-yl]-methanol as light brown solid.

MS: 237.1, 239.1, 241.1 (M)⁺.

Example 13

(2-Methyl-4-{methyl-[6-(4-trifluoromethoxy-phenyl)-pyridin-3-ylmethyl]-amino}-phenoxy)-acetic acid A] The title compound was prepared in analogy to example 12, but using in step C] 5-chloromethyl-2-(4-trifluoromethoxy-phenyl)-pyridine (example 10C])instead of 5-chloromethyl-2-(4-chloro-phenyl)-pyridin, as off-white solid of mp. 137–138° C.

MS: 445.2 (M–H)$^-$.

Example 14

(2-(3-Methoxy-propyl)-4-{methyl-[6-(4-trifluoromethoxy-phenyl)-pyridin-3-ylmethyl]-amino}-phenoxy)-acetic acid A] The title compound was prepared in analogy to example 13, but using in step C] [2-(3-methoxy-propyl)-4-methylamino-phenoxy]-acetic acid ethyl ester (example 1H]) instead of (2-methyl-4-methylamino-phenoxy)-acetic acid ethyl ester, as light brown solid of mp. 73–75° C.

MS: 505.5 (M+H)$^+$.

Example 15

(2-Methyl-4-{methyl-[6-(4-trifluoromethyl-phenyl)-pyridin-3-ylmethyl]-amino}-phenoxy)-acetic acid A] The title compound was prepared in analogy to example 13, but using in step C] 5-chloromethyl-2-(4-trifluoromethyl-phenyl)-pyridine instead of 5-chloromethyl-2-(4-trifluoromethoxy-phenyl)-pyridine, as off-white solid of mp. 199° C.

MS: 431.3 (M+H)$^+$.

The necessary intermediate

B] 5-Chloromethyl-2-(4-trifluoromethyl-phenyl)-pyridine was prepared in analogy to example 10C] as white solid of mp. 73° C.

MS: 272.1, 274.1 (M+H)$^+$.

Example 16

(2-(3-Methoxy-propyl)-4-{methyl-[6-(4-trifluoromethyl-phenyl)-pyridin-3-ylmethyl]-amino}-phenoxy)-acetic acid The title compound was prepared in analogy to example 15, but using in step C] [2-(3-methoxy-propyl)-4-methylamino-phenoxy]-acetic acid ethyl ester instead of (2-methyl-4-methylamino-phenoxy)-acetic acid methyl ester, as light brown solid of mp. 72–76° C.

MS: 487.2 (M–H)$^-$.

Example 17

[rac]-(2-Methyl-4-{1-[2-methyl-6-(4-trifluoromethyl-phenyl)-pyridin-3-yl]-ethylsulfanyl}-phenoxy)-acetic acid A] (2-Methyl-4-{1-[2-methyl-6-(4-trifluoromethyl-phenyl)-pyridin-3-yl]-ethylsulfanyl}-phenoxy)-acetic acid tert-butyl ester 0.224 g (0.75 mmol) of [rac]-3-(1-chloro-ethyl)-2-methyl-6-(4-trifluoromethyl-phenyl)-pyridine and 0.222 g (0.75 mmol) of (4-acetylsulfanyl-2-methyl-phenoxy)-acetic acid tert-butyl ester (prepared by standard acetylation of (4-mercapto-2-methyl-phenoxy)-acetic acid tert-butyl ester, described below in example 28A]-C]) were dissolved in 3.9 ml of acetonitrile and 0.2 ml of MeOH and treated with 0.292 g (1.2 eq.) of $Cs_2CO_3$. The reaction was then allowed to proceed over night. Pouring onto crashed ice, twofold extraction with AcOEt, washing with water, drying over sodium sulfate, and evaporation of the solvents, followed by flash chromatography ($SiO_2$, hexane/AcOEt=9/1), afforded in the less polar fractions 0.210 g of pure title compound and in the more polar fractions 0.112 g of the corresponding methyl ester as waxy solid.

B] [rac]-(2-Methyl-4-{1-[2-methyl-6-(4-trifluoromethyl-phenyl)-pyridin-3-yl]-ethylsulfanyl}-phenoxy)-acetic acid 0.322 g (0.62 mmol) of the above prepared (2-methyl-4-{1-[2-methyl-6-(4-trifluoromethyl-phenyl)-pyridin-3-yl]-ethylsulfanyl}-phenoxy)-acetic acid tert-butyl ester, containing some methyl ester, was dissolved in 3.8 ml of THF/EtOH=1/1, treated with 1.87 ml (3 eq.) of 1N NaOH, and kept at ambient temperature for 2 h. The reaction mixture was then poured onto crashed ice/HCl dil., extracted twice with AcOEt, washed with water, dried over sodium sulfate, and evaporated to dryness to leave, after crystallization from AcOEt/hexane, 0.276 g of the title compound as off-white solid of mp. 115–117° C.

MS: 460.3 (M–H)$^-$.

The necessary reagent

C] [rac]-3-(1-Chloro-ethyl)-2-methyl-6-(4-trifluoromethyl-phenyl)-pyridine

Was prepared in analogy to example 3A]-C], but starting the whole reaction sequence with 4-(trifluoromethyl) acetophenone instead of 3-(trifluoromethyl) acetophenone), as colorless oil.

MS: 299.1, 301.1 (M)$^+$.

Example 18

[rac]-(2-Methyl-4-{1-[2-methyl-6-(4-trifluoromethyl-phenyl)-pyridin-3-yl]-propylsulfanyl}-phenoxy)-acetic acid A] The title compound was prepared in analogy to example 17, but using [rac]-3-(1-chloro-propyl)-2-methyl-6-(4-trifluoromethyl-phenyl)-pyridine instead of [rac]-3-(1-chloro-ethyl)-2-methyl-6-(4-trifluoromethyl-phenyl)-pyridine, as off-white solid of mp. 126–128° C.

MS: 474.1 (M–H)$^-$.

The necessary reagent

B] [rac]-3-(1-Chloro-propyl)-2-methyl-6-(4-trifluoromethyl-phenyl)-pyridine was prepared in analogy to example 17C], but using for the Grignard-reaction ethyl magnesium chloride instead of the methyl derivative, as colorless oil.

MS: 314.2, 316.2 (M+H)$^+$.

Example 19

[rac]-(2-Methyl-4-{1-[2-methyl-6-(3-trifluoromethyl-phenyl)-pyridin-3-yl]-ethylsulfanyl}-phenoxy)-acetic acid A] The title compound was prepared in analogy to example 17, but using [rac]-3-(1-chloro-ethyl)-2-methyl-6-(3-trifluoromethyl-phenyl)-pyridine (example 3C]) instead of [rac]-3-(1-chloro-ethyl)-2-methyl-6-(4-trifluoromethyl-phenyl)-pyridine, as colorless foam.

MS: 460.3 (M−H)$^-$.

Example 20

[rac]-(2-Methyl-4-{1-[2-methyl-6-(4-trifluoromethyl-phenyl)-pyridin-3-yl]-ethoxy}-phenylsulfanyl)-acetic acid A] [rac[-(2-Methyl-4-{1-[2-methyl-6-(4-trifluoromethyl-phenyl)-pyridin-3-yl]-ethoxy]-phenylsulfanyl)-acetic acid tert-butyl ester To 0.118 g (0.39 mmol) of the above prepared [rac]-3-(1-chloro-ethyl)-2-methyl-6-(4-trifluoromethyl-phenyl)-pyridine (example 17C]) and 0.100 g (0.39 mmol) of (4-hydroxy-2-methyl-phenylsulfanyl)-acetic acid tert-butyl ester (see below example 20C]), dissolved in 2.0 ml of abs. acetone, were added successively 0.065 g (0.39 mmol) of KI and 0.154 g (0.47 mmol) of Cs$_2$CO$_3$. The reaction was allowed to proceed for 2 h at ambient temperature, when TLC still indicated large amounts of starting material. Therefore, stirring was continued over night at 40° C. Pouring onto crashed ice, extraction with AcOEt, filtration over Celite, washing of the organic layer with water, drying over sodium sulfate, and evaporation of the solvents, followed by flash chromatography (SiO$_2$, hexane/AcOEt=9/1), produced 0.143 g of the title compound as colorless oil.

MS: 518.4 (M+H)$^+$.

B] [rac]-(2-Methyl-4-{1-[2-methyl-6-(4-trifluoromethyl-phenyl)-pyridin-3-yl]-ethoxy}-phenylsulfanyl)-acetic acid 0.143 g (0.28 mmol) of the above prepared [rac]-(2-methyl-4-{1-[2-methyl-6-(4-trifluoromethyl-phenyl)-pyridin-3-yl]-ethoxy}-phenylsulfanyl)-acetic acid tert-butyl ester was dissolved in 2.75 ml of THF/EtOH=1/1, treated with 1.38 ml (3 eq.) of 1N NaOH and kept at ambient temperature for 5 h. The reaction mixture was then poured onto crashed ice/AcOEt/HCl dil., the organic layer was washed with water, dried over sodium sulfate, and evaporated to dryness to leave, since recrystallisation from AcOEt/hexane failed, 0.095 g of the title compound as colorless foam.

MS: 460.1 (M−H)$^-$.

The necessary reagent used in 20A] was prepared as follows:

C] (4-Hydroxy-2-methyl-phenylsulfanyl)-acetic acid tert-butyl ester

A solution of 10 g (71 mmol) of 4-mercapto-3-methyl-phenol (DE 2101359) and 10.5 ml (1 eq., 71 mmol) of bromo-acetic acid tert-butyl ester in 250 ml of THF was treated at room temperature with 12.2 ml (1 eq., 71 mmol) of N-ethyldiisopropylamine. The suspension was heated at reflux for 1 h, cooled to ambient temperature, and treated with water. The reaction mixture was then poured onto 0.1 M HCl/AcOEt, the organic layer was separated, washed with water and brine, dried over magnesium sulfate, and evaporated to dryness. Purification by flash chromatography (SiO$_2$, heptane/toluene/AcOEt=10/1/1) afforded finally 5.6 g of the title product as white solid.

MS: 253 (M−H)$^-$.

Example 21

[rac]-(2-Methyl-4-{1-[2-methyl-6-(4-trifluoromethyl-phenyl)-pyridin-3-yl]-butoxy}-phenylsulfanyl)-acetic acid A] The title compound was prepared in analogy to example 20, but using [rac]-3-(1-chloro-butyl)-2-methyl-6-(4-trifluoromethyl-phenyl)-pyridine instead of [rac]-3-(1-chloro-ethyl)-2-methyl-6-(3-trifluoromethyl-phenyl)-pyridine, as colorless foam.

MS: 488.1 (M−H)$^-$.

The necessary reagent

B] [rac -3-(1-chloro-butyl)-2-methyl-6-(4-trifluoromethyl-phenyl)-pyridine

Was prepared in analogy to example 17C], but using for the Grignard-reaction propyl magnesium chloride instead of the methyl derivative, as colorless oil.

MS: 328.2, 330.3 (M+H)$^+$.

Example 22

[rac]-(2-Methyl-4-{1-[2-methyl-6-(4-trifluoromethyl-phenyl)-pyridin-3-yl]-butylsulfanyl}-phenoxy)-acetic acid A] The title compound was prepared in analogy to example 17, but using in step A] [rac]-3-(1-chloro-butyl)-2-methyl-6-(4-trifluoromethyl-phenyl)-pyridine (example 21B]) instead of [rac]-3-(1-chloro-ethyl)-2-methyl-6-(4-trifluoromethyl-phenyl)-pyridine, as colorless foam.

MS: 488.0 (M−H)$^-$.

Example 23

[rac]-(4-{Cyclopentyl-[2-methyl-6-(4-trifluoromethyl-phenyl)-pyridin-3-yl]-methylsulfanyl}-2-methyl-phenoxy)-acetic acid A] The title compound was prepared in analogy to example 17, but using in step A] [rac]-3-(chloro-cyclopentyl-methyl)-2-methyl-6-(4-trifluoromethyl-phenyl)-pyridine instead of [rac]-3-(1-chloro-ethyl)-2-methyl-6-(4-trifluoromethyl-phenyl)-pyridine, as colorless foam.

MS: 514.2 (M–H)⁻.

Example 24

2-{4-[6-(4-Fluoro-3-trifluoromethyl-phenyl)-2-methyl-pyridin-3-ylmethoxy]-2-methyl-phenoxy}-2-methyl-propionic acid A] The title compound was prepared in analogy to example 8, but using in step A] 3-chloromethyl-6-(4-fluoro-3-trifluoromethyl-phenyl)-2-methyl-pyridine instead of 3-chloromethyl-2-methyl-6-(3-trifluoromethyl-phenyl)-pyridine, as white crystals of mp. 141–143° C.

MS: 476.1 (M–H)⁻.

The necessary reagent

B] 3-Chloromethyl-6-(4-fluoro-3-trifluoromethyl-phenyl)-2-methyl-pyridine was prepared in analogy to example 1K]-N], but starting the whole reaction sequence with 1-(4-fluoro-3-trifluoromethyl-phenyl)-ethanone instead of 4-(trifluoromethyl) acetophenone, as off-white solid.

MS: 303.1, 305.1 (M)⁺.

Example 25

[rac]-2-Methyl-2-(2-methyl-4-}1-[2-methyl-6-(3-trifluoromethyl-phenyl)-pyridin-3-yl]-ethoxy}-phenoxy)-propionic acid A] The title compound was prepared in analogy to example 8, but using in step A] [rac]-3-(1-chloro-ethyl)-2-methyl-6-(3-trifluoromethyl-phenyl)-pyridine (example 3C]) instead of 3-chloromethyl-2-methyl-6-(3-trifluoromethyl-phenyl)-pyridine, as white solid.

MS: 472.1 (M–H)⁻.

Example 26

2-Methyl-2-[3-(methyl-{2-[2-methyl-6-(4-trifluoromethyl-phenyl)-pyridin-3-yl]-acetyl}-amino)-phenoxy]-propionic acid A] 2-Methyl-2-(3-methylamino-phenoxy)-propionic acid ethyl ester In analogy to the procedures described in example 5D], 5E] and 5F], 2-(3-amino-phenoxy)-2-methyl-propionic acid ethyl ester [PCT Int. Appl. WO 2003/063794 A2] was converted into the corresponding tert-butoxycarbonylamino derivative, methylated at N and deprotected again to yield the title compound as light yellow oil.

MS: 238.1 (M+H)⁺; 224.1 [(M+H)⁺of the corresponding methyl ester present as impurity].

B] 2-Methyl-2-[3-(methyl-{2-[2-methyl-6-(4-trifluoromethyl-phenyl)-pyridin-3-yl]-acetyl}-amino)-phenoxy]-propionic acid ethyl ester 0.24 g (1.00 mmol) of the above prepared 2-methyl-2-(3-methylamino-phenoxy)-propionic acid ethyl ester and 0.31 g (1.05 mmol) of [2-methyl-6-(4-trifluoromethyl-phenyl)-pyridin-3-yl]-acetic acid (example 26E]) were dissolved in 15 ml of CH₂Cl₂. This solution was cooled down to 0° C. and then 0.24 g (1.20 mmol) of N-(3-dimethylamino-propyl)-N'-ethyl-carbodiimide-hydrochloride and 0.19 g (1.50 mmol) of N,N-dimethylaminopyridine were added and the reaction stirred for 20 hours at ambient temperature. It was subsequently poured into crashed ice/HCl and extracted two fold with CH₂Cl₂; the organic layers were washed with water, dried over magnesium sulfate, filtered and evaporated. The crude product was purified by chromatography (SiO₂; n-heptane/AcOEt=95:5 to 4:1) to give 0.50 g of the title compound as a light yellow oil.

MS: 515.3 (M+H)⁺.

C] 2-Methyl-2-[3-(methyl-{2-[2-methyl-6-(4-trifluoromethyl-phenyl)-pyridin-3-yl]-acetyl}-amino)-phenoxy]-propionic acid 0.50 g (0.97 mmol) of the above prepared 2-methyl-2-[3-(methyl-{2-[2-methyl-6-(4-trifluoromethyl-phenyl)-pyridin-3-yl]-acetyl}-amino)-phenoxy]-propionic acid ethyl ester was dissolved in 15 ml of THF/MeOH=2:1. To the stirred solution was added 1.16 ml of a LiOH-solution (1 molar in water). After 6 hours, the reaction mixture was poured into crashed ice/HCl and extracted twice with CH₂Cl₂; the organic layers were washed with water, dried over magnesium sulfate, filtered and evaporated to give 0.47 g of pure title compound as colorless foam.

MS: 485.3 (M–H)⁻.

The necessary building block [2-methyl-6-(4-trifluoromethyl-phenyl)-pyridin-3-yl]-acetic acid used in procedure 26B] was prepared as follows:

D] [2-Methyl-6-(4-trifluoromethyl-phenyl)-pyridin-3-yl]-acetonitrile 27.2 g (95.2 mmol) of 3-chloromethyl-2-methyl-6-(4-trifluoromethyl-phenyl)-pyridine (example 1N]) was dissolved in 100 ml of dimethyl sulfoxide; 5.9 g of sodium cyanide (120 mmol) was added and the mixture was stirred at room temperature for 18 hours. Then, the reaction mixture was poured into a mixture of ice and water and was subsequently extracted with 3 portions of 400 ml of tert-butyl methyl ether. The combined organic phases were washed with water, then with brine and dried over anhydrous sodium sulfate. After evaporation of the solvent, 25.2 g of the title compound was obtained as a pale yellow solid.

MS: 276.1 (M)⁺.

E] [2-Methyl-6-(4-trifluoromethyl-phenyl)-pyridin-3-yl]-acetic acid

A mixture of 25 g (90 mmol) of the above prepared [2-methyl-6-(4-trifluoromethyl-phenyl)-pyridin-3-yl]-acetonitrile, 20 g of sodium hydroxide (500 mmol), 60 ml of water and 250 ml of propanol was stirred vigorously at 100° C. Hydrolysis was complete after 2 hours. The reaction mixture was then evaporated to dryness and the residue was dissolved in 70 ml of water; then, 60 ml of cold 8 N aqueous HCl was added and the compound was extracted with three portions of 250 ml of ethyl acetate; the combined organic phases were washed with water and brine, dried over anhydrous sodium sulfate and evaporated to dryness to yield 25.1 g of the title product as pale yellow solid.

MS: 296.0 (M+H)⁺.

Example 27

(4-{[4-Cyclopropyl-2-(4-trifluoromethyl-phenyl)-pyrimidin-5-ylmethyl]-methyl-amino}-2-methyl-phenoxy)-acetic acid

A] (4-{[4-Cyclopropyl-2-(4-trifluoromethyl-phenyl)-pyrimidin-5-ylmethyl]-methyl-amino}-2-methyl-phenoxy)-acetic acid methyl ester To a solution of 400 mg (1.28 mmol) 5-chloromethyl-4-cyclopropyl-2-(4-trifluoromethyl-phenyl)-pyrimidine (example 27F]) and 268 mg (1.28 mmol) of (2-methyl-4-methylamino-phenoxy)-acetic acid methyl ester (example 5F]) in 8 ml of DMSO was added 194 mg (1.41 mmol) potassium carbonate and 192 mg (1.28 mmol) sodium iodide. The reaction mixture was stirred for 20 min at RT. It was then taken up in ether and washed with aqueous 10% $KHSO_4$-solution (10%) and water. The crude product was purified by chromatography over silica gel with AcOEt/heptane 1:3, to give 403 mg of pure (4-{[4-cyclopropyl-2-(4-trifluoromethyl-phenyl)-pyrimidin-5-ylmethyl]-methyl-amino}-2-methyl-phenoxy)-acetic acid methyl ester.

MS: 486.4 $(M+H)^+$.

B] (4-{[4-Cyclopropyl-2-(4-trifluoromethyl-phenyl)-pyrimidin-5-ylmethyl]-methyl-amino}-2-methyl-phenoxy)-acetic acid A solution of 351 mg (0.72 mmol) (4-{[4-cyclopropyl-2-(4-trifluoromethyl-phenyl)-pyrimidin-5-ylmethyl]-methyl-amino}-2-methyl-phenoxy)-acetic acid methyl ester and 1.45 ml 1N LiOH in 4 ml of THF was stirred for 3 h at RT. The reaction mixture was taken up in ether and washed with 1N HCl and water. The crude product was suspended in AcOEt/heptane 1:19 to give 95.64 mg of pure (4-{[4-cyclopropyl-2-(4-trifluoromethyl-phenyl)-pyrimidin-5-ylmethyl]-methyl-amino}-2-methyl-phenoxy)-acetic acid.

MS: 472.3 $(M+H)^+$.

5-Chloromethyl-4-cyclopropyl-2-(4-trifluoromethyl-phenyl)-pyrimidine used in 27A] was synthesized as follows:

C] (E,Z)-2-Cyclopropanecarbonyl-3-ethoxy-acrylic acid methyl ester

A solution of 10 g (70.34 mmol) 3-cyclopropyl-3-oxo-propionic acid methyl ester, 23.4 ml (140.68 mmol) of triethyl orthoformate in 100 ml acetic anhydride was refluxed at 150° C. for 5 h. The reaction mixture was concentrated at 95° C. under reduced pressure to give 14.35 g of crude (E,Z)-2-cyclopropanecarbonyl-3-ethoxy-acrylic acid methyl ester.

MS: 199.3 $(M+H)^+$.

D] 4-Cyclopropyl-2-(4-trifluoromethyl-phenyl)-pyrimidine-5-carboxylic acid ethyl ester To a solution of 4.74 g (18.19 mmol) 4-trifluoromethyl-benzamidine HCl in 50 ml of ethanol was added 1.818 g (18.186 mmol) of sodium tert-butoxide. After 2 min, 3.605 g of crude (E,Z)-2-cyclopropanecarbonyl-3-ethoxy-acrylic acid methyl ester was added and the reaction mixture was then stirred over night at RT. The ethanol was removed under reduced pressure, the residue taken up in ether and washed with 1N HCl and water. The ether solution was concentrated under reduced pressure and the crude product purified by chromatography over silica gel with AcOEt/heptane 1:3 to give 4.25 g of pure 4-cyclopropyl-2-(4-trifluoromethyl-phenyl)-pyrimidine-5-carboxylic acid ethyl ester.

MS: 337.1 $(M+H)^+$

E] [4-Cyclopropyl-2-(4-trifluoromethyl-phenyl)-pyrimidin-5-yl]-methanol

Within 10 min was dropped 31.6 ml (37.9 mmol) of 1.2 M DIBALH solution in toluene to a dry ice cooled (−50° C.) solution of 4.25 g (12.64 mmol) 4-cyclopropyl-2-(4-trifluoromethyl-phenyl)-pyrimidine-5-carboxylic acid ethyl ester in 50 ml of THF. The reaction mixture was stirred 30 min at −50° C. and after letting rise the temperature to RT, the reaction was stirred for 1 h at RT. The reaction mixture was taken up in ether and washed with 1N HCL and water. The solvent was removed under reduced pressure to give 3.72 g of pure [4-cyclopropyl-2-(4-trifluoromethyl-phenyl)-pyrimidin-5-yl]-methanol.

MS: 295.1 $(M+H)^+$.

F] 5-Chloromethyl-4-cyclopropyl-2-(4-trifluoromethyl-phenyl)-pyrimidine

A mixture of 1.9 g (6.456 mmol) of [4-cyclopropyl-2-(4-trifluoromethyl-phenyl)-pyrimidin-5-yl]-methanol and 0.515 ml (7.1 mmol) thionylchloride in 20 ml dichloromethane was stirred for 1 h at RT. The reaction mixture was taken up in ether and washed with sodium bicarbonate solution and water. The ether phase was concentrated under reduced pressure to give 1.97 g of pure 5-chloromethyl-4-cyclopropyl-2-(4-trifluoromethyl-phenyl)-pyrimidine.

MS: 313.1 $(M+H)^+$.

Example 28

[rac]-(4-{1-[4-Cyclopropyl-2-(4-trifluoromethyl-phenyl)-pyrimidin-5-yl]-ethylsulfanyl}-2-methyl-phenoxy)-acetic acid

A] 4,4'-Dithio-bis-(2-methyl-phenol)

To a solution of 5 g (46.23 mmol) o-cresol and 6.15 ml (48.54 mmol) chloro-trimethyl-silane in 50 ml dichloromethane was dropped under ice cooling 6.76 ml (48.55 mmol) triethyl amine within 5 min. The reaction mixture was stirred at RT for 30 min and then it was chilled to −40° C. At this temperature was dropped 1.86 ml (23.13 mmol) di-sulfur-di-chloride to the mixture, within 10 min. The reaction was allowed to come to RT and was stirred at this temperature for 1 h. The lot was taken up in ether and washed with water. The crude product was purified by chromatography over silica gel with AcOEt/heptane 1:3 providing 4 g pure 4,4'-dithio-bis-(2-methyl-phenol).

MS: 277.3 $(M-H)^-$.

B] [4-(4-tert-Butoxycarbonylmethoxy-3-methyl-phenyldisulfanyl)-2-methyl-phenoxy]-acetic acid tert-butyl ester To an ice cooled solution of 4.75 g (17.06 mmol) 4,4'-dithio-bis-(2-methyl-phenol) and 5.55 ml (37.6 mmol) bromo-acetic acid tert-butyl ester in 50 ml DMF was added 204 mg (85.3 mmol) sodium hydride (55% in oil). The reaction mixture was stirred over night at RT and then it was taken up in ether, washed with 1N HCl and water. The crude product was purified by chromatography over silica gel with AcOEt/heptane 1:4 providing 3.4 g pure [4-(4-tert-butoxy-carbonylmethoxy-3-methyl-phenyldisulfanyl)-2-methyl-phenoxy]-acetic acid tert-butyl ester.

MS: 524 (M+NH$_4$)$^+$.

C] (4-Mercapto-2-methyl-phenoxy)-acetic acid tert-butyl ester

To a solution of 3.3 g (6.51 mmol) [4-(4-tert-butoxycarbonylmethoxy-3-methyl-phenyldisulfanyl)-2-methyl-phenoxy]-acetic acid tert-butyl ester in 30 ml dichloromethane was added under ice cooling 4.26 g (65.1 mmol) zinc powder, 15 ml acetic acid and a few drops of HCl (25%). After a few minutes, the reaction completed. Then the solution filtered, taken up in ether and washed with water. The ether solution was concentrated under reduced pressure, providing 2.86 g of almost pure (4-mercapto-2-methyl-phenoxy)-acetic acid tert-butyl ester.

MS: 225 (M+H)$^+$.

D] [rac]-(4-{1-[4-Cyclopropyl-2-(4-trifluoromethyl-phenyl)-pyrimidin-5-yl]-ethylsulfanyl}-2-methyl-phenoxy)-acetic acid tert-butyl ester To a solution of 180 mg (0.551 mmol) [rac]-5-(1-chloro-ethyl)-4-cyclopropyl-2-(4-trifluoromethyl-phenyl)-pyrimidine (example 28H]) and 140 mg (0.551 mmol) (4-mercapto-2-methyl-phenoxy)-acetic acid tert-butyl ester in 3 ml DMF was added 315 mg (0.66 mmol) cesium carbonate. The reaction mixture was stirred for 3 h at RT and then partitioned between ether, 1N HCl and water. The crude product was purified by chromatography over silica gel with AcOEt/Heptan 1:9 to give 150 mg of pure [rac]-(4-{1-[4-cyclopropyl-2-(4-trifluoromethyl-phenyl)-pyrimidin-5-yl]-ethylsulfanyl}-2-methyl-phenoxy)-acetic acid tert-butyl ester.

MS: 544.64 (M+H)$^+$.

E] [rac]-(4-{1-[4-Cyclopropyl-2-(4-trifluoromethyl-phenyl)-pyrimidin-5-yl]-ethylsulfanyl}-2-methyl-phenoxy)-acetic acid To a solution of 146 mg (0.268 mmol) [rac]-(4-{1-[4-cyclopropyl-2-(4-trifluoromethyl-phenyl)-pyrimidin-5-yl]-ethylsulfanyl}-2-methyl-phenoxy)-acetic acid tert-butyl ester in 2 ml dichloromethane was added 0.5 ml trifluoroacetic acid. The reaction mixture was stirred for 4 h and then the trifluoroacetic acid was removed under reduced pressure. The crude product was suspended in AcOEt/heptane 1:19. The resulting crystalline product was filtered off to give 118 mg of pure [rac]-(4-{1-[4-cyclopropyl-2-(4-trifluoromethyl-phenyl)-pyrimidin-5-yl]-ethylsulfanyl}-2-methyl-phenoxy)-acetic acid.

MS: 487.2 (M–H)$^-$.

[rac]-5-(1-Chloro-ethyl)-4-cyclopropyl-2-(4-trifluoromethyl-phenyl)-pyrimidine used in 28D] was synthesized as follows:

F] 4-Cyclopropyl-2-(4-trifluoromethyl-phenyl)-pyrimidine-5-carbaldehyde

To a dry ice cooled solution of 0.86 ml (12 mmol) DMSO in 10 ml dichloromethane was added 0.68 ml (7.79 mmol) oxalylchloride. After the reaction mixture was stirred for 5 min at –70° C., 1.8 g (5.99 mmol) of [4-cyclopropyl-2-(4-trifluoromethyl-phenyl)-pyrimidin-5-yl]-methanol, dissolved in 8 ml dichloromethane, was added by dropping within 5 min. The reaction mixture was then stirred for further ten minutes at –70° C. and after 4.17 ml (30 mmol) triethylamine was added, the reaction mixture was allowed to come to RT and it was stirred for 1 h at RT. The mixture was taken up in ether and washed with 1N HCl and water. The ether phase was concentrated under reduced pressure to give 1.75 g of pure 4-cyclopropyl-2-(4-trifluoromethyl-phenyl)-pyrimidine-5-carbaldehyde.

MS: 264.1 (M–CO)

G] [rac]-1-[4-Cyclopropyl-2-(4-trifluoromethyl-phenyl)-pyrimidin-5-yl]-ethanol To a dry ice chilled solution of 0.75 g (2.57 mmol) 4-cyclopropyl-2-(4-trifluoromethyl-phenyl)-pyrimidine-5-carbaldehyde in 5 ml THF was dropped a solution of 1.11 ml (3.33 mmol) 3M methylmagnesium bromide in 2.5 ml THF. The reaction mixture was allowed to warm to RT and it was stirred for 15 min at this temperature. The reaction mixture was then taken up in ether and washed with 1N HCl and water. The crude product was purified by chromatography over silica gel with AcOEt/dichloromethane 1:6, to give 384 mg of pure [rac]-1-[4-cyclopropyl-2-(4-trifluoromethyl-phenyl)-pyrimidin-5-yl]-ethanol.

MS: 309.1 (M+H)$^+$.

H] [rac]-5-(1-Chloro-ethyl)-4-cyclopropyl-2-(4-trifluoromethyl-phenyl)-pyrimidine A solution of 357 mg (1.16 mmol) [rac]-1-[4-cyclopropyl-2-(4-trifluoromethyl-phenyl)-pyrimidin-5-yl]-ethanol and 0.09 ml (1.22 mmol) thionylchloride in 4 ml dichloromethane were stirred for 1 h at RT. The reaction mixture was concentrated under reduced pressure to provide 390 mg of pure [rac]-5-(1-chloro-ethyl)-4-cyclopropyl-2-(4-trifluoromethyl-phenyl)-pyrimidine.

MS: 327.4 (M+H)$^+$.

Example 29

[rac]-(4-{1-[4-Cyclopropyl-2-(4-trifluoromethyl-phenyl)-pyrimidin-5-yl]-ethoxy}-2-methyl-phenoxy)-acetic acid

A] [rac]-(4-{1-[4-Cyclopropyl-2-(4-trifluoromethyl-phenyl)-pyrimidin-5-yl]-ethoxy}-2-methyl-phenoxy)-acetic acid ethyl ester 180 mg (0.551 mmol) of [rac]-5-(1-chloro-ethyl)-4-cyclopropyl-2-(4-trifluoromethyl-phenyl)-pyrimidine (example 28H), 116 mg (0.551 mmol) of (4-hydroxy-2-methyl-phenoxy)-acetic acid ethyl ester (WO02092590) and 31 mg (0.71 mmol) sodium hydride (55% in oil) were stirred in 3 ml DMF over night. The reaction mixture was partitioned between ether and water. The crude product was purified by chromatography over silica gel with AcOEt/heptane 1:4 to give 157 mg of pure [rac]-(4-{1-[4-cyclopropyl-2-(4-trifluoromethyl-phenyl)-pyrimidin-5-yl]-ethoxy}-2-methyl-phenoxy)-acetic acid ethyl ester.

MS: 501.4 (M+H)$^+$.

B] [rac]-(4-{1-[4-Cyclopropyl-2-(4-trifluoromethyl-phenyl)-pyrimidin-5-yl]-ethoxy}-2-methyl-phenoxy)-acetic acid 154 mg (0.307 mmol) of [rac]-(4-{1-[4-cyclopropyl-2-(4-trifluoromethyl-phenyl)-pyrimidin-5-yl]-ethoxy}-2-methyl-phenoxy)-acetic acid ethyl ester and 0.62 ml 1N LiOH in 1.6 ml THF were stirred for 2 h at RT. The reaction mixture was taken up in ether and washed with 1N HCl and water. The crude product was suspended in AcOEt/heptane 1:19 and the resulting crystals were filtered off to give 125 mg of pure [rac]-(4-{1-[4-cyclopropyl-2-(4-trifluoromethyl-phenyl)-pyrimidin-5-yl]-ethoxy}-2-methyl-phenoxy)-acetic acid.

MS: 471.1 (M−H)$^−$.

Example 30

[rac]-(4-{1-[4-Cyclopropyl-2-(4-trifluoromethyl-phenyl)-pyrimidin-5-yl]-butylsulfanyl}-2-methyl-phenoxy)-acetic acid A] [rac]-(4-{1-[4-Cyclopropyl-2-(4-trifluoromethyl-phenyl)-pyrimidin-5-yl]-butylsulfanyl}-2-methyl-phenoxy)-acetic acid tert-butyl ester 231 mg (0.7 mmol) cesium carbonate was added to a solution of 210 mg (0.59 mmol) [rac]-5-(1-chloro-butyl)-4-cyclopropyl-2-(4-trifluoromethyl-phenyl)-pyrimidine (example 30D]) and 151 mg (0.59 mmol) (4-mercapto-2-methyl-phenoxy)-acetic acid tert-butyl ester (example 28C]) in 3 ml DMF. After stirring for 3 h at RT, the reaction mixture was taken up in ether and washed with 1N HCl and water. The crude product was purified by chromatography over silica gel with AcOEt/heptane 1:9 providing 257 mg of pure [rac]-(4-{1-[4-cyclopropyl-2-(4-trifluoromethyl-phenyl)-pyrimidin-5-yl]-butylsulfanyl}-2-methyl-phenoxy)-acetic acid tert-butyl ester.

MS: 573.4 (M+H)$^+$.

B] [rac]-(4-{1-[4-Cylopropyl-2-(4-trifluoromethyl-phenyl)-pyrimidin-5-yl]-butylsulfanyl}-2-methyl-phenoxy)-acetic acid A solution of 234 mg (0.44 mmol) [rac]-(4-{1-[4-cyclopropyl-2-(4-trifluoromethyl-phenyl)-pyrimidin-5-yl]-butylsulfanyl}-2-methyl-phenoxy)-acetic acid tert-butyl ester and 0.5 ml trifluoroacetic acid in 2.5 ml dichloromethane were stirred at RT for 4 h. The solution was concentrated under reduced pressure and the crude product was repeatedly concentrated in vacuo with ether until a foam of 155 mg pure [rac]-(4-{1-[4-cyclopropyl-2-(4-trifluoro-methyl-phenyl)-pyrimidin-5-yl]-butylsulfanyl}-2-methyl-phenoxy)-acetic acid resulted.

MS: 515.2 (M−H)$^−$.

[rac]-5-(1-Chloro-butyl)-4-cyclopropyl-2-(4-trifluoromethyl-phenyl)-pyrimidine used in 30A] was synthesized as follows:

C] [rac]-1-[4-Cyclopropyl-2-(4-trifluoromethyl-phenyl)-pyrimidin-5-yl]-butan-1-ol The synthesis was accomplished in the same way like 28C] and 28D], with the difference that methylmagnesium bromide was replaced by propylmagnesium bromide. [rac]-1-[4-cyclopropyl-2-(4-trifluoromethyl-phenyl)-pyrimidin-5-yl]-butan-1-ol was received.

MS: 337.0 (M+H)$^+$.

D] [rac]-5-(1-Chloro-butyl)-4-cyclopropyl-2-(4-trifluoromethyl-phenyl)-pyrimidine A solution of 392 mg (1.17 mmol) [rac]-1-[4-cyclopropyl-2-(4-trifluoromethyl-phenyl)-pyrimidin-5-yl]-butan-1-ol and 0.09 ml (1.22 mmol) thionylchloride in 4 ml dichloromethane were stirred at RT for 1 h. After concentration under reduced pressure 421 mg of pure [rac]-5-(1-chloro-butyl)-4-cyclopropyl-2-(4-trifluoromethyl-phenyl)-pyrimidine was isolated.

MS: 355.81 (M+H)$^+$.

Example 31

[rac]-(4-{1-[4-Cyclopropyl-2-(4-trifluoromethyl-phenyl)-pyrimidin-5-yl]-butoxy}-2-methyl-phenoxy)-acetic acid A] [rac]-(4-{1-[4-Cyclopropyl-2-(4-trifluoromethyl-phenyl)-pyrimidin-5-yl]-butoxy}-2-methyl-phenoxy)-acetic acid tert-butyl ester 28 mg (0.0.642 mmol) sodium hydride (55% in oil) was added to a solution of 175 mg (0.49 mmol) [rac]-5-(1-chloro-butyl)-4-cyclopropyl-2-(4-trifluoromethyl-phenyl)-pyrimidine (example 30D]) and 104 mg (0.49 mmol) (4-hydroxy-2-methyl-phenoxy)-acetic acid ethyl ester (WO02/092590) in 3 ml DMF. After stirring for 3 h at RT, the reaction mixture was taken up in ether and washed with 1N HCl and water. The crude product was purified by chromatography over silica gel with AcOEt/heptane 1:4 providing 165 mg of pure [rac]-(4-{1-[4-cyclopropyl-2-(4-trifluoromethyl-phenyl)-pyrimidin-5-yl]-butoxy}-2-methyl-phenoxy)-acetic acid tert-butyl ester.

MS: 529.0 (M+H)$^+$.

B] [rac]-(4-{1-[4-Cyclopropyl-2-(4-trifluoromethyl-phenyl)-pyrimidin-5-yl]-butoxy}-2-methyl-phenoxy)-acetic acid A solution of 150 mg (0.261 mmol) [rac]-(4-{1-[4-cyclopropyl-2-(4-trifluoromethyl-phenyl)-pyrimidin-5-yl]-butoxy}-2-methyl-phenoxy)-acetic acid tert-butyl ester and 0.52 ml 1N lithium hydroxide solution in 1.5 ml THF were stirred at RT for 2 h. The solution was partitioned between ether, 1N HCl and water and the ether layer then concentrated under reduced pressure. The crude product was repeatedly concentrated in with ether until a foam of 121 mg pure [rac]-(4-{1-[4-cyclopropyl-2-(4-trifluoromethyl-phenyl)-pyrimidin-5-yl]-butoxy}-2-methyl-phenoxy)-acetic acid was obtained.

MS: 478.49 (M−H)$^−$.

Example 32

2-{4-[4-Cyclopropyl-2-(4-trifluoromethyl-phenyl)-pyrimidin-5-ylmethoxy-2-methyl-phenoxy}-2-methyl-propionic acid A] 2-{4-[4-Cyclopropyl-2-(4-trifluoromethyl-phenyl)-pyrimidin-5-ylmethoxy]-2-methyl-phenoxy}-2-methyl-propionic acid ethyl ester In analogy to the procedure described in example 29A], 2-(4-hydroxy-2-methyl-phenoxy)-2-methyl-propionic acid ethyl ester (described in WO 02/092590) was reacted with 5-chloromethyl-4-cyclopropyl-2-(4-trifluoromethyl-phenyl)-pyrimidine (example 27F]) to give the title compound as colorless solid.

MS: 515.3 (M+H)$^+$.

B] 2-{4-[4-Cyclopropyl-2-(4-trifluoromethyl-phenyl)-pyrimidin-5-ylmethoxy]-2-methyl-phenoxy-}2-methyl-propionic acid In analogy to the procedure described in example 29B], saponification of 2-{4-[4-cyclopropyl-2-(4-trifluoromethyl-phenyl)-pyrimidin-5-ylmethoxy]-2-methyl-phenoxy}-2-methyl-propionic acid ethyl ester yielded the title compound as white crystals of mp. 191.0–192.2° C.

MS: 485.5 (M–H)$^-$.

Example 33

(2-Methyl-4-{methyl-[5-(4-trifluoromethyl-phenyl)-pyrazin-2-ylmethyl]-amino}-phenoxy)-acetic acid A] (2-Methyl-4-{methyl-[5-(4-trifluoromethyl-phenyl)-pyrazin-2-ylmethyl]-amino}-phenoxy)-acetic acid methyl ester A suspension of 53 mg (0.39 mmol) potassium carbonate and 52 mg (0.35 mmol) sodium iodide and 73 mg (0.35 mmol) (2-methyl-4-methylamino-phenoxy)-acetic acid methyl-ester (example 5F) in 2 ml of DMSO was treated with 32 mg (0.12 mmol) of 2-chloromethyl-5-(4-trifluoromethyl-phenyl)-pyrazine (example 33E]). After 1.5 h at RT, the second portion of 32 mg (0.12 mmol) of 2-chloromethyl-5-(4-trifluoromethyl-phenyl)-pyrazine was added. The third part was added after 2 h. The reaction mixture was stirred for total 19 h at RT. It was then taken up in ether and washed with aqueous 10% KHSO$_4$-solution and water. The organic phase was washed with NaCl (10%), dried (Na$_2$SO$_4$) and evaporated. Purification by flash chromatography (SiO$_2$, heptane/AcOEt=9/1) gave 126 mg of pure (2-methyl-4-{methyl-[5-(4-trifluoromethyl-phenyl)-pyrazin-2-ylmethyl]-amino}-phenoxy)-acetic acid methyl ester.

MS: 446.3 (M+H)$^+$.

B] (2-Methyl-4-{methyl-[5-(4-trifluoromethyl-phenyl)-pyrazin-2-ylmethyl]-amino}-phenoxy)-acetic acid A solution of 110 mg (0.25 mmol) (2-methyl-4-{methyl-[5-(4-trifluoromethyl-phenyl)-pyrazin-2-ylmethyl]-amino}-phenoxy)-acetic acid methyl ester in 0.75 ml of THF and 0.75 ml ethanol was treated at 0° C. with 0.74 ml 1N LiOH and stirred for 45 min at RT. The reaction was extracted with aqueous 10% KHSO$_4$/Et$_2$O (3×). The organic phase was washed with aqueous 10% NaCl, dried over Na$_2$SO$_4$ and evaporated. The product was crystallized from ether to give pure (2-methyl-4-{methyl-[5-(4-trifluoromethyl-phenyl)-pyrazin-2-ylmethyl]-amino}-phenoxy)-acetic acid.

MS: 432.4 (M+H)$^+$.

2-Chloromethyl-5-(4-trifluoromethyl-phenyl)-pyrazine used in 33A] was synthesized as follows:

C] 5-(4-Trifluoromethyl-phenyl)-pyrazine-2-carboxylic acid methyl ester

[Following a procedure of Ford, Alan; Sinn, Ekkehard; Woodward, Simon. Exploitation of differential reactivity of the carbon-chlorine bonds in 1,3-dichloroisoquinoline. Routes to new N,N-chelate ligands and 1,3-disubstituted isoquinolines. Journal of the Chemical Society, Perkin Transactions 1: Organic and Bio-Organic Chemistry (1997), (6), 927–934]

A solution of 5.18 g (30 mmol) methyl 5-chloropyrazine-2-carboxylate in 150 ml degassed DMF was treated with 3.47 g (0.1 mmol) tetrakis(triphenylphosphine)palladium and heated at 80° C. 6.27 g (33 mmol) of 4-(trifluoromethyl)benzeneboronic acid and 14 66 g (45 mmol) of cesium carbonate were added and heated for 3.5 h. The reaction was cooled to RT and extracted with H$_2$O (0° C.)/Et$_2$O (3×). The organic phases were washed with aqueous 10% NaCl, dried (NaSO$_4$) and evaporated. Purification by flash-chromatography on silica gel (heptane/AcOEt 95:5 to 2:1) gave 2.3 g (27%) of 5-(4-trifluoromethyl-phenyl)-pyrazine-2-carboxylic acid methyl ester.

MS: 283 (M+H)$^+$.

D] [5-(4-Trifluoromethyl-phenyl)-pyrazin-2-yl]-methanol 0.585 g (2.07 mmol) of the above synthesized 5-(4-trifluoromethyl-phenyl)-pyrazine-2-carboxylic acid methyl ester in 10 ml of abs. THF was cooled down to –30° C. and reacted with 5.18 ml of DIBAL-H-solution (1.2 M in toluene, 3 eq.) for 10 min. The reaction was warmed up during 2.5 h to 10° C. and stirred 1 h at RT. Careful quenching at 0° C. with saturated NaCl solution, twofold extraction with ether, washing with brine, drying over sodium sulfate, and evaporation of the solvents left a crude product which was purified by flash chromatography (SiO$_2$, heptane/AcOEt=4/1) to deliver finally 0.325 g of the title compound as yellow solid.

MS: 254.1 (M)$^+$.

E] 2-Chloromethyl-5-(4-trifluoromethyl-phenyl)-pyrazine 0.20 g (0.79 mmol) of the above prepared [5-(4-trifluoromethyl-phenyl)-pyrazin-2-yl]-methanol was dissolved in 8 ml of CH$_2$Cl$_2$ and treated dropwise at 0° C. with 0.11 ml (2 eq.) of SOCl$_2$. The reaction mixture was kept at 0° C. for 1 h, at RT for 18 h and 6 h at 30° C. Evaporation of the solvents and dissolution in ether and heptane with consecutive evaporation afforded 0.21 g of pure title compound as light brown solid.

MS: 272.1 (M, 1Cl)$^+$.

Example 34

2-Methyl-2-{2-methyl-4-[2-methyl-6-(4-trifluoromethyl-phenyl)-pyridin-3-ylmethoxy]-phenoxy}-propionic acid A] 2-Methyl-{2-2-methyl-4-[2-methyl-6-(4-trifluoromethyl-phenyl)-pyridin-3-ylmethoxy]-phenoxy}-propionic acid ethyl ester To 0.119 g (0.499 mmol) of 2-(4-hydroxy-2-methyl-phenoxy)-2-methyl-propionic acid ethyl ester (described in WO 02/092590) and 0.150 g (0.525 mmol) of the above prepared (example 1N]) 3-chloromethyl-2-methyl-6-(4-trifluoromethyl-phenyl)-pyridine, dissolved in 3.3 ml of abs. acetonitrile, was added 0.179 g of $Cs_2CO_3$ (0.549 mmol). The reaction was stirred over night at ambient temperature. Pouring onto crashed ice/$NH_4Cl$-solution, twofold extraction with AcOEt, washing with water, drying over sodium sulfate, and evaporation of the solvents, followed by flash chromatography ($SiO_2$, hexane/AcOEt=8/2) yielded 0.221 g of pure title compound as colorless oil.

MS: 488.4 $(M+H)^+$.

B] 2-Methyl-2-{2-methyl-4-[2-methyl-6-(4-trifluoromethyl-phenyl)-pyridin-3-ylmethoxy]-phenoxy}-propionic acid 0.221 g (0.453 mmol) of the above prepared 2-methyl-2-{2-methyl-4-[2-methyl-6-(4-trifluoromethyl-phenyl)-pyridin-3-ylmethoxy]-phenoxy}-propionic acid ethyl ester was dissolved in 2.7 ml of THF/EtOH=1/1, treated with 1.35 ml (3 eq.) of 1N NaOH and kept at ambient temperature for 4 h. The reaction mixture was then poured onto crashed ice/AcOEt/HCl dil., the aqueous phase extracted again with AcOEt, the combined organic layers were washed with water, dried over sodium sulfate, and evaporated to dryness. Recrystallisation from AcOEt/hexane afforded finally 0.194 g of the title compound as white solid of mp. 164–165° C.

MS: 458.2 $(M-H)^-$.

Example 35

[rac]-2-Methyl-2-(2-methyl-4-{1-[2-methyl-6-(4-trifluoromethyl-phenyl)-pyridin-3-yl]-butoxy}-phenoxy)-propionic acid A] The title compound was prepared in analogy to example 34, via [rac]-2-methyl-2-(2-methyl-4-{1-[2-methyl-6-(4-trifluoromethyl-phenyl)-pyridin-3-yl]-butoxy}-phenoxy)-propionic acid ethyl ester, but using in step A] [rac]-3-(1-chloro-butyl)-2-methyl-6-(4-trifluoromethyl-phenyl)-pyridine (example 21B]) instead of 3-chloromethyl-2-methyl-6-(4-trifluoromethyl-phenyl)-pyridine, as colorless foam.

MS: 500.2 $(M-H)^-$.

Example 36

A] [rac]-2-Methyl-2-(2-methyl-4-{1-[2-methyl-6-(4-trifluoromethyl-phenyl)-pyridin-3-yl]-propoxy}-phenoxy)-propionic acid The title compound was prepared in analogy to example 34, via [rac]-2-methyl-2-(2-methyl-4-{1-[2-methyl-6-(4-trifluoromethyl-phenyl)-pyridin-3-yl]-propoxy}-phenoxy)-propionic acid, but using in step A] [rac]-3-(1-chloro-propyl)-2-methyl-6-(4-trifluoromethyl-phenyl)-pyridine (example 36B]) instead of 3-chloromethyl-2-methyl-6-(4-trifluoromethyl-phenyl)-pyridine, as colorless foam.

MS: 486.3 $(M-H)^-$.

[rac]-3-(1-Chloro-propyl)-2-methyl-6-(4-trifluoromethyl-phenyl)-pyridine used in 36A] was synthesized as follows:

B] [rac]-3-(1-Chloro-propyl)-2-methyl-6-(4-trifluoromethyl-phenyl)-pyridine

Was prepared in analogy to example 17C], but using for the Grignard-reaction ethyl magnesium chloride instead of the methyl derivative, as colorless oil.

MS: 314.2, 316.2 $(M^+H)^+$.

Example 37

[rac]-2-Methyl-2-(2-methyl-4-{1-[2-methyl-6-(4-trifluoromethyl-phenyl)-pyridin-3-yl]-ethoxy}-phenoxy)-propionic acid A] The title compound was prepared in analogy to example 34, via [rac]-2-methyl-2-(2-methyl-4-{1-[2-methyl-6-(4-trifluoromethyl-phenyl)-pyridin-3-yl]-ethoxy}-phenoxy)-propionic acid, but using in step A] [rac]-3-(1-chloro-ethyl)-2-methyl-6-(4-trifluoromethyl-phenyl)-pyridine (example 17C]) instead of 3-chloromethyl-2-methyl-6-(4-trifluoromethyl-phenyl)-pyridine, as off-white foam.

MS: 472.1 $(M-H)^-$.

Example 38

2-{4-[6-(3-Fluoro-4-trifluoromethyl-phenyl)-2-methyl-pyridin-3-ylmethoxy]-2-methyl-phenoxy}-2-methyl-propionic acid A] 2-{4-[6-(3-Fluoro-4-trifluoromethyl-phenyl)-2-methyl-pyridin-3-ylmethoxy]-2-methyl-phenoxy}-2-methyl-propionic acid ethyl ester To 0.139 g (0.583 mmol) of 2-(4-hydroxy-2-methyl-phenoxy)-2-methyl-propionic acid ethyl ester (described in WO 02/092590) and 0.177 g (0.583 mmol) of 3-chloromethyl-6-(3-fluoro-4-trifluoromethyl-phenyl)-2-methyl-pyridine (example 38C]), dissolved in 3 ml of abs. acetonitrile, was added 0.228 g of $Cs_2CO_3$ (0.700 mmol). The reaction mixture was stirred during 3 h at ambient temperature. Pouring onto crashed ice/$NH_4Cl$-solution, twofold extraction with AcOEt, washing with water and brine, drying over magnesium sulfate, and evaporation of the solvents, followed by flash chromatography ($SiO_2$, hexane/AcOEt=88/12) yielded 0.219 g of pure title compound as white solid.

MS: 506.4 $(M+H)^+$.

B] 2-{4-[6-(3-Fluoro-4-trifluoromethyl-phenyl)-2-methyl-pyridin-3-ylmethoxy]-2-methyl-phenoxy}-2-methyl-propionic acid 0.214 g (0.423 mmol) of the above prepared 2-{4-[6-(3-fluoro-4-trifluoromethyl-phenyl)-2-methyl-pyridin-3-ylmethoxy]-2-methyl-phenoxy}-2-methyl-propionic acid ethyl ester was dissolved in 0.85 ml of THF/EtOH=1/1, treated with 1.27 ml (3 eq.) of 1N NaOH and kept at ambient temperature for 2 h. The reaction mixture was then poured onto crashed ice/AcOEt/HCl dil., the aqueous phase extracted again with AcOEt; the combined organic layers were washed with water and brine, dried over magnesium sulfate, and evaporated to dryness. Recrystallisation from AcOEt/hexane yielded finally 0.191 g of the title compound as white crystals of mp. 175–76°C.

MS: 476.1 (M−H)⁻.

3-Chloromethyl-6-(3-fluoro-4-trifluoromethyl-phenyl)-2-methyl-pyridine used in 38A] was synthesized as follows:

C] 3-Chloromethyl-6-(3-fluoro-4-trifluoromethyl-phenyl)-2-methyl-pyridine was prepared in analogy to example 24B], but starting the whole reaction sequence with 1-(3-fluoro-4-trifluoromethyl-phenyl)-ethanone instead of 1-(4-fluoro-3-trifluoromethyl-phenyl)-ethanone, as off-white solid.

MS: 303.1, 305.1 (M)⁺.

Example 39

2-Methyl-2-{2-methyl-4-[2-methyl-6-(4-trifluoromethoxy-phenyl)-pyridin-3-ylmethoxy]-phenoxy}-propionic acid

A] 2-Methyl-6-(4-trifluoromethoxy-phenyl)-nicotinic acid methyl ester was prepared in analogy to example 1L], but starting the whole reaction sequence with 4-(trifluoromethoxy) acetophenone instead of 4-(trifluoromethyl) acetophenone, as beige solid.

MS: 311.0 (M)⁺.

B] [2-Methyl-6-(4-trifluoromethoxy-phenyl)-pyridin-3-yl]-methanol 1.54 g (4.95 mmol) of the above synthesized 2-methyl-6-(4-trifluoromethoxy-phenyl)-nicotinic acid methyl ester in 25 ml of abs. THF was cooled down to −20° C. and reacted with 14.84 ml of DIBAL-H-solution (1.0 M in toluene, 3 eq.) for 0.5 h. Careful quenching with ice/HCl dil., twofold extraction with AcOEt, washing with water, drying over sodium sulfate, and evaporation of the solvents left a crude product which was purified by flash chromatography (SiO₂, hexane/AcOEt=1/1) to deliver finally 0.877 g of the title compound as off-white solid of mp. 68–69° C.

MS: 283.0 (M)⁺.

C] 3-Chloromethyl-2-methyl-6-(4-trifluoromethoxy-phenyl)-pyridine 0.300 g (1.059 mmol) of the above prepared [2-methyl-6-(4-trifluoromethoxy-phenyl)-pyridin-3-yl]-methanol was dissolved in 5.3 ml of CH₂Cl₂ and treated dropwise at 0° C. with 0.15 ml (2 eq.) of SOCl₂. The reaction mixture was kept at 0° C. for 5 Min. and at RT for 30 Min. Pouring onto crashed ice/NaHCO₃, twofold extraction with AcOEt, washing with water, drying over sodium sulfate and evaporation of the solvents generated 0.315 g of pure title compound as light yellow oil.

MS: 301.0, 303.0 (M)⁺.

D] 2-Methyl-2-{2-methyl-4-[2-methyl-6-(4-trifluoromethoxy-phenyl)-pyridin-3-ylmethoxy]-phenoxy}-propionic acid ethyl ester To 0.123 g (0.516 mmol) of 2-(4-hydroxy-2-methyl-phenoxy)-2-methyl-propionic acid ethyl ester (described in WO 02/092590) and 0.163 g (0.540 mmol) of the above prepared 3-chloromethyl-2-methyl-6-(4-trifluoromethoxy-phenyl)-pyridine, dissolved in 4.7 ml of abs. acetonitrile, was added 0.184 g of Cs₂CO₃ (0.565 mmol). The reaction was stirred over night at ambient temperature. Pouring onto crashed ice/NH₄Cl-solution, twofold extraction with AcOEt, washing with water, drying over sodium sulfate, and evaporation of the solvents, followed by flash chromatography (SiO₂, hexane/AcOEt=8/2) yielded 0.243 g of pure title compound as colorless oil.

MS: 504.5 (M+H)⁺.

E] 2-Methyl-2-{2-methyl-4-[2-methyl-6-(4-trifluoromethoxy-phenyl)-pyridin-3-ylmethoxy]-phenoxy}-propionic acid 0.243 g (0.483 mmol) of the above prepared 2-methyl-2-{2-methyl-4-[2-methyl-6-(4-trifluoromethoxy-phenyl)-pyridin-3-ylmethoxy]-phenoxy}-propionic acid ethyl ester was dissolved in 2.9 ml of THF/EtOH=1/1, treated with 1.45 ml (3 eq.) of 1N NaOH and kept at room temperature for 4 h. The reaction mixture was then poured onto crashed ice/AcOEt/HCl dil., the aqueous phase extracted again with AcOEt; the combined organic layers were washed with water, dried over sodium sulfate, and evaporated to dryness. Recrystallisation from AcOEt/hexane produced finally 0.221 g of the title compound as white solid of mp. 149–151° C.

MS: 474.1 (M−H)⁻.

Example 40

2-{4-[2-Cyclopropyl-6-(4-trifluoromethyl-phenyl)-pyridin-3-ylmethoxy]-2-methyl-phenoxy}-2-methyl-propionic acid

A] 3-Amino-3-cyclopropyl-acrylic acid ethyl ester

To 6.54 g of activated (by successively washing with 2N HCl, water, EtOH, and ether) and dried Zn dust (100 mmol) in 60 ml of abs. EtOH was added 0.4 ml of ethyl bromoacetate and the mixture refluxed under Ar for 20 Min., whereby the color turned greenish. 1.342 g of cyclopropyl cyanide (20 mmol) was then added, followed by the remaining 8.47 ml of ethyl bromoacetate (in total 80 mmol), and refluxing continued for another hour. The reaction mixture was cooled down, poured carefully onto crashed ice/NaHCO₃, and filtrated over Celite. The aqueous phase was extracted once more with AcOEt, the combined organic layers were washed with water and brine, dried over magnesium sulfate, and evaporated to dryness. Flash chromatography. (SiO₂, hexane/AcOEt=8/2) yielded 3.21 g of material containing according to NMR and GC/MS mainly the desired title compound, besides some 3-cyclopropyl-3-oxo-propionic acid ethyl ester (product of hydrolysis) and 3-oxo-butyric acid ethyl ester (selfcondensation of the reagent); however, it was used as such.

MS: 155 (M)⁺.

B] 2-Cyclopropyl-6-(4-trifluoromethyl-phenyl)-nicotinic acid ethyl ester 0.657 g (2.33 mmol) of the above prepared (example 1L]) 3-dimethylamino-1-(4-trifluoromethyl-phenyl)-propan-1-one hydrochloride and 0.362 g (1.0 eq., not corrected for impurities) of the above synthesised 3-amino-3-cyclopropyl-acrylic acid ethyl ester was dissolved in 7 ml of AcOH and heated to reflux for 3 h. After cooling, the bulk of the solvent was evaporated i. V. Ensuing flash chromatography (SiO$_2$, hexane/AcOEt=93/7) yielded 0.101 g of the title compound as light yellow solid.

MS: 336.2 (M+H)$^+$.

C] [2-Cyclopropyl-6-(4-trifluoromethyl-phenyl)-pyridin-3-yl]-methanol 0.193 g (0.576 mmol) of the above prepared 2-cyclopropyl-6-(4-trifluoromethyl-phenyl)-nicotinic acid ethyl ester in 3.0 ml of abs. THF was cooled down to 0° C. and reacted with 1.5 ml of DIBAL-H-solution (1.0 M in toluene, 2.6 eq.) for 1 h. Careful quenching with ice, filtration over Celite, separation of the layers, reextraction of the aqueous phase with AcOEt, washing of the combined organic layers with NH$_4$Cl, and drying over magnesium sulfate was followed by evaporation of the solvents. The crude product was finally purified by flash chromatography (SiO$_2$, hexane/AcOEt=7/3) to deliver 0.128 g of the title compound as white crystals.

MS: 293.1 (M)$^+$.

D] 3-Chloromethyl-2-cyclopropyl-6-(4-trifluoromethyl-phenyl)-pyridine 0.127 g (0.433 mmol) of the above prepared [2-cyclopropyl-6-(4-trifluoromethyl-phenyl)-pyridin-3-yl]-methanol was dissolved in 2.0 ml of CH$_2$Cl$_2$ and treated at 0° C. with 0.063 ml (2 eq.) of SOCl$_2$. The reaction mixture was kept at 0° C. for 5 Min. and at RT for 60 Min. Pouring onto crashed ice/NaHCO$_3$, twofold extraction with AcOEt, washing with water and brine, drying over magnesium sulfate, and evaporation of the solvents afforded 0.137 g of pure title compound as off-white solid.

MS: 312.1, 314.0 (M+H)$^+$.

E] 2-{4-[2-Cyclopropyl-6-(4-trifluoromethyl-phenyl)-pyridin-3-ylmethoxy]-2-methyl-phenoxy}-2-methyl-propionic acid ethyl ester To 0.102 g (0.428 mmol) of 2-(4-hydroxy-2-methyl-phenoxy)-2-methyl-propionic acid ethyl ester (described in WO 02/092590) and 0.134 g (0.429 mmol) of the above prepared 3-chloromethyl-2-cyclopropyl-6-(4-trifluoromethyl-phenyl)-pyridine, dissolved in 2.5 ml of abs. acetonitrile, was added 0.168 g of Cs$_2$CO$_3$ (0.516 mmol). The reaction was stirred over night at ambient temperature. Pouring onto crashed ice/NH$_4$Cl-solution, twofold extraction with AcOEt, washing with water and brine, drying over magnesium sulfate, and evaporation of the solvents, followed by flash chromatography (SiO$_2$, hexane/AcOEt=88/12) yielded 0.221 g of pure title compound as colorless oil.

MS: 514.5 (M+H)$^+$.

F] 2-{4-[2-Cyclopropyl-6-(4-trifluoromethyl-phenyl)-pyridin-3-ylmethoxy-2-methyl-phenoxy}-2-methyl-propionic acid 0.220 g (0.428 mmol) of the above prepared 2-{4-[2-cyclopropyl-6-(4-trifluoromethyl-phenyl)-pyridin-3-yl-methoxy]-2-methyl-phenoxy}-2-methyl-propionic acid ethyl ester was dissolved in 2.6 ml of THF/EtOH=1/1, treated with 1.30 ml (3 eq.) of 1N NaOH and kept at room temperature for 2 h. The reaction mixture was then poured onto crashed ice/AcOEt/HCl dil., the aqueous phase extracted again with AcOEt; the combined organic layers were washed with water and brine, dried over magnesium sulfate, and evaporated to dryness. Recrystallisation from AcOEt/hexane afforded eventually 0.198 g of the title compound as white crystals of mp. 170–171° C.

MS: 484.2 (M–H)$^-$.

Example 41

[rac]-2-Methyl-2-(2-methyl-4-{1-[2-methyl-6-(3-trifluoromethyl-phenyl)-pyridin-3-yl]-butoxy}-phenoxy)-propionic acid A] The title compound was prepared in analogy to example 8, via [rac]-2-methyl-2-(2-methyl-4-{1-[2-methyl-6-(3-trifluoromethyl-phenyl)-pyridin-3-yl]-butoxy}-phenoxy)-propionic acid ethyl ester, but using instep A] [rac]-3-(1-chloro-butyl)-2-methyl-6-(3-trifluoromethyl-phenyl)-pyridine (example 4B]) instead of 3-chloromethyl-2-methyl-6-(3-trifluoromethyl-phenyl)-pyridine, as white foam.

MS: 500.2 (M–H)$^-$.

Example 42

2-{4-[4-Cyclopropyl-2-(3-trifluoromethyl-phenyl)-pyrimidin-5-ylmethoxy-2-methyl-phenoxy}-2-methyl-propionic acid

A] 4-Cyclopropyl-2-(3-trifluoromethyl-phenyl)-pyrimidine-5-carboxylic acid ethyl ester To a solution of 0.953 g (4.24 mmol) commercially available 3-trifluoromethyl-benzamidine hydrochloride in 10 ml of ethanol was added 0.408 g (4.25 mmol) of sodium tert-butoxide. Two Min. later, 0.901 g (4.25 mmol) of crude (E,Z)-2-cyclopropane-carbonyl-3-ethoxy-acrylic acid methyl ester (example 27C], containing some Et-ester) was added and the reaction allowed to proceed over night at RT. The mixture was then poured onto crashed ice/AcOEt/HCl dil., the aqueous phase extracted again with AcOEt, the combined organic layers were washed with water, dried over sodium sulfate, and evaporated to dryness. Flash chromatography (SiO$_2$, hexane/AcOEt=9/1) yielded finally 1.253 g of title compound as white waxy solid (mixture of Me/Et-ester).

MS: 322.1, 336.0 (M)$^+$.

B] [4-Cyclopropyl-2-(3-trifluoromethyl-phenyl)-pyrimidin-5-yl]-methanol 1.250 g (3.717 mmol) of the above prepared 4-cyclopropyl-2-(3-trifluoromethyl-phenyl)-pyrimidine-5-carboxylic acid ethyl ester in 19 ml of abs. THF was cooled down to −15° C. and reacted with 11.2 ml of DIBAL-H-solution (1.0 M in toluene, 3 eq.) for 1/2 h. Careful quenching with ice/HCl dil., twofold extraction with AcOEt, washing with water, drying over sodium sulfate, and evaporation of the solvents left a crude product which was purified by flash chromatography (SiO$_2$, hexane/AcOEt=1/11) to yield finally 1.096 g of the title compound as white solid of mp. 108–09° C.

MS: 294.1 (M)$^+$.

C] 5-Chloromethyl-4-cyclopropyl-2-(3-trifluoromethyl-phenyl)-pyrimidine 0.300 g (1.019 mmol) of the above prepared [4-cyclopropyl-2-(3-trifluoromethyl-phenyl)-pyrimidin-5-yl]-methanol was dissolved in 5 ml of CH$_2$Cl$_2$ and treated at 0° C. with 0.15 ml (2 eq.) of SOCl$_2$. The reaction mixture was kept at 0° C. for 5 Min. and at ambient temperature for 30 Min. Pouring onto crashed ice/NaHCO$_3$, twofold extraction with AcOEt, washing with water, drying over sodium sulfate, and evaporation of the solvents gave 0.315 g of pure title compound as white solid of mp. 92–95° C.

MS: 312.1, 314.0 (M)$^+$.

D] 2-{4-[4-Cyclopropyl-2-(3-trifluoromethyl-phenyl)-pyrimidin-5-ylmethoxy-2-methyl-phenoxy}-2-methyl-propionic acid ethyl ester To 0.114 g (0.478 mmol) of 2-(4-hydroxy-2-methyl-phenoxy)-2-methyl-propionic acid ethyl ester (described in WO 02/092590) and 0.157 g (0.502 mmol) of the above prepared 5-chloromethyl-4-cyclopropyl-2-(3-trifluoromethyl-phenyl)-pyrimidine, dissolved in 4.4 ml of abs. acetonitrile, was added 0.171 g of Cs$_2$CO$_3$ (0.525 mmol). The reaction was stirred over night at ambient temperature. Pouring onto crashed ice/HCl dil.-solution, twofold extraction with AcOEt, washing with water, drying over sodium sulfate, and evaporation of the solvents, followed by flash chromatography (SiO$_2$, hexane/AcOEt=8/2) yielded 0.240 g of pure title compound as white waxy solid.

MS: 515.4 (M+H)$^+$.

E] 2-{4-[4-Cyclopropyl-2-(3-trifluoromethyl-phenyl)-pyrimidin-5-ylmethoxy]-2-methyl-phenoxy}-2-methyl-propionic acid 0.240 g (0.466 mmol) of the above prepared 2-{4-[4-cyclopropyl-2-(3-trifluoromethyl-phenyl)-pyrimidin-5-yl-methoxy]-2-methyl-phenoxy}-2-methyl-propionic acid ethyl ester was dissolved in 2.8 ml of THF/EtOH=1/1, treated with 1.40 ml (3 eq.) of 1N NaOH and kept at ambient temperature for 7 h. The reaction mixture was then poured onto crashed ice/AcOEt/HCl dil., the aqueous phase extracted again with AcOEt; the combined organic layers were washed with water, dried over sodium sulfate, and evaporated to dryness. Recrystallisation from AcOEt/hexane afforded finally 0.196 g of the title compound as white solid of mp. 175–176° C.

MS: 485.2 (M–H)$^-$.

Example 43

2-Methyl-2-(2-methyl-4-{2-[2-methyl-6-(4-trifluoromethyl-phenyl)-pyridin-3-yl]-ethoxy}-phenoxy)-propionic acid

A] [2-Methyl-6-(4-trifluoromethyl-phenyl)-pyridin-3-yl]-acetonitrile 27.2 g of the above (example 1N]) prepared 3-chloromethyl-2-methyl-6-(4-trifluoromethyl-phenyl)-pyridine (95.2 mmol) was dissolved in 100 ml of dimethyl sulfoxide; 5.9 g of sodium cyanide (120 mmol) was added and the mixture was stirred at room temperature for 18 hours. The reaction mixture was then poured onto a mixture of ice and water and was subsequently extracted with 3 portions of 400 ml of tert-butyl methyl ether. The combined organic layers were washed with water, then with brine, and dried over sodium sulfate. After evaporation of the solvents, 25.2 g of the title compound was obtained as pale yellow solid.

MS: 276.1 (M)$^+$.

B] [2-Methyl-6-(4-trifluoromethyl-phenyl)-pyridin-3-yl]-acetic acid

A mixture of 25 g (90 mmol) of the above prepared [2-methyl-6-(4-trifluoromethyl-phenyl)-pyridin-3-yl]-acetonitrile, 20 g of sodium hydroxide (500 mmol), 60 ml of water, and 250 ml of propanol was stirred vigorously at 100° C. Hydrolysis was complete after 2 hours. The reaction mixture was then evaporated to dryness and the residue was redissolved in 70 ml of water; 60 ml of cold 8 N aqueous HCl was then added and the acid extracted with three portions of 250 ml of ethyl acetate; the combined organic phases were washed with water and brine, dried over sodium sulfate, and evaporated to dryness. Thereby, 25.1 g of the title product was obtained as pale yellow solid.

MS: 296.0 (M+H)$^+$.

C] [2-Methyl-6-(4-trifluoromethyl-phenyl)-pyridin-3-yl]-acetic acid methyl ester A solution of 2.55 g (8.63 mmol) of the above prepared [2-methyl-6-(4-trifluoromethyl-phenyl)-pyridin-3-yl]-acetic acid in 25 ml of methanol was cooled to –10° C.; 1.88 ml (25.9 mmol) of thionyl chloride was added and the reaction mixture was then stirred at ambient temperature for 2 hours. Subsequently, the solution was poured onto ice water, then extracted with three portions of 50 ml of tert.-butyl methyl ether. The combined organic layers were washed with water, aqueous NaHCO$_3$-solution and brine, and dried over sodium sulfate. After evaporation of the solvents, 2.60 g of the title compound was obtained as light brown solid.

MS: 309.1 (M)$^+$.

D] 2-[2-Methyl-6-(4-trifluoromethyl-phenyl)-pyridin-3-yl]-ethanol 2.60 g (8.40 mmol) of the above prepared [2-methyl-6-(4-trifluoromethyl-phenyl)-pyridin-3-yl]-acetic acid methyl ester, dissolved in 15 ml of dry tetrahydrofuran, was added under an argon atmosphere within 15 minutes to a stirred suspension of 0.38 g (10 mmol) of lithium aluminum hydride in 5 ml of tetrahydrofuran. The reaction was exothermic. Subsequently, the mixture was stirred at room temperature for 1 hour to complete the reduction. Then, 1 ml of ethyl acetate was added dropwise to destroy the excess of reagent, followed by water, drop after drop, under argon, with stirring and cooling. The reaction mixture was diluted with 50 ml of ethyl acetate, dried over sodium sulfate, and filtered. The filtrate was evaporated i. V. and the residue was purified by chromatography on SiO$_2$ with a mixture of dichloromethane and tert.-butyl methyl ether (4:1) as eluent. Thereby, 1.88 g of the title compound was obtained as white solid.

MS: 281.1 (M)$^+$.

E] 2-Methyl-2-(2-methyl-4-{2-[2-methyl-6-(4-trifluoromethyl-phenyl)-pyridin-3-yl]-ethoxy}-phenoxy)-propionic acid ethyl ester 0.181 g (0.642 mmol) of the above prepared 2-[2-methyl-6-(4-trifluoromethyl-phenyl)-pyridin-3-yl]-ethanol and 0.153 g (0.642 mmol) of 2-(4-hydroxy-2-methyl-phenoxy)-2-methyl-propionic acid ethyl ester (described in WO 02/092590) were dissolved in 8 ml of abs. THF and treated successively at 0° C. with 0.156 g (0.771 mmol) of tributylphosphine and 0.133 g (0.770 mmol) of N,N,N',N'-tetramethylazodicarboxamide. The cooling bath was then removed and stirring continued for one night. Filtration over a pad of Celite, evaporation of the solvent, followed by flash chromatography (SiO$_2$, hexane/AcOEt=85/15), delivered 0.070 g of the title compound as colorless oil.

MS: 502.4 (M+H)$^+$.

F] 2-Methyl-2-(2-methyl-4-{2-[2-methyl-6-(4-trifluoromethyl-phenyl)-pyridin-3-yl]-ethoxy}-phenoxy)-propionic acid 0.070 g (0.140 mmol) of the above prepared 2-methyl-2-(2-methyl-4-{2-[2-methyl-6-(4-trifluoromethyl-phenyl)-pyridin-3-yl]-ethoxy}-phenoxy)-propionic acid ethyl ester was dissolved in 0.84 ml of THF/EtOH=1/1, treated with 0.42 ml (3 eq.) of 1N NaOH and kept at ambient temperature for 4 h. The reaction mixture was then poured onto crashed ice/AcOEt/HCl dil., the aqueous phase extracted again with AcOEt; the combined organic layers were washed with water, dried over sodium sulfate, and evaporated to dryness to yield 0.057 g of the title product as light yellow foam.

MS: 472.1 (M−H)$^-$.

Example 44

2-Methyl-2-{2-methyl-4-[6-(4-trifluoromethyl-phenyl)-pyridazin-3-ylmethoxy]-phenoxy]-propionic acid A] 6-(4-Trifluoromethyl-phenyl)-pyridazine-3-carboxylic acid methyl ester 0.400 g (2.32 mmol) of the known 6-chloro-pyridazine-3-carboxylic acid methyl ester was dissolved in 12 ml of abs. DMF and treated with 0.268 g (0.232 mmol) of Pd(Ph$_3$P)$_4$. After heating to 80° C., 0.572 g (3.01 mmol) of 4-(trifluoromethyl)benzeneborinic acid and 1.133 g (3.48 mmol) of Cs$_2$CO$_3$ was added and the reaction allowed to proceed for 3.5 h at the same temperature. After cooling, the mixture was poured onto crashed ice, extracted twice with AcOEt, washed with brine and water, and dried over sodium sulfate. Evaporation of the solvents i. V., followed by flash chromatography (SiO$_2$, hexane/AcOEt=1/1) delivered 0.316 g of a reddish solid which was recrystallised from hexane/AcOEt to remove remaining impurities. Thereby, 0.230 g of the title compound was isolated.

MS: 282.1 (M)$^+$.

B] [6-(4-Trifluoromethyl-phenyl)-pyridazin-3-yl]-methanol 0.582 g (2.062 mmol) of the above prepared 6-(4-trifluoromethyl-phenyl)-pyridazine-3-carboxylic acid methyl ester in 20 ml of abs. THF was cooled down to −15° C. and reacted with 5.16 ml of DIBAL-H-solution (1.0 M in toluene, 2.5 eq.) for ½ h. Careful quenching with ice/HCl dil., twofold extraction with AcOEt, washing with water, drying over sodium sulfate, and evaporation of the solvents left a crude product which was purified by flash chromatography (SiO$_2$, AcOEt) to yield 0.155 g of the title compound as light brown solid.

MS: 254.1 (M)$^+$.

C] 2-Methyl-2-{2-methyl-4-[6-(4-trifluoromethyl-phenyl)-pyridazin-3-ylmethoxy]-phenoxy}-propionic acid ethyl ester 0.170 g (0.669 mmol) of the above prepared [6-(4-trifluoromethyl-phenyl)-pyridazin-3-yl]-methanol and 0.163 g (0.684 mmol) of 2-(4-hydroxy-2-methyl-phenoxy)-2-methyl-propionic acid ethyl ester (described in WO 02/092590) were dissolved in 8 ml of abs. THF and treated successively at 0° C. with 0.162 g (0.800 mmol) of tributylphosphine and 0.139 g (0.804 mmol) of N,N,N',N'-tetramethylazodicarboxamide. The cooling bath was then removed and stirring continued for one night. The reaction mixture was then poured onto crashed ice, extracted twice with AcOEt, washed with water, and dried over sodium sulfate. Evaporation of the solvents i. V., followed by flash chromatography (SiO$_2$, hexane/AcOEt=7/3) yielded, after recrystallisation from hexane/AcOEt, 0.208 g of a colorless solid.

MS: 475.4 (M+H)$^+$.

D] 2-Methyl-2-{2-methyl-4-[6-(4-trifluoromethyl-phenyl)-pyridazin-3-ylmethoxy]-phenoxy}-propionic acid 0.183 g (0.386 mmol) of the above prepared 2-methyl-2-{2-methyl-4-[6-(4-trifluoromethyl-phenyl)-pyridazin-3-ylmethoxy]-phenoxy}-propionic acid ethyl ester was dissolved in 8 ml of THF/EtOH=1/1, treated with 1.16 ml (3 eq.) of 1N NaOH and kept at ambient temperature over night. The reaction mixture was then poured onto crashed ice/AcOEt/HCl dil., the aqueous phase extracted again with AcOEt; the combined organic layers were washed with water, dried over sodium sulfate, and evaporated to dryness to yield, after recrystallisation from hexane/AcOEt, 0.160 g of the title compound as light yellow crystals of mp. 191–192° C.

MS: 445.1 (M−H)$^-$.

Example 45

2-{4-[2-Methoxymethyl-6-(4-trifluoromethyl-phenyl)-pyridin-3-ylmethoxy]-2-methyl-phenoxy}-2-methyl-propionic acid A] 2-Bromomethyl-6-(4-trifluoromethyl-phenyl)-nicotinic acid methyl ester 1.97 g (6.67 mmol) of 2-methyl-6-(4-trifluoromethyl-phenyl)-nicotinic acid methyl ester (example 1L]) was dissolved in 20 ml of CCl$_4$ and treated with 1.781 g (10.0 mmol) of N-bromosuccinimide and 0.126 g (0.669 mmol) of dibenzoyl peroxide. The mixture was refluxed (oilbath temperature 95° C.) and the course of the bromination followed by GC. After 5 h, the reaction mixture was poured onto crashed ice, extracted twice with AcOEt, washed with water and brine, and dried over magnesium sulfate. Evaporation of the solvents i. V., followed by careful flash chromatography (SiO₂, hexane/AcOEt=92/8), afforded 1.39 g of the title compound as white crystals, contaminated with roughly 5% of the dibromo-analogue.

MS: 373.9, 375.9 (M)⁺.

B] 2-Methoxymethyl-6-(4-trifluoromethyl-phenyl)-nicotinic acid methyl ester

To 0.401 g (1.072 mmol) of the above prepared 2-bromomethyl-6-(4-trifluoromethyl-phenyl)-nicotinic acid methyl ester, dissolved in 4.0 ml of abs. MeOH, was added 0.116 g (2.15 mmol) of sodium methoxide and the mixture stirred for 4 h at ambient temperature, when TLC indicated the complete disappearance of starting material. Pouring onto crashed ice/NH₄Cl-solution, twofold extraction with AcOEt, washing with water and brine, drying over magnesium sulfate, and evaporation of the solvents, followed by flash chromatography (SiO₂, hexane/AcOEt=9/1), produced 0.279 g of pure title compound as white solid.

MS: 326.2 (M+H)⁺.

C] [2-Methoxymethyl-6-(4-trifluoromethyl-phenyl)-pyridin-3-yl]-methanol 0.364 g (1.119 mmol) of the above prepared 2-methoxymethyl-6-(4-trifluoromethyl-phenyl)-nicotinic acid methyl ester in 6 ml of abs. THF was cooled down to 0° C. and reacted with 2.8 ml of DIBAL-H-solution (1.0 M in toluene, 2.5 eq.) for 1 h. Careful quenching with icewater, filtration over a pad of Celite, twofold extraction with AcOEt, washing with NH₄Cl-solution, drying over magnesium sulfate, and evaporation of the solvents left a crude product which was purified by flash chromatography (SiO₂, hexane/AcOEt=1/1) to yield finally 0.312 g of the title compound as colorless oil.

MS: 298.1 (M+H)⁺.

D] 3-Chloromethyl-2-methoxymethyl-6-(4-trifluoromethyl-phenyl)-pyridine 0.311 g (1.046 mmol) of the above prepared [2-methoxymethyl-6-(4-trifluoromethyl-phenyl)-pyridin-3-yl]-methanol was dissolved in 4 ml of CH₂Cl₂ and treated at 0C. with 0.15 ml (2 eq.) of SOCl₂. The reaction mixture was kept at 0° C. for 5 Min. and at ambient temperature for 60 Min. Pouring onto crashed ice/NaHCO₃, twofold extraction with AcOEt, washing with water and brine, drying over magnesium sulfate, and evaporation of the solvents produced 0.330 g of pure title compound as colorless oil.

MS: 316.0, 318.0 (M+H)⁺.

E] 2-{4-[2-Methoxymethyl-6-(4-trifluoromethyl-phenyl)-pyridin-3-ylmethoxy]-2-methyl-phenoxy}-2-methyl-propionic acid ethyl ester To 0.097 g (0.407 mmol) of 2-(4-hydroxy-2-methyl-phenoxy)-2-methyl-propionic acid ethyl ester (described in WO 02/092590) and 0.145 g (0.459 mmol) of the above prepared 3-chloromethyl-2-methoxymethyl-6-(4-trifluoromethyl-phenyl)-pyridine, dissolved in 2.5 ml of abs. acetonitrile, was added 0.180 g of Cs₂CO₃ (0.552 mmol). The reaction was stirred for 22 h at ambient temperature. Pouring onto crashed ice/NH₄Cl-solution, twofold extraction with AcOEt, washing with water and brine, drying over magnesium sulfate, and evaporation of the solvents, followed by flash chromatography (SiO₂, hexane/AcOEt=88/12), gave 0.214 g of pure title compound as colorless oil.

MS: 518.3 (M+H)⁺.

F] 2-{4-[2-Methoxymethyl-6-(4-trifluoromethyl-phenyl)-pyridin-3-ylmethoxy-2-methyl-phenoxy}-2-methyl-propionic acid 0.213 g (0.412 mmol) of the above prepared 2-{4-[2-methoxymethyl-6-(4-trifluoromethyl-phenyl)-pyridin-3-ylmethoxy]-2-methyl-phenoxy}-2-methyl-propionic acid ethyl ester was dissolved in 2.6 ml of THF/EtOH=1/1, treated with 1.3 ml (3 eq.) of 1N NaOH and kept at ambient temperature over night. The reaction mixture was then poured onto crashed ice/AcOEt/HCl dil., the aqueous phase extracted again with AcOEt; the combined organic layers were washed with water, dried over magnesium sulfate, and evaporated to dryness to yield, after recrystallisation from hexane/AcOEt, 0.186 g of the title compound as white crystals of mp. 121–122° C.

MS: 488.2 (M–H)⁻.

Example 46

[rac]-(2-Methyl-4-{1-[2-methyl-6-(4-trifluoromethyl-phenyl)-pyridin-3-yl]-butoxy}-phenoxy)-acetic acid A] The title compound was prepared in analogy to example 35, via [rac]-(2-methyl-4-{1 -[2-methyl-6-(4-trifluoromethyl-phenyl)-pyridin-3-yl]-butoxy}-phenoxy)-acetic acid ethyl ester, but using in step A] (4-hydroxy-2-methyl-phenoxy)-acetic acid ethyl ester (WO02092590) instead of 2-(4-hydroxy-2-methyl-phenoxy)-2-methyl-propionic acid ethyl ester, as colorless, viscous oil.

MS: 472.1 (M–H)⁻.

Example 47

[rac]-(2-Methyl-4-{1-[2-methyl-6-(3-trifluoromethyl-phenyl)-pyridin-3-yl]-ethoxy}-phenoxy)-acetic acid A] The title compound was prepared in analogy to example 46, via [rac]-(2-methyl-4-{1-[2-methyl-6-(3-trifluoromethyl-phenyl)-pyridin-3-yl]-ethoxy}-phenoxy)-acetic acid ethyl ester, but using in step A] [rac]-3-(1-chloroethyl)-2-methyl-6-(3-trifluoromethyl-phenyl)-pyridine (example 3C]) instead of [rac]-3-(1-chloro-butyl)-2-methyl-6-(4-trifluoromethyl-phenyl)-pyridine as colorless solid.

MS: 444.1 (M–H)⁻.

Example 48

[rac]-(2-Methyl-4-{1-[2-methyl-6-(3-trifluoromethyl-phenyl)-pyridin-3-yl]-butoxy}-phenoxy)-acetic acid A] The title compound was prepared in analogy to example 47, via [rac]-(2-methyl-4-{1-[2-methyl-6-(3-trifluoromethyl-phenyl)-pyridin-3-yl]-butoxy}-phenoxy)-acetic acid ethyl ester, but using in step A] [rac]-3-(1-chloro-butyl)-2-methyl-6-(3-trifluoromethyl-phenyl)-pyridine (example 4B]) instead of [rac]-3-(1-chloro-ethyl)-2-methyl-6-(3-trifluoromethyl-phenyl)-pyridine as light yellow oil.

MS: 472.1 (M–H)⁻.

Example 49

[rac]-(2-Methyl-4-{1-[2-methyl-6-(4-trifluoromethyl-phenyl)-pyridin-3-yl]-propoxy}-phenoxy)-acetic acid A] The title compound was prepared in analogy to example 48, via [rac]-(2-methyl-4-{1-[2-methyl-6-(4-trifluoromethyl-phenyl)-pyridin-3-yl]-propoxy}-phenoxy)-acetic acid ethyl ester, but using in step A] [rac]-3-(1-chloro-propyl)-2-methyl-6-(4-trifluoromethyl-phenyl)-pyridine (example 36B]) instead of [rac]-3-(1-chloro-butyl)-2-methyl-6-(3-trifluoromethyl-phenyl)-pyridine as light yellow foam.

MS: 458.2 (M–H)⁻.

Example 50

[rac]-(2-Methyl-4-{1-[2-methyl-6-(4-trifluoromethyl-phenyl)-pyridin-3-yl]-ethoxy}-phenoxy)-acetic acid A] The title compound was prepared in analogy to example 49, via [rac]-(2-methyl-4-{1-[2-methyl-6-(4-trifluoromethyl-phenyl)-pyridin-3-yl]-ethoxy}-phenoxy)-acetic acid ethyl ester, but using in step A] [rac]-3-(1-chloro-ethyl)-2-methyl-6-(4-trifluoromethyl-phenyl)-pyridine (example 17C]) instead of [rac]-3-(1-chloro-propyl)-2-methyl-6-(4-trifluoromethyl-phenyl)-pyridine as off-white foam.

MS: 444.1 (M–H)⁻.

Example 51

2-{4-[2-Dimethylaminomethyl-6-(4-trifluoromethyl-phenyl)-pyridin-3-ylmethoxy]-2-methyl-phenoxy}-2-methyl-propionic acid A] 2-Dimethylaminomethyl-6-(4-trifluoromethyl-phenyl)-nicotinic acid methyl ester 0.102 g (0.273 mmol) of the above (example 45A]) prepared 2-bromomethyl-6-(4-trifluoromethyl-phenyl)-nicotinic acid methyl ester was dissolved in 1.5 ml of acetonitrile and treated with 0.027 g (0.331 mmol) of dimethylamine hydrochloride and 0.080 ml (2 eq.) of triethylamine. After stirring for 2 h at ambient temperature, the reaction mixture was poured onto crashed ice/KHSO₄-solution and extracted twice with AcOEt. Washing with water and brine, drying over magnesium sulfate, and evaporation of the solvents, followed by flash chromatography (SiO₂, AcOEt/MeOH/NEt₃=9/1/0.05), produced 0.047 g of pure title compound as off-white crystals.

MS: 339.2 (M+H)⁺.

B] [2-Dimethylaminomethyl-6-(4-trifluoromethyl-phenyl)-pyridin-3-yl]-methanol 0.046 g (0.136 mmol) of the above prepared 2-dimethylaminomethyl-6-(4-trifluoro-methyl-phenyl)-nicotinic acid methyl ester was dissolved in 1 ml of abs. diethylether and cooled down to –10°. 0.005 g (1 mol-eq.) of LiAlH₄ was added and stirring continued for 2 h at the same temperature. The reaction mixture was then quenched with 2 drops of conc. NaOH and, after vigorously stirring for another 3 h, filtered over a pad of Celite. Careful washing with AcOEt and evaporation of the solvents left finally 0.038 g of the title compound as light yellow solid.

MS: 311.2 (M+H)⁺.

C] 2-{4-[2-Dimethylaminomethyl-6-(4-trifluoromethyl-phenyl)-pyridin-3-ylmethoxy]-2-methyl-phenoxy}-2-methyl-propionic acid ethyl ester 0.170 g (0.548 mmol) of the above prepared [2-dimethylaminomethyl-6-(4-trifluoromethyl-phenyl)-pyridin-3-yl]-methanol and 0.122 g (0.512 mmol) of 2-(4-hydroxy-2-methyl-phenoxy)-2-methyl-propionic acid ethyl ester (described in WO 02/092590) were dissolved in 6 ml of abs. THF and treated successively at 0° C. with 0.133 g (0.658 mmol) of tributylphosphine and 0.114 g (0.659 mmol) of N,N,N',N'-tetramethylazodicarboxamide. The cooling bath was then removed and stirring continued for additional 6 h. The reaction mixture was then poured onto crashed ice, extracted twice with AcOEt, washed with water and brine, and dried over magnesium sulfate. Evaporation of the solvents i. V., followed by flash chromatography (SiO₂, hexane/AcOEt=25/75) yielded 0.016 g of the title product as yellow oil.

MS: 531.3 (M+H)⁺.

D] 2-{4-[2-Dimethylaminomethyl-6-(4-trifluoromethyl-phenyl)-pyridin-3-ylmethoxy-2-methyl-phenoxy}-2-methyl-propionic acid 0.015 g (0.028 mmol) of the above prepared 2-{4-[2-dimethylaminomethyl-6-(4-trifluoromethyl-phenyl)-pyridin-3-ylmethoxy]-2-methyl-phenoxy}-2-methyl-propionic acid ethyl ester was dissolved in 1.0 ml of THF/EtOH=1/1, treated with 0.5 ml (18 eq.) of 1N NaOH and kept at ambient temperature over night. The reaction mixture was then poured onto crashed ice/HCl dil. to adjust the pH to 3, the aqueous phase was extracted twice with AcOEt, the combined organic layers were washed with water and brine, dried over sodium sulfate, and evaporated to dryness to yield 0.014 g of the title compound as off-white amorphous solid.

MS: 503.4 (M+H)⁺.

Example 52

2-Methyl-2-{3-[(methyl-{2-[2-methyl-6-(4-trifluoromethyl-phenyl)-pyridin-3-yl]-acetyl}-amino)-methyl]-phenoxy}-propionic acid A] 2-(3-Cyano-phenoxy)-2-methyl-propionic acid ethyl ester 5.0 g (42.0 mmol) of 3-hydroxybenzonitrile and 16.25 ml=21.29 g (109 mmol) of ethyl-bromoisobutyrate were dissolved in 70 ml acetonitrile; then, 17.40 g (126 mmol) of potassium carbonate were added and the reaction mixture stirred for 16 hours at 80° C. (reflux). It was then cooled down to ambient temperature and the solvent was evaporated. The residue was partitioned between water and ether and extracted twice with ether; the organic phases were washed with water, dried (MgSO₄) and evaporated. The crude product was purified by flash chromatography (SiO₂, heptane/AcOEt) to finally give 9.10 g of the title compound as colorless oil.

MS: 233.2 (M)⁺.

B] 2-(3-Aminomethyl-phenoxy)-2-methyl-propionic acid ethyl ester 8.56 g (36.7 mmol) of 2-(3-cyano-phenoxy)-2-methyl-propionic acid ethyl ester was dissolved in 65 ml ethanol; then, 6.5 ml acetic acid was added, followed by 0.9 g Pd—C (10%) and the reaction mixture was hydrogenated under 1 atm of $H_2$-pressure during 5 hours. Then, it was filtered (Celite), the filter cake was washed twice with ethanol and the solvents were evaporated. The residue was partitioned between crashed ice/1N NaOH/EtOAc and extracted twice with EtOAc; the organic phases were washed with water, dried ($MgSO_4$) and evaporated. The crude product was purified by flash chromatography ($SiO_2$, $MeCl_2$/MeOH) to give 7.71 g of the title compound as colorless oil.

MS: 238.3 $(M+H)^+$.

C] 2-Methyl-2-(3-methylaminomethyl-phenoxy)-propionic acid ethyl ester

In analogy to the procedures described in example 5D], 5E] and 5F], 2-(3-aminomethyl-phenoxy)-2-methyl-propionic acid ethyl ester was converted into the corresponding tert-butoxycarbonylamino derivative by treatment with di-tert-butyl dicarbonate and sodium hydrogen carbonate in dioxane/water at r.t., methylated at N and deprotected again to yield the title compound as a yellow oil.

MS: 252.2 $(M+H)^+$.

D] 2-Methyl-2-{3-[(methyl-{2-[2-methyl-6-(4-trifluoromethyl-phenyl)-pyridin-3-yl]-acetyl}-amino)-methyl]-phenoxy}-propionic acid In analogy to the procedures described in example 26B] and 26C], 2-methyl-2-(3-methylaminomethyl-phenoxy)-propionic acid ethyl ester was reacted with [2-methyl-6-(4-trifluoromethyl-phenyl)-pyridin-3-yl]-acetic acid (example 26E]) to give 2-methyl-2-{3-[(methyl-{2-[2-methyl-6-(4-trifluoromethyl-phenyl)-pyridin-3-yl]-acetyl}-amino)-methyl]-phenoxy}-propionic acid ethyl ester, which was subsequently saponified to yield the title compound as colorless foam.

MS: 499.1 $(M–H)^-$.

Example 53

2-[3-({[4-Cyclopropyl-2-(4-trifluoromethyl-phenyl)-pyrimidine-5-carbonyl]-methyl-amino}-methyl)-phenoxy]-2-methyl-propionic acid A ] In analogy to the procedures described in example 26B] and 26C], 2-methyl-2-(3-methylaminomethyl-phenoxy)-propionic acid ethyl ester (example 52C]) was reacted with 4-cyclopropyl-2-(4-trifluoromethyl-phenyl)-pyrimidine-5-carboxylic acid (example 53B]) to give 2-[3-({[4-cyclopropyl-2-(4-trifluoromethyl-phenyl)-pyrimidine-5-carbonyl]-methyl-amino}-methyl-phenoxy]-2-methyl-propionic acid ethyl ester, which was subsequently saponified to yield the title compound as colorless solid.

MS: 512.2 $(M–H)^-$.

The necessary building block 4-cyclopropyl-2-(4-trifluoromethyl-phenyl)-pyrimidine-5-carboxylic acid used in procedure above was prepared as follows:

B] 4-Cyclopropyl-2-(4-trifluoromethyl-phenyl)-pyrimidine-5-carboxylic acid

The solutions of 3.6 g (10.7 mmol) of 4-cyclopropyl-2-(4-trifluoromethyl-phenyl)-pyrimidine-5-carboxylic acid ethyl ester (example 27D]) in 40 ml of ethanol and of 1.07 g (26.7 mmol) of sodium hydroxide in 5 ml of $H_2O$ were mixed and then refluxed for 1 hour. After cooling to ambient temperature, 6.7 ml of 4N aqueous hydrochloric acid was added. The reaction mixture was extracted with three portions of ethyl acetate. The combined organic phases were washed with water and brine and dried over anhydrous sodium sulfate. The 4-cyclopropyl-2-(4-trifluoromethyl-phenyl)-pyrimidine-5-carboxylic acid crystallized upon concentrating the solution by evaporation. After cooling in an ice bath, 3.08 g of white crystals were obtained (84% of theory).

MS: 307.2 $(M–H)^-$.

Example 54

2-Methyl-2-[3-({methyl-[2-methyl-6-(4-trifluoromethyl-phenyl)-pyridine-3-carbonyl]-amino}-methyl)-phenoxy]-propionic acid In analogy to the procedures described in example 26B] and 26C], 2-methyl-2-(3-methylaminomethyl-phenoxy)-propionic acid ethyl ester (example 52C]) was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-methyl-2-[3-({methyl-[2-methyl-6-(4-trifluoromethyl-phenyl)-pyridine-3-carbonyl]-amino}-methyl)-phenoxy]-propionic acid ethyl ester, which was subsequently saponified to yield the title compound as colorless amorphous solid.

MS: 485.3 $(M–H)^-$.

Example 55

2-Methyl-2-[3-(2-{2-[2-methyl-6-(4-trifluoromethyl-phenyl)-pyridin-3-yl]-acetylamino}-ethyl)-phenoxy]-propionic acid

A] 2-(3-Formyl-phenoxy)-2-methyl-propionic acid ethyl ester

In analogy to the procedure described in example 52A], 3-hydroxy-benzaldehyde was reacted with ethyl-bromoisobutyrate to give the title compound in form of a grey viscous oil.

B] 2-Methyl-2-[3-((E)-2-nitro-vinyl)-phenoxy-propionic acid ethyl ester 7.8 g (33 mmol) of 2-(3-formyl-phenoxy)-2-methyl-propionic acid ethyl ester was dissolved in 50 ml glacial acetic acid; then, 10.7 ml=12.09 g (198 mmol) of nitromethane and 7.93 g (106 mmol) of ammonium acetate were added and the reaction mixture heated for 30 min. at reflux temperature. After cooling to ambient temperature, it was poured into crashed ice and extracted twice with ethyl acetate. The combined organic phases were washed with water and brine and dried over anhydrous magnesium sulfate. After evaporation of the solvent, the crude product was purified by flash chromatography ($SiO_2$, heptane/EtOAc) to give 6.56 g of the title compound as yellow oil.

MS: 279.2 $(M)^+$.

C] 2-[3-(2-Amino-ethyl)-phenoxy-2-methyl-propionic acid ethyl ester 7.82 g (28.0 mmol) of 2-methyl-2-[3-((E)-2-nitro-vinyl)-phenoxy]-propionic acid ethyl ester was dissolved in 150 ml ethanol; 6.2 ml (39.7 mmol) hydrochloric acid in ethanol and 1.6 g of Pd-charcoal (10%) were added and the reaction mixture was then hydrogenated under 1 atm of $H_2$-pressure during 5 hours. It was subsequently filtered (Celite), the filter cake was washed twice with ethanol and filtrate was evaporated. The residue was then partitioned between crashed ice/$Na_2CO_3$-solution/$MeCl_2$ and extracted twice with $MeCl_2$; the organic phases were washed with water, dried ($MgSO_4$) and evaporated. The crude product was purified by flash chromatography ($SiO_2$, $MeCl_2$/MeOH) to give 4.36 g of the title compound as yellow oil.

MS: 252.1 $(M+H)^+$.

D] 2-Methyl-2-[3-(2-{2-[2-methyl-6-(4-trifluoromethyl-phenyl)-pyridin-3-yl]-acetylamino}-ethyl)-phenoxy-propionic acid In analogy to the procedures described in example 26B] and 26C], 2-[3-(2-amino-ethyl)-phenoxy]-2-methyl-propionic acid ethyl ester was reacted with [2-methyl-6-(4-trifluoromethyl-phenyl)-pyridin-3-yl]-acetic acid (example 26E]) to give 2-methyl-2-[3-(2-{2-[2-methyl-6-(4-trifluoromethyl-phenyl)-pyridin-3-yl]-acetylamino}-ethyl)-phenoxy]-propionic acid ethyl ester, which was subsequently saponified to yield the title compound as colorless solid.

MS: 499.1 $(M-H)^-$.

Example 56

2-Methyl-2-[3-(2-{[2-methyl-6-(4-trifluoromethyl-phenyl)-pyridine-3-carbonyl]-amino}-ethyl)-phenoxy]-propionic acid In analogy to the procedures described in example 26B] and 26C], 2-[3-(2-amino-ethyl)-phenoxy]-2-methyl-propionic acid ethyl ester (example 55C]) was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-methyl-2-[3-(2-{[2-methyl-6-(4-trifluoromethyl-phenyl)-pyridine-3-carbonyl]-amino}-ethyl)-phenoxy]-propionic acid ethyl ester, which was subsequently-saponified to yield the title compound as colorless solid.

MS: 485.3 $(M-H)^-$.

Example 57

2-[3-(2-{[4-Cyclopropyl-2-(4-trifluoromethyl-phenyl)-pyrimidine-5-carbonyl-amino}-ethyl)-phenoxy]-2-methyl-propionic acid In analogy to the procedures described in example 26B] and 26C], 2-[3-(2-amino-ethyl)-phenoxy]-2-methyl-propionic acid ethyl ester (example 55C]) was reacted with 4-cyclopropyl-2-(4-trifluoromethyl-phenyl)-pyrimidine-5-carboxylic acid (example 53B]) to give 2-[3-(2-{[4-cyclopropyl-2-(4-trifluoromethyl-phenyl)-pyrimidine-5-carbonyl]-amino}-ethyl)-phenoxy]-2-methyl-propionic acid ethyl ester, which was subsequently saponified to yield the title compound as colorless solid.

MS: 512.2 $(M-H)^-$.

Example 58

2-[3-({2-[4-Butyl-2-(4-trifluoromethyl-phenyl)-pyrimidin-5-yl]-acetyl}-methyl-amino)-phenoxy]-2-methyl-propionic acid In analogy to the procedures described in example 26B] and 26C], 2-methyl-2-(3-methylamino-phenoxy)-propionic acid ethyl ester (example 26 A]) was reacted with [4-butyl-2-(4-trifluoromethyl-phenyl)-pyrimidin-5-yl]-acetic acid (prepared starting from 3-oxo-heptanoic acid ethyl ester in analogy to the sequences described in examples 27C] to 27F] and examples 26D] and 26E]) to give 2-[3-({2-[4-butyl-2-(4-trifluoromethyl-phenyl)-pyrimidin-5-yl]-acetyl}-methyl-amino)-phenoxy]-2-methyl-propionic acid ethyl ester, which was subsequently saponified to yield the title compound as light yellow amorphous solid.

MS: 528.1 $(M-H)^-$.

Example 59

2-Methyl-2-(3-{methyl-[2-methyl-6-(4-trifluoromethyl-phenyl)-pyridin-3-ylmethyl]-carbamoyl}-phenoxy)-propionic acid

A] 3-(1-Ethoxycarbonyl-1-methyl-ethoxy)-benzoic acid 3.33 g (14.1 mmol) of 2-(3-formyl-phenoxy)-2-methyl-propionic acid ethyl ester (example 55A]) was dissolved in 60 ml of tert.-butanol; 7.5 ml (70.5 mmol) of 2-methyl-2-butene was added, followed by a solution of 4.14 g (36.6 mmol) of sodium chlorite and 3.30 g (21.1 mmol) of sodium dihydrogen phosphate in 35 ml of water. After 2 hours, the reaction mixture was poured into crashed ice/EtOAc and extracted twice with EtOAc; the organic phases were washed with water, dried ($MgSO_4$) and evaporated. The crude product was purified by recrystallisation from EtOAc/heptane to give 3.19 g of the title compound as colorless solid.

MS: 251.0 (M–H)–.

B] 2-Methyl-2-(3-methylcarbamoyl-phenoxy)-propionic acid ethyl ester 1.0 g (4.0 mmol) of 3-(1-ethoxycarbonyl-1-methyl-ethoxy)-benzoic acid was dissolved in 50 ml of methylene chloride; then, 1.5 ml (4.0 mmol) of a methylamine-solution in ethanol was added. The reaction mixture was cooled down to 0° C. and 0.91 g (4.8 mmol) of N-(3-dimethylaminopropyl)-N'-ethylcarbodiimide hydrochloride and 1.50 g (11.9 mmol) of 4-dimethylaminopyridine were added. After stirring for two hours at ambient temperature, it was poured into crashed ice/HCl (1N) and extracted twice with $MeCl_2$. The combined organic phases were washed with water and brine and dried over anhydrous magnesium sulfate. After evaporation of the solvent, the crude product was purified by flash chromatography ($SiO_2$, $MeCl_2$/MeOH) to give 0.97 g of the title compound in form of colorless needles.

MS: 266.3 $(M+H)^+$.

C] 2-Methyl-2-(3-{methyl-[2-methyl-6-(4-trifluoromethyl-phenyl)-pyridin-3-ylmethyl]-carbamoyl}-phenoxy)-propionic acid ethyl ester 0.28 g (1.05 mmol) of 2-methyl-2-(3-methylcarbamoyl-phenoxy)-propionic acid ethyl ester and 0.36 g (1.05 mmol) of methanesulfonic acid 2-methyl-6-(4-trifluoromethyl-phenyl)-pyridin-3-ylmethyl ester (example 59E]) were dissolved in 15 ml of DMF. The reaction mixture was cooled down to 0° C. and 0.05 g (1.20 mmol) of sodium hydride (55% in mineral oil) was added. After stirring for sixteen hours at ambient temperature, the reaction mixture was poured into crashed ice and extracted twice with $Et_2O$. The combined organic phases were washed with water and brine and dried over anhydrous magnesium sulfate. After evaporation of the solvent, the crude product was purified by flash chromatography (SiO2, heptane/EtOAc) to give 0.249 g of the title compound as yellow oil.

MS: 515.4 $(M+H)^+$.

D] 2-Methyl-2-(3-{methyl-[2-methyl-6-(4-trifluoromethyl-phenyl)-pyridin-3-ylmethyl]-carbamoyl}-phenoxy)-propionic acid In analogy to the procedure described in example 26C], 2-methyl-2-(3-{methyl-[2-methyl-6-(4-trifluoromethyl-phenyl)-pyridin-3-ylmethyl]-carbamoyl}-phenoxy)-propionic acid ethyl ester was saponified to yield the title compound as a light yellow solid.

MS: 485.2 (M–H)–.

The methanesulfonic acid 2-methyl-6-(4-trifluoromethyl-phenyl)-pyridin-3-ylmethyl ester used in example 59C] was synthesized as follows:

E] Methanesulfonic acid 2-methyl-6-(4-trifluoromethyl-phenyl)-pyridin-3-ylmethyl Ester 2.60 g (9.7 mmol) of [2-methyl-6-(4-trifluoromethyl-phenyl)-pyridin-3-yl]-methanol (example 1M]) were dissolved in 50 ml $MeCl_2$ and cooled down to 0° C. 2.55 ml=1.93 g (14.6 mmol) of N-ethyl diisopropylamine was added, followed by 0.85 ml=1.25 g (10.7 mmol) of methane sulfonylchloride, drop by drop. After stirring for 30 min. at ambient temperature, the reaction mixture was poured into crashed ice and extracted twice with $MeCl_2$. The combined organic phases were washed with water and brine, dried over anhydrous magnesium sulfate and evaporated. This gave 3.44 g of crude title compound as yellow solid.

MS: 345.0 $(M)^+$.

Example 60

3-{4-[4-Cyclopropyl-2-(4-trifluoromethyl-phenyl)-pyrimidin-5-ylmethoxy]-2-methyl-phenyl}-propionic acid

A] (E)-3-(4-Benzyloxy-2-methyl-phenyl)-acrylic acid ethyl ester

A mixture of 11.2 g (50 mmol) of 4-benzyloxy-2-methyl-benzaldehyde [PCT Int. Appl. (2002), WO 2002/092084/A1] and of 12.33 g (55 mmol) of triethyl phosphonoacetate in 25 ml of absolute ethanol was added to a cooled solution (0° C.) of sodium ethylate (freshly prepared from 1.38 g (60 mmol) of sodium and 25 ml of absolute ethanol). Subsequently, the mixture was stirred at ambient temperature for 2 hours. Then, the solvent was evaporated and the residue was partioned between tert.-butyl methyl ether and water. The organic layer was washed with brine, dried over anhydrous sodium sulfate and finally evaporated. After crystallization from a mixture of dichloromethane and n-heptane, 12.9 g of (E)-3-(4-benzyloxy-2-methyl-phenyl)-acrylic acid ethyl ester was obtained as beige crystals (87% of theory).

MS: 296.1 $(M)^+$.

B] 3-(4-Hydroxy-2-methyl-phenyl)-propionic acid ethyl ester 5 g (16.8 mmol) of the above prepared (E)-3-(4-benzyloxy-2-methyl-phenyl)-acrylic acid ethyl ester was dissolved in 50 ml of tetrahydrofuran and hydrogenated over 0.8 g of 10% of palladium on charcoal as catalyst at ambient temperature and atmospheric pressure. Filtering off the catalyst and evaporating the solvent yielded 3.5 g of the title compound as light yellow oil (100% of theory).

MS: 208.1 $(M)^+$.

C] 3-{4-[4-Cyclopropyl-2-(4-trifluoromethyl-phenyl)-pyrimidin-5-ylmethoxy-2-methyl-phenyl}-propionic acid In analogy to the procedures described in examples 8A] and 31B], 3-(4-hydroxy-2-methyl-phenyl)-propionic acid ethyl ester was reacted with 5-chloromethyl-4-cyclopropyl-2-(4-trifluoromethyl-phenyl)-pyrimidine (example 27F]) to give 3-{4-[4-cyclopropyl-2-(4-trifluoromethyl-phenyl)-pyrimidin-5-ylmethoxy]-2-methyl-phenyl}-propionic acid ethyl ester, which was subsequently saponified to yield the title compound as colorless solid.

MS: 455.8 (M–H)–.

Example 61

3-{4-[4-Cyclopropyl-2-(4-trifluoromethyl-phenyl)-pyrimidin-5-ylmethoxy]-3-ethoxy-phenyl}-propionic acid In analogy to the procedures described in examples 8A] and 31B], 3-(3-ethoxy-4-hydroxy-phenyl)-propionic acid ethyl ester [Eur. Pat. Appl. (1996), EP 710659/A1] was reacted with 5-chloromethyl-4-cyclopropyl-2-(4-trifluoromethyl-phenyl)-pyrimidine (example 27F]) to give 3-{4-[4-cyclopropyl-2-(4-trifluoromethyl-phenyl)-pyrimidin-5-ylmethoxy]-3-ethoxy-phenyl}-propionic acid ethyl ester, which was subsequently saponified to yield the title compound as colorless solid.

MS: 485.3 (M–H)–.

Example 62

3-{3-Ethoxy-4-[2-methyl-6-(4-trifluoromethyl-phenyl)-pyridin-3-ylmethoxy]-phenyl}-propionic acid In analogy to the procedures described in examples 8A] and 31B], 3-(3-ethoxy-4-hydroxy-phenyl)-propionic acid ethyl ester [Eur. Pat. Appl. (1996), EP 710659/A1] was reacted with 3-chloromethyl-2-methyl-6-(4-trifluoromethyl-phenyl)-pyridine (example 1N]) to give 3-{3-ethoxy-4-[2-methyl-6-(4-trifluoromethyl-phenyl)-pyridin-3-ylmethoxy]- phenyl}-propionic acid ethyl ester, which was subsequently saponified to yield the title compound as colorless solid.

MS: 458.4 (M−H)−.

Example 63

3-{2-Methyl-4-[5-(4-trifluoromethyl-phenyl)-pyrimidin-2-ylmethoxy]-phenyl}-propionic acid A] In analogy to the procedures described in examples 8A] and 31B], 3-(4-hydroxy-2-methyl-phenyl)-propionic acid ethyl ester (example 60B]) was reacted with 2-bromomethyl-5-(4-trifluoromethyl-phenyl)-pyrimidine (example 63C]) to give 3-{2-methyl-4-[5-(4-trifluoromethyl-phenyl)-pyrimidin-2-ylmethoxy]-phenyl}-propionic acid ethyl ester, which was subsequently saponified to yield the title compound as off-white solid.

MS: 415.2 (M−H)−.

The necessary building block 2-bromomethyl-5-(4-trifluoromethyl-phenyl)-pyrimidine used in the procedure above was prepared as follows:

B] 2-Methyl-5-(4-trifluoromethyl-phenyl)-pyrimidine

A solution of 7.95 g (75 mmol) of sodium carbonate in 15 ml of water was added to a mixture of 2.6 g (15 mmol) of 5-bromo-2-methylpyrimidine [Coll. Czech.Chem. Comm. 14 (1949), 223–235], of 4 g (21 mmol) of 4-(trifluoromethyl)benzeneboronic acid and of 0.52 g (0.45 mmol) of tetrakis(triphenylphosphine)palladium in a mixture of 50 ml of 1,2-dimethoxy-ethane and of 30 ml of ethanol. The reaction mixture was stirred at 80° C. for 2 hours; afterwards, it was concentrated by distilling off the major part of the organic solvents. Subsequently, the residue was extracted with 3 portions of tert.-butyl methyl ether. The combined organic phases were washed with water and brine, dried over anhydrous sodium sulfate and finally evaporated. The residue was chromatographed on silicagel with a mixture of dichloromethane/tert.-butyl methyl ether (9/1 vol./vol.) as eluent. 3 g of the title compound was obtained as greenish solid.

MS: 239.2 (M+H)+.

C] 2-Bromomethyl-5-(4-trifluoromethyl-phenyl)-pyrimidine 0.31 g (1.3 mmol) of 2-methyl-5-(4-trifluoromethyl-phenyl)-pyrimidine, 0.255 g (1.43 mmol) of N-bromosuccinimide and 0.15 g (0.91 mmol) of 2,2'-azobis-(2-methyl-propionitril) were dissolved in 5 ml of carbon tetrachloride and the mixture was stirred at 75° C. Two portions of 0.13 g (0.73 mmol) of N-bromosuccinimide and of 0.075 g (0.046 mmol) of 2,2'-azobis-(2-methyl-propionitril) were added to the reaction mixture, after 4 and 8 hours, respectively, and heating was continued for additional 16 hours. After cooling to ambient temperature, the mixture was chromatographed on silicagel with dichloromethane as eluent. 0.145 g of the title compound was obtained as pale yellow solid.

MS: 316.0 (M)+, 1Br.

Example 64

2-[3-({2-[4-Cyclopropyl-2-(4-trifluoromethyl-phenyl)-pyrimidin-5-yl]-acetyl}-methyl-amino)-phenoxy]-2-methyl-propionic acid In analogy to the procedures described in example 26B] and 26C], 2-methyl-2-(3-methylamino-phenoxy)-propionic acid ethyl ester (example 26 A]) was reacted with [4-cyclopropyl-2-(4-trifluoromethyl-phenyl)-pyrimidin-5-yl]-acetic acid (prepared from 5-chloromethyl-4-cyclopropyl-2-(4-trifluoromethyl-phenyl)-pyrimidine (example 27F]) in analogy to the sequences described in examples 26D] and 26E]) to give 2-[3-({2-[4-cyclopropyl-2-(4-trifluoromethyl-phenyl)-pyrimidin-5-yl]-acetyl}-methyl-amino)-phenoxy]-2-methyl-propionic acid ethyl ester, which was subsequently saponified to yield the title compound as colorless solid.

MS: 512.2 (M−H)−.

Example 65

2-[3-(2-{2-[4-Cyclopropyl-2-(4-trifluoromethyl-phenyl)-pyrimidin-5-yl]-acetylamino}-ethyl)-phenoxy]-2-methyl-propionic acid In analogy to the procedures described in example 26B] and 26C], 2-[3-(2-amino-ethyl)-phenoxy]-2-methyl-propionic acid ethyl ester (example 55C]) was reacted with [4-cyclopropyl-2-(4-trifluoromethyl-phenyl)-pyrimidin-5-yl]-acetic acid (prepared from 5-chloromethyl-4-cyclopropyl-2-(4-trifluoromethyl-phenyl)-pyrimidine (example 27F]) in analogy to the sequences described in examples 26D] and 26E]) to give 2-[3-(2-{2-[4-cyclopropyl-2(4-trifluoromethyl-phenyl)-pyrimidin-5-yl]-acetylamino}-ethyl)-phenoxy]-2-methyl-propionic acid ethyl ester, which was subsequently saponified to yield the title compound as colorless solid.

MS: 526.1 (M−H)−.

Example 66

2-[3-({[4-Cyclopropyl-2-(4-trifluoromethyl-phenyl)-pyrimidine-5-carbonyl]-amino}-methyl)-phenoxy]-2-methyl-propionic acid In analogy to the procedures described in example 26B] and 26C], 2-(3-aminomethyl-phenoxy)-2-methyl-propionic acid ethyl ester (example 52B]) was reacted with 4-cyclopropyl-2-(4-trifluoromethyl-phenyl)-pyrimidine-5-carboxylic acid (example 53B]) to give 2-[3-({[4-cyclopropyl-2-(4-trifluoromethyl-phenyl)-pyrimidine-5-carbonyl]-amino}-methyl)-phenoxy]-2-methyl-propionic acid ethyl ester, which was subsequently saponified to yield the title compound as colorless amorphous solid.

MS: 498.1 (M−H)−.

Example 67

2-Methyl-2-[3-({2-[2-methyl-6-(4-trifluoromethyl-phenyl)-pyridin-3-yl]-acetylamino}-methyl)-phenoxy]-propionic acid In analogy to the procedures described in example 26B] and 26C], 2-(3-aminomethyl-phenoxy)-2-methyl-propionic acid ethyl ester (example 52B]) was reacted with [2-methyl-6-(4-trifluoromethyl-phenyl)-pyridin-3-yl]-acetic acid (example 26E]) to give 2-methyl-2-[3-({2-[2-methyl-6-(4-trifluoromethyl-phenyl)-pyridin-3-yl]-acetylamino}-methyl)-phenoxy]-propionic acid ethyl ester, which was subsequently saponified to yield the title compound as colorless solid.

MS: 485.3 (M−H)⁻.

Example 68

2-[3-({2-[4-Cyclopropyl-2-(4-trifluoromethyl-phenyl)-pyrimidin-5-yl]-acetylamino}-methyl)-phenoxy]-2-methyl-propionic acid In analogy to the procedures described in example 26B] and 26C], 2-(3-aminomethyl-phenoxy)-2-methyl-propionic acid ethyl ester (example 52B]) was reacted with [4-cyclopropyl-2-(4-trifluoromethyl-phenyl)-pyrimidin-5-yl]-acetic acid (prepared from 5-chloromethyl-4-cyclopropyl-2-(4-trifluoromethyl-phenyl)-pyrimidine (example 27F]) in analogy to the sequences described in examples 26D] and 26E]) to give 2-[3-({2-[4-cyclopropyl-2-(4-trifluoromethyl-phenyl)-pyrimidin-5-yl]-acetylamino}-methyl)-phenoxy]-2-methyl-propionic acid ethyl ester, which was subsequently saponified to yield the title compound as colorless solid.

MS: 512.2 (M−H)⁻.

Example 69

2-Methyl-2-[3-({[2-methyl-6-(4-trifluoromethyl-phenyl)-pyridine-3-carbonyl]-amino}-methyl)-phenoxy]-propionic acid In analogy to the procedures described in example 26B] and 26C], 2-(3-aminomethyl-phenoxy)-2-methyl-propionic acid ethyl ester (example 52B]) was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-methyl-2-[3-({[2-methyl-6-(4-trifluoromethyl-phenyl)-pyridine-3-carbonyl]-amino}-methyl)-phenoxy]-propionic acid ethyl ester, which was subsequently saponified to yield the title compound as amorphous colorless solid.

MS: 471.1 (M−H)⁻.

Example 70

2-Methyl-2-(2-methyl-5-{2-[2-methyl-6-(4-trifluoromethyl-phenyl)-pyridin-3-yl]-ethoxy}-phenoxy)-propionic acid A] 2-(5-Hydroxy-2-methyl-phenoxy)-2-methyl-propionic acid ethyl ester 5.10 g (14.9 mmol) 2-(5-benzyloxy-2-formyl-phenoxy)-2-methyl-propionic acid ethyl ester (prepared from 4-benzyloxy-2-hydroxybenzaldehyde and ethyl-bromoisobutyrate in analogy to the procedure described in example 52A]) was dissolved in 100 ml of ethanol and hydrogenated with 1.0 g of Pd—C (5%), 2 bar H₂, 25° C., for two hours. The reaction mixture was filtered (Celite), the filter cake was washed twice with EtOH and the filtrate was evaporated. The crude product was purified by flash chromatography (SiO₂, heptane/EtOAc) to give 3.37 g of the title compound as light yellow oil.

MS: 237.0 (M−H)⁻.

B] 2-Methyl-2-(2-methyl-5-{2-[2-methyl-6-(4-trifluoromethyl-phenyl)-pyridin-3-yl]-ethoxy}-phenoxy)-propionic acid ethyl ester 0.24 g (1.0 mmol) of the above prepared 2-(5-hydroxy-2-methyl-phenoxy)-2-methyl-propionic acid ethyl ester, 0.31 g (1.10 mmol) of 2-[2-methyl-6-(4-trifluoromethyl-phenyl)-pyridin-3-yl]-ethanol (see below example 70E]) and 0.32 g (1.20 mmol) of triphenylphosphine were dissolved in 10 ml of THF. The stirred reaction mixture was cooled down to 0° C. and a solution of 0.27 g (1.15 mmol) of di-tert.-butyl azodicarboxylate in 5 ml of THF was added drop by drop. Then, the reaction warmed up to ambient temperature. After 20 hours, the solvent was evaporated and the residue purified by chromatography (SiO2, heptane/EtOAc=95:5 to 9:1) to give 0.23 g of the title compound as colorless oil.

MS: 502.4 (M+H)⁺.

C] 2-Methyl-2-(2-methyl-5-{2-[2-methyl-6-(4-trifluoromethyl-phenyl)-pyridin-3-yl]-ethoxy}-phenoxy)-propionic acid In analogy to the procedure described in example 26C], 2-methyl-2-(2-methyl-5-{2-2-methyl-6-(4-trifluoromethyl-phenyl)-pyridin-3-yl]-ethoxy}-phenoxy)-propionic acid ethyl ester was saponified to yield the title compound as colorless solid.

MS: 472.1 (M−H)⁻.

The necessary building block 2-[2-methyl-6-(4-trifluoromethyl-phenyl)-pyridin-3-yl]-ethanol used in the procedure above was prepared as follows:

D] [2-Methyl-6-(4-trifluoromethyl-phenyl)-pyridin-3-yl]-acetic acid ethyl ester

A solution of 2.55 g (8.63 mmol) of [2-methyl-6-(4-trifluoromethyl-phenyl)-pyridin-3-yl]-acetic acid (example 26E]) in 25 ml of methanol was cooled to −10° C.; 1.88 ml (25.9 mmol) of thionyl chloride was added. The reaction mixture was then stirred at ambient temperature for 2 hours. Subsequently, the solution was stirred with ice water, then extracted with three portions of 50 ml of tert.-butyl methyl ether. The combined organic layers were washed with water, aqueous sodium hydrogen carbonate and brine, and dried over anhydrous sodium sulfate. After evaporation of the solvent, 2.6 g of the title compound was obtained as light brown solid.

MS: 309.1(M)⁺.

E] 2-[2-Methyl-6-(4-trifluoromethyl-phenyl)-pyridin-3-yl]-ethanol 2.6 g (8.40 mmol) of the above prepared [2-methyl-6-(4-trifluoromethyl-phenyl)-pyridin-3-yl]-acetic acid methyl ester dissolved in 15 ml of dry tetrahydrofuran was added under an argon atmosphere within 15 minutes to a stirred suspension of 0.38 g (10 mmol) of lithium aluminum hydride in 5 ml of tetrahydrofuran. The reaction was exothermic. Subsequently, the mixture was stirred at room temperature for 1 hour. Then, 1 ml of ethyl acetate was dropped into the reaction mixture, followed by water, drop after drop, under argon, with stirring and cooling until the gas evolution ceased. The reaction mixture was then diluted with 50 ml of ethyl acetate, dried over anhydrous sodium sulfate, and filtered. The filtrate was evaporated i. V. and the residue was chromatographed on SiO$_2$ with a mixture of dichloromethane and tert.-butyl methyl ether (4/1 vol./vol.) as eluent. Thereby, 1.88 g of the title compound was obtained as white solid.

MS: 281.1 (M)$^+$.

Example 71

2-Methyl-2-{2-methyl-5-[2-methyl-6-(4-trifluoromethyl-phenyl)-pyridin-3-ylmethoxy]-phenoxy}-propionic acid In analogy to the procedures described in examples 70B] and 26C], 2-(5-hydroxy-2-methyl-phenoxy)-2-methyl-propionic acid ethyl ester (example 70A]) was reacted with [2-methyl-6-(4-trifluoromethyl-phenyl)-pyridin-3-yl]-methanol (example 1M]) in the presence of triphenylphosphine and di-tert.-butyl azodicarboxylate to give 2-methyl-2-{2-methyl-5-[2-methyl-6-(4-trifluoromethyl-phenyl)-pyridin-3-ylmethoxy]-phenoxy}-propionic acid ethyl ester which was subsequently saponified to yield the title compound as colorless solid.

MS: 458.2 (M–H)$^-$.

Example 72

[rac]-3-(2-Methyl-4-{1-[2-methyl-6-(4-trifluoromethyl-phenyl)-pyridin-3-yl]-ethoxy}-phenyl)-propionic acid In analogy to the procedures described in examples 8A] and 31B], 3-(4-hydroxy-2-methyl-phenyl)-propionic acid ethyl ester (example 60B]) was reacted with [rac]-3-(1-chloro-ethyl)-2-methyl-6-(4-trifluoromethyl-phenyl)-pyridine (example 17C]) to give [rac]-3-(2-methyl-4-{1-[2-methyl-6-(4-trifluoromethyl-phenyl)-pyridin-3-yl]-ethoxy}-phenyl)-propionic acid ethyl ester, which was subsequently saponified to yield the title compound as light yellow solid.

MS: 442.2 (M–H)–.

Example 73

3-{3-Methyl-4-[2-methyl-6-(4-trifluoromethyl-phenyl)-pyridin-3-ylmethoxy]-phenyl}-propionic acid A] 3-(4-Hydroxy-3-methyl-phenyl)-propionic acid ethyl ester In analogy to the procedures described in examples 60A] and 60B], 4-benzyloxy-3-methyl-benzaldehyde [Bioorganic & Medicinal Chemistry Letters (2003), 13(3), 399–403] was reacted with triethyl phosphonoacetate to give (E)-3-(4-benzyloxy-3-methyl-phenyl)-acrylic acid ethyl ester, which was subsequently hydrogenated to yield the title compound in form of a grey solid.

MS: 208.1 (M)$^+$.

B] 3-{3-Methyl-4-[2-methyl-6-(4-trifluoromethyl-phenyl)-pyridin-3-ylmethoxy]-phenyl}-propionic acid In analogy to the procedures described in examples 8A] and 31B], 3-(4-hydroxy-3-methyl-phenyl)-propionic acid ethyl ester was reacted with 3-chloromethyl-2-methyl-6-(4-trifluoromethyl-phenyl)-pyridine (example 1N]) to give 3-{3-methyl-4-[2-methyl-6-(4-trifluoromethyl-phenyl)-pyridin-3-ylmethoxy]-phenyl}-propionic acid ethyl ester, which was subsequently saponified to yield the title compound as colorless solid.

MS: 428.3 (M–H)–.

Example 74

[rac]-3-(3-Methyl-4-{1-[2-methyl-6-(4-trifluoromethyl-phenyl)-pyridin-3-yl]-ethoxy}-phenyl)-propionic acid In analogy to the procedures described in examples 8A] and 31B], 3-(4-hydroxy-3-methyl-phenyl)-propionic acid ethyl ester (example 73A]) was reacted with [rac]-3-(1-chloro-ethyl)-2-methyl-6-(4-trifluoromethyl-phenyl)-pyridine (example 17C]) to give [rac]-3-(3-methyl-4-{1-[2-methyl-6-(4-trifluoromethyl-phenyl)-pyridin-3-yl]-ethoxy}-phenyl)-propionic acid ethyl ester, which was subsequently saponified to yield the title compound as colorless solid.

MS: 442.2 (M–H)–.

Example 75

2-[3-({2-[4-Cyclopropyl-2-(4-trifluoromethyl-phenyl)-pyrimidin-5-yl]-acetyl}-methyl-amino)-5-trifluoromethyl-phenoxy]-2-methyl-propionic acid A] 2-Methyl-2-(3-nitro-5-trifluoromethyl-phenoxy)-propionic acid ethyl ester In analogy to the procedure described in example 52A], 3-nitro-5-trifluoromethyl-phenol [PCT Int. Appl. (1994), WO 94/20467A1] was reacted with ethyl bromoisobutyrate to yield the title compound as yellow oil.

MS: 321.0 (M)$^+$.

B] 2-(3-Amino-5-trifluoromethyl-phenoxy)-2-methyl-propionic acid ethyl ester 13.8 g (43 mmol) of 2-methyl-2-(3-nitro-5-trifluoromethyl-phenoxy)-propionic acid ethyl ester was dissolved in 300 ml of ethanol and hydrogenated with 1.14 g of Pd—C (10%), 1 bar H$_2$, 25° C., for two hours. The reaction mixture was then filtered (Celite), the filter cake was washed twice with ethanol and the filtrate was evaporated. The crude product was purified by flash chromatography (SiO$_2$, heptane/EtOAc) which gave 11.0 g of the title compound as yellow oil.

MS: 292.2 (M+H)$^+$.

C] 2-Methyl-2-(3-methylamino-5-trifluoromethyl-phenoxy)-propionic acid ethyl ester In analogy to the procedures described in example 5D], 5E] and 5F], 2-(3-amino-5-trifluoromethyl-phenoxy)-2-methyl-propionic acid ethyl ester was converted into 2-(3-tert-butoxycarbonylamino-5-trifluoromethyl-phenoxy)-2-methyl-propionic acid ethyl ester by treatment with di-tert-butyl dicarbonate and sodium hydrogen carbonate in dioxane/water at r.t., methylated at nitrogen to yield 2-[3-(tert-butoxycarbonyl-methyl-amino)-5-trifluoromethyl-phenoxy]-2-methyl-propionic acid ethyl ester and deprotected again to yield the title compound as light yellow oil.

MS: 306.3 (M+H)+.

D] 2-[3-({2-[4-Cyclopropyl-2-(4-trifluoromethyl-phenyl)-pyrimidin-5-yl]-acetyl}-methyl-amino)-5-trifluoromethyl-phenoxy]-2-methyl-propionic acid In analogy to the procedures described in example 26B] and 26C], 2-methyl-2-(3-methylamino-5-trifluoromethyl-phenoxy)-propionic acid ethyl ester was reacted with [4-cyclopropyl-2-(4-trifluoromethyl-phenyl)-pyrimidin-5-yl]-acetic acid (prepared from 5-chloromethyl-4-cyclopropyl-2-(4-trifluoromethyl-phenyl)-pyrimidine (example 27F]) in analogy to the sequences described in examples 26D] and 26E]) to give 2-[3-({2-[4-cyclopropyl-2-(4-trifluoromethyl-phenyl)-pyrimidin-5-yl]-acetyl}-methyl-amino)-5-trifluoromethyl-phenoxy)-2-methyl-propionic acid ethyl ester, which was subsequently saponified to yield the title compound as light yellow oil.

MS: 580.1 (M–H)−.

Example 76

2-Methyl-2-[3-(methyl-{2-[2-methyl-6-(4-trifluoromethyl-phenyl)-pyridin-3-yl]-acetyl}-amino)-5-trifluoromethyl-phenoxy]-propionic acid In analogy to the procedures described in example 26B] and 26C], 2-methyl-2-(3-methylamino-5-trifluoromethyl-phenoxy)-propionic acid ethyl ester (example 75C]) was reacted with [2-methyl-6-(4-trifluoromethyl-phenyl)-pyridin-3-yl]-acetic acid (example 26E]) to give 2-methyl-2-[3-(methyl-{2-[2-methyl-6-(4-trifluoromethyl-phenyl)-pyridin-3-yl]-acetyl}-amino)-5-trifluoromethyl-phenoxy]-propionic acid ethyl ester, which was subsequently saponified to yield the title compound as light yellow oil.

MS: 553.1 (M–H)−.

Example 77

2-[4-({2-[4-Cyclopropyl-2-(4-trifluoromethyl-phenyl)-pyrimidin-5-yl]-acetylamino}-methyl)-phenoxy]-2-methyl-propionic acid In analogy to the procedures described in example 26B] and 26C], 2-(4-aminomethyl-phenoxy)-2-methyl-propionic acid ethyl ester [PCT Int. Appl. (2002), WO 2002/096895A1] was reacted with [4-cyclopropyl-2-(4-trifluoromethyl-phenyl)-pyrimidin-5-yl]-acetic acid (prepared from 5-chloromethyl-4-cyclopropyl-2-(4-trifluoromethyl-phenyl)-pyrimidine (example 27F]) in analogy to the sequences described in examples 26D] and 26E]) to give 2-[4-({2-[4-cyclopropyl-2-(4-trifluoromethyl-phenyl)-pyrimidin-5-yl]-acetylamino}-methyl)-phenoxy]-2-methyl-propionic acid ethyl ester, which was subsequently saponified to yield the title compound as colorless solid.

MS: 512.2 (M–H)−.

Example 78

2-Methyl-2-[4-({2-[2-methyl-6-(4-trifluoromethyl-phenyl)-pyridin-3-yl]-acetylamino}-methyl)-phenoxy]-propionic acid In analogy to the procedures described in example 26B] and 26C), 2-(4-aminomethyl-phenoxy)-2-methyl-propionic acid ethyl ester [PCT Int. Appl. (2002), WO 2002/096895A1] was reacted with [2-methyl-6-(4-trifluoromethyl-phenyl)-pyridin-3-yl]-acetic acid (example 26E]) to give 2-methyl-2-[4-({2-[2-methyl-6-(4-trifluoromethyl-phenyl)-pyridin-3-yl]-acetylamino}-methyl)-phenoxy]-propionic acid ethyl ester, which was subsequently saponified to yield the title compound as colorless amorphous solid.

MS: 485.2 (M–H)−.

Example 79

2-[4-({[4-Cyclopropyl-2-(4-trifluoromethyl-phenyl)-pyrimidine-5-carbonyl]-amino}-methyl)-phenoxy]-2-methyl-propionic acid In analogy to the procedures described in example 26B] and 26C], 2-(4-aminomethyl-phenoxy)-2-methyl-propionic acid ethyl ester [PCT Int. Appl. (2002), WO 2002/096895A1] was reacted with 4-cyclopropyl-2-(4-trifluoromethyl-phenyl)-pyrimidine-5-carboxylic acid (example 53B]) to give 2-[4-({[4-cyclopropyl-2-(4-trifluoromethyl-phenyl)-pyrimidine-5-carbonyl]-amino}-methyl)-phenoxy]-2-methyl-propionic acid ethyl ester, which was subsequently saponified to yield the title compound as colorless oil.

MS: 498.1 (M–H)−.

Example 80

2-Methyl-2-[4-({[2-methyl-6-(4-trifluoromethyl-phenyl)-pyridine-3-carbonyl]-amino}-methyl)-phenoxy]-propionic acid In analogy to the procedures described in example 26B] and 26C], 2-(4-aminomethyl-phenoxy)-2-methyl-propionic acid ethyl ester [PCT Int. Appl. (2002), WO 2002/096895A1] was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-methyl-2-[4-({[2-methyl-6-(4-trifluoromethyl-phenyl)-pyridine-3-carbonyl]-amino}-methyl)-phenoxy]-propionic acid ethyl ester, which was subsequently saponified to yield the title compound as colorless oil.

MS: 471.1 (M–H)−.

Example 81

2-Methyl-2-(3-{methyl-[4-methyl-2-(4-trifluoromethyl-phenyl)-pyrimidin-5-ylmethyl]-carbamoyl}-phenoxy)-propionic acid In analogy to the procedures described in examples 59C] and 26C], 2-methyl-2-(3-methylcarbamoyl-phenoxy)-propionic acid ethyl ester (example 59B]) was reacted 5-chloromethyl-4-methyl-2-(4-trifluoromethyl-phenyl)-pyrimidine (prepared from methylacetoacetate in analogy to the procedures described in examples 27C] to 27F]) to give 2-methyl-2-(3-}methyl-[4-methyl-2-(4-trifluoromethyl-phenyl)-pyrimidin-5-ylmethyl]-carbamoyl}-phenoxy)-propionic acid ethyl ester, which was subsequently saponified to yield the title compound as light brown oil.

MS: 486.3 (M–H)−.

Example 82

2-(3-{[4-(2-Methoxy-ethyl)-6-methyl-2-(4-trifluoromethyl-phenyl)-pyrimidin-5-ylmethyl]-methyl-carbamoyl}-phenoxy)-2-methyl-propionic acid In analogy to the procedures described in examples 59C] and 26C], 2-methyl-2-(3-methylcarbamoyl-phenoxy)-propionic acid ethyl ester (example 59B]) was reacted 5-chloromethyl-4-(2-methoxy-ethyl)-6-methyl-2-(4-trifluoromethyl-phenyl)-pyrimidine (example 118G]) to give 2-(3-{[4-(2-methoxy-ethyl)-6-methyl-2-(4-trifluoromethyl-phenyl)-pyrimidin-5-ylmethyl]-methyl-carbamoyl}-phenoxy)-2-methyl-propionic acid ethyl ester, which was subsequently saponified to yield the title compound as light brown solid.

MS: 544.2 (M−H)$^-$.

Example 83

2-Methyl-2-{4-[(methyl-{2-[2-methyl-6-(4-trifluoromethyl-phenyl)-pyridin-3-yl]-acetyl}-amino)-methyl]-phenoxy}-propionic acid

A] 2-Methyl-2-(4-methylaminomethyl-phenoxy)-propionic acid ethyl ester

In analogy to the procedure described in example 52A], (4-hydroxy-benzyl)-carbamic acid tert-butyl ester was reacted with ethyl-bromoisobutyrate to give 2-[4-(tert-butoxycarbonylamino-methyl)-phenoxy]-2-methyl-propionic acid ethyl ester; this compound was then reacted with sodium hydride, methyl iodide in analogy to the procedure described in example 5E] to give 2-{4-[(tert-butoxycarbonyl-methyl-amino)-methyl]-phenoxy}-2-methyl-propionic acid ethyl ester, subsequent deprotection in analogy to the procedure described in example 5F] gave the title compound as light brown oil.

MS: 252.2 (M+H)$^+$.

B] 2-Methyl-2-{4-[(methyl-{2-[2-methyl-6-(4-trifluoromethyl-phenyl)-pyridin-3-yl]-acetyl}-amino)-methyl]-phenoxy}-propionic acid In analogy to the procedures described in example 26B] and 26C], 2-methyl-2-(4-methylaminomethyl-phenoxy)-propionic acid ethyl ester was reacted with [2-methyl-6-(4-trifluoromethyl-phenyl)-pyridin-3-yl]-acetic acid (example 26E]) to give 2-methyl-2-{4-[(methyl-{2-[2-methyl-6-(4-trifluoromethyl-phenyl)-pyridin-3-yl]-acetyl}-amino)-methyl]-phenoxy}-propionic acid ethyl ester, which was subsequently saponified to yield the title compound as colorless solid.

MS: 499.1 (M−H)$^-$.

Example 84

2-Methyl-2-[4-(2-{[2-methyl-6-(4-trifluoromethyl-phenyl)-pyridine-3-carbonyl]-amino}-ethyl)-phenoxy]-propionic acid

A] 2-[4-(2-Amino-ethyl)-phenoxy]-2-methyl-propionic acid ethyl ester

In analogy to the procedure described in example 52A], [2-(4-hydroxy-phenyl)-ethyl]-carbamic acid tert-butyl ester was reacted with ethyl-bromoisobutyrate to give 2-[4-(2-tert-butoxycarbonylamino-ethyl)-phenoxy]-2-methyl-propionic acid ethyl ester, subsequent deprotection in analogy to the procedure described in example 5F] the title compound as yellow oil.

MS: 252.2 (M+H)$^+$.

B] 2-Methyl-2-[4-(2-{2-methyl-6-(4-trifluoromethyl-phenyl)-pyridine-3-carbonyl]-amino}-ethyl)-phenoxy-propionic acid In analogy to the procedures described in example 26B] and 26C], 2-[4-(2-amino-ethyl)-phenoxy]-2-methyl-propionic acid ethyl ester was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-methyl-2-[4-(2-{[2-methyl-6-(4-trifluoromethyl-phenyl)-pyridine-3-carbonyl]-amino}-ethyl)-phenoxy]-propionic acid ethyl ester, which was subsequently saponified to yield the title compound as colorless solid.

MS: 485.2 (M−H)$^-$.

Example 85

2-[4-(2-{[4-Cyclopropyl-2-(4-trifluoromethyl-phenyl)-pyrimidine-5-carbonyl]-amino}-ethyl)-phenoxy]-2-methyl-propionic acid In analogy to the procedures described in example 26B] and 26C], 2-[4-(2-amino-ethyl)-phenoxy]-2-methyl-propionic acid ethyl ester (example 84A]) was reacted with 4-cyclopropyl-2-(4-trifluoromethyl-phenyl)-pyrimidine-5-carboxylic acid (example 53B]) to give 2-[4-(2-{[4-cyclopropyl-2-(4-trifluoromethyl-phenyl)-pyrimidine-5-carbonyl]-amino}-ethyl)-phenoxy]-2-methyl-propionic acid ethyl ester, which was subsequently saponified to yield the title compound as colorless solid.

MS: 512.2 (M−H)$^-$.

Example 86

2-Methyl-2-[4-(2-{2-[2-methyl-6-(4-trifluoromethyl-phenyl)-pyridin-3-yl]-acetylamino}-ethyl)-phenoxy]-propionic acid In analogy to the procedures described in example 26B] and 26C], 2-[4-(2-amino-ethyl)-phenoxy]-2-methyl-propionic acid ethyl ester (example 84A]) was reacted with [2-methyl-6-(4-trifluoromethyl-phenyl)-pyridin-3-yl]-acetic acid (example 26E]) to give 2-methyl-2-[4-(2-{2-[2-methyl-6-(4-trifluoromethyl-phenyl)-pyridin-3-yl]-acetylamino}-ethyl)-phenoxy]-propionic acid ethyl ester, which was subsequently saponified to yield the title compound as colorless solid.

MS: 501.3 (M+H)$^+$.

Example 87

2-[4-(2-{2-[4-Cyclopropyl-2-(4-trifluoromethyl-phenyl)-pyrimidin-5-yl]-acetylamino}-ethyl)-phenoxy]-2-methyl-propionic acid In analogy to the procedures described in example 26B] and 26C], 2-[4-(2-amino-ethyl)-phenoxy]-2-methyl-propionic acid ethyl ester (example 84A] ) was reacted with

[4-cyclopropyl-2-(4-trifluoromethyl-phenyl)-pyrimidin-5-yl]-acetic acid (prepared from 5-chloromethyl-4-cyclopropyl-2-(4-trifluoromethyl-phenyl)-pyrimidine (example 27F]) in analogy to the sequences described in examples 26D] and 26E]) to give 2-[4-(2-{2-[4-cyclopropyl-2-(4-trifluoromethyl-phenyl)-pyrimidin-5-yl]-acetylamino}-ethyl)-phenoxy]-2-methyl-propionic acid ethyl ester, which was subsequently saponified to yield the title compound as colorless solid.

MS: 528.4 (M+H)$^+$.

Example 88

2-Methyl-2-{4-[2-(methyl-{2-[2-methyl-6-(4-trifluoromethyl-phenyl)-pyridin-3-yl]-acetyl}-amino)-ethyl]-phenoxy}-propionic acid

A] 2-Methyl-2-[4-(2-methylamino-ethyl)-phenoxy-propionic acid ethyl ester

In analogy to the procedure described in example 52A], [2-(4-hydroxy-phenyl)-ethyl]-carbamic acid tert-butyl ester was reacted with ethyl-bromoisobutyrate to give 2-[4-(2-tert-butoxycarbonylamino-ethyl)-phenoxy]-2-methyl-propionic acid ethyl ester; this compound was subsequently reacted with sodium hydride, methyl iodide in analogy to the procedure described in example 5E] to give 2-{4-[2-(tert-butoxycarbonyl-methyl-amino)-ethyl]-phenoxy}-2-methyl-propionic acid ethyl ester; subsequent deprotection in analogy to the procedure described in example 5F] gave the title compound as light brown oil.

MS: 266.2 (M+H)$^{+-}$.

B] 2-Methyl-2-{4-[2-(methyl-{2-[2-methyl-6-(4-trifluoromethyl-phenyl)-pyridin-3-yl]-acetyl}-amino)-ethyl]-phenoxy-propionic acid In analogy to the procedures described in example 26B] and 26C], 2-methyl-2-[4-(2-methylamino-ethyl)-phenoxy]-propionic acid ethyl ester was reacted with [2-methyl-6-(4-trifluoromethyl-phenyl)-pyridin-3-yl]-acetic acid (example 26E]) to give 2-methyl-2-{4-[2-(methyl-{2-[2-methyl-6-(4-trifluoromethyl-phenyl)-pyridin-3-yl]-acetyl}-amino)-ethyl]-phenoxy}-propionic acid ethyl ester, which was subsequently saponified to yield the title compound as colorless solid.

MS: 513.3 (M−H)$^-$.

Example 89

2-Methyl-2-[4-(2-{methyl-[2-methyl-6-(4-trifluoromethyl-phenyl)-pyridine-3-carbonyl]-amino}-ethyl)-phenoxy]-propionic acid In analogy to the procedures described in example 26B] and 26C], 2-methyl-2-[4-(2-methylamino-ethyl)-phenoxy]-propionic acid ethyl ester (example 88A]) was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-methyl-2-[4-(2-{methyl-[2-methyl-6-(4-trifluoromethyl-phenyl)-pyridine-3-carbonyl]-amino}-ethyl)-phenoxy]-propionic acid ethyl ester, which was subsequently saponified to yield the title compound as colorless solid.

MS: 501.4 (M+H)$^+$.

Example 90

2-{2-Methoxy-4-[2-methyl-6-(4-trifluoromethyl-phenyl)-pyridin-3-ylmethoxy]-phenoxy}-2-methyl-propionic acid

A] 2-(4-Hydroxy-2-methoxy-phenoxy)-2-methyl-propionic acid ethyl ester

In analogy to the procedures described in examples 52A] and 60B], 4-benzyloxy-2-methoxy-phenol [Journal of Organic Chemistry (1980), 45(2), 208–12] was reacted with ethyl-bromoisobutyrate to give 2-(4-benzyloxy-2-methoxy-phenoxy)-2-methyl-propionic acid ethyl ester, which was subsequently hydrogenated to yield the title compound in form of a grey viscous oil.

MS: 253.1 (M−H)$^-$.

B] 2-{2-Methoxy-4-[2-methyl-6-(4-trifluoromethyl-phenyl)-pyridin-3-ylmethoxy-phenoxy}-2-methyl-propionic acid In analogy to the procedures described in examples 8A] and 31B], 2-(4-hydroxy-2-methoxy-phenoxy)-2-methyl-propionic acid ethyl ester was reacted with 3-chloromethyl-2-methyl-6-(4-trifluoromethyl-phenyl)-pyridine (example 1N]) to give 2-{2-methoxy-4-[2-methyl-6-(4-trifluoromethyl-phenyl)-pyridin-3-ylmethoxy]-phenoxy}-2-methyl-propionic acid ethyl ester, which was subsequently saponified to yield the title compound as light yellow solid.

MS: 474.1 (M−H)$^-$.

Example 91

[rac]-2-(2-Methoxy-4-{1-[2-methyl-6-(4-trifluoromethyl-phenyl)-pyridin-3-yl]-ethoxy}-phenoxy)-2-methyl-propionic acid In analogy to the procedures described in examples 8A] and 31B], 2-(4-hydroxy-2-methoxy-phenoxy)-2-methyl-propionic acid ethyl ester (example 90A]) was reacted with [rac]-3-(1-chloro-ethyl)-2-methyl-6-(4-trifluoromethyl-phenyl)-pyridine (example 17C]) to give [rac]-2-(2-methoxy-4-{1-[2-methyl-6-(4-trifluoromethyl-phenyl)-pyridin-3-yl]-ethoxy}-phenoxy)-2-methyl-propionic acid ethyl ester, which was subsequently saponified to yield the title compound as light yellow solid.

MS: 488.1 (M−H)$^-$.

Example 92

3-{2-Methoxy-4-[2-methyl-6-(4-trifluoromethyl-phenyl)-pyridin-3-ylmethoxy]-phenyl}-propionic acid

A] 3-(4-Hydroxy-2-methoxy-phenyl)-propionic acid ethyl ester

In analogy to the procedures described in examples 60A] and 60B], 4-benzyloxy-2-methoxy-benzaldehyde was reacted with triethyl phosphonoacetate to give (E)-3-(4-benzyloxy-2-methoxy-phenyl)-acrylic acid ethyl ester B] 3-{2-Methoxy-4-[2-methyl-6-(4-trifluoromethyl-phenyl)-pyridin-3-ylmethoxy]-phenyl}-propionic acid In analogy to the procedures described in examples 8A] and 31B], 3-(4-hydroxy-2-methoxy-phenyl)-propionic acid ethyl ester was reacted with 3-chloromethyl-2-methyl-6-(4-trifluoromethyl-phenyl)-pyridine (example 1N]) to give 3-{2-methoxy-4-[2-methyl-6-(4-trifluoromethyl-phenyl)-pyridin-3-ylmethoxy]-phenyl}-propionic acid ethyl ester, which was subsequently saponified to yield the title compound as colorless solid.

MS: 444.1 (M−H)$^-$.

Example 93

2-[3-Methoxy-5-(2-{[2-methyl-6-(4-trifluoromethyl-phenyl)-pyridine-3-carbonyl]-amino}-ethyl)-phenoxy]-2-methyl-propionic acid A] 2-[3-(2-Amino-ethyl)-5-methoxy-phenoxy-2-methyl-propionic acid ethyl ester In analogy to the procedure described in example 52A], 3-hydroxy-5-methoxy-benzaldehyde [Journal of Organic Chemistry (1985), 50(13), 2236–40] was reacted with ethyl-bromoisobutyrate to give 2-(3-formyl-5-methoxy-phenoxy)-2-methyl-propionic acid ethyl ester; this compound was subsequently transformed in analogy to procedures described in examples 55B] and 55C] into 2-(3-methoxy-5-((E)-2-nitro-vinyl)-phenoxy)-2-methyl-propionic acid ethyl ester which was then hydrogenated to give 2-[3-(2-amino-ethyl)-5-methoxy-phenoxy]-2-methyl-propionic acid ethyl ester as yellow oil.

MS: 282.2 (M+H)$^+$.

B] 2-[3-Methoxy-5-(2-{[2-methyl-6-(4-trifluoromethyl-phenyl)-pyridine-3-carbonyl]-amino}-ethyl)-phenoxy-2-methyl-propionic acid In analogy to the procedures described in example 26B] and 26C], 2-[3-(2-amino-ethyl)-5-methoxy-phenoxy]-2-methyl-propionic acid ethyl ester was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-[3-methoxy-5-(2-{[2-methyl-6-(4-trifluoromethyl-phenyl)-pyridine-3-carbonyl]-amino}-ethyl)-phenoxy]-2-methyl-propionic acid ethyl ester, which was subsequently saponified to yield the title compound as colorless solid.

MS: 515.2 (M−H)$^-$.

Example 94

2-[3-(2-{[4-Cyclopropyl-2-(4-trifluoromethyl-phenyl)-pyrimidine-5-carbonyl]-amino}-ethyl)-5-methoxy-phenoxy]-2-methyl-propionic acid In analogy to the procedures described in example 26B] and 26C], 2-[3-(2-amino-ethyl)-5-methoxy-phenoxy]-2-methyl-propionic acid ethyl ester (example 93A]) was reacted with 4-cyclopropyl-2-(4-trifluoromethyl-phenyl)-pyrimidine-5-carboxylic acid (example 53B]) to give 2-[3-(2-{[4-cyclopropyl-2-(4-trifluoromethyl-phenyl)-pyrimidine-5-carbonyl]-amino}-ethyl)-5-methoxy-phenoxy]-2-methyl-propionic acid ethyl ester, which was subsequently saponified to yield the title compound as colorless solid.

MS: 542.2 (M−H)$^-$.

Example 95

2-[3-(2-{2-[4-Cyclopropyl-2-(4-trifluoromethyl-phenyl)-pyrimidin-5-yl]-acetylamino}-ethyl)-5-methoxy-phenoxy]-2-methyl-propionic acid In analogy to the procedures described in example 26B] and 26C], 2-[3-(2-amino-ethyl)-5-methoxy-phenoxy]-2-methyl-propionic acid ethyl ester (example 93A]) was reacted with [4-cyclopropyl-2-(4-trifluoromethyl-phenyl)-pyrimidin-5-yl]-acetic acid (prepared from 5-chloromethyl-4-cyclopropyl-2-(4-trifluoromethyl-phenyl)-pyrimidine (example 27F]) in analogy to the sequences described in examples 26D] and 26E]) to give 2-[3-(2-{2-[4-cyclopropyl-2-(4-trifluoromethyl-phenyl)-pyrimidin-5-yl]-acetylamino}-ethyl)-5-methoxy-phenoxy]-2-methyl-propionic acid ethyl ester, which was subsequently saponified to yield the title compound as colorless solid.

MS: 556.1 (M+H)$^+$.

Example 96

2-[3-Methoxy-5-(2-{2-[2-methyl-6-(4-trifluoromethyl-phenyl)-pyridin-3-yl]-acetylamino}-ethyl)-phenoxy]-2-methyl-propionic acid In analogy to the procedures described in example 26B] and 26C], 2-[3-(2-amino-ethyl)-5-methoxy-phenoxy]-2-methyl-propionic acid ethyl ester (example 93A]) was reacted with [2-methyl-6-(4-trifluoromethyl-phenyl)-pyridin-3-yl]-acetic acid (example 26E]) to give 2-[3-methoxy-5-(2-{2-[2-methyl-6-(4-trifluoromethyl-phenyl)-pyridin-3-yl]-acetylamino}-phenoxy]-2-methyl-propionic acid ethyl ester, which was subsequently saponified to yield the title compound as colorless solid.

MS: 529.2 (M−H)$^-$.

Example 97

2-Methyl-2-[2-methyl-4-({[2-methyl-6-(4-trifluoromethyl-phenyl)-pyridine-3-carbonyl]-amino}-methyl)-phenoxy]-propionic acid A] 2-[4-(Z,E-Hydroxyimino-methyl)-2-methyl-phenoxy-2-methyl-propionic acid ethyl ester 19.35 g (77.3 mmol) of 2-(4-formyl-2-methyl-phenoxy)-2-methyl-propionic acid ethyl ester (prepared from 4-hydroxy-3-methyl-benzaldehyde and ethyl-bromoisobutyrate in analogy to the procedure described in example 52A]) was dissolved in 200 ml ethanol; while stirring, 8.68 g (123.7 mmol) hydroxylamine hydrochloride were added, followed by a solution of 19.22 g (232.0 mmol) of sodium acetate in 200 ml water. After stirring of the reaction mixture for 18 hours at ambient temperature, the solvent was removed by evaporation at reduced pressure, the residue was then poured into crashed ice and extracted three times with MeCl$_2$. The combined organic phases were washed with water and brine, dried over anhydrous magnesium sulfate and evaporated. The crude product was purified by flash chromatography (SiO$_2$, heptane/EtOAc) to give 20.61 g of the title compound as light yellow oil.

MS: 266.2 (M+H)$^+$.

B] 2-(4-Aminomethyl-2-methyl-phenoxy)-2-methyl-propionic acid ethyl ester 19.9 g (75.0 mmol) of 2-[4-(Z,E-hydroxyimino-methyl)-2-methyl-phenoxy]-2-methyl-propionic acid ethyl ester was dissolved in 300 ml of glacial acetic acid and heated to 65° C. While stirring, 44.13 g (675 mmol) zinc dust was added in several small portions. After 90 min., the reaction mixture was cooled down to ambient temperature, filtered (Celite) and the filtrate was evaporated. The residue was partitioned between water and ethyl acetate, the pH was adjusted to >12 with NaOH/H$_2$O, the mixture was filtered again (Celite) and the filtrate extracted twice with ethyl acetate. The combined organic phases were washed with water and brine, dried over anhydrous magnesium sulfate and evaporated. The crude product was purified by flash chromatography (SiO$_2$, MeCl2/MeOH) to give 15.72 g of the title compound as light yellow oil.

MS: 252.2 (M+H)$^+$.

C] 2-Methyl-2-[2-methyl-4-({[2-methyl-6-(4-trifluoromethyl-phenyl)-pyridine-3-carbonyl]-amino}-methyl)-phenoxy]-propionic acid In analogy to the procedures described in example 26B] and 26C], 2-(4-aminomethyl-2-methyl-phenoxy)-2-methyl-propionic acid ethyl ester was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-methyl-2-[2-methyl-4-({[2-methyl-6-(4-trifluoromethyl-phenyl)-pyridine-3-carbonyl]-amino}-methyl)-phenoxy]-propionic acid ethyl ester, which was subsequently saponified to yield the title compound as light yellow foam.

MS: 485.3 (M−H)$^-$.

Example 98

2-[4-({[4-Cyclopropyl-2-(4-trifluoromethyl-phenyl)-pyrimidine-5-carbonyl]-amino}-methyl)-2-methyl-phenoxy]-2-methyl-propionic acid In analogy to the procedures described in example 26B] and 26C], 2-(4-aminomethyl-2-methyl-phenoxy)-2-methyl-propionic acid ethyl ester (example 97B]) was reacted with 4-cyclopropyl-2-(4-trifluoromethyl-phenyl)-pyrimidine-5-carboxylic acid (example 53B]) to give 2-[4-({[4-cyclopropyl-2-(4-trifluoromethyl-phenyl)-pyrimidine-5-carbonyl]-amino}-methyl)-2-methyl-phenoxy]-2-methyl-propionic acid ethyl ester, which was subsequently saponified to yield the title compound as light yellow foam.

MS: 512.2 (M−H)$^-$.

Example 99

2-[4-({[4-Methoxymethyl-2-(4-trifluoromethyl-phenyl)-pyrimidine-5-carbonyl]-amino}-methyl)-2-methyl-phenoxy]-2-methyl-propionic acid In analogy to the procedures described in example 26B] and 26C], 2-(4-aminomethyl-2-methyl-phenoxy)-2-methyl-propionic acid ethyl ester (example 97B]) was reacted with 4-methoxymethyl-2-(4-trifluoromethyl-phenyl)-pyrimidine-5-carboxylic acid (prepared from 4-methoxy-3-oxo-butyric acid methyl ester, in analogy to the procedures described in examples 27C] and 27D] followed by saponification in analogy to the procedure described in example 53B]) to give 2-[4-({[4-methoxymethyl-2-(4-trifluoromethyl-phenyl)-pyrimidine-5-carbonyl]-amino}-methyl)-2-methyl-phenoxy]-2-methyl-propionic acid ethyl ester, which was subsequently saponified to yield the title compound as light yellow foam.

MS: 516.2 (M−H)$^-$.

Example 100

2-[4-({[4-(2-Methoxy-ethyl)-2-(4-trifluoromethyl-phenyl)-pyrimidine-5-carbonyl]-amino}-methyl)-2-methyl-phenoxy]-2-methyl-propionic acid In analogy to the procedures described in example 26B] and 26C], 2-(4-aminomethyl-2-methyl-phenoxy)-2-methyl-propionic acid ethyl ester (example 97B]) was reacted with 4-(2-methoxy-ethyl)-2-(4-trifluoromethyl-phenyl)-pyrimidine-5-carboxylic acid (prepared from 5-methoxy-3-oxo-pentanoic acid methyl ester, in analogy to the procedures described in examples 27C] and 27D] followed by saponification in analogy to the procedure described in example 53B]) to give 2-[4-({[4-(2-methoxy-ethyl)-2-(4-trifluoromethyl-phenyl)-pyrimidine-5-carbonyl]-amino}-methyl)-2-methyl-phenoxy]-2-methyl-propionic acid ethyl ester, which was subsequently saponified to yield the title compound as light yellow oil.

MS: 530.2 (M−H)$^-$.

Example 101

2-{4-[4-(2-Ethoxy-ethyl)-2-(6-trifluoromethyl-pyridin-3-yl)-pyrimidin-5-ylmethoxy]-2-methyl-phenoxy}-2-methyl-propionic acid A] 2-{4-[4-(2-Methoxy-ethyl)-2-(6-trifluoromethyl-pyridin-3-yl)-pyrimidin-5-ylmethoxy]-2-methyl-phenoxy}-2-methyl-propionic acid ethyl ester To a solution of 133 mg (0.40 mmol) 5-chloromethyl-4-(2-methoxy-ethyl)-2-(6-trifluoromethyl-pyridin-3-yl)-pyrimidine (example 101F]) and 95 mg (0.40 mmol) 2-(4-hydroxy-2-methyl-phenoxy)-2-methyl-propionic acid ethyl ester (described in WO 02/092590) in 12 ml of acetonitrile was added 143 mg (0.44 mmol) cesium carbonate. The reaction mixture was stirred for 16 h at RT. The mixture was filtered, taken up in dichloromethane dried (Na$_2$SO$_4$) and evaporated. The crude product was purified by flash chromatography over silica gel with heptane/AcOEt 9:1, to give 119 mg of the title compound as light yellow viscous oil.

MS: 534.5 (M+H)$^+$.

B] 2-{4-[4-(2-Ethoxy-ethyl)-2-(6-trifluoromethyl-pyridin-3-yl)-pyrimidin-5-ylmethoxy]-2-methyl-phenoxy}-2-methyl-propionic acid A solution of 110 mg (0.21 mmol) 2-{4-[4-(2-methoxy-ethyl)-2-(6-trifluoromethyl-pyridin-3-yl)-pyrimidin-5-ylmethoxy]-2-methyl-phenoxy}-2-methyl-propionic acid ethyl ester in 1.2 ml of THF/EtOH (1:1) was cooled (0° C.) treated with 0.62 ml 1N LiOH and stirred for 15 h at RT. The reaction mixture was taken up in ether and washed with aqueous 10% KHSO$_4$ solution and aqueous 10% NaCl. The organic phase was dried (Na$_2$SO$_4$) and evaporated. The crude product was suspended in ether/petane and filtered to give 87 mg of the title compound as a white powder of mp. 122–124° C., dec.

MS: 518.2 (M−H)$^-$.

5-Chloromethyl-4-(2-methoxy-ethyl)-2-(6-trifluoromethyl-pyridin-3-yl)-pyrimidine used in 101A] was synthesized as follows:

C] (E,Z)-2-[1-Ethoxy-methylidene-5-methoxy-3-oxo-pentanoic acid methyl ester A solution of 21.96 g (116.5 mmol) 5-methoxy-3-oxovaleric acid methyl ester, 35.25 ml (233.1 mmol) of triethyl orthoformate in 240 ml acetic anhydride was refluxed at 150° C. for 2.5 h. The reaction mixture was concentrated at 50° C. under reduced pressure to give 29.06 g of crude (E,Z)-2-[1-ethoxy-methylidene]-5-methoxy-3-oxo-pentanoic acid methyl ester.

MS: 217.2 (M+H)$^+$.

D] 4-(2-Methoxy-ethyl)-2-(6-trifluoromethyl-pyridin-3-yl)-pyrimidine-5-carboxylic acid Methyl Ester and 4-(2-methoxy-ethyl)-2-(6-trifluoromethyl-pyridin-3-yl)-pyrimidine-5-carboxylic acid ethyl ester To a solution of 16.24 g (72.0 mmol) 6-(trifluoromethyl) pyridine-3-benzamidine HCl in 200 ml of ethanol was added 7.61 g (96.1 mmol) of sodium tert-butoxide. After 5 min, 15.57 g (72.0 mmol) of crude (E,Z)-2-[1-ethoxy-methylidene]-5-methoxy-3-oxo-pentanoic acid methyl ester in 70 ml ethanol was added. The reaction mixture was then stirred over night at 90° C. The ethanol was removed partially under reduced pressure, the residue taken up in ether and washed with 1N HCl and water. The ether solution was concentrated under reduced pressure and the crude product purified by flash chromatography over silica gel with dichloromethane/ether 99:1 to 95:5 to give 18.36 g of a mixture of 4-(2-methoxy-ethyl)-2-(6-trifluoromethyl-pyridin-3-yl)-pyrimidine-5-carboxylic acid methyl ester and 4-(2-methoxy-ethyl)-2-(6-trifluoromethyl-pyridin-3-yl)-pyrimidine-5-carboxylic acid ethyl ester.

MS: 342.2 and 356.3 (M+H)$^+$.

E] [4-(2-Methoxy-ethyl)-2-(6-trifluoromethyl-pyridin-3-yl)-pyrimidin-5-yl]-methanol Within 20 min was dropped 50 ml (60 mmol) of DIBALH (1.2 M solution in toluene) to a dry ice cooled (−30° C.) solution of 6.83 g (20 mmol) 4-(2-methoxy-ethyl)-2-(6-trifluoromethyl-pyridin-3-yl)-pyrimidine-5-carboxylic acid methyl ester and 4-(2-methoxy-ethyl)-2-(6-trifluoromethyl-pyridin-3-yl)-pyrimidine-5-carboxylic acid ethyl ester in 100 ml of THF. The reaction was warmed up (0° C. for 1 h) and stirred 1 h at RT. The reaction was cooled (0° C.) and neutralized with KHSO$_4$ solution (10%). The mixture was extracted with ether (3×), the organic phase was washed with a NaCl solution (10%), dried (Na$_2$SO$_4$) and evaporated. The crude product was crystallized (dichloromethane/ether, 0° C.) to give 6.72 g of pure [4-(2-methoxy-ethyl)-2-(6-trifluoromethyl-pyridin-3-yl)-pyrimidin-5-yl]-methanol.

MS: 314.2 (M+H)$^+$.

F] 5-Chloromethyl-4-(2-methoxy-ethyl)-2-(6-trifluoromethyl-pyridin-3-yl)-pyrimidine A cooled (0° C.) solution of 0.94 g (3 mmol) of [4-(2-methoxy-ethyl)-2-(6-trifluoromethyl-pyridin-3-yl)-pyrimidin-5-yl]-methanol in 30 ml dichloromethane was treated with 0.44 ml (6 mmol) thionylchloride and stirred for 2.5 h at RT. The reaction was evaporated, dissolved twice in heptane an evaporated to give 1.0 g of pure 5-chloromethyl-4-(2-methoxy-ethyl)-2-(6-trifluoromethyl-pyridin-3-yl)-pyrimidine.

MS: 332.2 (M+H, 1Cl)$^+$.

Example 102

2-{4-[4-(2-Methoxy-ethyl)-2-(6-trifluoromethyl-pyridin-3-yl)-pyrimidin-5-ylmethoxy]-2-methyl-phenoxy}-2-methyl-propionic acid A solution of 133 mg (0.25 mmol) 2-{4-[4-(2-methoxy-ethyl)-2-(6-trifluoromethyl-pyridin-3-yl)-pyrimidin-5-ylmethoxy]-2-methyl-phenoxy}-2-methyl-propionic acid ethyl ester (example 101A]) in 1.5 ml of THF/MeOH (1:1) was cooled (0° C.) treated with 0.75 ml 1N LiOH and stirred for 15 h at RT. The reaction mixture was taken up in ether and washed with aqueous 10% KHSO$_4$ solution and aqueous 10% NaCl. The organic phase was dried (Na$_2$SO$_4$) and evaporated. The crude product was suspended in ether (RT to 4° C.) and filtered to give 66 mg of the title compound as a white powder of mp. 140.5–141.5° C., dec.

MS: 504.2 (M−H)$^-$.

Example 103

2-{4-[4-(2-Hydroxy-ethyl)-2-(6-trifluoromethyl-pyridin-3-yl)-pyrimidin-5-ylmethoxy]-2-methyl-phenoxy}-2-methyl-propionic acid

A] 2-{4-[4-(2-Hydroxy-ethyl)-2-(6-trifluoromethyl-pyridin-3-yl)-pyrimidin-5-ylmethoxy -2-methyl-phenoxy}-2-methyl-propionic acid ethyl ester To a solution of 133 mg (0.25 mmol) 2-{4-[4-(2-methoxy-ethyl)-2-(6-trifluoromethyl-pyridin-3-yl)-pyrimidin-5-ylmethoxy]-2-methyl-phenoxy}-2-methyl-propionic acid ethyl ester (example 101A]) in 1 ml of dichloromethan was treated at −78° C. with 0.31 ml BBr$_3$ (1M in dichloromethane, 0.31 mmol). The reaction was warmed up (RT for 2.5 h) and stirred 30 min at RT. The reaction was treated with saturated NaHCO$_3$-solution. The mixture was extracted with ether (3×), the organic phase was washed with a NaCl solution (10%), dried (Na$_2$SO$_4$) and evaporated. The crude product was purified by flash chromatography over silica gel with heptane/AcOEt 9:1 to 4:1, to give 21 mg of the title compound as an off-white viscous oil.

MS: 520.5 (M+H)$^+$.

B] 2-{4-[4-(2-Hydroxy-ethyl)-2-(6-trifluoromethyl-pyridin-3-yl)-pyrimidin-5-ylmethoxy]-2-methyl-phenoxy}-2-methyl-propionic acid In analogy to the saponification described in examples 102], 2-{4-[4-(2-hydroxy-ethyl)-2-(6-trifluoromethyl-pyridin-3-yl)-pyrimidin-5-ylmethoxy]-2-methyl-phenoxy}-2-methyl-propionic acid ethyl ester gave the title compound as a white powder of mp. 187–188° C., dec. MS: 490.2 (M–H)$^-$.

Example 104

2-{4-[4-Methoxymethyl-2-(4-trifluoromethyl-phenyl)-pyrimidin-5-ylmethoxy]-2-methyl-phenoxy}-2-methyl-propionic acid In analogy to the procedures described in example 101A], 2-(4-hydroxy-2-methyl-phenoxy)-2-methyl-propionic acid ethyl ester (described in WO 02/092590) was reacted with 5-chloromethyl-4-methoxymethyl-2-(4-trifluoromethyl-phenyl)-pyrimidine (prepared from methyl 4-methoxyacetoacetate and 6-(trifluoromethyl)pyridine-3-benzamidine hydrochloride, in analogy to the procedures described in examples 101C] to 101F]) to give 2-{4-[4-methoxymethyl-2-(4-trifluoromethyl-phenyl)-pyrimidin-5-ylmethoxy]-2-methyl-phenoxy}-2-methyl-propionic acid ethyl ester, which was subsequently saponified in analogy to the procedure described in example 101B] to yield the title compound as off-white crystals of mp. 120–121° C.

MS: 489.1 (M–H)$^-$.

Example 105

2-{4-[4-Cyclopropyl-2-(6-trifluoromethyl-pyridin-3-yl)-pyrimidin-5-ylmethoxy]-2-methyl-phenoxy}-2-methyl-propionic acid In analogy to the procedures described in example 101A], 2-(4-hydroxy-2-methyl-phenoxy)-2-methyl-propionic acid ethyl ester (described in WO 02/092590) was reacted with 5-chloromethyl-4-cyclopropyl-2-(6-trifluoromethyl-pyridin-3-yl)-pyrimidine (prepared from methyl 3-cyclopropyl-3-oxopropanoate and 4-(trifluoromethyl)benzamidine hydrochloride, in analogy to the procedures described in examples 101C] to 101F]) to give 2-{4-[4-cyclopropyl-2-(6-trifluoromethyl-pyridin-3-yl)-pyrimidin-5-ylmethoxy]-2-methyl-phenoxy}-2-methyl-propionic acid ethyl ester, which was subsequently saponified in analogy to the procedure described in example 101B] to yield the title compound as off-white crystals of mp. 185.0–185.5° C.

MS: 486.3 (M–H)$^-$.

Example 106

2-{4-[4-Cyclopropyl-2-(4-trifluoromethyl-phenyl)-pyrimidin-5-ylmethoxy]-2,3-dimethyl-phenoxy}-2-methyl-propionic acid A] 2-(4-Hydroxy-2,3-dimethyl-phenoxy)-2-methyl-propionic acid ethyl ester To a suspension of 8.0 g (57.9 mmol) 2,3-dimethylhydroquinone and 39.6 g (121.6 mmol) cesium carbonate in 100 ml DMF was treated with 9.45 ml (63.7 mmol) of ethyl 2-bromo-2-methylpropionate and stirred for 2 days at RT. The reaction was poured on a mixture of saturated NH$_4$Cl-solution and ice and extracted with AcOEt (3×). The organic phase was washed with aqueous 10% NaCl, dried (Na$_2$SO$_4$) and evaporated. The crude product was purified by flash chromatography over silica gel with heptane/AcOEt 9:1, to give 5.4 g of the title compound as dark brown oil.

MS: 252.1 (M$^+$).

B] 2-{4-[4-Cyclopropyl-2-(4-trifluoromethyl-phenyl)-pyrimidin-5-ylmethoxy]-2,3-dimethyl-phenoxy}-2-methyl-propionic acid In analogy to the procedures described in example 101A], 2-(4-hydroxy-2,3-dimethyl-phenoxy)-2-methyl-propionic acid ethyl ester (example 106A]) was reacted with 5-chloromethyl-4-cyclopropyl-2-(4-trifluoromethyl-phenyl)-pyrimidine (example 27F]) to give 2-{4-[4-cyclopropyl-2-(4-trifluoromethyl-phenyl)-pyrimidin-5-ylmethoxy]-2,3-dimethyl-phenoxy}-2-methyl-propionic acid ethyl, which was subsequently saponified in analogy to the procedure described in example 101B] to yield the title compound as off-white powder of mp. 214–215° C., dec.

MS: 499.1 (M–H)$^-$.

Example 107

2-Methyl-2-{2-methyl-4-[4-trifluoromethyl-2-(4-trifluoromethyl-phenyl)-pyrimidin-5-ylmethoxy]-phenoxy}-propionic acid A] 2-Methyl-2-{2-methyl-4-[4-trifluoromethyl-2-(4-trifluoromethyl-phenyl)-pyrimidin-5-ylmethoxy]-phenoxy}-propionic acid In analogy to the procedures described in example 101A], 2-(4-hydroxy-2-methyl-phenoxy)-2-methyl-propionic acid ethyl ester (described in WO 02/092590) was reacted with 5-chloromethyl-4-trifluoromethyl-2-(4-trifluoromethyl-phenyl)-pyrimidine (example 107D]) to give 2-methyl-2-{2-methyl-4-[4-trifluoromethyl-2-(4-trifluoromethyl-phenyl)-pyrimidin-5-ylmethoxy]-phenoxy}-propionic acid ethyl ester, which was subsequently saponified in analogy to the procedure described in example 101B] to yield the title compound as off-white powder of mp. 149–151° C., dec.

MS: 513.1 (M–H)$^-$.

5-Chloromethyl-4-trifluoromethyl-2-(4-trifluoromethyl-phenyl)-pyrimidine used in 107A] was synthesized as follows:

B] 4-Trifluoromethyl-2-(4-trifluoromethyl-phenyl)-pyrimidine-5-carboxylic acid ethyl ester In analogy to the procedures described in example 101C] and 101D], ethyl 4,4,4-trifluoroacetoacetate and 4-(trifluoromethyl)benzamidine hydrochloride gave the title compound as a light yellow powder.

MS: 363.9 (M)$^+$.

C] [4-Trifluoromethyl-2-(4-trifluoromethyl-phenyl)-pyrimidin-5-yl]-methanol

Within 10 min was dropped 5.5 ml (6.6 mmol) of DIBALH (1.2 M solution in toluene) to a dry ice cooled (–30° C.) solution of 1.09 g (3.0 mmol) 4-trifluoromethyl-2-(4-trifluoromethyl-phenyl)-pyrimidine-5-carboxylic acid ethyl ester in 15 ml of THF. The reaction was stirred for 2.5 h at −30° C., warmed up (0° C. for 2 h) and stirred 1 h at 0° C. The reaction was neutralized with saturated NaHCO₃ solution. The mixture was extracted with ether (3×), the organic phase was washed with a NaCl solution (10%), dried (Na₂SO₄) and evaporated. The crude product was purified by flash chromatography over silica gel with heptane/isopropanol 9:1, to give 0.16 g of pure [4-trifluoromethyl-2-(4-trifluoromethyl-phenyl)-pyrimidin-5-yl]-methanol as a yellow solid.

MS: 322.0 (M)⁺.

D] 5-Chloromethyl-4-trifluoromethyl-2-(4-trifluoromethyl-phenyl)-pyrimidine

A cooled (0° C.) solution of 0.081 g (0.25 mmol) of [4-trifluoromethyl-2-(4-trifluoromethyl-phenyl)-pyrimidin-5-yl]-methanol in 2.5 ml dichloromethane was treated with 0.04 ml (0.50 mmol) thionylchloride and stirred for 14 h at RT. The reaction was evaporated, dissolved in ether and twice in heptane and evaporated to give 0.077 g of pure 5-chloromethyl-4-trifluoromethyl-2-(4-trifluoromethyl-phenyl)-pyrimidine.

MS: 339.9 (M, 1Cl)⁺.

Example 108

2-Methyl-2-{2-methyl-4-[4-trifluoromethyl-6-(4-trifluoromethyl-phenyl)-pyridin-3-ylmethoxy]-phenoxy}-propionic acid A] 2-Methyl-2-{2-methyl-4-[4-trifluoromethyl-6-(4-trifluoromethyl-phenyl)-pyridin-3-ylmethoxy]-phenoxy}-propionic acid In analogy to the procedures described in example 101A], 2-(4-hydroxy-2-methyl-phenoxy)-2-methyl-propionic acid ethyl ester (described in WO 02/092590) was reacted with 5-chloromethyl-4-trifluoromethyl-2-(4-trifluoromethyl-phenyl)-pyridine (example 108D]) to give 2-methyl-2-{2-methyl-4-[4-trifluoromethyl-6-(4-trifluoromethyl-phenyl)-pyridin-3-ylmethoxy]-phenoxy}-propionic acid ethyl ester, which was subsequently saponified in analogy to the procedure described in example 101] to yield the title compound as off-white crystals of mp. 148–149° C.

MS: 512.1 (M−H)⁻.

5-Chloromethyl-4-trifluoromethyl-2-(4-trifluoromethyl-phenyl)-pyridine used in 108A] was synthesized as follows:

B] 4-Trifluoromethyl-6-(4-trifluoromethyl-phenyl)-nicotinic acid methyl Ester [Following a Procedure of Kaoru Inada and Norio Miyaura, Tetrahedron (2000), 56, 8661–8664]

A solution of 0.84 g (1.2 mmol) bis(triphenylphosphine) palladium(II)chloride, 9.58 g (40 mmol) methyl 6-chloro-4-(trifluoromethyl)nicotinate and 10.08 g (52 mmol) of 4-(trifluoromethyl)benzeneboronic acid in 200 ml degassed toluene was treated with 40 ml aqueous 2M K₃PO4 and heated at 80° C. for 16 h. The reaction was cooled to RT and extracted with H₂O (0° C.)/Et₂O (3x). The organic phases were washed with aqueous 10% NaCl, dried (NaSO₄) and evaporated. Purification by flash-chromatography on silica gel (dichloromethane/heptane 2:1 to 1:1) gave 9.91 g of the title compound as an off-white powder.

MS: 348.9 (M)⁺.

C] [4-Trifluoromethyl-6-(4-trifluoromethyl-phenyl)-pyridin-3-yl]-methanol

Within 15 min was dropped 25 ml (30 mmol) of DIBALH (1.2 M solution in toluene) to a dry ice cooled (−30° C.) solution of 3.49 g (10 mmol) 5-(4-trifluoromethyl-phenyl)-pyrazine-2-carboxylic acid methyl ester in 50 ml of THF. The reaction was stirred for 1.25 h at −30° C., and 1 h at 0° C. The reaction was neutralized with aqueous 10% KHSO₄ solution. The mixture was extracted with ether (3x), the organic phase was washed with a NaCl solution (10%), dried (Na₂SO₄) and evaporated to give 3.21 g of pure [4-trifluoromethyl-6-(4-trifluoromethyl-phenyl)-pyridin-3-yl]-methanol as a light yellow powder.

MS: 321.0 (M)⁺.

D] 5-Chloromethyl-4-trifluoromethyl-2-(4-trifluoromethyl-phenyl)-pyridine

In analogy to the procedures described in example 101F], [4-trifluoromethyl-6-(4-trifluoromethyl-phenyl)-pyridin-3-yl]-methanol (example 108C]) gave the title compound as off-white crystalls.

MS: 339.0 (M, 1Cl)⁺.

Example 109

2-{4-[4-Chloro-6-(4-trifluoromethoxy-phenyl)-pyridin-3-ylmethoxy]-2-methyl-phenoxy}-2-methyl-propionic acid A] 2-{4-[4-Chloro-6-(4-trifluoromethoxy-phenyl)-pyridin-3-ylmethoxy-2-methyl-phenoxy}-2-methyl-propionic acid In analogy to the procedures described in example 101A], 2-(4-hydroxy-2-methyl-phenoxy)-2-methyl-propionic acid ethyl ester (described in WO 02/092590) was reacted with 4-chloro-5-chloromethyl-2-(4-trifluoromethoxy-phenyl)-pyridine hydrochloride. (example 109B]) and 3.15 equivalent of cesium carbonate to give 2-{4-[4-chloro-6-(4-trifluoromethoxy-phenyl)-pyridin-3-ylmethoxy]-2-methyl-phenoxy}-2-methyl-propionic acid ethyl ester, which was subsequently saponified in analogy to the procedure described in example 101B] to yield the title compound as white crystals of mp. 179–181° C., dec.

MS: 494.2 (M−H, 1Cl)⁻.

4-Chloro-5-chloromethyl-2-(4-trifluoromethoxy-phenyl)-pyridine hydrochloride used in 109A] was synthesized as follows:

B] 4-Chloro-5-chloromethyl-2-(4-trifluoromethoxy-phenyl)-pyridine Hydrochloride

In analogy to the procedures described in examples 108B] to 108D], ethyl 2-chloro-4-(trifluoromethyl)pyrimidine-5-carboxylate and 4-(trifluoromethoxy)phenylboronic acid gave the title compound as a white powder.

MS: 321.0 (M, 2Cl)⁺.

Example 110

2-{4-[4-(2-Hydroxy-ethyl)-2-(4-trifluoromethyl-phenyl)-pyrimidin-5-ylmethoxy]-2-methyl-phenoxy}-2-methyl-propionic acid

A] 2-{4-[4-(2-Hydroxy-ethyl)-2-(4-trifluoromethyl-phenyl)-pyrimidin-5-ylmethoxy-2-methyl-phenoxy}-2-methyl-propionic acid In analogy to the procedures described in example 101A], 2-(4-hydroxy-2-methyl-phenoxy)-2-methyl-propionic acid ethyl ester (described in WO 02/092590) was reacted with 2-[5-chloromethyl-2-(4-trifluoromethyl-phenyl)-pyrimidin-4-yl]-ethanol. (example 110C]) and 5.1 equivalent of cesium carbonate in the presence of catalytic amount of sodium iodide to give 2-{4-[4-(2-hydroxy-ethyl)-2-(4-trifluoromethyl-phenyl)-pyrimidin-5-ylmethoxy]-2-methyl-phenoxy}-2-methyl-propionic acid ethyl ester, which was subsequently saponified in analogy to the procedure described in example 101B] to yield the title compound as white crystals of mp. 155.0–155.5° C.

MS: 489.1 (M–H,)⁻.

2-[5-Chloromethyl-2-(4-trifluoromethyl-phenyl)-pyrimidin-4-yl]-ethanol used in 110A] was synthesized as follows:

B] 5-Chloromethyl-4-(2-methoxy-ethyl)-2-(4-trifluoromethyl-phenyl)-pyrimidine In analogy to the procedures described in examples 101C] to 101F], 5-methoxy-3-oxovaleric acid methyl ester and 4-(trifluoromethyl)benzamidine hydrochloride gave the title compound as a yellow oil.

MS: 329.9 (M, 1Cl)⁺.

C] 2-[5-Chloromethyl-2-(4-trifluoromethyl-phenyl)-pyrimidin-4-yl]-ethanol

In analogy to the procedures described in examples 103A], 5-chloromethyl-4-(2-methoxy-ethyl)-2-(4-trifluoromethyl-phenyl)-pyrimidine and BBr₃ (1M in dichloromethane) gave the title compound as a yellow oil, which was used without further purification. MS: 317.1 (M+H, Cl)⁺.

Example 111

2-Methyl-2-{2-methyl-4-[2-(4-trifluoromethoxy-phenyl)-4-trifluoromethyl-pyrimidin-5-ylmethoxy]-phenoxy}-propionic acid

A] 2-Methyl-2-{2-methyl-4-[2-(4-trifluoromethoxy-phenyl)-4-trifluoromethyl-pyrimidin-5-ylmethoxy]-phenoxy}-propionic acid In analogy to the procedures described in example 101A], 2-(4-hydroxy-2-methyl-phenoxy)-2-methyl-propionic acid ethyl ester (described in WO 02/092590) was reacted with chlorosulfurous acid 2-(4-trifluoromethoxy-phenyl)-4-trifluoromethyl-pyrimidin-5-ylmethyl ester (example 111F]) to give 2-methyl-2-{2-methyl-4-[2-(4-trifluoromethoxy-phenyl)-4-trifluoromethyl-pyrimidin-5-ylmethoxy]-phenoxy}-propionic acid ethyl ester, which was subsequently saponified in analogy to the procedure described in example 101B] to yield the title compound as a white powder of mp. 153.5–154.5° C.

MS: 529.1 (M–H)⁻.

Chlorosulfurous acid 2-(4-trifluoromethoxy-phenyl)-4-trifluoromethyl-pyrimidin-5-ylmethyl ester used in 111A] was synthesized as follows:

B] 2-(4-Trifluoromethoxy-phenyl)-4-trifluoromethyl-pyrimidine-5-carboxylic acid ethyl ester In analogy to the procedures described in examples 108B], ethyl 2-chloro-4-(trifluoromethyl)pyrimidine-5-carboxylate and 4-(trifluoromethoxy)phenylboronic acid gave the title compound as an off-white powder.

MS: 379.9 (M)⁺.

C] 2-(4-Trifluoromethoxy-phenyl)-4-trifluoromethyl-pyrimidine-5-carboxylic acid In analogy to the procedures described in examples 101B], 2-(4-trifluoromethoxy-phenyl)-4-trifluoromethyl-pyrimidine-5-carboxylic acid ethyl ester gave the title compound as a white powder.

MS: 351.1 (M–H)⁻.

D] 2-(4-Trifluoromethoxy-phenyl)-4-trifluoromethyl-pyrimidine-5-carbonyl Chloride A solution of 0.43 g (1.22 mmol) of 2-(4-trifluoromethoxy-phenyl)-4-trifluoromethyl-pyrimidine-5-carboxylic acid in 8 ml of dichloromethane was treated at RT with 2 drops of DMF. 0.12 ml (1.34 mmol, 1.1 eq) of oxalyl chloride were added within 5 min and stirring was continued for 2 h. The solution was evaporated and dried under reduced pressure to give 0.45 g of the title compound.

MS: 370.0 (M, 1Cl)⁺.

E] [2-(4-Trifluoromethoxy-phenyl)-4-trifluoromethyl-pyrimidin-5-yl]-methanol 0.45 g (1.21 mmol) 2-(4-Trifluoromethoxy-phenyl)-4-trifluoromethyl-pyrimidine-5-carbonyl chloride in 4 ml tetrahydrofurane were cooled (-30° C.) and treated during 10 min with 2.23 ml (2.20 mmol) of a DIBALH-solution (1.2 M in toluene). The solution was allowed to come to 0° C. (1.5 h). The reaction was then powered to an ice-cooled aqueous 10% KHSO₄ solution and extracted with ether. The ether-phase was washed with aqueous 10% NaCl solution, dried (NaSO₄) and evaporated. The crude product was purified by flash chromatography over silica gel with heptane/AcOEt 9:1, to give 0.29 g of the title compound as an off-white solid.

MS: 338.0 (M)⁺.

F] Chlorosulfurous acid 2-(4-trifluoromethoxy-phenyl)-4-trifluoromethyl-pyrimidin-5-ylmethyl Ester A cooled (0° C.) solution of 0.40 g (1.20 mmol) of [2-(4-trifluoromethoxy-phenyl)-4-trifluoromethyl-pyrimidin-5-yl]-methanol in 12 ml dichloromethane was treated with 0.10 ml (1.32 mmol) thionylchloride and stirred for 30 min at RT. The reaction was cooled (0° C.), treated with 0.08 ml (1.08 mmol) thionylchloride and stirred for 30 min at RT. The solution was evaporated, dissolved in ether and twice in heptane and evaporated to give 0.44 g of the title compound as an off-white powder.

MS: 338.0 (M-SOCl)⁺, IR:1227 cm⁻¹.

Example 112

2-Methyl-2-{2-methyl-4-[2-methyl-6-(4-trifluoromethoxy-phenyl)-4-trifluoromethyl-pyridin-3-ylmethoxy]-phenoxy}-propionic acid

A] 2-Methyl-2-{2-methyl-4-[2-methyl-6-(4-trifluoromethoxy-phenyl)-4-trifluoromethyl-pyridin-3-ylmethoxy]-phenoxy}-propionic acid ethyl ester To an ice cold solution of 2-(4-hydroxy-2-methyl-phenoxy)-2-methyl-propionic acid ethyl ester (35 mg, 147 µmol; described in WO 02/092590), [2-methyl-6-(4-trifluoromethoxy-phenyl)-4-trifluoromethyl-pyridin-3-yl]-methanol (52 mg, 148 µmol, example 112E]) and tributylphosphine (50 µl, 178 µmol) in tetrahydrofuran (3.5 ml) was added N,N,N',N'-tetramethyl azodicarboxamide (30 mg, 178 mmol). The cooling bath was removed and stirring continued for 14 h. The mixture was filtered over celite and the solvent removed under reduced pressure to give a yellow oil which was purified by column chromatography (silica gel, heptane/AcOEt) to give 63 mg (110 µmol, 75%) of the title compound as colorless oil.

MS: 572.3 (M+H)$^+$.

B] 2-Methyl-2-{2-methyl-4-[2-methyl-6-(4-trifluoromethoxy-phenyl)-4-trifluoromethyl-pyridin-3-ylmethoxy]-phenoxy}-propionic acid In analogy to the procedure described in example 26C], 2-methyl-2-{2-methyl-4-[2-methyl-6-(4-trifluoromethoxy-phenyl)-4-trifluoromethyl-pyridin-3-ylmethoxy]-phenoxy}-propionic acid ethyl ester was treated with LiOH to obtain the title compound as colorless solid.

MS: 544.2 (M+H)$^+$.

[2-methyl-6-(4-trifluoromethoxy-phenyl)-4-trifluoromethyl-pyridin-3-yl]-methanol used in 112A] was synthesized as follows:

C] (Z)-4,4,4-Trifluoro-3-hydroxy-1-(4-trifluoromethoxy-phenyl)-but-2-en-1-one To a toluene (50 ml) suspension of potassium t-butoxide (3.3 g, 29 mmol) and 1-(4-trifluoromethoxy-phenyl)-ethanone (3.9 ml, 24 mmol) under an argon atmosphere was added dropwise ethyl trifluoroacetate (3.4 ml, 29 mmol) at 10° C. The suspension was stirred at ambient temperature for 14 h. The pH value of the mixture was adjusted to 6 with 10% H$_2$SO$_4$, the solution was extracted two times with t-butyl methylether and the combined extracts were washed with brine/ice water 1/1. The organic layer was dried over sodium sulfate, concentrated under reduced pressure and the residue purified by column chromatography (silica gel, n-heptane/ethyl acetate) to yield 2.9 g (9.7 mmol, 40%) of the title compound as orange oil.

MS: 319.2 (M+NH$_4$)$^+$.

D] 2-Methyl-6-(4-trifluoromethoxy-phenyl)-4-trifluoromethyl-nicotinic acid ethyl ester To an acetonitrile (35 ml) solution of (Z)-4,4,4-trifluoro-3-hydroxy-1-(4-trifluoromethoxy-phenyl)-but-2-en-1-one (2.9 g, 10 mmol) was added ethyl-3-aminocrotonate (2.5 g, 19 mmol) under an argon atmosphere. The mixture was heated at reflux for 12 h. The solvent was removed under reduced pressure and the residue purified by column chromatography (silica gel, n-heptane/ethyl acetate) to yield 1.9 g (4.8 mmol, 50%) of the title compound as yellow oil.

MS: 394.0 (M+H)$^+$.

E] [2-Methyl-6-(4-trifluoromethoxy-phenyl)-4-trifluoromethyl-pyridin-3-yl]-methanol A solution of 2-methyl-6-(4-trifluoromethoxy-phenyl)-4-trifluoromethyl-nicotinic acid ethyl ester (400 mg, 1 mmol) in diethyl ether (6 ml) was added to a suspension of lithium aluminium hydride (77 mg, 2 mmol) in diethyl ether (12 ml) under an argon atmosphere at ambient temperature within 5 min. The mixture was stirred at reflux for 12 h, cooled to 0° C. and treated cautiously with ice water (12 ml) and 10% aqueous NaOH (6 ml). The reaction mixture was filtered over celite, t-butyl methylether was added and the layers were separated. The aqueous layer was extracted one more time with t-butyl methylether, the combined organic layers were washed with ice water/brine 1/1 and dried over sodium sulfate. Removal of the solvent under reduced pressure gave an orange oil which was purified by column chromatography (silica gel, heptane/AcOEt) to yield 140 mg (400 □mol, 39%) of the title compound as colorless crystals.

MS: 352.3 (M+H)$^+$.

Example 113

2-{4-[4-Cyclopropyl-6-methoxymethyl-2-(4-trifluoromethyl-phenyl)-pyrimidin-5-ylmethoxy]-2-methyl-phenoxy}-2-methyl-propionic acid

A] 2-{4-[4-Cyclopropyl-6-methoxymethyl-2-(4-trifluoromethyl-phenyl)-pyrimidin-5-ylmethoxy]-2-methyl-phenoxy}-2-methyl-propionic acid ethyl ester A solution of 200 mg (0.56 mmol) 5-chloromethyl-4-cyclopropyl-6-methoxymethyl-2-(4-trifluoromethyl-phenyl)-pyrimidine (example 113H]), 134 mg (0.56 mmol) 2-(4-hydroxy-2-methyl-phenoxy)-2-methyl-propionic acid ethyl ester (described in WO 02/092590) and 237 mg (0.73 mmol) cesium carbonate in 3 ml DMF was stirred for 3 h at RT. The reaction mixture was taken up in ether and washed with 1N HCl and water. After purification of the crude product by chromatography over silica gel with AcOEt/heptane 1:3, 257 mg of pure 2-{4-[4-cyclopropyl-6-methoxymethyl-2-(4-trifluoromethyl-phenyl)-pyrimidin-5-yl-methoxy]-2-methyl-phenoxy-2-methyl-propionic acid ethyl ester could be isolated.

MS: 559.3 (M+H)$^+$.

B] 2-{4-[4-Cyclopropyl-6-methoxymethyl-2-(4-trifluoromethyl-phenyl)-pyrimidin-5-ylmethoxy-2-methyl-phenoxy}-2-methyl-propionic acid A solution of 215 mg (0.385 mmol) 2-{4-[4-cyclopropyl-6-methoxymethyl-2-(4-trifluoromethyl-phenyl)-pyrimidin-5-ylmethoxy]-2-methyl-phenoxy}-2-methyl-propionic acid ethyl ester and 1.1 ml 1N LiOH-solution in 2.5 ml tetrahydrofurane was stirred for 2 h at RT. The reaction mixture was taken up in ether and washed with 1N HCl and water. The crude residue was suspended in AcOEt/heptane 1:19. The resulting amorphous crystals were filtered off to provide 164 mg of pure 2-{4-[4-cyclopropyl-6-methoxymethyl-2-(4-trifluoromethyl-phenyl)-pyrimidin-5-ylmethoxy]-2-methyl-phenoxy}-2-methyl-propionic acid.

MS: 529.3 (M−H)⁻.

5-Chloromethyl-4-cyclopropyl-6-methoxymethyl-2-(4-trifluoromethyl-phenyl)-pyrimidine used in 113A] was synthesized as follows:

C] 2-Cylopropanecarbonyl-4-methoxy-3-oxo-butyric acid methyl ester

To an ice-cooled solution of 10 g (70.35 mmol) 3-cyclopropyl-3-oxo-propionic acid methyl ester and 6.69 g (70.35 mmol) anhydrous magnesium chloride was dropped within 10 min 11.3 2ml (140 7 mmol) pyridine. 15 min later, 12.54 g (77.38 mmol) methoxyacetic anhydride was added and the reaction mixture was then stirred at RT over night. The reaction mixture was concentrated under reduced pressure and then taken up in ether and washed with water, 1N HCl and again with water. The ether-phase was concentrated under reduced pressure providing 13.17 g crude 2-cyclopropanecarbonyl-4-methoxy-3-oxo-butyric acid methyl ester.

MS: 215.4 (M+H)⁺.

D] (E,Z)-2-Cyclopropanecarbonyl-3,4-dimethoxy-but-2-enoic acid methyl ester

An ice-cooled solution of 6.43 g (30 mmol) 2-cyclopropanecarbonyl-4-methoxy-3-oxo-butyric acid methyl ester in 60 ml acetonitrile was treated with 9.78 g (30 mmol) cesium carbonate. After the removal of the ice bath 3.39 ml (30 mmol) trifluoro-methanesulfonic acid methyl ester was added. The reaction mixture was stirred over night at RT, concentrated under reduced pressure, taken up in ether and washed with water. The ether-layers were concentrated under reduced pressure to provide 6.48 g crude (E,Z)-2-cyclopropanecarbonyl-3,4-dimethoxy-but-2-enoic acid methyl ester.

MS: 229.3 (M+H)⁺.

E] 4-Cylopropyl-6-methoxymethyl-2-(4-trifluoromethyl-phenyl)-pyrimidine-5-carboxylic acid methyl ester and

F] 4-Cyclopropyl-6-methoxymethyl-2-(4-trifluoromethyl-phenyl)-pyrimidine-5-carboxylic acid A solution of 7.4 g (28.28 mmol) 4-trifluoromethyl-benzamidine HCl in 40 ml ethanol was treated with 2.81 g (28.28 mmol) sodium tert.-butoxide. After 4 min, 6.48 g (28.28 mmol) of the crude (E,Z)-2-cyclopropanecarbonyl-3,4-dimethoxy-but-2-enoic acid methyl ester, in 30 ml ethanol, was added. The reaction mixture was stirred over night, taken up in ether and washed with 1N HCl and water. The crude product was purified by chromatography over silica gel with AcOEt/heptane 1:3, providing 2.86 g pure 4-cyclopropyl-6-methoxymethyl-2-(4-trifluoromethyl-phenyl)-pyrimidine-5-carboxylic acid methyl ester (example E]).

MS: 367.1 (M+H)⁺.

And 1.2 g of pure 4-cyclopropyl-6-methoxymethyl-2-(4-trifluoromethyl-phenyl)-pyrimidine-5-carboxylic acid (example F]).

MS: 351.4 (M−H)⁻.

G] [4-Cyclopropyl-6-methoxymethyl-2-(4-trifluoromethyl-phenyl)-pyrimidin-5-yl]-methanol To a solution of 2.86 g (7.8 mmol) 4-cyclopropyl-6-methoxymethyl-2-(4-trifluoromethyl-phenyl)-pyrimidine-5-carboxylic acid methyl ester in 30 ml tetrahydrofurane was dropped at −78° C., 20 ml (24 mmol) of a DIBALH-solution (1.2 M in toluene). The reaction was stirred for 15 min at −70° C., then the dry-ice bath was removed, the reaction temperature was allowed to come to RT and the solution was stirred for 2 h at RT. To the reaction mixture was then dropped carefully, under ice-cooling, 13 ml of 6N HCl. The reaction mixture was then taken up in ether and was washed with water. The ether-phase was concentrated under reduced pressure providing 1.29 g of pure crystalline [4-cyclopropyl-6-methoxymethyl-2-(4-trifluoromethyl-phenyl)-pyrimidin-5-yl]-methanol.

MS: 339.1 (M+H)⁺.

H] 5-Chloromethyl-4-cyclopropyl-6-methoxymethyl-2-(4-trifluoromethyl-phenyl)-pyrimidine A solution of 1.29 g (3.8 mmol) [4-cyclopropyl-6-methoxymethyl-2-(4-trifluoromethyl-phenyl)-pyrimidin-5-yl]-methanol in 12 ml dichloromethane was treated with 0.29 ml (3.99 mmol) thionylchloride. After 2 h stirring at RT, the mixture was partitioned between ether and water. The ether-phase was concentrated under reduced pressure giving 1.35 g pure crystalline 5-chloromethyl-4-cyclopropyl-6-methoxymethyl-2-(4-trifluoromethyl-phenyl)-pyrimidine.

MS: 357.3 (M+H)⁺.

Example 114

2-{4-[4-Cyclopropyl-6-methoxymethyl-2-(4-trifluoromethyl-phenyl)-pyrimidin-5-ylmethoxy]-phenoxy}-2-methyl-propionic acid

A] 2-{4-[4-Cyclopropyl-6-methoxymethyl-2-(4-trifluoromethyl-phenyl)-pyrimidin-5-ylmethoxy]-phenoxy}-2-methyl-propionic acid ethyl ester A solution of 200 mg (0.56 mmol) 5-chloromethyl-4-cyclopropyl-6-methoxymethyl-2-(4-trifluoromethyl-phenyl)-pyrimidine (example 113H]), 125 mg (0.56 mmol) 2-(4-hydroxy-phenoxy)-2-methyl-propionic acid ethyl ester [Newman, Melvin S.; Cella, James A. Monoalkylation of hydroquinone. Journal of Organic Chemistry (1974), 39(2), p 214–15] and 237 mg (0.73 mmol) cesium carbonate in 3 ml DMF was stirred for 3 h at RT. The reaction mixture was taken up in ether and washed with 1N HCl and water. After purification of the crude product by chromatography over silica gel with AcOEt/heptane 1:3, 223 mg of pure 2-{4-[4-Cyclopropyl-6-methoxymethyl-2-(4-trifluoromethyl-phenyl)-pyrimidin-5-ylmethoxy]-phenoxy}-2-methyl-propionic acid ethyl ester was isolated.

MS: 544.58 (M+H)⁺.

B] 2-{4-[4-Cyclopropyl-6-methoxymethyl-2-(4-trifluoromethyl-phenyl)-pyrimidin-5-ylmethoxy]-phenoxy}-2-methyl-propionic acid A solution of 198 mg (0.385 mmol) 2-{4-[4-cyclopropyl-6-methoxymethyl-2-(4-trifluoromethyl-phenyl)-pyrimidin-5-ylmethoxy]-2-methyl-phenoxy}-2-methyl-propionic acid ethyl ester and 1.1 ml 1N LiOH-solution in 2.5 ml tetrahydrofurane was stirred for 2 h at RT. The reaction mixture was taken up in ether and washed with 1N HCl and water. The crude residue was suspended in Ethylacetate/heptane 1:19. The resulting crystals were filtered off to provide 170 mg of pure 2-{4-[4-cyclopropyl-6-methoxymethyl-2-(4-trifluoromethyl-phenyl)-pyrimidin-5-ylmethoxy]-phenoxy}-2-methyl-propionic acid.

MS: 515.2 (M–H)$^-$.

Example 115

2-{4-[4-Butyl-2-(4-trifluoromethyl-phenyl)-pyrimidin-5-ylmethoxy]-2-methyl-phenoxy}-2-methyl-propionic acid A] 2-{4-[4-Butyl-2-(4-trifluoromethyl-phenyl)-pyrimidin-5-ylmethoxy]-2-methyl-phenoxy}-2-methyl-propionic acid ethyl ester To a solution of 400 mg (1.22 mmol) 4-butyl-5-chloromethyl-2-(4-trifluoromethyl-phenyl)-pyrimidine (example 115C]) and 290 mg (1.22 mmol) 2-(4-hydroxy-2-methyl-phenoxy)-2-methyl-propionic acid ethyl ester (described in WO 02/092590) in 4 ml DMF was added 90 mg (2.06 mmol) of sodium hydride (55% in oil). The reaction mixture was stirred for 2 h at RT, taken up in ether and washed with 1N HCl and water. The crude product was purified by chromatography over silica gel with AcOEt/heptane 1:4 to provide 347 mg pure 2-{4-[4-butyl-2-(4-trifluoromethyl-phenyl)-pyrimidin-5-ylmethoxy]-2-methyl-phenoxy}-2-methyl-propionic acid ethyl ester.

MS: 531.0 (M+H)$^+$.

B] 2-{4-[4-Butyl-2-(4-trifluoromethyl-phenyl)-pyrimidin-5-ylmethoxy]-2-methyl-phenoxy}-2-methyl-propionic acid 324 mg (0.61 mmol) of 2-{4-[4-butyl-2-(4-trifluoromethyl-phenyl)-pyrimidin-5-ylmethoxy]-2-methyl-phenoxy}-2-methyl-propionic acid ethyl ester and 1.83 ml 1N LiOH in 3 ml terahydrofurane were stirred over night at RT. The reaction mixture was taken up in ether and washed with 1N HCl and water. The crude product was suspended in AcOEt/heptane 1:19. The resulting crystals were filtered off providing 282 mg pure 2-{4-[4-butyl-2-(4-trifluoromethyl-phenyl)-pyrimidin-5-ylmethoxy]-2-methyl-phenoxy}-2-methyl-propionic acid.

MS: 501.5 (M–H)$^-$.

4-Butyl-5-chloromethyl-2-(4-trifluoromethyl-phenyl)-pyrimidine used in 115A] was synthesized as follows:

C] 4-Butyl-5-chloromethyl-2-(4-trifluoromethyl-phenyl)-pyrimidine

In analogy to the procedures described in example 27F], 3-oxo-heptanoic acid methyl ester and 4-trifluoromethyl-benzamidine HCl gave the title compound.

MS: 329.0 (M+H, 1Cl)$^+$.

Example 116

2-{4-[4-Butyl-2-(4-trifluoromethyl-phenyl)-pyrimidin-5-ylmethoxy]-phenoxy}-2-methyl-propionic acid A] 2-{4-[4-Butyl-2-(4-trifluoromethyl-phenyl)-pyrimidin-5-ylmethoxy]-phenoxy}-2-methyl-propionic acid ethyl ester A solution of 367 mg (1.11 mmol) 4-butyl-5-chloromethyl-2-(4-trifluoromethyl-phenyl)-pyrimidine (example 115C]) and 250 mg (1.11 mmol) 2-(4-hydroxy-phenoxy)-2-methyl-propionic acid ethyl ester [Newman, Melvin S.; Cella, James A. Monoalkylation of hydroquinone. Journal of Organic Chemistry (1974), 39(2), p 214–15] in 4 ml DMF was treated with 436 mg (1.34 mmol) cesium carbonate. The reaction mixture was stirred for 24 h at RT and then it was taken up in ether and washed with 1N HCl and water. The crude product was purified by chromatography over silica gel with AcOEt/heptane 1:4 to provide 344 mg pure 2-{4-[4-butyl-2-(4-trifluoromethyl-phenyl)-pyrimidin-5-ylmethoxy]-phenoxy}-2-methyl-propionic acid ethyl ester.

MS: 517.3 (M+H)$^+$.

B] 2-{4-[4-Butyl-2-(4-trifluoromethyl-phenyl)-pyrimidin-5-ylmethoxy]-phenoxy}-2-methyl-propionic acid 297 mg (0.575 mmol) 2-{4-[4-butyl-2-(4-trifluoromethyl-phenyl)-pyrimidin-5-ylmethoxy]-phenoxy}-2-methyl-propionic acid ethyl ester and 2 ml 1N LiOH in 3 ml terahydrofurane were stirred over night at RT. The reaction mixture was taken up in ether and washed with 1N HCl and water. The crude product was suspended in AcOEt/heptane 1:19. The resulting crystals were filtered off providing 258 mg pure 2-{4-[4-butyl-2-(4-trifluoromethyl-phenyl)-pyrimidin-5-ylmethoxy]-phenoxy}-2-methyl-propionic acid.

MS: 487.2 (M–H)$^-$.

Example 117

2-{4-[4-Cyclopropyl-2-(4-trifluoromethyl-phenyl)-pyrimidin-5-ylmethoxy]-phenoxy}-2-methyl-propionic acid A] 2-{4-[4-Cyclopropyl-2-(4-trifluoromethyl-phenyl)-pyrimidin-5-ylmethoxy]-phenoxy}-2-methyl-propionic acid ethyl ester A solution of 418 mg (1.34 mmol) 5-chloromethyl-4-cyclopropyl-2-(4-trifluoromethyl-phenyl)-pyrimidine and 300 mg (1.34 mmol) 2-(4-hydroxy-phenoxy)-2-methyl-propionic acid ethyl ester [Newman, Melvin S.; Cella, James A. Monoalkylation of hydroquinone. Journal of Organic Chemistry (1974), 39(2), p 214–15] in 5 ml DMF was treated with 523 mg (1.61 mmol) cesium carbonate. The reaction mixture was stirred 4 h at RT and then it was taken up in ether and washed with 1N HCl and water. The ether layers were concentrated under reduced pressure and the crude product was purified by chromatography over silica gel with AcOEt/heptane 1:4 giving 550 mg of pure 2-{4-[4-cyclopropyl-2-(4-trifluoromethyl-phenyl)-pyrimidin-5-ylmethoxy]-phenoxy}-2-methyl-propionic acid ethyl ester.

MS: 501.2 (M+H)$^+$.

B] 2-{4-[4-Cyclopropyl-2-(4-trifluoromethyl-phenyl)-pyrimidin-5-ylmethoxy]-phenoxy}-2-methyl-propionic acid 445 mg (0.889 mmol) of 2-{4-[4-cyclopropyl-2-(4-trifluoromethyl-phenyl)-pyrimidin-5-ylmethoxy]-phenoxy}-2-methyl-propionic acid ethyl ester and 2.7 ml 1N LiOH in 5 ml tetrahydrofurane were stirred at 50° C. over night. The reaction mixture was taken up in ether and washed with 1N HCl and water. The crude product was suspended with AcOEt/heptane 1:19. The resulting crystals were filtered off providing 393 mg pure 2-{4-[4-cyclopropyl-2-(4-trifluoromethyl-phenyl)-pyrimidin-5-ylmethoxy]-phenoxy}-2-methyl-propionic acid.

MS: 471.1 (M−H)⁻.

Example 118

2-{4-[4-(2-Methoxy-ethyl)-6-methyl-2-(4-trifluoromethyl-phenyl)-pyrimidin-5-ylmethoxy]-2-methyl-phenoxy}-2-methyl-propionic acid A] 2-{4-[4-(2-Methoxy-ethyl)-6-methyl-2-(4-trifluoromethyl-phenyl)-pyrimidin-5-ylmethoxy]-2-methyl-phenoxy}-2-methyl-propionic acid ethyl ester A solution of 350 mg (1 mmol) 5-chloromethyl-4-(2-methoxy-ethyl)-6-methyl-2-(4-trifluoromethyl-phenyl)-pyrimidine (example 118G]), 235 mg (1 mmol) 2-(4-hydroxy-2-methyl-phenoxy)-2-methyl-propionic acid ethyl ester (described in WO 02/092590) and 417 mg (1 mmol) cesium carbonate in 5 ml DMF was stirred for 3 h at RT. The reaction mixture was taken up in ether and washed with 1N HCl and water. After purification of the crude product by chromatography over silica gel with AcOEt/heptane 1:3, 283 mg of pure 2-{4-[4-(2-methoxy-ethyl)-6-methyl-2-(4-trifluoromethyl-phenyl)-pyrimidin-5-ylmethoxy]-2-methyl-phenoxy}-2-methyl-propionic acid ethyl ester was isolated.

MS: 547.3 (M+H)⁺.

B] 2-{4-[4-(2-Methoxy-ethyl)-6-methyl-2-(4-trifluoromethyl-phenyl)-pyrimidin-5-ylmethoxy]-2-methyl-phenoxy}-2-methyl-propionic acid A solution of 244 mg (0.446 mmol) 2-{4-[4-(2-methoxy-ethyl)-6-methyl-2-(4-trifluoromethyl-phenyl)-pyrimidin-5-ylmethoxy]-2-methyl-phenoxy}-2-methyl-propionic acid ethyl ester and 1.34 ml 1N LiOH-solution in 2.5 ml tetrahydrofurane was stirred for 2 h at RT. The reaction mixture was taken up in ether and washed with 1N HCl and water. The crude residue was suspended in AcOEt/heptane 1:19. The resulting crystals were filtered off providing 188 mg of pure 2-{4-[4-(2-methoxy-ethyl)-6-methyl-2-(4-trifluoromethyl-phenyl)-pyrimidin-5-ylmethoxy]-2-methyl-phenoxy}-2-methyl-propionic acid.

MS: 517.2 (M−H)⁻.

5-Chloromethyl-4-(2-methoxy-ethyl)-6-methyl-2-(4-trifluoromethyl-phenyl)-pyrimidine used in 118A] was synthesized as follows:

C] 2-Acetyl-5-methoxy-3-oxo-pentanoic acid methyl ester

To an ice cooled solution of 5.28 g (32.96 mmol) 5-methoxy-3-oxo-pentanoic acid methyl ester and 3.14 g (32.96 mmol) anhydrous magnesium chloride in 50 ml dichloromethane was dropped within 3 min 5.3 ml (65.92 mmol) pyridine. 3.27 ml (34.61 mmol) of acetic anhydride was then added within 3 min. The reaction mixture was stirred over night at RT and after concentration under reduced pressure it was partitioned between ether, 1N HCl and water. The ether solution was concentrated under reduced pressure to give 5.87 g pure 2-acetyl-5-methoxy-3-oxo-pentanoic acid methyl ester.

MS: 203.3 (M+H)⁺.

D] 5-Methoxy-2-[1-methoxy-eth-(E,Z)-ylidene]-3-oxo-pentanoic acid methyl ester

An ice-cooled solution of 5.87 g (29.02 mmol) 2-acetyl-5-methoxy-3-oxo-pentanoic acid methyl ester in 50 ml acetonitrile was treated with 9.46 g (29.02 mmol) cesium carbonate. After the removal of the ice bath 3.28 ml (29.02 mmol) trifluoro-methanesulfonic acid methyl ester was added. The reaction mixture was stirred for 2 h at RT, concentrated under reduced pressure, taken up in ether and washed with water. The ether-layers were concentrated under vacuum to provide 6 g of crude 5-methoxy-2-[1-methoxy-eth-(E,Z)-ylidene]-3-oxo-pentanoic acid methyl ester.

MS: 217.3 (M+H)⁺.

E] 4-(2-Methoxy-ethyl)-6-methyl-2-(4-trifluoromethyl-phenyl)-pyrimidine-5-carboxylic acid methyl ester A solution of 7.23 g (27.47 mmol) 4-trifluoromethyl-benzamidine HCl in 30 ml Ethanol was treated with 2.67 g (27.47 mmol) Sodium tert.Butoxide. After 4 min, 6 g (27.74 mmol) of the crude 5-methoxy-2-[1-methoxy-eth-(E,Z)-ylidene]-3-oxo-pentanoic acid methyl ester, in 30 ml Ethanol, was added. The reaction mixture was stirred over night, then taken up in ether and washed with 1N HCl and water. The crude product was purified by chromatography over silica gel with AcOEt/heptane 1:3, providing 4.9 g of pure 4-(2-methoxy-ethyl)-6-methyl-2-(4-trifluoromethyl-phenyl)-pyrimidine-5-carboxylic acid methyl ester.

MS: 355.4 (M+H)⁺.

F] [4-(2-Methoxy-ethyl)-6-methyl-2-(4-trifluoromethyl-phenyl)-pyrimidin-5-yl]-methanol To a dry-ice cooled solution of 4.9 g (13.83 mmol) 4-(2-methoxy-ethyl)-6-methyl-2-(4-trifluoromethyl-phenyl)-pyrimidine-5-carboxylic acid methyl ester in 50 ml tetrahydrofurane was dropped 34.57 ml (41.48 mmol) of DIBALH-solution (1.2 M in Toluene). The reaction mixture was stirred for 15 min at −70° C. and then the dry-ice bath was removed, the reaction temperature was allowed to come to RT and the reaction mixture was stirred for 2 h at RT. To the reaction mixture was then dropped carefully, under ice-cooling, 10 ml of 6N HCl. After 4 min was the whole taken up in ether and washed with water. The ether-phase was concentrated under reduced pressure providing 4.67 g pure crystalline [4-(2-methoxy-ethyl)-6-methyl-2-(4-trifluoromethyl-phenyl)-pyrimidin-5-yl]-methanol.

MS: 327.1 (M+H)⁺.

G] 5-Chloromethyl-4-(2-methoxy-ethyl)-6-methyl-2-(4-trifluoromethyl-phenyl)-pyrimidine A solution of 2.47 g (7.48 mmol) [4-(2-methoxy-ethyl)-6-methyl-2-(4-trifluoromethyl-phenyl)-pyrimidin-5-yl]-methanol in 25 ml Methylenchloride was treated with 0.57 ml (7.85 mmol) thionylchloride. After 2 h stirring at RT, the mixture was partitioned between ether and water. The ether-phase was concentrated under reduced pressure giving 2.42 g pure 5-chloromethyl-4-(2-methoxy-ethyl)-6-methyl-2-(4-trifluoromethyl-phenyl)-pyrimidine.

MS: 345.3 (M+H)$^+$.

Example 119

2-{4-[4-(2-Ethoxy-ethyl)-2-(4-trifluoromethyl-phenyl)-pyrimidin-5-ylmethoxy]-2-methyl-phenoxy}-2-methyl-propionic acid and 2-{4-[4-(2-Methoxy-ethyl)-2-(4-trifluoromethyl-phenyl)-pyrimidin-5-ylmethoxy]-2-methyl-phenoxy}-2-methyl-propionic acid (3:2)

A] 2-{4-[4-(2-Methoxy-ethyl)-2-(4-trifluoromethyl-phenyl)-pyrimidin-5-ylmethoxy]-2-methyl-phenoxy}-2-methyl-propionic acid ethyl ester In analogy to the procedures described in example 101A], 2-(4-hydroxy-2-methyl-phenoxy)-2-methyl-propionic acid ethyl ester (described in WO 02/092590) was reacted with 5-chloromethyl-4-(2-methoxy-ethyl)-2-(4-trifluoromethyl-phenyl)-pyrimidine (example 110B]) to give the title compound as light yellow oil.

MS: 533.5 (M+H)$^+$.

B] 2-{4-[4-(2-Ethoxy-ethyl)-2-(4-trifluoromethyl-phenyl)-pyrimidin-5-ylmethoxy]-2-methyl-phenoxy}-2-methyl-propionic acid and 2-{4-[4-(2-Methoxy-ethyl)-2-(4-trifluoromethyl-phenyl)-pyrimidin-5-ylmethoxy]-2-methyl-phenoxy}-2-methyl-propionic acid (3:2)

2-{4-[4-(2-Methoxy-ethyl)-2-(4-trifluoromethyl-phenyl)-pyrimidin-5-ylmethoxy]-2-methyl-phenoxy}-2-methyl-propionic acid ethyl ester was saponified in THF/EtOH in analogy to the procedure described in example 101B] to yield the title compounds as white crystalls.

MS: 519.5 and 505.4 (M−H)$^-$.

Example 120

[rac]-3-(2-Methyl-4-{3-methyl-1-[2-methyl-6-(4-trifluoromethyl-phenyl)-pyridin-3-yl]-butoxy}-phenyl)-propionic acid In analogy to the procedures described in examples 8A] and 31B], 3-(4-hydroxy-2-methyl-phenyl)-propionic acid ethyl ester (example 60B]) was reacted with [rac]-3-(1-chloro-3-methyl-butyl)-2-methyl-6-(4-trifluoromethyl-phenyl)-pyridine (prepared from [2-methyl-6-(4-trifluoromethyl-phenyl)-pyridin-3-yl]-methanol (example 1M]) by i) oxidation with MnO$_2$ in analogy to the procedure described in example 3A] to yield 2-methyl-6-(4-trifluoromethyl-phenyl)-pyridine-3-carbaldehyde; ii) treatment with isobutyl magnesium chloride and iii) reaction with SOCl$_2$ in analogy the procedures described in examples 4A] and 4B]) to give [rac]-3-(2-methyl-4-{3-methyl-1-[2-methyl-6-(4-trifluoromethyl-phenyl)-pyridin-3-yl]-butoxy}-phenyl)-propionic acid ethyl ester, which was subsequently saponified to yield the title compound as light yellow solid.

MS: 484.3 (M−H)$^-$.

Example 121

2-[4-({[4-Methoxymethyl-2-(4-trifluoromethyl-phenyl)-pyrimidine-5-carbonyl]-amino}-methyl)-phenoxy]-2-methyl-propionic acid In analogy to the procedures described in example 26B] and 26C], 2-(4-aminomethyl-phenoxy)-2-methyl-propionic acid ethyl ester [PCT Int. Appl. (2002), WO 2002/096895A1] was reacted with 4-methoxymethyl-2-(4-trifluoromethyl-phenyl)-pyrimidine-5-carboxylic acid (prepared from 4-methoxy-3-oxo-butyric acid methyl ester, in analogy to the procedures described in examples 27C] and 27D] followed by saponification in analogy to the procedure described in example 53B]) to give 2-[4-({[4-methoxymethyl-2-(4-trifluoromethyl-phenyl)-pyrimidine-5-carbonyl]-amino}-methyl)-phenoxy]-2-methyl-propionic acid ethyl ester, which was subsequently saponified to yield the title compound as light yellow foam.

MS: 502.1 (M−H)$^-$.

Example 122

2-[4-({[4-(2-Methoxy-ethyl)-2-(4-trifluoromethyl-phenyl)-pyrimidine-5-carbonyl]-amino}-methyl)-phenoxy]-2-methyl-propionic acid In analogy to the procedures described in example 26B] and 26C], 2-(4-aminomethyl-phenoxy)-2-methyl-propionic acid ethyl ester [PCT Int. Appl. (2002), WO 2002/096895A1] was reacted with 4-(2-methoxy-ethyl)-2-(4-trifluoromethyl-phenyl)-pyrimidine-5-carboxylic acid (prepared from 5-methoxy-3-oxo-pentanoic acid methyl ester, in analogy to the procedures described in examples 27C] and 27D] followed by saponification in analogy to the procedure described in example 53B]) to give 2-[4-({[4-(2-methoxy-ethyl)-2-(4-trifluoromethyl-phenyl)-pyrimidine-5-carbonyl]-amino}-methyl)-phenoxy]-2-methyl-propionic acid ethyl-ester, which was subsequently saponified to yield the title compound as light yellow solid.

MS: 516.3 (M−H)$^-$.

Example 123

2-(3-Methoxy-5-{methyl-[2-methyl-6-(4-trifluoromethyl-phenyl)-pyridin-3-ylmethyl]-carbamoyl}-phenoxy)-2-methyl-propionic acid A] In analogy to the procedures described in example 26B] and 26C], methyl-[2-methyl-6-(4-trifluoromethyl-phenyl)-pyridin-3-ylmethyl]-amine (example 123D]) was reacted with 3-(1-ethoxycarbonyl-1-methyl-ethoxy)-5-methoxy-benzoic acid (prepared from 3-hydroxy-5-methoxy-benzaldehyde [Journal of Organic Chemistry (1985), 50(13), 2236–40], by reaction with ethyl-bromoisobutyrate followed by oxidation with sodium chlorite in analogy to the procedures described in examples 52A] and 59A]) to give 2-(3-methoxy-5-{methyl-[2-methyl-6-(4-trifluoromethyl-phenyl)-pyridin-3-ylmethyl]-carbamoyl}-phenoxy)-2-methyl-propionic acid ethyl ester, which was subsequently saponified to yield the title compound as colorless solid.

MS: 515.2 (M–H)⁻.

The necessary building block methyl-[2-methyl-6-(4-trifluoromethyl-phenyl)-pyridin-3-ylmethyl]-amine used in procedure above was prepared as follows:

B] 2-[2-Methyl-6-(4-trifluoromethyl-phenyl)-pyridin-3-ylmethyl]-isoindole-1,3-dione 0.25 g (0.94 mmol) of [2-methyl-6-(4-trifluoromethyl-phenyl)-pyridin-3-yl]-methanol (example 1M]), 0.15 g (1.03 mmol) of phthalimide and 0.32 g (1.20 mmol) of triphenylphosphine were dissolved in 10 ml of THF. The stirred reaction mixture was cooled down to 0° C. and a solution of 0.27 g (1.15 mmol) of di-tert.-butyl azodicarboxylate in 2 ml of THF was added drop by drop. Then, the reaction was warmed up to ambient temperature. After 1 hour, the solvent was evaporated and the residue purified by crystallization from $MeCl_2$ and n-heptane to give 0.32 g of the title compound as a colorless solid.

MS: 396.0 (M)⁺.

C] [2-Methyl-6-(4-trifluoromethyl-phenyl)-pyridin-3-yl]-methylamine 3.04 ml=3.13 g (62.5 mmol) of hydrazine hydrate was added at the ambient temperature to a slurry of 6.20 g (15.6 mmol) of 2-[2-methyl-6-(4-trifluoromethyl-phenyl)-pyridin-3-ylmethyl]-isoindole-1,3-dione in 130 ml of EtOH. Then, the reaction mixture was stirred at reflux (oil bath=110° C.) for 1 hour. It was subsequently cooled down to ambient temperature, filtered and the filtrate was evaporated. The residue was partitioned between water and $MeCl_2$ and the pH was adjusted to >12 with $NaOH/H_2O$. The mixture was then extracted twice with $MeCl_2$, the combined organic phases were washed with water, dried over anhydrous magnesium sulfate and evaporated. The crude product was purified by flash chromatography ($SiO_2$, $MeCl_2/MeOH$) to give 4.10 g of the title compound as colorless solid.

MS: 267.2 (M+H)⁺.

D] Methyl-[2-methyl-6-(4-trifluoromethyl-phenyl)-pyridin-3-ylmethyl]-amine

In analogy to the procedures described in example 5D], 5E] and 5F], [2-methyl-6-(4-trifluoromethyl-phenyl)-pyridin-3-yl]-methylamine was converted into the corresponding tert-butoxycarbonylamino derivative by treatment with di-tert-butyl dicarbonate and sodium hydrogen carbonate in dioxane/water at r.t., methylated at N and deprotected again to yield the title compound as a yellow solid.

MS: 281.2 (M+H)⁺.

Example 124

2-Methyl-2-[4-({[2-methyl-6-(4-trifluoromethyl-phenyl)-pyridin-3-ylmethyl]-carbamoyl}-methyl)-phenoxy]-propionic acid A] 2-(4-Carboxymethyl-phenoxy)-2-methyl-propionic acid Tert-butyl Ester 6.27 g (20.3 mmol) of 2-(4-methoxycarbonylmethyl-phenoxy)-2-methyl-propionic acid tert-butyl ester (prepared from methyl 4-hydroxyphenylacetate and tert-butyl alpha-bromoisobutyrate, in analogy to the procedure described in example 52A]) was dissolved in 100 ml of dioxane; to the stirred solution, 40.7 ml of 1N LiOH solution was added drop by drop. After 30 min., the reaction mixture was poured into crashed ice, the pH was adjusted to <3 with $HCl/H_2O$ and it was extracted twice with AcOEt. The combined organic phases were washed with water, dried over anhydrous magnesium sulfate and evaporated to give 6.01 g of the title compound as a light yellow solid.

MS: 293.1 (M–H)⁻.

B] 2-Methyl-2-[4-({[2-methyl-6-(4-trifluoromethyl-phenyl)-pyridin-3-ylmethyl]-carbamoyl}-methyl)-phenoxy-propionic acid Tert-butyl Ester In analogy to the procedure described in example 26B], 2-(4-carboxymethyl-phenoxy)-2-methyl-propionic acid tert-butyl ester was reacted with [2-methyl-6-(4-trifluoromethyl-phenyl)-pyridin-3-yl]-methylamine (example 123C]) to give the title compound as colorless oil.

MS: 543.5 (M+H)⁺.

C] 2-Methyl-2-[4-({[2-methyl-6-(4-trifluoromethyl-phenyl)-pyridin-3-ylmethyl]-carbamoyl}-methyl)-phenoxy]-propionic acid 0.23 g (0.42 mmol) of 2-methyl-2-[4-({[2-methyl-6-(4-trifluoromethyl-phenyl)-pyridin-3-ylmethyl]-carbamoyl}-methyl)-phenoxy]-propionic acid tert-butyl ester was dissolved in 10 ml of $MeCl_2$. Then, 0.14 ml=0.139 g (1.28 mmol) of anisole was added followed by 0.32 ml=0.48 g (4.2 mmol) of trifluoroacetic acid. The reaction mixture was stirred at reflux (oil bath 50° C.) for 16 hours. It was then poured into crashed ice and extracted twice with $MeCl_2$. The combined organic phases were washed with water, dried over anhydrous magnesium sulfate and evaporated. The crude product was purified by flash chromatography ($SiO_2$, $MeCl_2/MeOH$) to give 0.17 g of the title compound as colorless solid.

MS: 485.3 (M–H)⁻.

Example 125

2-Methyl-2-(4-{[2-methyl-6-(4-trifluoromethyl-phenyl)-pyridin-3-ylcarbamoyl]-methyl}-phenoxy)-propionic acid A] In analogy to the procedures described in example 26B] and 124C], 2-methyl-6-(4-trifluoromethyl-phenyl)-pyridin-3-ylamine (example 125C]) was reacted with 2-(4-carboxymethyl-phenoxy)-2-methyl-propionic acid tert-butyl ester (example 124A]) to give 2-methyl-2-(4-{[2-methyl-6-(4-trifluoromethyl-phenyl)-pyridin-3-ylcarbamoyl]-methyl}-phenoxy)-propionic acid tert-butyl ester, which was subsequently cleaved with trifluoroacetic acid to yield the title compound as colorless solid.

MS: 471.1 (M–H)⁻.

The necessary building block 2-methyl-6-(4-trifluoromethyl-phenyl)-pyridin-3-ylamine used in procedure above was prepared as follows:

B] [2-Methyl-6-(4-trifluoromethyl-phenyl)-pyridin-3-yl]-carbamic acid Tert-butyl Ester 4.30 g (15.3 mmol) of 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) was dissolved in 85 ml of 2-methyl-2-propanol and 3.18 ml=2.32 g (22.9 mmol) of triethylamine was added. After 5 min., 4.97 ml=6.64 g (22.9 mmol) of diphenylphosphoryl azide (95%) was added. The reaction mixture was then stirred at reflux (oil bath 100° C.). After 10 min., 0.53 g (3.1 mmol) of anhydrous 4-toluene sulfonic acid was added and stirring continued for 1 hour at reflux. The solvent was then completely removed by evaporation at high vacuum; the residue was dissolved in Et$_2$O and washed with H$_2$O, 1N HCl, and NaHCO$_3$ solution. The combined organic phases were dried over anhydrous magnesium sulfate and evaporated. The crude product was purified by crystallization (EtOAc, n-heptane) to give 4.05 g of the title compound as colorless solid.

MS: 353.3 (M+H)$^+$.

C] 2-Methyl-6-(4-trifluoromethyl-phenyl)-pyridin-3-ylamine

In analog to the procedure described in example 5F], [2-methyl-6-(4-trifluoromethyl-phenyl)-pyridin-3-yl]-carbamic acid tert-butyl ester was reacted with trifluoroacetic acid to yield the title compound as colorless solid.

MS: 253.1 (M+H)$^+$.

Example 126

2-[3-Chloro-4-({[2-methyl-6-(4-trifluoromethyl-phenyl)-pyridine-3-carbonyl]-amino}-methyl)-phenoxy]-2-methyl-propionic acid In analogy to the procedures described in example 26B] and 26C], 2-(4-aminomethyl-3-chloro-phenoxy)-2-methyl-propionic acid ethyl ester (prepared from 2-chloro-4-hydroxy-benzaldehyde by reaction with ethyl-bromoisobutyrate as described in example 52A] followed by oxim formation and reduction as described in examples 97A] and 97B]) was reacted with 2-methyl-6-(4-trifluoromethyl-phenyl)-nicotinic acid (prepared from 2-methyl-6-(4-trifluoromethyl-phenyl)-nicotinic acid methyl ester (example 1L]) in analogy to the procedure described in example 53B]) to give 2-[3-chloro-4-({[2-methyl-6-(4-trifluoromethyl-phenyl)-pyridine-3-carbonyl]-amino}-methyl)-phenoxy]-2-methyl-propionic acid ethyl ester, which was subsequently saponified to yield the title compound as light yellow foam.

MS: 505.1 (M–H, 1Cl)$^-$.

Example 127

2-[3-Chloro-4-({[4-cyclopropyl-2-(4-trifluoromethyl-phenyl)-pyrimidine-5-carbonyl]-amino}-methyl)-phenoxy]-2-methyl-propionic acid In analogy to the procedures described in example 26B] and 26C], 2-(4-aminomethyl-3-chloro-phenoxy)-2-methyl-propionic acid ethyl ester (prepared from 2-chloro-4-hydroxy-benzaldehyde by reaction with ethyl-bromoisobutyrate as described in example 52A] followed by oxim formation and reduction as described in examples 97A] and 97B]) was reacted with 4-cyclopropyl-2-(4-trifluoromethyl-phenyl)-pyrimidine-5-carboxylic acid (example 53B]) to give 2-[3-chloro-4-({[4-cyclopropyl-2-(4-trifluoromethyl-phenyl)-pyrimidine-5-carbonyl]-amino}-methyl)-phenoxy]-2-methyl-propionic acid ethyl ester, which was subsequently saponified to yield the title compound as colorless solid.

MS: 532.2 (M–H, 1Cl)$^-$.

Example 128

2-[3-Chloro-4-({[4-methoxymethyl-2-(4-trifluoromethyl-phenyl)-pyrimidine-5-carbonyl]-amino}-methyl)-phenoxy]-2-methyl-propionic acid In analogy to the procedures described in example 26B] and 26C], 2-(4-aminomethyl-3-chloro-phenoxy)-2-methyl-propionic acid ethyl ester (prepared from 2-chloro-4-hydroxy-benzaldehyde by reaction with ethyl-bromoisobutyrate as described in example 52A] followed by oxim formation and reduction as described in examples 97A] and 97B]) was reacted with 4-methoxymethyl-2-(4-trifluoromethyl-phenyl)-pyrimidine-5-carboxylic acid (prepared from 4-methoxy-3-oxo-butyric acid methyl ester, in analogy to the procedures described in examples 27C] and 27D] followed by saponification in analogy to the procedure described in example 53B]) to give 2-[3-chloro-4-({[4-methoxymethyl-2-(4-trifluoromethyl-phenyl)-pyrimidine-5-carbonyl]-amino}-methyl)-phenoxy]-2-methyl-propionic acid ethyl ester, which was subsequently saponified to yield the title compound as light yellow foam.

MS: 536.2 (M–H, 1Cl)$^-$.

Example 129

2-[3-Chloro-4-({[4-(2-methoxy-ethyl)-2-(4-trifluoromethyl-phenyl)-pyrimidine-5-carbonyl]-amino}-methyl)-phenoxy]-2-methyl-propionic acid In analogy to the procedures described in example 26B] and 26C], 2-(4-aminomethyl-3-chloro-phenoxy)-2-methyl-propionic acid ethyl ester (prepared from 2-chloro-4-hydroxy-benzaldehyde by reaction with ethyl-bromoisobutyrate as described in example 52A] followed by oxim formation and reduction as described in examples 97A] and 97B]) was reacted with 4-(2-methoxy-ethyl)-2-(4-trifluoromethyl-phenyl)-pyrimidine-5-carboxylic acid (prepared from 5-methoxy-3-oxo-pentanoic acid methyl ester, in analogy to the procedures described in examples 27C] and 27D] followed by saponification in analogy to the procedure described in example 53B]) to give 2-[3-chloro-4-({[4-(2-methoxy-ethyl)-2-(4-trifluoromethyl-phenyl)-pyrimidine-5-carbonyl]-amino}-methyl)-phenoxy]-2-methyl-propionic acid ethyl ester, which was subsequently saponified to yield the title compound as light yellow oil.

MS: 550.1 (M–H, 1Cl)$^-$.

Example 130

2-(3-{[4-Cyclopropyl-2-(4-trifluoromethyl-phenyl)-pyrimidin-5-ylmethyl]-methyl-carbamoyl}-5-methoxy-phenoxy)-2-methyl-propionic acid A] In analogy to the procedures described in example 26B] and 26C], [4-cyclopropyl-2-(4-trifluoromethyl-phenyl)-pyrimidin-5-ylmethyl]-methyl-amine (example 130C]) was reacted with 3-(1-ethoxycarbonyl-1-methyl-ethoxy)-5-methoxy-benzoic acid (prepared from 3-hydroxy-5-methoxy-benzaldehyde [Journal of Organic Chemistry (1985), 50(13), 2236–40], by reaction with ethyl-bromoisobutyrate followed by oxidation with sodium chlorite in analogy to the procedures described in examples 52A] and 59A]) to give 2-(3-{[4-cyclopropyl-2-(4-trifluoromethyl-phenyl)-pyrimidin-5-ylmethyl]-methyl-carbamoyl}-5-methoxy-phenoxy)-2-methyl-propionic acid ethyl ester, which was subsequently saponified to yield the title compound as colorless solid.

MS: 542.2 (M–H)⁻.

The necessary building block [4-cyclopropyl-2-(4-trifluoromethyl-phenyl)-pyrimidin-5-ylmethyl]-methyl-amine used in procedure above was prepared as follows:

B] [4-Cyclopropyl-2-(4-trifluoromethyl-phenyl)-pyrimidin-5-ylmethyl]-methyl-carbamic acid ethyl ester 1.00 g (3.2 mmol) of 5-chloromethyl-4-cyclopropyl-2-(4-trifluoromethyl-phenyl)-pyrimidine (example 27F]) was dissolved in 20 ml of DMF. Then, the reaction mixture was cooled down to 0° C. 0.36 ml=0.366 g (3.52 mmol) of methyl-carbamic acid ethyl ester was added to the stirred solution, followed by 0.14 g (3.2 mmol) of sodium hydride (55%). After 18 hours, the reaction mixture was poured into crashed ice, the pH was adjusted to <3 with HCl/H$_2$O and it was then extracted twice with Et$_2$O. The combined organic phases were washed with water, dried over anhydrous magnesium sulfate and evaporated. The crude product was purified by flash chromatography (SiO$_2$, gradient of EtOAc, n-heptane) to give 0.87 g of the title compound as light yellow solid.

MS: 380.4 (M+H)⁺.

C] [4-Cyclopropyl-2-(4-trifluoromethyl-phenyl)-pyrimidin-5-ylmethyl]-methyl-amine 0.83 g (2.2 mmol) of [4-cyclopropyl-2-(4-trifluoromethyl-phenyl)-pyrimidin-5-ylmethyl]-methyl-carbamic acid ethyl ester was dissolved in 15 ml of ethylene glycol. Then, 1.72 g (26.4 mmol) of potassium hydroxide (86%) and 0.44 ml=0.46 g (9.0 mmol) of hydrazine hydrate were added and the reaction mixture heated up to 190° C. (oil bath, 210° C.) for 90 minutes. After cooling down below 80° C., some pieces of ice were added to the reaction mixture followed by EtOAc. It was then extracted twice with EtOAc; the combined organic phases were washed with water, dried over anhydrous magnesium sulfate and evaporated. The crude product was purified by flash chromatography (SiO$_2$, gradient of MeCl$_2$, MeOH) to give 0.59 g of the title compound as yellow solid.

MS: 308.2 (M+H)⁺.

Example 131

2-Methyl-2-[4-({methyl-[2-methyl-6-(4-trifluoromethyl-phenyl)-pyridin-3-yl]-carbamoyl}-methyl)-phenoxy]-propionic acid In analogy to the procedures described in example 26B] and 124C], methyl-[2-methyl-6-(4-trifluoromethyl-phenyl)-pyridin-3-yl]-amine (prepared from [2-methyl-6-(4-trifluoromethyl-phenyl)-pyridin-3-yl]-carbamic acid tert-butyl ester (example 125B] by N-methylation followed by Boc-cleavage in analogy to the procedures described in examples 5E] and 5F]) was reacted with 2-(4-carboxymethyl-phenoxy)-2-methyl-propionic acid tert-butyl ester (example 124A]) to give 2-methyl-2-[4-({methyl-[2-methyl-6-(4-trifluoromethyl-phenyl)-pyridin-3-yl]-carbamoyl}-methyl)-phenoxy]-propionic acid tert-butyl ester, which was subsequently cleaved with trifluoroacetic acid to yield the title compound as colorless solid.

MS: 485.3 (M–H)⁻.

Example 132

2-[3-Chloro-4-({[4-trifluoromethyl-6-(4-trifluoromethyl-phenyl)-pyridine-3-carbonyl]-amino}-methyl)-phenoxy]-2-methyl-propionic acid In analogy to the procedures described in example 26B] and 26C], 2-(4-aminomethyl-3-chloro-phenoxy)-2-methyl-propionic acid ethyl ester (prepared from 2-chloro-4-hydroxy-benzaldehyde by reaction with ethyl-bromoisobutyrate as described in example 52A] followed by oxim formation and reduction as described in examples 97A] and 97B]) was reacted with 4-trifluoromethyl-6-(4-trifluoromethyl-phenyl)-nicotinic acid (prepared from 4-trifluoromethyl-6-(4-trifluoromethyl-phenyl)-nicotinic acid methyl ester (example 108B]) by saponification in analogy to example 53B]) to give 2-[3-chloro-4-({[4-trifluoromethyl-6-(4-trifluoromethyl-phenyl)-pyridine-3-carbonyl]-amino}-methyl)-phenoxy]-2-methyl-propionic acid ethyl ester, which was subsequently saponified to yield the title compound as amorphous light yellow solid.

MS: 559.2 (M–H, 1Cl)⁻.

Example 133

2-[3-Chloro-4-({[4-trifluoromethyl-2-(4-trifluoromethyl-phenyl)-pyrimidine-5-carbonyl]-amino}-methyl)-phenoxy]-2-methyl-propionic acid In analogy to the procedures described in example 26B] and 26C], 2-(4-aminomethyl-3-chloro-phenoxy)-2-methyl-propionic acid ethyl ester (prepared from 2-chloro-4-hydroxy-benzaldehyde by reaction with ethyl-bromoisobutyrate as described in example 52A] followed by oxim formation and reduction as described in examples 97A] and 97B]) was reacted with 4-trifluoromethyl-2-(4-trifluoromethyl-phenyl)-pyrimidine-5-carboxylic acid (prepared by saponification from 4-trifluoromethyl-2-(4-trifluoromethyl-phenyl)-pyrimidine-5-carboxylic acid ethyl ester (example 107B]) in analogy to example 53B]) to give 2-[3-chloro-4-({[4-trifluoromethyl-2-(4-trifluoromethyl-phenyl)-pyrimidine-5-carbonyl]-amino}-methyl)-phenoxy]-2-methyl-propionic acid ethyl ester, which was subsequently saponified to yield the title compound as amorphous light yellow solid.

MS: 560.2 (M–H, 1Cl)⁻.

Example 134

2-Methyl-2-[4-({[4-trifluoromethyl-6-(4-trifluoromethyl-phenyl)-pyridine-3-carbonyl]-amino}-methyl)-phenoxy]-propionic acid In analogy to the procedures described in example 26B] and 26C], 2-(4-aminomethyl-phenoxy)-2-methyl-propionic acid ethyl ester [PCT Int. Appl. (2002), WO 2002/096895A1] was reacted with 4-trifluoromethyl-6-(4-trifluoromethyl-phenyl)-nicotinic acid (prepared from 4-trifluoromethyl-6-(4-trifluoromethyl-phenyl)-nicotinic acid methyl ester (example 108B]) by saponification in analogy to example 53B]) to give 2-methyl-2-[4-({[4-trifluoromethyl-6-(4-trifluoromethyl-phenyl)-pyridine-3-carbonyl]-amino}-methyl)-phenoxy]-propionic acid ethyl ester, which was subsequently saponified to yield the title compound as amorphous light yellow solid.

MS: 525.1 (M–H)⁻.

Example 135

2-Methyl-2-[4-({[4-trifluoromethyl-2-(4-trifluoromethyl-phenyl)-pyrimidine-5-carbonyl]-amino}-methyl)-phenoxy]-propionic acid In analogy to the procedures described in example 26B] and 26C], 2-(4-aminomethyl-phenoxy)-2-methyl-propionic acid ethyl ester [PCT Int. Appl. (2002), WO 2002/096895A1] was reacted with 4-trifluoromethyl-2-(4-trifluoromethyl-phenyl)-pyrimidine-5-carboxylic acid (prepared by saponification from 4-trifluoromethyl-2-(4-trifluoromethyl-phenyl)-pyrimidine-5-carboxylic acid ethyl ester (example 107B]) in analogy to example 53B]) to give 2-methyl-2-[4-({[4-trifluoromethyl-2-(4-trifluoromethyl-phenyl)-pyrimidine-5-carbonyl]-amino}-methyl)-phenoxy]-propionic acid ethyl ester, which was subsequently saponified to yield the title compound as colorless solid.

MS: 526.1 (M–H)$^-$.

Example 136

2-(4-{[4-Cyclopropyl-2-(4-trifluoromethyl-phenyl)-pyrimidin-5-ylcarbamoyl]-methyl}-phenoxy)-2-methyl-propionic acid In analogy to the procedures described in example 26B] and 124C], 4-cyclopropyl-2-(4-trifluoromethyl-phenyl)-pyrimidin-5-ylamine (prepared from 4-trifluoromethyl-2-(4-trifluoromethyl-phenyl)-pyrimidine-5-carboxylic acid, see example 133], in analogy to the procedures described in examples 125B] and 125C]) was reacted with 2-(4-carboxymethyl-phenoxy-2-methyl-propionic acid tert-butyl ester (example 124A]) to give 2-(4-{[4-cyclopropyl-2-(4-trifluoromethyl-phenyl)-pyrimidin-5-ylcarbamoyl]-methyl}-phenoxy)-2-methyl-propionic acid tert-butyl ester, which was subsequently cleaved with trifluoroacetic acid to yield the title compound as yellow solid.

MS: 498.1 (M–H)$^-$.

Example 137

2-(3-{[4-Cyclopropyl-2-(4-trifluoromethyl-phenyl)-pyrimidin-5-ylcarbamoyl]-methyl}-phenoxy)-2-methyl-propionic acid In analogy to the procedures described in example 26B] and 124C], 4-cyclopropyl-2-(4-trifluoromethyl-phenyl)-pyrimidin-5-ylamine (prepared from 4-trifluoromethyl-2-(4-trifluoromethyl-phenyl)-pyrimidine-5-carboxylic acid, see example 133], in analogy to the procedures described in examples 125B] and 125C]) was reacted with 2-(3-carboxymethyl-phenoxy)-2-methyl-propionic acid tert-butyl ester (prepared from (3-hydroxy-phenyl)-acetic acid methyl ester and tert-butyl alpha-bromoisobutyrate, in analogy to the procedure described in example 52A], followed by saponification in analogy the procedure described in example 124A]) to give 2-(3-{[4-cyclopropyl-2-(4-trifluoromethyl-phenyl)-pyrimidin-5-ylcarbamoyl]-methyl}-phenoxy)-2-methyl-propionic acid tert-butyl ester, which was subsequently cleaved with trifluoroacetic acid to yield the title compound as light yellow amorphous solid.

MS: 498.1 (M–H)$^-$.

Example 138

2-Methyl-2-(3-{[2-methyl-6-(4-trifluoromethyl-phenyl)-pyridin-3-ylcarbamoyl]-methyl}-phenoxy)-propionic acid In analogy to the procedures described in example 26B] and 124C], 2-methyl-6-(4-trifluoromethyl-phenyl)-pyridin-3-ylamine (example 125C]) was reacted with 2-(3-carboxymethyl-phenoxy)-2-methyl-propionic acid tert-butyl ester (prepared from (3-hydroxy-phenyl)-acetic acid methyl ester and tert-butyl alpha-bromoisobutyrate, in analogy to the procedure described in example 52A], followed by saponification in analogy the procedure described in example 124A]) to give 2-methyl-2-(3-{[2-methyl-6-(4-trifluoromethyl-phenyl)-pyridin-3-ylcarbamoyl]-methyl}-phenoxy)-propionic acid tert-butyl ester, which was subsequently cleaved with trifluoroacetic acid to yield the title compound as light yellow amorphous solid.

MS: 471.1 (M–H)$^-$.

Example 139

2-Methyl-2-(4-{[4-trifluoromethyl-6-(4-trifluoromethyl-phenyl)-pyridin-3-ylcarbamoyl]-methyl}-phenoxy)-propionic acid A] 2-Methyl-2-(4-{[4-trifluoromethyl-6-(4-trifluoromethyl-phenyl)-pyridin-3-ylcarbamoyl]-methyl}-phenoxy)-propionic acid Tert-butyl Ester 0.295 g (1.0 mmol) of 2-(4-carboxymethyl-phenoxy)-2-methyl-propionic acid tert-butyl ester (example 124A]) was dissolved in 10 ml methylenechloride at room temperature; then, one drop of DMF was added followed by addition of 0.09 ml (0.130 g=1.0 mmol) of oxalylchloride; after stirring of the reaction for 30 min., the solvent was removed by evaporation at 20° C. The residue was dissolved in 5 ml of methylenechloride and added to a solution of 0.33 ml=0.25 g (2.0 mmol) of N-ethyl-diisopropylamine in 5 ml methylenechloride. A solution of 0.279 g (0.95 mmol) of 4-trifluoromethyl-6-(4-trifluoromethyl-phenyl)-pyridin-3-ylamine (prepared from 4-trifluoromethyl-6-(4-trifluoromethyl-phenyl)-nicotinic acid (example 132]) and 2-methyl-2-propanol/diphenylphosphoryl azide followed by Boc cleavage with trifluoroacetic acid in analogy to the procedures described in examples 125 B] and 125C]) in 5 ml of methylenechloride was added at room temperature and the reaction mixture was stirred for 16 hours. Then, 0.18 g (1.5 mmol) of N,N'-dimethylaminopyridine was added and the reaction mixture heated at reflux for 8 hours. Subsequently, the solvent was removed by evaporation in vacuo and the residue was purified by chromatography on silica gel with a gradient of MeCl$_2$ and MeOH to give 0.39 g of the title compound as colorless oil.

MS: 582.3 (M)$^+$.

B] 2-Methyl-2-(4-{[4-trifluoromethyl-6-(4-trifluoromethyl-phenyl)-pyridin-3-ylcarbamoyl]-methyl}-phenoxy)-propionic acid In analogy to the procedure described in example 124C], 2-methyl-2-(4-{[4-trifluoromethyl-6-(4-trifluoromethyl-phenyl)-pyridin-3-ylcarbamoyl]-methyl}-phenoxy)-propionic acid tert-butyl ester was cleaved with trifluoroacetic acid to yield the title compound as light yellow oil.

MS: 525.1 (M–H)$^-$.

Example 140

2-{4-[4-(2-Methoxy-ethyl)-2-(4-trifluoromethyl-phenyl)-pyrimidin-5-ylmethoxy]-2-methyl-phenoxy}-2-methyl-propionic acid In analogy to the procedure described in example 101A], 2-(4-hydroxy-2-methyl-phenoxy)-2-methyl-propionic acid ethyl ester (described in WO 02/092590) was reacted with 5-chloromethyl-4-(2-methoxy-ethyl)-2-(4-trifluoromethyl-phenyl)-pyrimidine (example 110B]) in the presence of catalytic amount of sodium iodide to give 2-{4-[4-(2-methoxy-ethyl)-2-(4-trifluoromethyl-phenyl)-pyrimidin-5-ylmethoxy]-2-methyl-phenoxy}-2-methyl-propionic acid ethyl ester, which was subsequently saponified in analogy to the procedure described in example 102] to yield the title compound as white crystals of mp. 119.5–120.0° C.

MS: 503.2 (M–H)⁻.

Example 141

2-{4-[4-Cyclopropyl-2-(4-trifluoromethyl-phenyl)-pyrimidin-5-ylmethoxy]-3-fluoro-phenoxy}-2-methyl-propionic acid

A] 2-(4-Acetyl-3-fluoro-phenoxy)-2-methyl-propionic acid ethyl ester

A suspension of 12.0 g (77.9 mmol) of 2-fluoro-4-hydroxyacetophenone, 27.9 g (85.6 mmol) of cesium carbonate and 11.6 ml (77.9 mmol) of ethyl 2-bromo-2-methyl-propionate in 200 ml of DMF was heated at 50° C. for 3 days. Twice a day additional 12.7 g (38.9 mmol) of cesium carbonate and 5.8 ml (38.9 mmol) of ethyl 2-bromo-2-methylpropionate were added (total of 2.5 equivalent). The mixture was neutralized with aqueous 10% KHSO₄ and extracted with ether (3×). The organic phases were washed with aqueous 10% KHSO₄, aqueous 10% NaCl and dried over sodium sulfate. The crude product was purified by flash chromatography over silica gel with heptane/AcOEt 9:1 to 6:1, to give 16.7 g of the title compound as colorless oil.

MS: 268.2 (M)⁺.

B] 2-(4-Acetoxy-3-fluoro-phenoxy)-2-methyl-propionic acid ethyl ester

A solution of 3.0 g (11.2 mmol) of 2-(4-acetyl-3-fluoro-phenoxy)-2-methyl-propionic acid ethyl ester in 30 ml dichloromethane was treated with 4.1 g (70%, 16.8 mmol) of 3-chloro perbenzoic acid. The reaction was stirred at RT. After 1 day additional 1.2 g (70%, 4.7 mmol), after 2 days 0.8 g (70%, 3.1 mmol) and after 3 days 0.6 g (70%, 2.3 mmol) of 3-chloro perbenzoic acid were added. The mixture was poured on ice/aqueous 10% disodium pyroslfite solution and extracted with ether (3×). The organic phases were washed with aqueous 10% NaHCO₃, aqueous saturated NH₄Cl, aqueous 10% NaCl and dried over sodium sulfate to give 3.2 g of the title compound as light yellow oil.

MS: 302.2 (M+NH₄)⁺.

C] 2-(3-Fluoro-4-hydroxy-phenoxy)-2-methyl-propionic acid ethyl ester

A solution of 3.10 g (10.9 mmol) of 2-(4-acetoxy-3-fluoro-phenoxy)-2-methyl-propionic acid ethyl ester in 30 ml ethanol was treated at 0° C. with 2.26 g (16.4 mmol) of K₂CO₃. The mixture was stirred for 1 day at RT, the neutralized with aqueous 10% KHSO₄ and extracted with ether (3×). The organic phases were washed with aqueous 10% KHSO₄, aqueous 10% NaCl and dried over sodium sulfate. The crude product was purified by flash chromatography over silica gel with heptane/AcOEt 97.5:2.5 to 4:1, to give 2.48 g of the title compound as colorless crystalls.

MS: 242.3 (M)⁺.

D] 2-{4-[4-Cyclopropyl-2-(4-trifluoromethyl-phenyl)-pyrimidin-5-ylmethoxy]-3-fluoro-phenoxy}-2-methyl-propionic acid In analogy to the procedure described in example 101A], 2-(3-fluoro-4-hydroxy-phenoxy)-2-methyl-propionic acid ethyl ester was reacted with 5-chloromethyl-4-cyclopropyl-2-(4-trifluoromethyl-phenyl)-pyrimidine (example 27F]) in the presence of catalytic amount of sodium iodide to give 2-{4-[4-cyclopropyl-2-(4-trifluoromethyl-phenyl)-pyrimidin-5-ylmethoxy]-3-fluoro-phenoxy}-2-methyl-propionic acid ethyl ester, which was subsequently saponified in analogy to the procedure described in example 101B] to yield the title compound as white crystals of mp. 177.5–178.0° C.

MS: 489.1 (M–H)⁻.

Example 142

2-{4-[4-Cyclopropyl-2-(4-trifluoromethoxy-phenyl)-pyrimidin-5-ylmethylsulfanyl]-2-methyl-phenoxy}-2-methyl-propionic acid

A] 4,4'-Dithiodi-o-cresol

To a stirred solution of 33.0 g (825.6 mmol) NaOH in 200 ml water was added 44.0 g (266.3 mmol) of 2-methyl-4-thiocyanato-phenol at 85° C. [Wei, Zhi-Liang; Kozikowski, Alan P., A Short and Efficient Synthesis of the Pharmacological Research Tool GW501516 for the Peroxisome Proliferator-Activated Receptor delta, Journal of Organic Chemistry (2003), 68(23), 9116–9118]. The temperature was raised to 95° C. and the mixture stirred over night. After cooling (10° C.), ether and 90 ml of aqueous conc. HCl were added. The water phase was extracted with ether (2×). The organic phase was washed with brine, dried (Na₂SO₄) and evaporated. The residue was dissolved in 300 ml of DMSO and heated for 2 h at 95° C. Subsequently, the solution was poured onto ice water and extracted with three 1 l portions of TBME. The organic layers were washed with 700 ml of water, dried (Na₂SO₄) and evaporated to give 42.1 g of the title compound.

B] 2-{4-[4-(1-Ethoxycarbonyl-1-methyl-ethoxy)-3-methyl-phenyldisulfanyl]-2-methyl-phenoxy-2-methyl-propionic acid ethyl ester To a solution of 25.0 g (89.8 mmol) 4,4'-dithiodi-o-cresol and 52.7 ml (360 mmol) ethyl-bromoisobutyrate in 600 ml DMF 117 g (360 mmol) cesium carbonate were slowly added at 45° C. The reaction mixture was stirred for 5 h at C] 2-(4-Acetylsulfanyl-2-methyl-phenoxy)-2-methyl-propionic acid ethyl ester A solution of 9.2 g (31.7 mmol) of [(n-Bu)₃PH]BF₄ [Netherton, Matthew R.; Fu, Gregory C., Air-Stable Trialkylphosphonium Salts: Simple, Practical, and Versatile Replacements for Air-Sensitive Trialkylphosphines. Applications in Stoichiometric and Catalytic Processes, Organic Letters (2001), 3(26), 4295–4298] in 150 ml DMF (degassed with argon) was added to 11.5 g (22.6 mmol) of 2-{4-[4-(1-ethoxycarbonyl-1-methyl-ethoxy)-3-methyl-phenyldisulfanyl]-2-methyl-phenoxy}-2-methyl-propionic acid ethyl ester. 5.43 ml (31.7 mmol) N-ethyldiisopropylamine and 0.416 ml (23.1 mmol) of water were added. After 2 h 40 min, 5.14 ml (54.4 mmol) of acetic acid anhydride were added and after 1 h 20 min, the reaction was diluted with isobutyl acetate, washed with 0.1N HCl and brine. The organic phase was dried (Na₂SO₄), concentrated under reduced pressure and purified by chromatography over silica gel with EtOAc/n-heptane 1:4, to give 12.56 g of the title compound as colorless oil.

MS: 319 (M+Na)⁺.

D] 2-{4-[4-Cyclopropyl-2-(4-trifluoromethoxy-phenyl)-pyrimidin-5-ylmethylsulfanyl]-2-methyl-phenoxy}-2-methyl-propionic acid ethyl ester 0.399 g (1.2 mmol) of 5-Chloromethyl-4-cyclopropyl-2-(4-trifluoromethoxy-phenyl)-pyrimidine (example 150D]) and 0.300 g (1.0 mmol) of 2-(4-acetylsulfanyl-2-methyl-phenoxy)-2-methyl-propionic acid ethyl ester (example 142C]) were dissolved in 2.0 ml of acetonitrile and 0.08 ml of MeOH and treated with 0.462 g (1.4 mmol) of Cs₂CO₃. After vigorous stirring for 27 h at ambient temperature and filtration, the solvent was evaporated and the residue redissolved in dichloromethane and filtered again and evaporated. Purification by flash chromatography (SiO₂, dichloromethane/n-heptane 1:2 to 4:1 and then AcOEt) afforded 0.428 g of the title compound as colorless oil.

MS: 546.3 (M)⁺.

E] 2-{4-[4-Cyclopropyl-2-(4-trifluoromethoxy-phenyl)-pyrimidin-5-ylmethylsulfanyl]-2-methyl-phenoxy}-2-methyl-propionic acid 0.386 g (0.7 mmol) of the above prepared 2-{4-[4-cyclopropyl-2-(4-trifluoromethoxy-phenyl)-pyrimidin-5-ylmethylsulfanyl]-2-methyl-phenoxy}-2-methyl-propionic acid ethyl ester was dissolved in 12 ml of THF/EtOH (1:1), treated at 0° C. with 2.12 ml (2.1 mmol) of 1N LiOH, and kept at ambient temperature for 23 h. The reaction mixture was taken up in ether and washed with aqueous 10% KHSO₄ solution and aqueous 10% NaCl solution. The water phases were extracted with ether (2×). The organic phase was dried (Na₂SO₄) and evaporated. The crude product was precipitated in ether/pentane (RT to 4° C.) and filtered to give 0.289 g of the title compound as white crystals of mp. 127–128° C., dec.

MS: 517.3 (M–H)⁻.

Example 143

2-{4-[2-Cyclopropyl-6-(4-trifluoromethoxy-phenyl)-pyridin-3-ylmethylsulfanyl]-2-methyl-phenoxy}-2-methyl-propionic acid A] 2-{4-[2-Cyclopropyl-6-(4-trifluoromethoxy-phenyl)-pyridin-3-ylmethylsulfanyl]-2-methyl-phenoxy}-2-methyl-propionic acid ethyl ester In analogy to the procedure described in example 142D], 2-(4-acetylsulfanyl-2-methyl-phenoxy)-2-methyl-propionic acid ethyl ester (example 142C]) was reacted with 3-chloromethyl-2-cyclopropyl-6-(4-trifluoromethoxy-phenyl)-pyridine (example 143F]) to give the title compound as colorless oil.

MS: 545.3 (M)⁺.

B] 2-{4-[2-Cyclopropyl-6-(4-trifluoromethoxy-phenyl)-pyridin-3-ylmethylsulfanyl]-2-methyl-phenoxy}-2-methyl-propionic acid In analogy to the procedure described in example 142E], saponification of 2-{4-[2-cyclopropyl-6-(4-trifluoromethoxy-phenyl)-pyridin-3-ylmethylsulfanyl]-2-methyl-phenoxy}-2-methyl-propionic acid ethyl ester yielded the title compound as colorless oil.

MS: 516.2 (M–H)⁻.

3-Chloromethyl-2-cyclopropyl-6-(4-trifluoromethoxy-phenyl)-pyridine used in 143A] was prepared as follows:

C] (E)-3-Dimethylamino-1-(4-trifluoromethoxy-phenyl)-propenone (Following the procedure described in Gammill, R. B. A new and efficient synthesis of 3-halogenated 4H-1-benzopyran-4-ones. Synthesis (1979), (11), 901–3)

A solution of 20.4 g (100.0 mmol) 1-(4-trifluoromethoxy-phenyl)-ethanone in 20 ml (150.0 mmol) of dimethylformamide dimethylacetal were heated at 100° C. for 23.5 h. The reaction was evaporated and precipitated from ether/n-pentane to give 23.1 g of the title compound as a yellow solid.

MS: 260.1 (M+H)⁺.

D] 2-Cyclopropyl-6-(4-trifluoromethoxy-phenyl)-nicotinic acid methyl ester (Following the procedure described in Al-Saleh, Balkis; Abdelidalik, Mervat Mohammed; Eltoukhy, Afaf Mohammed; Elnagdi, Mohammed Hilmy. Enaminones in heterocyclic synthesis: A new regioselective synthesis of 2,3,6-trisubstituted pyridines, 6-substituted-3-aroylpyridines and 1,3,5-triaroylbenzenes. Journal of Heterocyclic Chemistry (2002), 39(5), 1035–1038)

A mixture of 2.0 g (7.72 mmol) (E)-3-dimethylamino-1-(4-trifluoromethoxy-phenyl)-propenone, 1.32 g (9.26 mmol) methyl 3-cyclopropyl-3-oxopropanoate and 0.77 (10.0 mmol) ammonium acetate in 8 ml acetic acid were heated under reflux for 1.5 h and cooled to room temperature. The reaction was neutralized with aqueous 10% KHSO₄ solution. The mixture was extracted with ether (3×); the organic phase was washed with aqueous 10% KHSO₄-solution, aqueous saturated NaHCO₃, dried (Na₂SO₄) and evaporated. The side product ((4-trifluoromethoxy-phenyl)-[6-(4-trifluoromethoxy-phenyl)-pyridin-3-yl]-methanone) was precipitated from ether/pentane and the mother liquor purified by flash chromatography (SiO$_2$, n-heptane/AcOEt=97.5/2.5) to give 1.07 g of the title compound as a yellow oil.

MS: 337.1 (M)$^+$.

E] [2-Cyclopropyl-6-(4-trifluoromethoxy-phenyl)-pyridin-3-yl]-methanol

In analogy to the procedure described in example 108C], reduction of 2-cyclopropyl-6-(4-trifluoromethoxy-phenyl)-nicotinic acid methyl ester yielded the title compound as white solid.

MS: 309.2 (M)$^+$.

F] 5-Chloromethyl-4-trifluoromethyl-2-(4-trifluoromethyl-phenyl)-pyridine

In analogy to the procedure described in example 101F], [2-cyclopropyl-6-(4-trifluoromethoxy-phenyl)-pyridin-3-yl]-methanol gave at 0° C., the title compound as off-white powder.

MS: 327.1 (M, 1Cl)$^+$.

Example 144

2-{4-[4-Cyclopropyl-2-(4-trifluoromethyl-phenyl)-pyrimidin-5-ylmethylsulfanyl]-2-methyl-phenoxy}-2-methyl-propionic acid

A] 2-{4-[4-Cyclopropyl-2-(4-trifluoromethyl-phenyl)-pyrimidin-5-ylmethylsulfanyl]-2-methyl-phenoxy-2-methyl-propionic acid ethyl ester In analogy to the procedure described in example 142D], 2-(4-acetylsulfanyl-2-methyl-phenoxy)-2-methyl-propionic acid ethyl ester (example 142C]) was reacted with 5-chloromethyl-4-cyclopropyl-2-(4-trifluoromethyl-phenyl)-pyrimidine (example 27F]) to give the title compound as colorless oil.

MS: 531.3 (M+H)$^+$.

B] 2-{4-[4-Cyclopropyl-2-(4-trifluoromethyl-phenyl)-pyrimidin-5-ylmethylsulfanyl]-2-methyl-phenoxy}-2-methyl-propionic acid In analogy to the procedure described in example 142E], saponification of 2-{4-[4-cyclopropyl-2-(4-trifluoromethyl-phenyl)-pyrimidin-5-ylmethylsulfanyl]-2-methyl-phenoxy}-2-methyl-propionic acid ethyl ester yielded after precipitation with ether/n-pentane (4° C.) the title compound as white crystals of mp. 129–131° C. MS: 501.2 (M–H)$^-$.

Example 145

2-{4-[2-Cyclopropyl-6-(4-trifluoromethoxy-phenyl)-pyridin-3-ylmethoxy]-2-methyl-phenoxy}-2-methyl-propionic acid

A] 2-{4-[2-Cyclopropyl-6-(4-trifluoromethoxy-phenyl)-pyridin-3-ylmethoxy]-2-methyl-phenoxy}-2-methyl-propionic acid ethyl ester In analogy to the procedure described in example 101A], 2-(4-hydroxy-2-methyl-phenoxy)-2-methyl-propionic acid ethyl ester (described in WO 02/092590) was reacted with 5-chloromethyl-4-trifluoromethyl-2-(4-trifluoromethyl-phenyl)-pyridine (example 143F]) to give the title compound as light yellow solid.

MS: 530.4 (M+H)$^+$.

B] 2-{4-[2-Cyclopropyl-6-(4-trifluoromethoxy-phenyl)-pyridin-3-ylmethoxy]-2-methyl-phenoxy}-2-methyl-propionic acid In analogy to the procedure described in example 101B], saponification of 2-{4-[2-cyclopropyl-6-(4-trifluoromethoxy-phenyl)-pyridin-3-ylmethoxy]-2-methyl-phenoxy}-2-methyl-propionic acid ethyl ester yielded the title compound as white crystals of mp. 131–133° C.

MS: 500.1 (M–H)$^-$.

Example 146

{2-Methyl-4-[2-methyl-6-(4-trifluoromethyl-phenyl)-pyridin-3-ylmethoxy]-phenylsulfanyl}-acetic acid In analogy to the procedure described in example 20A], (4-hydroxy-2-methyl-phenylsulfanyl)-acetic acid tert-butyl ester (example 20C]), was reacted with 3-chloromethyl-2-methyl-6-(4-trifluoromethyl-phenyl)-pyridine (example 1N]) to give {2-methyl-4-[2-methyl-6-(4-trifluoromethyl-phenyl)-pyridin-3-ylmethoxy]-phenylsulfanyl}-acetic acid tert-butyl ester, which was subsequently saponified in analogy to the procedure described in example 20B] to yield the title compound as white solid of mp. 168–169° C.

MS: 446.1 (M–H)$^-$.

Example 147

2-{4-[4-Methoxymethyl-6-methyl-2-(4-trifluoromethyl-phenyl)-pyrimidin-5-ylmethoxy]-phenoxy}-2-methyl-propionic acid

A] 2-{4-[4-Methoxymethyl-6-methyl-2-(4-trifluoromethyl-phenyl)-pyrimidin-5-ylmethoxy]-2-methyl-phenoxy}-2-methyl-propionic acid ethyl ester In analogy to the procedure described in example 113A], 2-(4-hydroxy-2-methyl-phenoxy)-2-methyl-propionic acid ethyl ester (described in WO 02/092590) was reacted with 5-chloromethyl-4-methoxymethyl-6-methyl-2-(4-trifluoromethyl-phenyl)-pyrimidine (example 147E]) to give the title compound as light brown oil.

MS: 533.3 (M+H)$^+$.

B] 2-{4-[2-Cyclopropyl-6-(4-trifluoromethoxy-phenyl)-pyridin-3-ylmethoxy]-2-methyl-phenoxy}-2-methyl-propionic acid In analogy to the procedure described in example 113B], saponification of 2-{4-[4-methoxymethyl-6-methyl-2-(4-trifluoromethyl-phenyl)-pyrimidin-5-ylmethoxy]-2-methyl-phenoxy}-2-methyl-propionic acid ethyl ester yielded the title compound as colorless solid.

MS: 503.1 (M–H)$^-$.

5-Chloromethyl-4-methoxymethyl-6-methyl-2-(4-trifluoromethyl-phenyl)-pyrimidine used in 147A] was prepared as follows:

C] (E,Z)-3-Methoxy-2-(2-methoxy-acetyl)-but-2-enoic acid methyl ester

In analogy to the procedures described in example 113C] and 113D], 4-methoxy-3-oxo-butyric acid methyl ester and methoxyacetic anhydride (from methoxyacetyl chloride and methoxyacetic acid with pyridine) gave the title compound as a light brown oil.

MS: 203.1 (M+H)$^+$.

D] [4-Methoxymethyl-6-methyl-2-(4-trifluoromethyl-phenyl)-pyrimidin-5-yl]-methanol In analogy to the procedures described in example 113E] and 113G], (E,Z)-3-methoxy-2-(2-methoxy-acetyl)-but-2-enoic acid methyl ester and 4-trifluoromethyl-benzamidine HCl gave the title compound as light yellow crystals.

MS: 313.1 (M+H)$^+$.

E] 5-Chloromethyl-4-methoxymethyl-6-methyl-2-(4-trifluoromethyl-phenyl)-pyrimidine In analogy to the procedure described in example 113H], [4-methoxymethyl-6-methyl-2-(4-trifluoromethyl-phenyl)-pyrimidin-5-yl]-methanol and thionylchloride gave the title compound as a light red oil.

MS: 331.1 (M+H, 1Cl)$^+$.

Example 148

2-{4-[4-Methoxymethyl-6-methyl-2-(3-trifluoromethyl-phenyl)-pyrimidin-5-ylmethoxy]-2-methyl-phenoxy}-2-methyl-propionic acid A] 2-{4-[4-Methoxymethyl-6-methyl-2-(3-trifluoromethyl-phenyl)-pyrimidin-5-ylmethoxy]-2-methyl-phenoxy}-2-methyl-propionic acid ethyl ester In analogy to the procedure described in example 113A], 2-(4-hydroxy-2-methyl-phenoxy)-2-methyl-propionic acid ethyl ester (described in WO 02/092590) was reacted with 5-chloromethyl-4-methoxymethyl-6-methyl-2-(3-trifluoromethyl-phenyl)-pyrimidine (example 148D]) to give the title compound as light yellow viscous oil.

MS: 533.4 (M+H)$^+$.

B] 2-{4-[4-Methoxymethyl-6-methyl-2-(3-trifluoromethyl-phenyl)-pyrimidin-5-ylmethoxy]-2-methyl-phenoxy}-2-methyl-propionic acid In analogy to the procedure described in example 113B], saponification of 2-{4-[4-methoxymethyl-6-methyl-2-(3-trifluoromethyl-phenyl)-pyrimidin-5-ylmethoxy]-2-methyl-phenoxy}-2-methyl-propionic acid ethyl ester yielded the title compound as light yellow solid.

MS: 503.3 (M–H)$^-$.

5-Chloromethyl-4-methoxymethyl-6-methyl-2-(3-trifluoromethyl-phenyl)-pyrimidine used in 148A] was prepared as follows:

C] [4-Methoxymethyl-6-methyl-2-(3-trifluoromethyl-phenyl)-pyrimidin-5-yl]-methanol In analogy to the procedures described in example 113E] and 113G], (E,Z)-3-methoxy-2-(2-methoxy-acetyl)-but-2-enoic acid methyl ester (example 147C]) and 3-trifluoromethyl-benzamidine HCl gave the title compound as light yellow crystals.

MS: 313.1 (M+H)$^+$.

D] 5-Chloromethyl-4-methoxymethyl-6-methyl-2-(3-trifluoromethyl-phenyl)-pyrimidine In analogy to the procedure described in example 113H], [4-methoxymethyl-6-methyl-2-(3-trifluoromethyl-phenyl)-pyrimidin-5-yl]-methanol and thionylchloride gave the title compound as a brown viscous oil.

MS: 331.1 (M+H, 1Cl)$^+$.

Example 149

2-{4-[4-Methoxymethyl-6-methyl-2-(4-trifluoromethoxy-phenyl)-pyrimidin-5-ylmethoxy]-2-methyl-phenoxy}-2-methyl-propionic acid A] 2-{4-[4-Methoxymethyl-6-methyl-2-(4-trifluoromethoxy-phenyl)-pyrimidin-5-ylmethoxy]-2-methyl-phenoxy}-2-methyl-propionic acid ethyl ester In analogy to the procedure described in example 113A], 2-(4-hydroxy-2-methyl-phenoxy)-2-methyl-propionic acid ethyl ester (described in WO 02/092590) was reacted with 5-chloromethyl-4-methoxymethyl-6-methyl-2-(4-trifluoromethoxy-phenyl)-pyrimidine (example 149D]) to give the title compound as light yellow viscous oil.

MS: 549.3 (M+H)$^+$.

B] 2-{4-[4-Methoxymethyl-6-methyl-2-(4-trifluoromethoxy-phenyl)-pyrimidin-5-ylmethoxy]-2-methyl-phenoxy}-2-methyl-propionic acid In analogy to the procedure described in example 113B], saponification of 2-{4-[4-methoxymethyl-6-methyl-2-(4-trifluoromethoxy-phenyl)-pyrimidin-5-ylmethoxy]-2-methyl-phenoxy}-2-methyl-propionic acid ethyl ester yielded the title compound as a colorless solid.

MS: 519.5 (M–H)$^-$.

5-Chloromethyl-4-methoxymethyl-6-methyl-2-(4-trifluoromethoxy-phenyl)-pyrimidine used in 149A] was prepared as follows:

C] [4-Methoxymethyl-6-methyl-2-(4-trifluoromethoxy-phenyl)-pyrimidin-5-yl]-methanol In analogy to the procedures described in example 113E] and 113G], (E,Z)-3-methoxy-2-(2-methoxy-acetyl)-but-2-enoic acid methyl ester (example 147C]) and 4-trifluoromethoxy-benzamidine HCl gave the title compound as a light yellow oil.

MS: 329.3 (M+H)$^+$.

D] 5-Chloromethyl-4-methoxymethyl-6-methyl-2-(4-trifluoromethoxy-phenyl)-pyrimidine In analogy to the procedure described in example 113H], [4-methoxymethyl-6-methyl-2-(4-trifluoromethoxy-phenyl)-pyrimidin-5-yl]-methanol and thionylchloride gave the title compound as a brown oil.

MS: 347.5 (M+H, 1Cl)$^+$.

Example 150

2-{4-[4-Cyclopropyl-2-(4-trifluoromethoxy-phenyl)-pyrimidin-5-ylmethoxy]-2-methyl-phenoxy}-2-methyl-propionic acid A] 2-{4-[4-Cyclopropyl-2-(4-trifluoromethoxy-phenyl)-pyrimidin-5-ylmethoxy]-2-methyl-phenoxy}-2-methyl-propionic acid ethyl ester In analogy to the procedure described in example 113A], 2-(4-hydroxy-2-methyl-phenoxy)-2-methyl-propionic acid ethyl ester (described in WO 02/092590) was reacted with 5-chloromethyl-4-cyclopropyl-2-(4-trifluoromethoxy-phenyl)-pyrimidine (example 150D]) to give the title compound as light yellow viscous oil.

MS: 531.3 (M+H)$^+$.

B] 2-{4-[4-Cyclopropyl-2-(4-trifluoromethoxy-phenyl)-pyrimidin-5-ylmethoxy]-2-methyl-phenoxy}-2-methyl-propionic acid In analogy to the procedure described in example 113B], saponification of 2-{4-[4-cyclopropyl-2-(4-trifluoromethoxy-phenyl)-pyrimidin-5-ylmethoxy]-2-methyl-phenoxy}-2-methyl-propionic acid ethyl ester yielded the title compound as a colorless solid.

MS: 501.4 (M–H)$^-$.

5-Chloromethyl-4-cyclopropyl-2-(4-trifluoromethoxy-phenyl)-pyrimidine used in 150A] was prepared as follows:

C] [4-Cyclopropyl-2-(4-trifluoromethoxy-phenyl)-pyrimidin-5-yl]-methanol

In analogy to the procedures described in example 27D] and 27E], (E,Z)-2-cyclopropanecarbonyl-3-ethoxy-acrylic acid methyl ester (example 27C]) and 4-trifluoromethoxy-benzamidine HCl gave the title compound as a colorless solid.

MS: 311.0 (M+H)$^+$.

D] 5-Chloromethyl-4-cyclopropyl-2-(4-trifluoromethoxy-phenyl)-pyrimidine

In analogy to the procedure described in example 113H], [4-cyclopropyl-2-(4-trifluoromethoxy-phenyl)-pyrimidin-5-yl]-methanol and thionylchloride gave the title compound as a light brown solid.

MS: 329.0 (M+H, 1Cl)$^+$.

Example 151

2-Methyl-2-{2-methyl-4-[6-(4-trifluoromethoxy-phenyl)-4-trifluoromethyl-pyridin-3-ylmethoxy]-phenoxy}-propionic acid A] 6-(4-Trifluoromethoxy-phenyl)-4-trifluoromethyl-nicotinic acid methyl ester In analogy to the procedure described in example 108B], 4-(trifluoromethoxy)-phenylboronic acid was reacted with methyl 6-chloro-4-(trifluoromethyl)nicotinate in the presence of bis(triphenylphosphine)palladium(II)chloride and aqueous 2M K$_3$PO$_4$ solution to give the title compound as yellow crystals.

MS: 366.0 (M+H)$^+$.

B] [6-(4-Trifluoromethoxy-phenyl)-4-trifluoromethyl-pyridin-3-yl]-methanol

In analogy to the procedure described in example 43D], 6-(4-trifluoromethoxy-phenyl)-4-trifluoromethyl-nicotinic acid methyl ester was treated with lithium aluminium hydride in tetrahydrofuran under reflux conditions for 12 h to give the title compound as yellow oil.

MS: 338.0 (M+H)$^+$.

C] 2-Methyl-2-{2-methyl-4-[6-(4-trifluoromethoxy-phenyl)-4-trifluoromethyl-pyridin-3-ylmethoxy]-phenoxy}-propionic acid ethyl ester In analogy to the procedure described in example 43E], 2-(4-hydroxy-2-methyl-phenoxy)-2-methyl-propionic acid ethyl ester (described in WO 02/092590) was reacted with [6-(4-trifluoromethoxy-phenyl)-4-trifluoromethyl-pyridin-3-yl]-methanol in the presence of N,N,N',N'-tetramethylazodicarboxamide and tributylphosphine to give the title compound as colorless oil.

MS: 557.8 (M+H)$^+$.

D] 2-Methyl-2-{2-methyl-4-[6-(4-trifluoromethoxy-phenyl)-4-trifluoromethyl-pyridin-3-ylmethoxy]-phenoxy}-propionic acid In analogy to the procedure described in example 26C], 2-methyl-2-{2-methyl-4-[6-(4-trifluoromethoxy-phenyl)-4-trifluoromethyl-pyridin-3-ylmethoxy]-phenoxy}-propionic acid ethyl ester was treated with 1 N aqueous LiOH solution to give the title compound as yellow crystals.

MS: 530.0 (M+H)$^+$.

Example 152

2-{4-[2-Cyclopropylmethyl-6-(4-trifluoromethoxy-phenyl)-4-trifluoromethyl-pyridin-3-ylmethoxy]-2-methyl-phenoxy}-2-methyl-propionic acid A] 2-Cyclopropyl-acetimidic acid methyl ester Hydrochloride To a solution of 11.2 ml (120 mmol) cyclopropylacetonitrile in 60 ml diethyl ether, 4.9 ml (120 mmol) methanol were added. The solution was cooled to 4° C. and HCl gas was bubbled through the solution for 3 h. The mixture was stirred for 14 h at ambient temperature and the solvent removed under reduced pressure. The residue was washed with pentane and diethyl ether to give 10.3 g (69 mmol, 58%) of the title compound as colorless crystals which were used in the next step without further purification.

B] 5-(1-Amino-2-cyclopropyl-ethylidene)-2,2-dimethyl-[1,3]dioxane-4,6-dione 1 g (7 mmol) 2-Cyclopropyl-acetimidic acid methyl ester hydrochloride, 963 mg (7 mmol) 2,2-dimethyl-[1,3]dioxane-4,6-dione and 1.07 ml (8 mmol) triethylamine were heated under reflux in 7 ml chloroform for 14 h. The mixture was diluted with dichloromethane, washed neutral with brine/ice water 1/1 and the organic layer was dried over sodium sulfate. The solvent was removed under reduced pressure and the residue purified by flash chromatography (silica gel, heptane/AcOEt) to give 128 mg (0.6 mmol, 9%) of the title compound as yellow crystals.

C] 3-Amino-4-cyclopropyl-but-2-enoic acid ethyl ester 397 mg (2 mmol) 5-(1-Amino-2-cyclopropyl-ethylidene)-2,2-dimethyl-[1,3]dioxane-4,6-dione were added to a solution of 45 mg (2 mmol) sodium in 3 ml ethanol. The reaction mixture was heated under reflux for 14 h, diluted with dichloromethane and poured onto ice water/brine 1/1. The organic layer was dried over sodium sulfate and the solvent removed under reduced pressure to give 231 mg (1.4 mmol, 77%) of the title compound as orange oil.

MS: 170.3 (M+H)$^+$.

D] (Z)-4,4,4-Trifluoro-3-hydroxy-1-(4-trifluoromethoxy-phenyl)-but-2-en-1-one 25 g (122 mmol) 1-(4-Trifluoromethoxy-phenyl)-ethanone were added to a suspension of 16.5 g (147 mmol) potassium-tert-butylate in 250 ml toluene. The suspension was cooled to 2° C. and 17.5 ml (147 mmol) ethyltrifluoroacetate were added within 15 min. The mixture was stirred at ambient temperature for 14 h, cooled to 2° C. and brought to pH 6 with 10% aqueous $H_2SO_4$. Twofold extraction with tert-butyl methylether was followed by washing of the combined extracts with brine/ice water 1/1 and drying of the organic layer over sodium sulfate. The solvent was removed under reduced pressure and the residue purified by flash chromatography (silica gel, dichloromethane) to give 30.5 g (102 mmol, 83%) of the title compound as red oil.

MS: 301.9 (M+H)$^+$.

E] 2-Cyclopropylmethyl-6-(4-trifluoromethoxy-phenyl)-4-trifluoromethyl-nicotinic acid ethyl ester 231 mg (1.4 mmol) 3-Amino-4-cyclopropyl-but-2-enoic acid ethyl ester were added to a solution of 819 mg (2.7 mmol) (Z)-4,4,4-trifluoro-3-hydroxy-1-(4-trifluoromethoxy-phenyl)-but-2-en-1-one in 2.7 ml acetonitrile. The mixture was heated under reflux conditions for 12 h, the solvent was removed under reduced pressure and the residue purified by flash chromatography (silica gel, heptane/AcOEt) to give 242 mg (0.56 mmol, 41%) of the title compound as yellow oil.

MS: 434.3 (M+H)$^+$.

F] [2-Cyclopropylmethyl-6-(4-trifluoromethoxy-phenyl)-4-trifluoromethyl-pyridin-3-yl]-methanol In analogy to the procedure described in example 43D], 2-cyclopropylmethyl-6-(4-trifluoromethoxy-phenyl)-4-trifluoromethyl-nicotinic acid ethyl ester was treated with lithium aluminium hydride to give the title compound as colorless crystals.

MS: 392.3 (M+H)$^+$.

G] 2-{4-[2-Cyclopropylmethyl-6-(4-trifluoromethoxy-phenyl)-4-trifluoromethyl-pyridin-3-ylmethoxy]-2-methyl-phenoxy}-2-methyl-propionic acid ethyl ester In analogy to the procedure described in example 43E], 2-(4-hydroxy-2-methyl-phenoxy)-2-methyl-propionic acid ethyl ester (described in WO 02/092590) was reacted with [2-cyclopropylmethyl-6-(4-trifluoromethoxy-phenyl)-4-trifluoromethyl-pyridin-3-yl]-methanol in the presence of N,N,N',N'-tetramethylazodicarboxamide and tributylphosphine to give the title compound as colorless crystals.

MS: 593.3 (M+H)$^+$.

H] 2-{4-[2-Cyclopropylmethyl-6-(4-trifluoromethoxy-phenyl)-4-trifluoromethyl-pyridin-3-ylmethoxy]-2-methyl-phenoxy}-2-methyl-propionic acid In analogy to the procedure described in example 26C], 2-{4-[2-cyclopropylmethyl-6-(4-trifluoromethoxy-phenyl)-4-trifluoromethyl-pyridin-3-ylmethoxy]-2-methyl-phenoxy}-2-methyl-propionic acid ethyl ester was treated with 1 N aqueous LiOH solution to give the title compound as off-white crystals.

MS: 584.3 (M+H)$^+$.

Example 153

2-{4-[2-Cyclopropyl-6-(4-trifluoromethoxy-phenyl)-4-trifluoromethyl-pyridin-3-ylmethoxy]-2-methyl-phenoxy}-2-methyl-propionic acid A] 2-Cyclopropyl-6-(4-trifluoromethoxy-phenyl)-4-trifluoromethyl-nicotinic acid ethyl ester In analogy to the procedure described in example 152E], 3-amino-3-cyclopropyl-acrylic acid ethyl ester (J. P. Célérier, E. Deloisy, P. Kapron, G. Lhommet, P. Maitte, *Synthesis* 1981, 130–133) was reacted with (Z)-4,4,4-trifluoro-3-hydroxy-1-(4-trifluoromethoxy-phenyl)-but-2-en-1-one (example 152D]) to give the title compound as colorless oil.

MS: 420.3 (M+H)$^+$.

B] [2-Cyclopropyl-6-(4-trifluoromethoxy-phenyl)-4-trifluoromethyl-pyridin-3-yl]-methanol In analogy to the procedure described in example 43D], 2-cyclopropyl-6-(4-trifluoromethoxy-phenyl)-4-trifluoromethyl-nicotinic acid ethyl ester was treated with lithium aluminium hydride to give the title compound as colorless crystals.

MS: 378.3 (M+H)$^+$.

C] 2-{4-[2-Cyclopropyl-6-(4-trifluoromethoxy-phenyl)-4-trifluoromethyl-pyridin-3-ylmethoxy]-2-methyl-phenoxy}-2-methyl-propionic acid ethyl ester In analogy to the procedure described in example 43E], 2-(4-hydroxy-2-methyl-phenoxy)-2-methyl-propionic acid ethyl ester (described in WO 02/092590) was reacted with [2-cyclopropyl-6-(4-trifluoromethoxy-phenyl)-4-trifluoromethyl-pyridin-3-yl]-methanol in the presence of N,N,N',N'-tetramethylazodicarboxamide and tributylphosphine to give the title compound as colorless crystals.

MS: 598.3 (M+H)$^+$.

D] 2-{4-[2-Cyclopropyl-6-(4-trifluoromethoxy-phenyl)-4-trifluoromethyl-pyridin-3-ylmethoxy-2-methyl-phenoxy-2-methyl-propionic acid In analogy to the procedure described in example 26C], 2-{4-[2-cyclopropyl-6-(4-trifluoromethoxy-phenyl)-4-trifluoromethyl-pyridin-3-ylmethoxy)-2-methyl-phenoxy}-2- methyl-propionic acid ethyl ester was treated with 1 N aqueous LiOH solution to give the title compound as colorless foam.

MS: 570.3 (M+H)+.

Example 154

2-Methyl-2-{2-methyl-4-[6-(4-trifluoromethoxy-phenyl)-2-trifluoromethyl-pyridin-3-ylmethoxy]-phenoxy}-propionic acid A] 6-(4-Trifluoromethoxy-phenyl)-2-trifluoromethyl-nicotinic acid ethyl ester In analogy to the procedure described in example 143D], (E)-3-dimethylamino-1-(4-trifluoromethoxy-phenyl)-propenone (example 143C]) was reacted with 4,4,4-trifluoro-3-oxobutanoic acid ethyl ester in the presence of ammonium acetate and acetic acid to give the title compound as yellow oil.

MS: 380.3 (M+H)+.

B] [6-(4-Trifluoromethoxy-phenyl)-2-trifluoromethyl-pyridin-3-yl]-methanol

In analogy to the procedure described in example 43D], 6-(4-trifluoromethoxy-phenyl)-2-trifluoromethyl-nicotinic acid ethyl ester was treated with lithium aluminium hydride to give the title compound as colorless crystals.

MS: 338.0 (M+H)+.

C] 2-Methyl-2-{2-methyl-4-[6-(4-trifluoromethoxy-phenyl)-2-trifluoromethyl-pyridin-3-ylmethoxy]-phenoxy}-propionic acid ethyl ester In analogy to the procedure described in example 43E], 2-(4-hydroxy-2-methyl-phenoxy)-2-methyl-propionic acid ethyl ester (described in WO 02/092590) was reacted with [6-(4-trifluoromethoxy-phenyl)-2-trifluoromethyl-pyridin-3-yl]-methanol in the presence of N,N,N',N'-tetramethylazodicarboxamide and tributylphosphine to give the title compound as colorless oil.

MS: 558.3 (M+H)+.

D] 2-Methyl-2-{2-methyl-4-[6-(4-trifluoromethoxy-phenyl)-2-trifluoromethyl-pyridin-3-ylmethoxy]-phenoxy}-propionic acid In analogy to the procedure described in example 26C], 2-methyl-2-{2-methyl-4-[6-(4-trifluoromethoxy-phenyl)-2-trifluoromethyl-pyridin-3-ylmethoxy]-phenoxy}-propionic acid ethyl ester was treated with 1 N aqueous LiOH solution to give the title compound as colorless oil.

MS: 528.1 (M–H)−.

Example 155

2-{4-[4-Methoxymethyl-2-(4-trifluoromethoxy-phenyl)-pyrimidin-5-ylmethoxy]-2-methyl-phenoxy}-2-methyl-propionic acid A] 2-{4-[4-Methoxymethyl-2-(4-trifluoromethoxy-phenyl)-pyrimidin-5-ylmethoxy]-2-methyl-phenoxy}-2-methyl-propionic acid ethyl ester In analogy to the procedure described in example 113A], 2-(4-hydroxy-2-methyl-phenoxy)-2-methyl-propionic acid ethyl ester (described in WO 02/092590) was reacted with 5-chloromethyl-4-methoxymethyl-2-(4-trifluoromethoxy-phenyl)-pyrimidine (example 155E]) to give the title compound as brown oil.

MS: 535.1 (M+H)+.

B] 2-{4-[4-Methoxymethyl-2-(4-trifluoromethoxy-phenyl)-pyrimidin-5-ylmethoxy]-2-methyl-phenoxy}-2-methyl-propionic acid In analogy to the procedure described in example 113B], saponification of 2-{4-[4-methoxymethyl-2-(4-trifluoromethoxy-phenyl)-pyrimidin-5-ylmethoxy]-2-methyl-phenoxy}-2-methyl-propionic acid ethyl ester yielded the title compound as off-white solid.

MS: 505.2 (M–H)−.

5-Chloromethyl-4-methoxymethyl-2-(4-trifluoromethoxy-phenyl)-pyrimidine used in 155A] was prepared as follows:

C] (E,Z)-2-Ethoxymethylene-4-methoxy-3-oxo-butyric acid methyl ester

In analogy to the procedures described in example 27C], methyl 4-methoxyacetoacetate and triethyl orthoformate gave the title compound as orange oil.

MS: 201.9 (M)+.

D] [4-Methoxymethyl-2-(4-trifluoromethoxy-phenyl)-pyrimidin-5-yl]-methanol

In analogy to the procedures described in example 27D] and 27E], (E,Z)-2-ethoxymethylene-4-methoxy-3-oxo-butyric acid methyl ester and 4-trifluoromethoxy-benzamidine HCl gave the title compound as off-white solid.

MS: 315.1 (M+H)+.

E] 5-Chloromethyl-4-methoxymethyl-2-(4-trifluoromethoxy-phenyl)-pyrimidine

In analogy to the procedure described in example 113H], [4-methoxymethyl-2-(4-trifluoromethoxy-phenyl)-pyrimidin-5-yl]-methanol and thionylchloride gave the title compound as a brown oil.

MS: 333.1 (M+H, 1Cl)+.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |

-continued

| Ingredients | Per tablet | |
|---|---|---|
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavoring additives and filled into sachets.

What is claimed:
1. A Compound of the formula

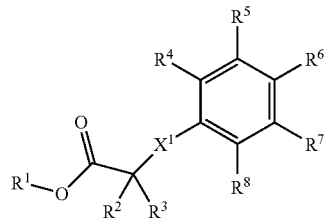

and enantiomers and pharmaceutically acceptable salts or esters thereof, wherein
  $X^1$ is O, S, $CH_2$
  $R^1$ is hydrogen or $C_{1-7}$-alkyl;
  $R^2$ is hydrogen or $C_{1-7}$-alkyl,
    or, if $X^1$ is $CH_2$, $R^2$ is hydrogen, $C_{1-7}$-alkyl or $C_{1-7}$-alkoxy;
  $R^3$ is hydrogen or $C_{1-7}$-alkyl;
  $R^4$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
  $R^5$, $R^6$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
  and one of $R^5$, $R^6$ and $R^7$ is

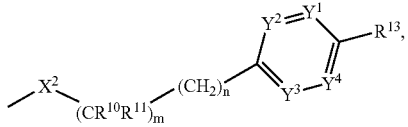

wherein
  $X^2$ is selected from the group consisting of S, O, $NR^9$, $(CH_2)_p NR^9 CO$, or $(CH_2)_p CONR^9$,
  $R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl;
  $Y^1$, $Y^2$, $Y^3$ and $Y^4$ are N or C—$R^{12}$, and 1 or 2 of $Y^1$, $Y^2$, $Y^3$ and $Y^4$ are N and the other ones are C—$R^{12}$;
  $R^{10}$ is $C_{1-7}$-alkyl, $C_{3-7}$-cycloalkyl, fluoro-$C_{1-7}$-alkyl, or $C_{1-7}$-alkoxy-$C_{1-7}$-alkyl;
  $R^{11}$ is hydrogen, $C_{1-7}$-alkyl, $C_{1-7}$-alkoxy-$C_{1-7}$-alkyl;
  $R^{12}$ independently from each other is selected from the group consisting of hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;
  $R^{13}$ is aryl or heteroaryl;
  m is 0 or 1, n is 0, 1, 2 or 3, and p is 0, 1 or 2, and the sum of m, n and p is 1, 2, 3 or 4;
provided that compounds of formula I are excluded, wherein
  $X^1$ is O, $R^2$ and $R^3$ are hydrogen,
  $R^6$ is equal to

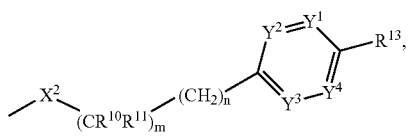

$X^2$ is O or S, and m is 0.
2. The Compound of claim 1, wherein
  $X^2$ is $NR^9$, $(CH_2)_p NR^9 CO$ or $(CH_2)_p CONR^9$,
  $R^9$ is hydrogen, $C_{1-7}$-alkyl, $C_{3-7}$-cycloalkyl, fluoro-$C_{1-7}$-alkyl, hydroxy-$C_{2-7}$-alkyl, or
  $C_{1-7}$-alkoxy-$C_{2-7}$-alkyl; and p is 0, 1 or 2.
3. The Compound of claim 2, wherein $X^2$ is $NR^9$, and $R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl.
4. The Compound of claim 1, wherein
  $X^2$ is $(CH_2)_p NR^9 CO$, or $(CH_2)_p CONR^9$,
  $R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl; and p is 0, 1 or 2.
5. The Compound of claim 4, wherein $R^9$ is $C_{1-7}$-alkyl.
6. The Compound of claim 2, wherein said compound is selected from the group consisting of
  (2-(3-methoxy-propyl)-4-{methyl-[2-methyl-6-(4-trifluoromethyl-phenyl)-pyridin-3-ylmethyl]-amino}-phenoxy)-acetic acid,
  [rac]-[2-methyl-4-(methyl-{1-[2-methyl-6-(3-trifluoromethyl-phenyl)-pyridin-3-yl]-butyl}-amino)-phenoxy]-acetic acid,
  (4-{[6-(4-chloro-phenyl)-pyridin-3-ylmethyl]-methyl-amino}-2-methyl-phenoxy)-acetic acid, 2-methyl-2-[3-(methyl-{2-[2-methyl-6-(4-trifluoromethyl-phenyl)-pyridin-3-yl]-acetyl}-amino)-phenoxy]-propionic acid, and
  (4-{[4-cyclopropyl-2-(4-trifluoromethyl-phenyl)-pyrimidin-5-ylmethyl]-methyl-amino}-2-methyl-phenoxy)-acetic acid.
7. The Compound of claim 4, wherein said compound is selected from the group consisting of 2-methyl-2-(3-{methyl-[2-methyl-6-(4-trifluoromethyl-phenyl)-pyridin-3-ylmethyl]-carbamoyl}-phenoxy)-propionic acid,
  2-[3-([]2-[4-cyclopropyl-2-(4-trifluoromethyl-phenyl)-pyrimidin-5-yl]-acetyl}-methyl-amino)-phenoxy]-2-methyl-propionic acid,
  2-methyl-2-[3-(methyl-{2-[2-methyl-6-(4-trifluoromethyl-phenyl)-pyridin-3-yl]-acetyl}-amino)-5-trifluoromethyl-phenoxy]-propionic acid,
  2-[4-({[4-cyclopropyl-2-(4-trifluoromethyl-phenyl)-pyrimidine-5-carbonyl]-amino}-methyl)-phenoxy]-2-methyl-propionic acid, and
  2-methyl-2-(4-{[2-methyl-6-(4-trifluoromethyl-phenyl)-pyridin-3-ylcarbamoyl]-methyl}-phenoxy)-propionic acid.
8. The Compound of claim 4, wherein said compound is selected from the group consisting of
  2-[3-chloro-4-({[4-trifluoromethyl-2-(4-trifluoromethyl-phenyl)-pyrimidine-5-carbonyl]-amino}-methyl)-phenoxy]-2-methyl-propionic acid,
  2-methyl-2-[4-({[4-trifluoromethyl-2-(4-trifluoromethyl-phenyl)-pyrimidine-5-carbonyl]-amino}-methyl)-phenoxy]-propionic acid; and
  2-(4-{[4-cyclopropyl-2-(4-trifluoromethyl-phenyl)-pyrimidin-5-ylcarbamoyl]-methyl}-phenoxy)-2-methyl-propionic acid.
9. The Compound of claim 1, wherein $X^1$ and $X^2$ are O and $R^2$ is $C_{1-7}$-alkyl.
10. The Compound of claim 1, wherein $X^1$ and $X^2$ are O and $R^2$ and $R^3$ are $C_{1-7}$-alkyl.
11. The Compound of claim 10, wherein said compound is selected from the group consisting of
  2-methyl-2-{2-methyl-4-[2-methyl-6-(3-trifluoromethyl-phenyl)-pyridin-3-ylmethoxy]-phenoxy}-propionic acid,
  2-methyl-2-{2-methyl-4-[6-(4-trifluoromethoxy-phenyl)-pyridin-3-ylmethoxy]-phenoxy}-propionic acid, and
  2-{4-[4-cyclopropyl-2-(4-trifluoromethyl-phenyl)-pyrimidin-5-ylmethoxy]-2-methyl-phenoxy}-2-methyl-propionic acid.
12. The Compound of claim 10, wherein said compound is selected from the group consisting of
  2-methyl-2-{2-methyl-4-[2-methyl-6-(4-trifluoromethoxy-phenyl)-pyridin-3-ylmethoxy]-phenoxy}-propionic acid,
  2-{4-[4-cyclopropyl-2-(3-trifluoromethyl-phenyl)-pyrimidin-5-ylmethoxy]-2-methyl-phenoxy}-2-methyl-propionic acid, and
  2-{4-[4-(2-methoxy-ethyl)-6-methyl-2-(4-trifluoromethyl-phenyl)-pyrimidin-5-ylmethoxy]-2-methyl-phenoxy}-2-methyl-propionic acid.
13. The Compound of claim 10, wherein said compound is selected from the group consisting of
  2-{4-[2-cyclopropyl-6-(4-trifluoromethoxy-phenyl)-pyridin-3-ylmethoxy]-2-methyl-phenoxy}-2-methyl-propionic acid,
  2-{4-[4-methoxymethyl-6-methyl-2-(3-trifluoromethyl-phenyl)-pyrimidin-5-ylmethoxy-2-methyl-phenoxy}-2-methyl-propionic acid,
  2-{4-[2-cyclopropyl-6-(4-trifluoromethoxy-phenyl)-4-trifluoromethyl-pyridin-3-ylmethoxy]-2-methyl-phenoxy}-2-methyl-propionic acid,
  2-{4-[4-methoxymethyl-2-(4-trifluoromethoxy-phenyl)-pyrimidin-5-ylmethoxy]-2-methyl-phenoxy}-2-methyl-propionic acid, 2-{4-[2-cyclopropyl-6-(4-trifluoromethoxy-phenyl)-4-trifluoromethyl-pyridin-3-ylmethoxy]-2-methyl-phenoxy}-2-methyl-propionic acid, and 2-{4-[4-methoxymethyl-2-(4-trifluoromethoxy-phenyl)-pyrimidin-5-ylmethoxy]-2-methyl-phenoxy}-2-methyl-propionic acid.

14. The Compound of claim 1, wherein $X^1$ and $X^2$ are O and m is 1.

15. The Compound of claim 14, wherein said compound is selected from the group consisting of

[rac]-(4-{1-[4-Cyclopropyl-2-(4-trifluoromethyl-phenyl)-pyrimidin-5-yl]-ethoxy}-2-methyl-phenoxy)-acetic acid, and

[rac]-(4-{1-[4-Cyclopropyl-2-(4-trifluoromethyl-phenyl)-pyrimidin-5-yl]-butoxy}-2-methyl-phenoxy)-acetic acid.

16. The Compound of claim 1, wherein $X^1$ is S.

17. The Compound of claim 16, wherein said compound is selected from the group consisting of

[rac]-(2-methyl-4-{1-[2-methyl-6-(4-trifluoromethyl-phenyl)-pyridin-3-yl]-ethoxy}-phenylsulfanyl)-acetic acid, and

[rac]-(2-methyl-4-{1-[2-methyl-6-(4-trifluoromethyl-phenyl)-pyridin-3-yl]-butoxy}-phenylsulfanyl)-acetic acid.

18. The Compound of claim 1, wherein $X^1$ is O, $X^2$ is S and m is 1.

19. The Compound of claim 18, wherein said compound is selected from the group consisting of

[rac]-(2-methyl-4-{1-[2-methyl-6-(4-trifluoromethyl-phenyl)-pyridin-3-yl]-ethylsulfanyl}-phenoxy)-acetic acid, and

[rac]-(4-{1-[4-Cyclopropyl-2-(4-trifluoromethyl-phenyl)-pyrimidin-5-yl]-ethylsulfanyl}-2-methyl-phenoxy)-acetic acid.

20. The Compound of claim 1, wherein $R^{13}$ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano.

21. The Compound of claim 20, wherein $R^{13}$ is unsubstituted phenyl or phenyl substituted with one to three groups selected from $C_{1-7}$-alkyl, $C_{1-7}$-alkoxy, halogen, fluoro-$C_{1-7}$-alkyl and cyano.

22. The Compound of claim 21, wherein $R^{13}$ is phenyl substituted with halogen or fluoro-$C_{1-7}$-alkyl.

23. The Compound of claim 20, wherein R13 is phenyl substituted with fluoro-$C_{1-7}$-alkoxy.

24. The Compound of claim 23, wherein $R^1$ is hydrogen.

25. The Compound of claim 1, wherein $R^3$ is $C_{1-7}$-alkyl.

26. The Compound of claim 1, wherein 2 of $Y^1$, $Y^2$, $Y^3$ and $Y^4$ are N and the other ones are C—$R^{12}$.

27. A process for the manufacture of a compound of claim 1, which process comprises a) reacting a compound of formula

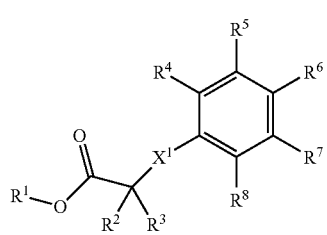

II wherein $R^1$ is $C_{1-7}$-alkyl, $R^2$ to $R^8$ are as defined as in claim 1 and one of $R^5$, $R^6$ or $R^7$ is selected from —OH, —SH or —NHR$^9$, wherein $R^9$ is as defined in claim 1, with a compound of formula

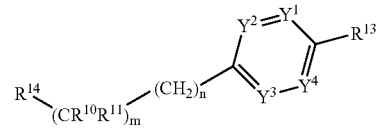

III wherein $Y^1$ to $Y^4$, $R^{10}$, $R^{11}$, $R^{13}$, m and n are as defined in claim 1 and $R^{14}$ is —OH, —Cl, —Br, —I or another leaving group, to obtain a compound of formula

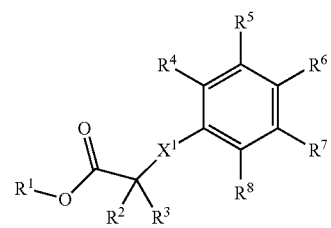

I-1 wherein one of $R^5$, $R^6$ and $R^7$ is

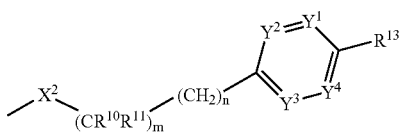

and wherein $X^2$ is O, S or —NR$^9$, $R^1$ is $C_{1-7}$-alkyl and $X^1$, $Y^1$ to $Y^4$, $R^2$ to $R^{13}$ and m and n are as defined in claim 1, and optionally hydrolysing the ester group to obtain a compound of formula I, wherein $R^1$ is hydrogen;

or, alternatively, b) reacting a compound of formula

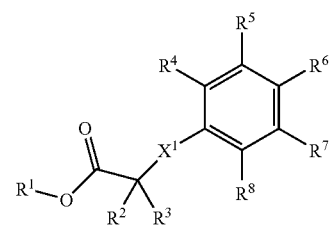

IV wherein $R^1$ is $C_{1-7}$-alkyl, $R^2$ to $R^8$ are as defined as in claim 1 and one of $R^5$, $R^6$or $R^7$ is —(CH$_2$)$_p$—NHR$^9$, wherein $R^9$ and p are as defined in claim 1, with a compound of formula

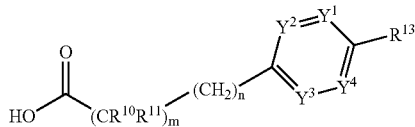

V wherein $Y^1$ to $Y^4$, $R^{10}$, $R^{11}$, $R^{13}$, m and n are as defined in claim 1, to obtain a compound of formula

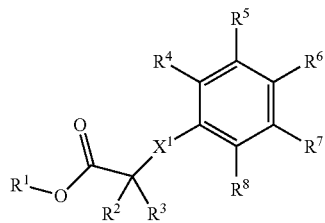

I-2 wherein one of $R^5$, $R^6$ and $R^7$ is

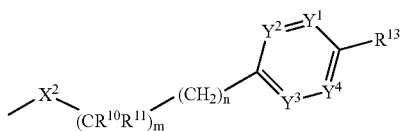

and wherein $X^2$ is $—(CH_2)_p—NR^9CO—$, $R^1$ is $C_{1-7}$-alkyl and $X^1$, $Y^1$ to $Y^4$, $R^2$ to $R^{13}$ and m, n and p are as defined in claim 1, and optionally hydrolysing the ester group to obtain a compound of formula I, wherein $R^1$ is hydrogen;

or, alternatively, c) reacting a compound of formula

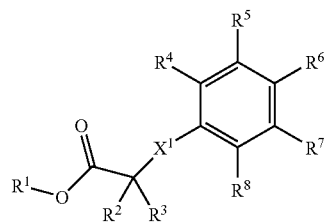

VI wherein $R^1$ is $C_{1-7}$-alkyl, $R^2$ to $R^8$ are as defined as in claim 1 and one of $R^5$, $R^6$ or $R^7$ is $—(CH_2)_p—COOH$, and p is defined as in claim 1, with a compound of formula

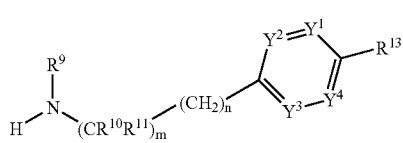

VII wherein $Y^1$ to $Y^4$, $R^9$, $R^{10}$, $R^{11}$, $R^{13}$, m and n are as defined in claim 1, to obtain a compound of formula

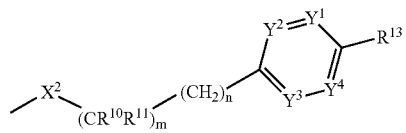

I-3 wherein one of $R^5$, $R^6$ and $R^7$ is

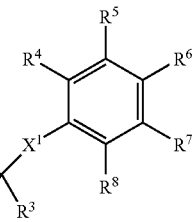

and wherein $X^2$ is $—(CH_2)_p—CONR^9$, $R^1$ is $C_{1-7}$-alkyl and $X^1$, $Y^1$ to $Y^4$, $R^2$ to $R^{13}$ and m, n and p are as defined in claim 1, and optionally hydrolysing the ester group to obtain a compound of formula I, wherein $R^1$ is hydrogen.

28. A pharmaceutical composition which comprises a compound of the formula

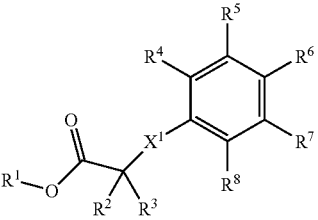

I and enantiomers and pharmaceutically acceptable salts and esters thereof, wherein $X^1$ is O, S, $CH_2$ $R^1$ is hydrogen or $C_{1-7}$-alkyl;

$R^2$ is hydrogen or $C_{1-7}$-alkyl, or, if $X^1$ is $CH_2$, $R^2$ is hydrogen, $C_{1-7}$-alkyl or $C_{1-7}$-alkoxy;

$R^3$ is hydrogen or $C_{1-7}$-alkyl;

$R^4$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

$R^5$, $R^6$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^5$, $R^6$ and $R^7$ is

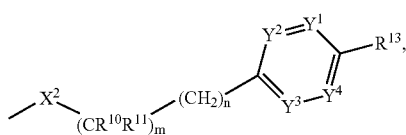

wherein
- $X^2$ is selected from the group consisting of S, O, $NR^9$, $(CH_2)_p NR^9 CO$, or $(CH_2)_p CONR^9$,
- $R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl;
- $Y^1$, $Y^2$, $Y^3$ and $Y^4$ are N or C—$R^{12}$, and 1 or 2 of $Y^1$, $Y^2$, $Y^3$ and $Y^4$ are N and the other ones are
- $R^{10}$ is $C_{1-7}$-alkyl, $C_{3-7}$-cycloalkyl, fluoro-$C_{1-7}$-alkyl, or $C_{1-7}$-alkoxy-$C_{1-7}$-alkyl;
- $R^{11}$ is hydrogen, $C_{1-7}$-alkyl, $C_{1-7}$-alkoxy-$C_{1-7}$-alkyl;
- $R^{12}$ independently from each other in each occurance is selected from the group consisting of hydrogen, $C_{1-7}$-alkyl, $C_{3-7}$-cycloalkyl, fluoro-$C_{1-7}$-aklyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;
- $R^{13}$ is aryl or heteroaryl;
- m is 0 or 1, n is 0, 1, 2 or 3, and p is 0, 1 or 2, and the sum of m, n and p is 1, 2, 3 or 4;

provided that compounds of formula I are excluded, wherein $X^1$ is O, $R^2$ and $R^3$ are hydrogen, $R^6$ is equal to

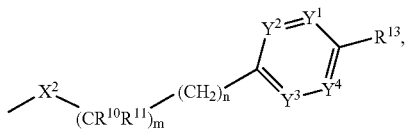

$X^2$ is O or S, and m is 0 together with a pharmaceutically acceptable carrier or excipient.

* * * * *